(12) United States Patent
Myers et al.

(10) Patent No.: US 10,640,528 B2
(45) Date of Patent: *May 5, 2020

(54) MACROLIDES WITH MODIFIED DESOSAMINE SUGARS AND USES THEREOF

(71) Applicant: President and Fellows of Harvard College, Cambridge, MA (US)

(72) Inventors: Andrew G. Myers, Boston, MA (US); Ian Bass Seiple, San Francisco, CA (US); Ziyang Zhang, San Francisco, CA (US)

(73) Assignee: President and Fellows of Havard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/558,896

(22) PCT Filed: Mar. 25, 2016

(86) PCT No.: PCT/US2016/024333
§ 371 (c)(1),
(2) Date: Sep. 15, 2017

(87) PCT Pub. No.: WO2016/154591
PCT Pub. Date: Sep. 29, 2016

(65) Prior Publication Data
US 2018/0066008 A1 Mar. 8, 2018

Related U.S. Application Data

(60) Provisional application No. 62/138,198, filed on Mar. 25, 2015, provisional application No. 62/138,168, filed on Mar. 25, 2015.

(51) Int. Cl.
*C07H 17/08* (2006.01)
*C07H 1/00* (2006.01)
*C07H 15/26* (2006.01)

(52) U.S. Cl.
CPC ............ *C07H 17/08* (2013.01); *C07H 1/00* (2013.01); *C07H 15/26* (2013.01)

(58) Field of Classification Search
CPC ........... C07H 1/00; C07H 17/08; C07H 15/26
See application file for complete search history.

(56) References Cited

U.S. PATENT DOCUMENTS

| | | |
|---|---|---|
| 5,656,607 A | 8/1997 | Roussel et al. |
| 6,262,030 B1 | 7/2001 | Wu et al. |
| 6,399,582 B1 | 6/2002 | Hlasta et al. |
| 6,777,543 B2 | 8/2004 | Wu et al. |
| 6,939,861 B2 | 9/2005 | Gary et al. |
| 7,601,695 B2 | 10/2009 | Liang et al. |
| 7,767,797 B1 | 8/2010 | Gutke et al. |
| 8,012,943 B2 | 9/2011 | Liang et al. |
| 8,063,021 B2 | 11/2011 | Li et al. |
| 8,343,936 B2 | 1/2013 | Duffield et al. |
| 8,759,500 B2 | 6/2014 | Pereira et al. |
| 8,791,080 B2 | 7/2014 | Fernandes |
| 8,796,232 B2 | 8/2014 | Fernandes et al. |
| 8,796,474 B1 | 8/2014 | Williams et al. |
| 9,982,005 B2 | 5/2018 | Myers et al. |

(Continued)

FOREIGN PATENT DOCUMENTS

| | | |
|---|---|---|
| CN | 1984918 A | 6/2007 |
| CN | 101103039 A | 1/2008 |

(Continued)

OTHER PUBLICATIONS

Partial Supplementary European Search Report for Application No. EP 14779590.0, dated Oct. 26, 2016.

(Continued)

*Primary Examiner* — Jonathan S Lau
(74) *Attorney, Agent, or Firm* — Wolf, Greenfield & Sacks, P.C.

(57) ABSTRACT

Provided herein are macrolide compounds of Formula (I) and (I-N) for the treatment of infectious diseases and inflammatory conditions. The 14-membered ketolides and 14-, 15-, and 16-membered azaketolides described herein comprise modified sugars which are desosamine or mycaminose analogs. Pharmaceutical compositions and methods of treating infection diseases and inflammatory conditions using the inventive macrolides are also provided. This disclosure additionally provides methods of preparing the macrolides by the coupling of an eastern and western half.

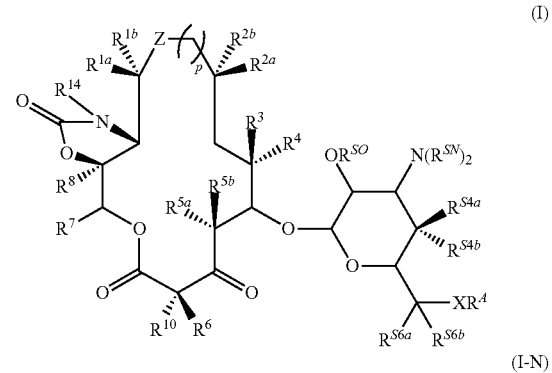

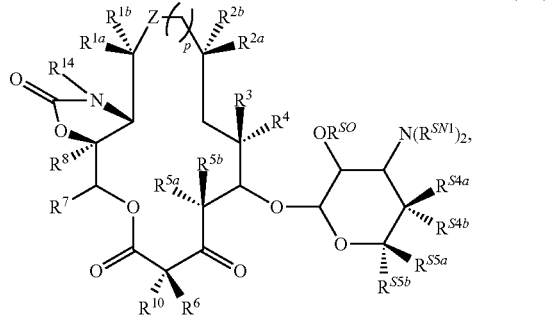

20 Claims, 3 Drawing Sheets

(56) References Cited

U.S. PATENT DOCUMENTS

| | | |
|---|---|---|
| 2002/0013281 A1 | 1/2002 | Agouridas et al. |
| 2002/0128212 A1 | 9/2002 | Or et al. |
| 2003/0199458 A1 | 10/2003 | Kosan et al. |
| 2005/0090461 A1 | 4/2005 | Leadlay et al. |
| 2006/0096158 A1 | 5/2006 | Robinson |
| 2006/0141589 A1 | 6/2006 | Okuda et al. |
| 2008/0021226 A1 | 1/2008 | Kanada et al. |
| 2008/0287376 A1 | 11/2008 | Das et al. |
| 2009/0170790 A1 | 7/2009 | Das et al. |
| 2009/0209547 A1 | 8/2009 | Kim et al. |
| 2010/0035832 A1 | 2/2010 | Heggelund et al. |
| 2010/0216731 A1 | 8/2010 | Pereira et al. |
| 2011/0195920 A1 | 8/2011 | Fernandes |
| 2011/0201566 A1 | 8/2011 | Fernandes et al. |
| 2012/0058963 A1 | 3/2012 | Alihoszic et al. |
| 2012/0172323 A1 | 7/2012 | Fernandes |
| 2013/0018008 A1 | 1/2013 | Pereira et al. |
| 2013/0045937 A1 | 2/2013 | Fernandes |
| 2013/0066056 A1 | 3/2013 | Pereira et al. |
| 2013/0172280 A1 | 7/2013 | Pereira et al. |
| 2013/0178429 A1 | 7/2013 | Liu et al. |
| 2013/0345410 A1 | 12/2013 | Liang et al. |
| 2014/0213515 A1 | 7/2014 | Liu et al. |
| 2015/0105339 A1 | 4/2015 | Fernandes et al. |
| 2016/0052951 A1 | 2/2016 | Myers et al. |
| 2017/0305953 A1 | 10/2017 | Myers et al. |
| 2018/0111956 A1 | 4/2018 | Myers et al. |
| 2018/0298048 A1 | 10/2018 | Myers et al. |

FOREIGN PATENT DOCUMENTS

| | | |
|---|---|---|
| CN | 101142225 A | 3/2008 |
| CN | 101631795 A | 1/2010 |
| CN | 102690297 A | 9/2012 |
| EP | 14779590.0 | 10/2016 |
| EP | 14779590.0 | 2/2017 |
| EP | 15848340.4 | 6/2018 |
| EP | 16769811.7 | 7/2018 |
| EP | 15848340.4 | 9/2018 |
| EP | 16769811.7 | 10/2018 |
| FR | 2692579 A1 | 12/1993 |
| JP | 2001-247595 A | 9/2001 |
| JP | 2002-542254 A | 12/2002 |
| JP | 2003-507487 A | 2/2003 |
| JP | 2012-506872 A | 3/2012 |
| WO | WO 98/56801 A1 | 12/1998 |
| WO | WO 1999/00125 A1 | 1/1999 |
| WO | WO 99/21866 A1 | 5/1999 |
| WO | WO 2000/63223 A1 | 10/2000 |
| WO | WO 2001/10879 A1 | 2/2001 |
| WO | WO 2001/14397 A1 | 3/2001 |
| WO | WO 02/32918 A2 | 4/2002 |
| WO | WO 2003/050132 A1 | 6/2003 |
| WO | WO 2004/080319 A1 | 9/2004 |
| WO | WO 2004/080391 A2 | 9/2004 |
| WO | WO 2004/101591 A1 | 11/2004 |
| WO | WO 2005/030227 A1 | 4/2005 |
| WO | WO 2006/074962 A2 | 7/2006 |
| WO | WO 2006/087644 A2 | 8/2006 |
| WO | WO 2006/120541 A1 | 11/2006 |
| WO | WO 2007/012464 A1 | 2/2007 |
| WO | WO 2007/091393 A1 | 8/2007 |
| WO | WO 2008/110918 A2 | 9/2008 |
| WO | WO 2009/055557 A1 | 4/2009 |
| WO | WO 2010/015703 A2 | 2/2010 |
| WO | WO 2010/048599 A1 | 4/2010 |
| WO | WO 2010/048600 A1 | 4/2010 |
| WO | WO 2010/048601 A1 | 4/2010 |
| WO | WO 2011/018510 A1 | 2/2011 |
| WO | WO 2011/032052 A1 | 3/2011 |
| WO | WO 2011/119604 A1 | 9/2011 |
| WO | WO 2011/131749 A1 | 10/2011 |
| WO | WO 2011/146829 A1 | 11/2011 |
| WO | WO 2012/034058 A1 | 3/2012 |
| WO | WO 2012/051126 A2 | 4/2012 |
| WO | WO 2012/127351 A1 | 9/2012 |
| WO | WO 2013/148891 A1 | 10/2013 |
| WO | PCT/US2014/033025 | 8/2014 |
| WO | WO 2014/145210 A1 | 9/2014 |
| WO | WO 2014/152326 A1 | 9/2014 |
| WO | PCT/US2014/033025 | 10/2014 |
| WO | WO 2014/165792 A2 | 10/2014 |
| WO | PCT/US2014/033025 | 10/2015 |
| WO | PCT/US2015/054700 | 1/2016 |
| WO | PCT/US2016/024333 | 5/2016 |
| WO | PCT/US2016/024210 | 8/2016 |
| WO | PCT/US2016/024333 | 8/2016 |
| WO | PCT/US2015/054700 | 4/2017 |
| WO | PCT/US2016/024210 | 10/2017 |
| WO | PCT/US2018/030002 | 9/2018 |

OTHER PUBLICATIONS

Extended European Search Report for Application No. EP 14779590. 0, dated Feb. 6, 2017.

Invitation to Pay Additional Fees for PCT/US2014/033025, dated Aug. 14, 2014.

International Search Report and Written Opinion for PCT/US2014/ 033025, dated Oct. 28, 2014.

International Preliminary Report on Patentability for PCT/US2014/ 033025, dated Oct. 15, 2015.

International Preliminary Report on Patentability for PCT/US2015/ 054700, dated Apr. 20, 2017.

International Search Report and Written Opinion for PCT/US2015/ 054700, dated Jan. 11, 2016.

International Search Report and Written Opinion for PCT/US2016/ 024210, dated Aug. 12, 2016.

International Preliminary Report on Patentability for PCT/US2016/ 024210, dated Oct. 5, 2017.

Invitation to Pay Additional Fees for PCT/US2016/024333, dated May 18, 2016.

International Search Report and Written Opinion for PCT/US2016/ 024333, dated Aug. 5, 2016.

[No Author Listed], PubChem Substance Summary for CID 10839468. Deposit date Oct. 26, 2006.

Alihodzic et al., Synthesis and antibacterial activity of isomeric 15-membered azalides. J Antibiot (Tokyo). Dec. 2006;59(12):753-69.

Amsden, Anti-inflammatory effects of macrolides—an underappreciated benefit in the treatment of community-acquired respiratory tract infections and chronic inflammatory pulmonary conditions? Journal of Antimicribial Chemotherapy. 2005;55:10-21.

Asaka et al., Recent developments in macrolide antimicrobial research. Curr Top Med Chem (Sharjah, United Arab Emirates). 2003;961-989.

Baer et al., A Stereospecific Synthesis of L-Desosamine. Canadian Journal of Chemistry. 1974;52(1):122-4.

Baer et al., Reactions of nitro sugars. V. Some reactions with methyl 3-deoxy-3-nitro-a, d-hexopyranoside. Canadian J Chem. 1967;45:983-990.

Berge et al., Pharmaceutical salts. J. Pharm. Sci., Jan. 1977;66: 1-19. doi:10.1002/jps.2600660104.

Bertrand et al., Molecular characterization of off-target activities of telithromycin: a potential role for nicotinic acetylcholine receptors. Antimicrob Agents Chemother. Dec. 2010;54(12):5399-402. doi: 10.1128/AAC.00840-10. Epub Sep. 20, 2010.

Boeckman et al., A new, highly efficient, selective methodology for formation of medium-ring and macrocyclic lactones via intramolecular ketene trapping: an application to a convergent synthesis of (−)-kromycin. J Am Chem Soc. 1989;111:8286-8288.

Breton et al., Total synthesis of erythromycin B. Tetrahedron. Jan. 25, 2007;63(26):5709-29.

Bright et al., Synthesis, in vitro and in vivo activity of novel 9-deoxo-9a-AZA-9a-homoerythromycin A derivatives; a new class of macrolide antibiotics, the azalides. J Antibiot. 1988;41:1029-1047.

Bryskier, Ketolides-telithromycin, an example of a new class of antibacterial agents. Clin Microbiol Infect. Dec. 2000;6(12):661-9.

(56) References Cited

OTHER PUBLICATIONS

Bulkley et al., Revisiting the structures of several antibiotics bound to the bacterial ribosome. Proc Natl Acad Sci U.S.A. 2010;107:17158-17163.

Bulman et al., Synthesis of enantiomerically pure tertiary 1,2-aminoalcohols by the highly diastereoselective reductive ring opening of oxazolidines. Tetrahedron. Nov. 2007;63(45):10991-10999.

Burger et al., Synthesis and antibacterial activity of novel C12 ethyl ketolides. Bioorg Med Chem. Aug 15, 2006;14(16):5592-604. Epub May 11, 2006.

Chen et al., Synthesis and antibacterial activity of novel modified 5-O-desosamine ketolides. Bioorg Med Chem Lett. Dec. 15, 2012;22(24):7402-5. Doi: 10.1016/j.bmcl.2012.10.064. Epub Oct. 23, 2012.

Clark et al., Synthesis and antibacterial activity of novel 6-O-substituted erythromycin A derivatives. Bioorganic & Medicinal Chemistry Letters. 2000;10:815-819.

Cossy et al., Formal total synthesis of methynolide. Tetrahedron. 2002;58:5909-5922.

Davidson et al., Stereoselective synthesis of d-desosamine and related glycals via tungsten-catalyzed alkynol cycloisomerization. Org Lett. May 13, 2004;6(10):1601-3.

Denis et al., Synthesis of 6-O-methyl-azithromycin and its ketolide analogue via Beckmann rearrangement of 9€-6-O-methyl-erythromycin oxime. Bioorg Med Chem Lett. Sep. 22, 1998;8(18):2427-32.

Djokic et al., Erythromycin series. XII. Antibacterial in vitro evaluation of 10-dihydro-10-deoxo-11-azaerythromycin A: synthesis and structure-activity relationship of its acyl derivatives. J Antibiot. 1987;40:1006-1015.

Douthwaite et al., Macrolide-ketolide inhibition of MLS-resistant ribosomes is improved by alternative drug interaction with domain II of 23S rRNA. Mol Microbiol. 2000;36:183-192.

Dunkle et al., Structures of the *Escherichia coli* ribosome with antibiotics bound near the peptidyl transferase center explain spectra of drug action. Proc Natl Acad Sci U.S.A. 2010;107: 17152-17157.

Fajdetic et al., Synthesis and structural properties of novel tricyclic 15-membered azilides. Croatia Chemica Acta. 2009;82(4):715-23.

Farrell et al., The in vitro evaluation of solithromycin (CEM-101) against pathogens isolated in the United States and Europe (2009). J Infect. Dec. 2010;61(6):476-83. doi: 10.1016/j.jinf.2010.08.010. Epub Sep. 8, 2010.

Giguere et al., Enantioselective de novo synthesis of 4-deoxy-D-hexopyranoses via hetero-Diels-Alder cycloadditions: total synthesis of ezoaminuroic acid and neosidomycin. J Org Chem. Dec. 2, 2011;76(23):9687-98. Doi: 10.1021/jo201673w. Epub Nov. 10, 2011.

Girard et al., Pharmacokinetic and in vivo studies with azithromycin (CP-62,993), a new macrolide with an extended half-life and excellent tissue distribution. Antimicrob Agents Chemother. 1987;31:1948-1954.

Goldman et al., Binding of novel macrolide structures to macrolides-lincosamides-streptogramin B-resistant ribosomes inhibits protein synthesis and bacterial growth. Antimicrob Agents Chemother. Jul. 1989;33(7):1058-66.

Hansen et al., Structures of five antibiotics bound at the peptidyl transferase center of the large ribosomal subunit. J Mol Biol. 2003;330:1061-1075.

Hansen et al., The macrolide-ketolide antibiotic binding site is formed by structures in domains II and V of 23S ribosomal RNA. Mol Microbiol. 1999;31:623-631.

Hansen et al., The structures of four macrolide antibiotics bound to the large ribosomal subunit. Mol Cell. 2002;10:117-128.

He et al., Formation of unusual sugars: mechanistic studies and biosynthetic applications. Annu Rev Biochem. 2002;71:701-54. Epub Nov. 9, 2001.

Hikota et al., Chiral synthesis of polyketide-derived natural products. 27. Stereoselective synthesis of erythronolide A via an extremely efficient macrolactonization by the modified Yamaguchi method. J. Org. Chem., Jan. 1990;55(1):7-9. DOI: 10.1021/jo00288a004.

Jakopovic et al., Novel desosamine-modified 14- and 15-membered macrolides without antibacterial activity. Bioorg Med Chem Lett. May 15, 2012;22(10):3527-30. Doi: 10.1016/j.bmcl.2012.03.076. Epub Mar. 29, 2012.

Jones et al., New macrolide antibiotics. Synthesis of a 14-membered azalide. J Org Chem. 1992;57:4361-4367.

Kanemasa et al., Asymmetric anti-Selective Aldol Reactions of Titanium Z-Enolates Derived from N-Alkylideneglycinamides Bearing a 2,2-Dimethyloxazolidine Chiral Controller. Tetrahedron Letts. Dec. 1993;34(51):8293-96.

Kim et al., Total synthesis of azithromycin. Angew Chem Int Ed Engl. 2009;48(10):1827-9. doi: 10.1002/anie.200805334.

Kummer et al., Stereocontrolled Alkylative Construction of Quaternary Carbon Centers. J Am Chem Soc. Sep. 13, 2008;130(40):13231-13233.

Kurath et al., Acid degradation of erythromycin A and erythromycin B. Experientia. 1971;27:362.

Leclercq et al., Bacterial resistance to macrolide, lincosamide, and streptogramin antibiotics by target modification. Antimicrob Agents Chemother. 1991;35:1267-1272.

Leclercq et al., Intrinsic and unusual resistance to macrolide, lincosamide, and streptogramin antibiotics in bacteria. Antimicrob Agents Chemother. 1991;35:1273-1276.

Lee et al., Chemistry and biology of macrolide antiparasitic agents. J Med Chem. 2011;54:2792-2804.

Letorneau et al., Synthesis and antibacterial activity of desosamine-modified macrolide derivatives. Bioorg Med Chem Lett. Jul. 15, 2012;22(14):4575-8. Doi: 10.1016/j.bmcl.2012.05.110. Epub Jun. 6, 2012.

Li et al., Single and dual mutations at positions 2058, 2503 and 2504 of 23S rRNA and their relationship to resistance to antibiotics that target the large ribosomal subunit. J Antimicrob Chemother. Sep. 2011;66(9):1983-6. doi: 10.1093/jac/dkr268. Epub Jun. 23, 2011.

Liang et al., Synthesis and biological activity of new 5-O-sugar modified ketolide and 2-fluoro-ketolide antibiotics. Bioorg Med Chem Lett. 2005;15:1307-1310.

Llano-Sotelo et al., Binding and action of CEM-101, a new fluoroketolide antibiotic that inhibits protein synthesis. Antimicrob Agents Chemother. 2010;54:4961-4970.

Ma et al., Significant breakthroughs in search for anti-infectious agents derived from erythromycin A. Curr Med Chem. 2011;18:1993-2015.

Ma et al., Various novel erthyromycin derivatives obtained by different modifications: recent advance in macrolide antibiotics. Mini-Rev Med Chem. 2010;10:272-286.

Mankin et al., Macrolide myths. Curr Opin Microbiol. Oct. 2008;11(5):414-21. doi: 10.1016/j.mib.2008.08.003. Epub Oct. 3, 2008.

Martins et al., Antimicrobial activity of chitosan derivatives containing N-quaternized moieties in its backbone: a review. Int J Mol Sci. Nov. 13, 2014;15(11):20800-32. Doi: 10.3390/ijms151120800.

Marusic et al., Novel 9a, 11-bridged azalides: One-pot synthesis of N'-substituted 2-imino-1,3-oxazolidines condensed to an azalide aglycome. Bioorg Med Chem. 2011;19:556-66.

Marusic et al., Novel 9a-carbamoyl-and9a-thiocarbamoyl-3-decladinosyl-6-hydroxy and 6-methoxy derivatives of 15-membered macrolides. Bioorg Med Chem. 2007;15:4498-4510.

Morales et al., Pseudoephenamine: a practical chiral auxiliary for asymmetric synthesis. Angew Chem Int Ed Engl. May 7, 2012;51(19):4568-71. doi: 10.1002/anie.201200370. Epub Mar. 27, 2012.

Morimoto et al., Chemical modification of erythromycins. I. Synthesis and antibacterial activity of 6-O-methylerythromycins A. J Antibiot (Tokyo). Feb. 1984;37(2):187-9.

Morimoto et al., Chemical modification of erythromycins. II. Synthesis and antibacterial activity of O-alkyl derivatives of erythromycin A. J Antibiot (Tokyo). 1990;43:286-294.

Mutak, Azalides from azithromycin to new azalide derivatives. J Antibiot. 2007;60:85-122.

(56) References Cited

OTHER PUBLICATIONS

Myers et al., Greatly Simplified Procedures for the Synthesis of α-Amino Acids by the Direct Alkylation of Pseudoephedrine Glycinamide Hydrate. J Org Chem. Apr. 16, 1999;64(9):3322-27.
Myers et al., Practical Syntheses of Enantiomerically Enriched γ-Lactones and γ-Hydroxy Ketones by the Alkylation of Pseudoephedrine Amides with Epoxides and Their Derivatives. J Org Chem. Apr. 5, 1996;61(7):2428-2420.
Myers et al., Pseudoephedrine as a Practical Chiral Auxiliary for the Synthesis of Highly Enantiomerically Enriched Carboxylic Acids, Alcohols, Aldehydes, and Ketones. J Am Chem Soc. Jul. 16, 1997;119(28):6496-6511.
Myers et al., Synthesis of tertiary alkyl fluoride centers by asymmetric C☐C(F) bond formation. Tetrahedron Letts. Oct. 6, 1997;38(40):7037-40.
Myers et al., Use of Pseudoephedrine as a Practical Chiral Auxiliary for Asymmetric Synthesis. J Am Chem Soc. Oct. 1994; 116(20):9361-62.
Nakasutka et al., Total synthesis of FK506 and an FKBP probe reagent, [C(8),C(9)-13C2]-FK506. J Am Chem Soc. 1990;112:5583-5601.
Nakata et al., Total synthesis of 6-deoxyerythronolide B. J Am Chem Soc. 1981;103:1568.
Newman, Degradation and Synthesis of Desosamine. J Org Chem. 1964;29(6):1461-8.
Oh et al., Total synthesis of methymycin. Org. Biomol Chem. 2009;7:4458-4463.
Paterson et al., Total Synthesis of Denticulatins A and B Using Efficient Methods of Acyclic Stereocontrol. Tetrahedron. 1996;52:1811-1834.
Paterson, Tetrahedron report No. 190: Recent developments in the total synthesis of macrolide antibiotics. Tetrahedron. 1985;41:3569-3624.
Pavlovic et al., Novel hybrids of 15-membered 8a- and 9a-azahomoerythromycin A ketolides and quinolones as potent antibacterials. Bioorg Med Chem. 2010;18:8566-8582.
Pereira et al., Synthesis and antibacterial activity of novel 4-aryl-[1,2,3]-triazole containing macrolides. Bioorg Med Chem Lett. Jan. 1, 2011;21(1):510-3. doi: 10.1016/j.bmcl.2010.10.091. Epub Oct. 25, 2010.
Phan et al., Synthesis and antibacterial activity of a novel class of 4'-substituted 16-membered ring macrolides derived from tylosin. J Med Chem. Jun. 3, 2004;47(12):2965-8.
Prunier et al., Clinical isolates of *Staphylococcus aureus* with ribosomal mutations conferring resistance to macrolides. Antimicrob Agents Chemother. 2002;46:3054-3056.
Putnam et al., Antimicrobial characterisation of solithromycin (CEM-101), a novel fluoroketolide: activity against staphylococci and enterococci. Int J Antimicrob Agents. Jan. 2011;37(1):39-45. doi: 10.1016/j.ijantimicag.2010.08.021.
Retsema et al., Spectrum and mode of action of azithromycin (CP-62,993), a new 15-membered-ring macrolide with improved potency against gram-negative organisms. Antimicrob Agents Chemother. 1987;31:1939-1947.
Richardson, A stereospecific synthesis of desosamine hydrochloride. Proceedings of the Chemical Society. 1963:131.
Romero et al., An efficient entry to new sugar modified ketolide antibiotics. Tetrahedron Lett. 2005;46:1483-1487.
Rück, Asymmetric Alkylation of Amide Enolates with Pseudoephedrine and Ephedrine as Chiral Auxiliaries—Unexpected Influence of Additives? Angewandte Chemie. International Edition. Mar. 7, 1995;34(4):433-35.
Seiple et al., A platform for the discovery of new macrolide antibiotics. Nature. May 18, 2016;533(7603):338-45. doi: 10.1038/nature17967.
Shvekhgeimer et al., Aliphatic nitro alcohols. Synthesis, chemical transformations and applications. Russian Chemical Reviews. 1998;67(1):35-68.

Sutcliffe et al., *Streptococcus pneumoniae* and *Streptococcus pyogenes* resistant to macrolides but sensitive to clindamycin: a common resistance pattern mediated by an efflux system. Antimicrob Agents Chemother. 1996;40:1817-1824.
Tu et al., Structures of MLSBK antibiotics bound to mutated large ribosomal subunits provide a structural explanation for resistance. Cell. 2005;121:257-270.
Van Summeren et al., New approaches towards the synthesis of the side-chain of mycolactones A and B. J Org Biomol Chem. 2005;3:2524-2533.
Velvadapu et al., Concise syntheses of D-desosamine, 2-thiopyrimidinyl desosamine donors, and methyl desosaminide analogues from D-glucose. Carbohydr Res. 2008;343:145-150.
Velvadapu et al., Desmethyl Macrolide Analogues to Address Antibiotic Resistance: Total Synthesis and Biological Evaluation of 4,8,10-Tridesmethyl Telithromycin. ACS Med Chem Lett. Jan. 13, 2011;2(1):68-72.
Velvadapu et al., Desmethyl Macrolides: Synthesis and Evaluation of 4,10-Didesmethyl Telithromycin. ACS Med Chem Lett. Mar. 8, 2012;3(3):211-215. Epub Jan. 15, 2012.
Velvadapu et al., Total synthesis of (−)-4,8,10-tridesmethyl telithromycin. J Org Chem. Sep. 16, 2011;76(18):7516-27. doi: 10.1021/jo201319b. Epub Aug. 24, 2011.
Vester et al., Macrolide resistance conferred by base substitutions in 23S rRNA. Antimicrob Agents Chemother. 2001;45:1-12.
Vicario et al., Asymmetric aldol reactions using (S,S)-(+)-pseudoephedrine-based amides: stereoselective synthesis of alpha-methyl-beta-hydroxy acids, esters, ketones, and 1,3-Syn and 1,3-anti diols. J Org Chem. Jun. 16, 2000;65(12):3754-60.
Wagh et al., Desmethyl Macrolides: Synthesis and Evaluation of 4,8-Didesmethyl Telithromycin. ACS Med Chem Lett. Dec. 12, 2012;3(12):1013-1018.
Washington et al., Erythromycin: a microbial and clinical perspective after 30 years of clinical use (1). Mayo Clin Proc. 1985;60:189-203.
Washinigton et al., Erythromycin: a microbial and clinical perspective after 30 years of clinical use (2). Mayo Clin Proc. 1985;60:271-278.
Watanabe et al., Chemical modification of erythromycins. IX. Selective methylation at the C-6 hydroxyl group of erythromycin A oxime derivatives and preparation of clarithromycin. J Antibiot (Tokyo). Apr. 1993;46(4):647-60.
Watanabe et al., Chemical modification of erythromycins. XII. A facile synthesis of clarithromycin (6-O-methylerythromycin A) via 2'-silylethers of erythromycin A derivatives. J Antibiot (Tokyo). Jul. 1993;46(7):1163-7.
Watanabe et al., Tetronothiodin, a novel cholecystokinin type-B receptor antagonist produced by *Streptomyces* sp. NR0489. I. Taxonomy, yield improvement and fermentation. J Antibiot (Tokyo). Jan. 1993;46(1):1-10.
Weisblum, Erythromycin resistance by ribosome modification. Antimicrob Agents Chemother. 1995;39:577-585.
Wilkening et al., The synthesis of novel 8a-AZA-8a-homoerythromycin derivatives via the Beckman rearrangement of (9z)-erythrromycin a oxime. Bioorg Med Chem. 1993;3(6):1287-92.
Wondrack et al., Clinical strain of *Staphylococcus aureus* inactivates and causes efflux of macrolides. Antimicrob Agents Chemother. 1996;40:992-998.
Woodward et al., Asymmetric total synthesis of erythromcin. 1. Synthesis of an erythronolide A secoacid derivative via asymmetric induction. J Am Chem Soc. 1981;103(11):3210-3213.
Woodward et al., Asymmetric total synthesis of erythromycin. 2. Synthesis of an erythronolide A lactone system. J Am Chem Soc. 1981;103(11):3213-3215.
Woodward et al., Asymmetric total synthesis of erythromycin. 3. Total synthesis of erythromycin. J Am Chem Soc. 1981;103(11):3215-3217.
Worch et al., Unexpected formation of complex bridged tetrazoles via intramolecular 1,3-dipolar cycloaddition of 1,2-O-cyanoalkylidene derivatives of 3-azido-3-deoxy-D-allose. Carbohydr Res. Aug. 11, 2008;343(12):2118-29. Epub Nov. 6, 2007.

(56) References Cited

OTHER PUBLICATIONS

Wright et al., Molecular mechanisms of antibiotic resistance. Chem Commun (Camb). Apr. 14, 2011;47(14):4055-61. doi: 10.1039/c0cc05111j. Epub Feb. 1, 2011.
Wu et al., Highlights of semi-synthetic developments from erythromycin A. Curr Pharm Des. Jan. 2000;6(2):181-223.
Wu et al., Recent developments on ketolides and macrolides. Curr Med Chem. Dec. 2001;8(14):1727-58.
Zhanel et al., The ketolides: a critical review. Drugs. 2002;62(12):1771-804.
Zhang et al., Synthesis of D-Desosamine and Analogs by Rapid Assembly of 3-Amino Sugars. Angewandte Chemie Int Ed. Jan. 11, 2016;55(2):523-7. Epub Nov. 27, 2015.
Zindel et al., Synthesis of 3-(trans-2'-Nitrocyclopropyl)alanine, a Constituent of the Natural Peptide-Lactone Hormaomycin. J. Org. Chem. 1995;60(10):2968-73.
U.S. Appl. No. 14/781,719, filed Oct. 1, 2015, Myers et al.
U.S. Appl. No. 15/946,658, filed Apr. 5, 2018, Myers et al.
U.S. Appl. No. 15/517,843, filed Apr. 7, 2017, Myers et al.
Partial Supplementary European Search Report for Application No. EP 15848340.4 dated Jun. 22, 2018.
Extended European Search Report for EP 15848340, dated Sep. 26, 2018.
Partial Supplementary European Search Report for Application No. EP 16769811.7, dated Jul. 17, 2018.
Extended European Search Report for Application No. EP 16769811.7, dated Oct. 24, 2018.
Invitation to Pay Additional Fees for PCT/US2018/030002, dated Sep. 25, 2018.
[No Author Listed] 2005 Caplus entry for AN 2005:124660 (Romero).
[No Author Listed] 2016 Caplus entry for AN 2016:590903 (Myers).
[No Author Listed] 2005 CAS Registry No. 849407-75-6.
Falzari et al., In vitro and in vivo activities of macrolide derivatives against *Mycobacterium tuberculosis*. Antimicrob Agents Chemother. Apr. 2005;49(4):1447-54.
Griesgraber et al., Anhydrolide macrolides. 2. Synthesis and antibacterial activity of 2,3-anhydro-6-O-methyl 11,12-carbazate erythromycin A analogues. J Med Chem. May 7, 1998;41(10):1660-70.
Gunnes et al., Chemoselective synthesis of erythromycin A ketolides substituted in the C10-methyl group. Bioorganic & Medicinal Chemistry Jan. 2007;15(1):119-129.
Hoye et al., Dual macrolactonization/pyran-hemiketal formation via acylketenes: applications to the synthesis of (−)-callipeltoside A and a lyngbyaloside B model system. Angew Chem Int Ed Engl. 2008;47(50):9743-6.
Hoye et al., Total synthesis of (−)-callipeltoside A. J Org Chem. Nov. 5, 2010;75(21):7052-60.
Knapp et al., Synthesis of the Ezomycin Nucleoside Disaccharide. Org. Lett. 2000;2(10):1391-1393.
Ma et al., Regioselective Synthesis of Bifunctional Macrolides for Probing Ribosomal Binding. Org. Lett. 2002;4(6):987-990.
Song et al., Protein Phosphatase 2A-SUR-6/B55 Regulates Centriole Duplication in C. elegans by Controlling the Levels of Centriole Assembly Factors. Dev Cell. Apr. 19, 2011; 20(4): 563-571.
Wang et al., Synthesis of novel 6,11-O-bridged bicyclic ketolides via a palladium-catalyzed bis-allylation. Org Lett. Nov. 25, 2004;6(24):4455-8.

erythromycin (1)
14-membered macrolide
Preparation: fermentation from *S. erythraea*
US FDA Approval: 1952 clarithromycin (2)
14-membered macrolide
semi-synthesis: 6 steps from erythromycin
1991 azithromycin (3)
15-membered azalide
semi-synthesis: 4 steps from erythromycin
1991 telithromycin (4)
14-membered ketolide
semi-synthesis: 12 steps from erythromycin
2004 solithromycin (5)
14-membered ketolide
semi-synthesis: 16 steps from erythromycin
(Clinic Phase II)

cethromycin (7)
14-membered ketolide
(Clinic Phase III)

tylosin (6)
16-membered macrolide
fermentation from *S. fradiae*
(veterinary medicine)

MACROLIDES WITH MODIFIED DESOSAMINE SUGARS AND USES THEREOF

RELATED APPLICATIONS

The present application is a national stage filing under 35 U.S.C. § 371 of international PCT application, PCT/US2016/024333, filed Mar. 25, 2016, which claims priority under 35 U.S.C. § 119(e) to U.S. provisional patent applications, U.S. Ser. No. 62/138,198, filed Mar. 25, 2015, and U.S. Ser. No. 62/138,168, filed Mar. 25, 2015, each of which is incorporated herein by reference.

BACKGROUND

Emerging resistance to existing antibiotics is rapidly developing as a crisis of global proportions, especially for *Staphylococcus aureus, Streptococcus pyogenes*, and *Streptococcus pneumonia* infections. Pathogenic bacteria can transmit genes coding for antibiotic resistance both vertically (to their progeny) and horizontally (to neighboring bacteria of different lineages), and as a result antibiotic resistance can evolve quickly, particularly in nosocomial (hospital) settings. See, e.g., Wright, *Chem. Commun.* (2011) 47:4055-4061. This year, >99,000 people will die in the U.S. from healthcare-associated infections, more than all casualties from car accidents, HIV, and breast cancer combined, creating an estimated burden of up to $45 billion in U.S. healthcare costs. See, e.g., Klevens et al., *Public Health Rep* (2007) 122:160-166. The current crisis is exacerbated by the fact that most major pharmaceutical companies have essentially abandoned research in the development of new antibiotics. See, e.g., Projan, *Curr. Opin. Microbiol.* (2003) 6:427-430. The current rate of introduction of new antibiotics does not adequately address growing resistance, and with the ease of international travel and increasing population densities, the need for innovation in the field has never been higher.

The macrolides are one of the few major clinically important classes of antibiotics for which the only practical access has been through semi-synthesis, or chemical manipulation of structurally complex fermentation products, in routes as long as 16 steps. See, e.g., Paterson, *Tetrahedron* (1985) 41:3569-3624; Omura, Ed., *Macrolide Antibiotics: Chemistry, Biology, and Practice, Second Edition*; Academic Press, 2002. The macrolide class of antibiotics has proven safe and effective in the battle against pathogenic bacteria since the discovery of erythromycin over 60 years ago. See, e.g., Wu et al., *Curr. Med. Chem.* (2001) 8:1727-1758. Erythromycin displays a spectrum of antibacterial activity against Gram-positive bacteria similar to that of penicillin but has a lesser propensity to induce allergic interactions, and has been routinely prescribed for upper and lower respiratory tract infections and urogenital infections. See, e.g., Washington et al., *Mayo. Clin. Proc.* (1985) 60:189-203; Washington et al., *Mayo. Clin. Proc.* (1985) 60:271-278. However, erythromycin is known to undergo acid-promoted internal ketalization (cyclization of the C6 and C12 hydroxyl groups onto the C9 ketone) in the gut, which leads to adverse gastrointestinal events. See, e.g., Kurath et al., *Experientia* (1971) 27:362. Second-generation macrolide antibiotics clarithromycin and azithromycin addressed issues of acid instability and were prepared semi-synthetically in 4-6 steps from erythromycin, which is readily available through large-scale fermentation. See, e.g., Ma et al., *Curr. Med. Chem.* (2011) 18:1993-2015; Wu et al., *Curr. Pharm. Des.* (2000) 6:181-223; Ma et al., *Mini-Rev. Med. Chem.* (2010) 10:272-286; Asaka et al., *Curr. Top. Med. Chem. (Sharjah, United Arab Emirates)* (2003) 3:961-989; Morimoto et al., *J. Antibiot.* (1990) 43:286-294; Morimoto et al., *J. Antibiot.* (1984) 37:187-189; Watanabe et al., *J. Antibiot.* (1993) 46: 1163-1167; Watanabe et al., *J. Antibiot.* (1993) 46:647-660; Bright et al., *J. Antibiot.* (1988) 41: 1029-1047; Djokic et al., *J. Antibiot.* (1987) 40:1006-1015; Mutak et al., *J. Antibiot.* (2007) 60: 85-122; and Retsema et al., *Antimicrob. Agents Chemother.* (1987) 31:1939-1947. Azithromycin has been shown to exhibit markedly improved efficacy against Gram-negative organisms, and has a longer half-life and higher tissue distribution than the other macrolide antibiotics, thought to correlate with its 15-membered ring containing a tertiary amine. See, e.g., Ferwerda et al., *J. Antimicrob. Chemother.* (2001) 47:441-446; Girard et al., *Antimicrob. Agents Chemother.* (1987) 31:1948-1954. The natural product tylosin, a 16-membered macrolide used in veterinary medicine, has been shown by X-ray crystallography to occupy the same binding pocket as erythromycin and azithromycin, suggesting that there is a high tolerance for variability in ring size and composition of the macrocycle.

The three primary causes of resistance to macrolides in bacterial organisms are ribosome methylation encoded by erm genes, mutations in ribosomal RNA or peptides, and cell efflux mediated by mef and msr genes. See, e.g., Leclercq et al., *Antimicrob. Agents Chemother.* (1991) 35:1273-1276; Leclercq et al., *Antimicrob. Agents Chemother.* (1991) 35:1267-1272; Weisblum, *Antimicrob. Agents Chemother.* (1995) 39:577-585; Vester et al., *Antimicrob. Agents Chemother.* (2001) 45:1-12; Prunier et al., *Antimicrob. Agents Chemother.* (2002) 46:3054-3056; Li et al., *J. Antimicrob. Chemother.* (2011) 66:1983-1986; Sutcliffe et al., *Antimicrob. Agents Chemother.* (1996) 40:1817-1824; Wondrack et al., *Antimicrob. Agents Chemother.* (1996) 40: 992-998. Ketolides such as telithromycin and solithromycin defeat the efflux mechanism of resistance by replacement of the C3 cladinose sugar with a carbonyl group (hence the name "ketolides"), and are thought to exhibit greatly increased binding by virtue of favorable interactions between the novel aryl-alkyl sidechain and the ribosome. See, e.g., Ma et al., *Curr. Med. Chem.* (2011) 18:1993-2015; Ma et al., *Mini-Rev. Med. Chem.* (2010) 10:272-286. Despite greatly improved ribosomal binding, ketolides such as telithromycin and solithromycin have not addressed several of the newest forms of macrolide resistance that have evolved in nosocomial settings, especially ribosome methylation and RNA point mutations.

SUMMARY

Macrolides are an important class of antibiotics, and have proven to be safe and effective in the treatment of infectious diseases for decades. A critical component of erythromycin, and many other macrolide antibiotics (e.g., azithromycin, carbomycin, cethromycin, clarithromycin, roxithromycin, solithromycin, telithromycin, tylosin), is the desosamine or mycaminose sugar at the C5 position of the macrolide. For example, in erythromycin (shown below with the typical carbon numbering for a 14-membered macrolide), the C5 sugar is D-desosamine.

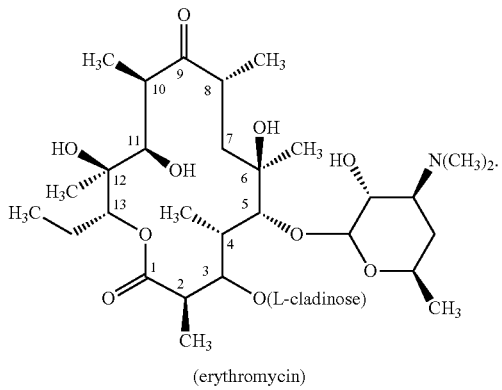

(erythromycin)

X-ray crystallographic studies reveal that the C5 sugar makes extensive contacts with the 23S subunit of bacterial ribosomal RNA as shown in FIG. 2, and thus it is thought that it plays a key role in antibiotic activity of macrolides. See, e.g., Tu et al., *Cell* (2005) 121:257-270; Mankin et al., *Current Opinion in Microbiology* (2008) 11:414-421. Variation of the sugar at the C5 position of the macrolide (e.g., desosamine and mycaminose analogs) affords macrolide antibiotics with desired and/or improved pharmaceutical properties (e.g., efficacy against resistant strains, improved pharmacokinetics, reduced side-effects). As described herein, the C3 position and/or C6 position of the sugar (e.g., desosamine or mycaminose) can be modified to afford novel macrolide antibiotics.

The compounds described herein comprise macrolides with a modified sugar (e.g., desosamine and mycaminose) at the C5 position of the macrolide. In certain embodiments, the sugar at the C5 position of the macrolide is modified at the C6 position of the sugar. Such compounds are provided as macrolides of Formula (I):

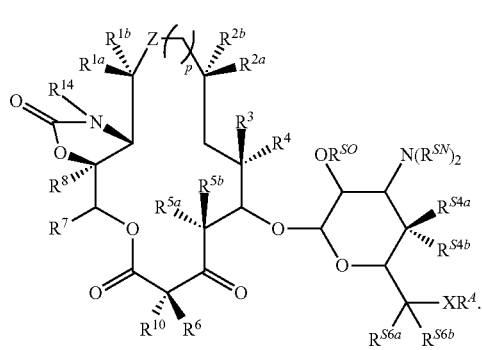

(I)

In another aspect, the present invention provides compounds which are macrolides with a modified sugar moiety, wherein the sugar is modified at the C3 position of the sugar (e.g., the amine moiety of desosamine or mycaminose). Such compounds are provided as macrolides of Formula (I-N):

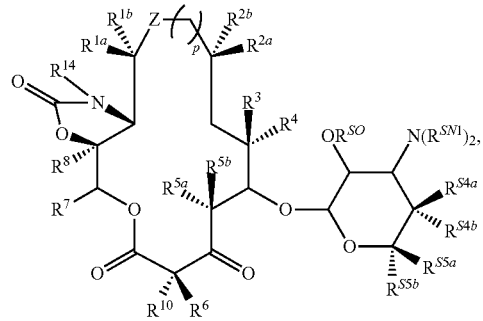

(I-N)

wherein at least one of $R^{SN1}$ is not methyl.

Specifically, the invention provides 14-membered ketolides of Formula (I-a) and 14-, 15-, and 16-membered azaketolides of Formulae (I-b), (I-c), and (I-d), respectively, as described herein.

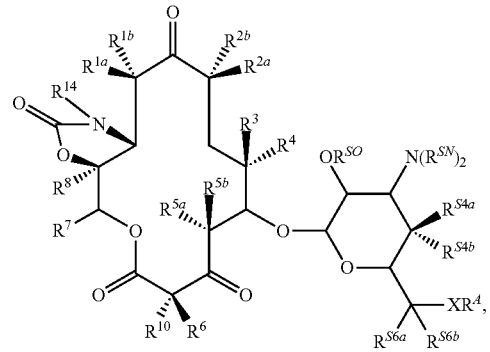

(I-a)

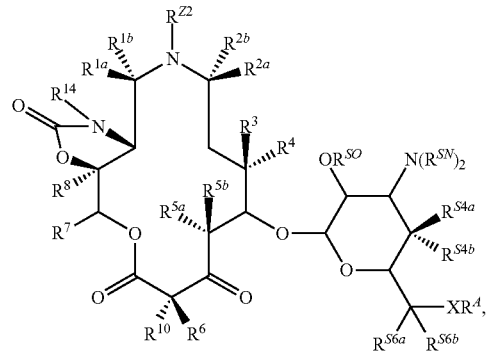

(I-b)

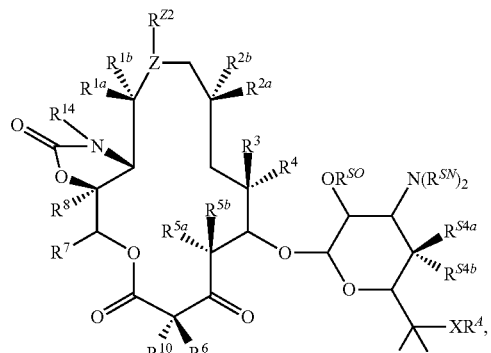

(I-c)

-continued

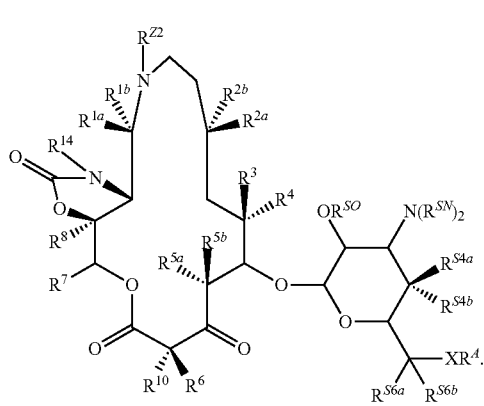

In other embodiments, the invention provides 14-membered ketolides of Formula (I-a-N) and 14-, 15-, and 16-membered azaketolides of Formulae (I-b-N), (I-c-N), and (I-d-N), respectively, as described herein:

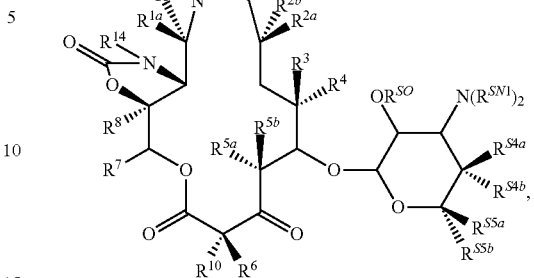

The macrolides of the invention have anti-microbial activity and may be used to treat and/or prevent infectious diseases and inflammatory conditions. Pharmaceutical compositions of the compounds, and methods of treatment using the compounds or compositions thereof are provided herein. Infectious diseases which may be treated with a compound of the invention include, but are not limited to, bacterial infections caused by *Staphylococcus, Bacillus, Strepococcus, Escherichia*, and *Haemophilus* species.

Methods of preparing macrolides with modified C5 sugars are also provided herein. The general synthetic methodology involves construction of eastern and western halves of the macrolide, and coupling of the eastern and western halves followed by macrocyclization. Variation of macrolide substituents may be accomplished at any stage of the synthesis (e.g., during synthesis of the two halves, after coupling, or after macrocyclization), and many positions may be varied independently to access a diverse range of macrolides. The modified sugar moiety (e.g., desosamine or mycaminose analog) is typically installed during synthesis of the eastern half, for example, via the glycosylation of a hydroxyl group at the C5 position with the desired glycosyl donor (e.g., a thioglycoside sugar). The sugar may also be attached at other stages of the synthesis, for example, after assembly of the macrolide by deprotecting a C5 hydroxyl and treating the macrolide with a glycosyl donor. The invention also provides intermediates in the preparation of the macrolides described herein.

The details of certain embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

The accompanying drawings, which constitute a part of this specification, illustrate several embodiments of the invention and together with the description, serve to explain the principles of the invention.

DETAILED DESCRIPTION OF CERTAIN EMBODIMENTS

Figure 1:
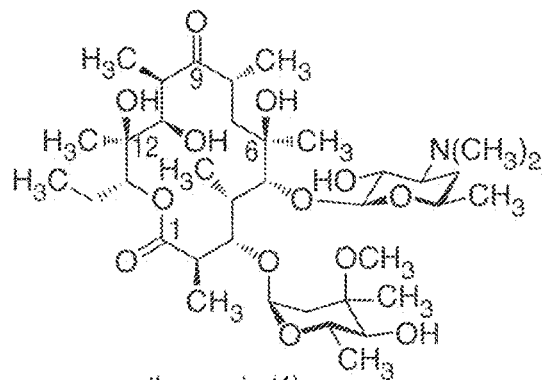
FIG. 1 depicts exemplary 14-, 15-, and 16-membered macrolide antibiotics.
Figure 1:
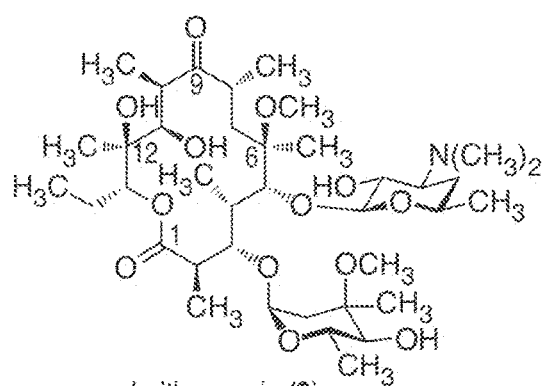
Figure 1:
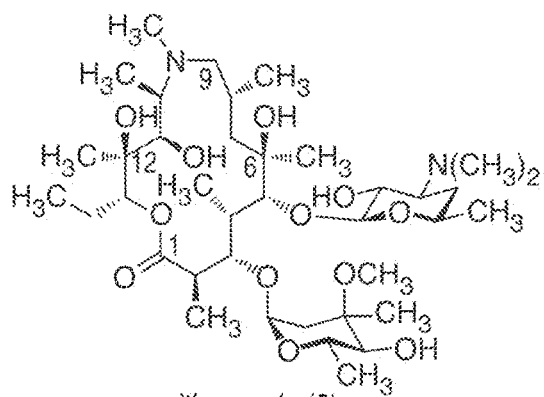
Figure 1:
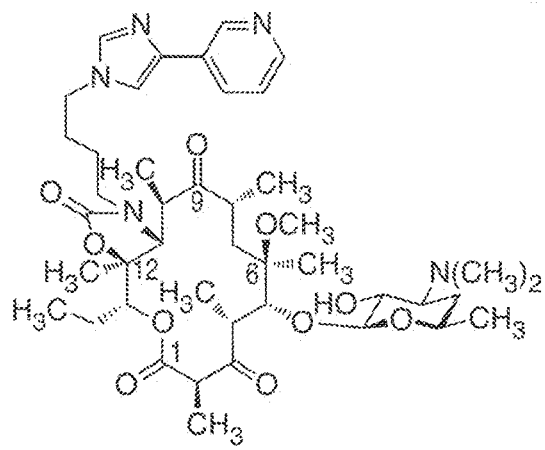
Figure 1:
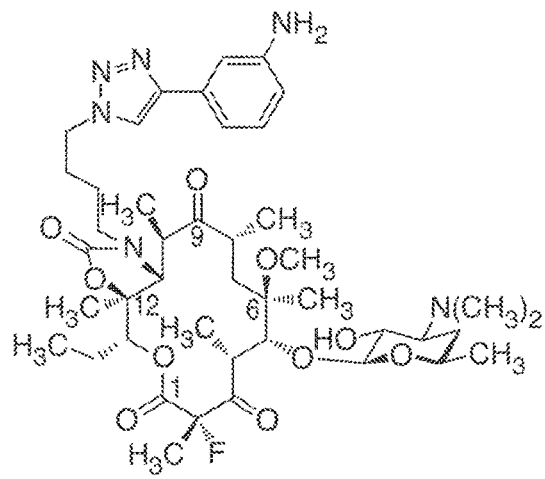
Figure 1:
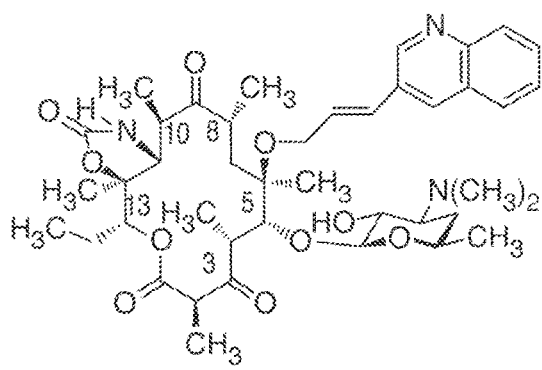
Figure 1:
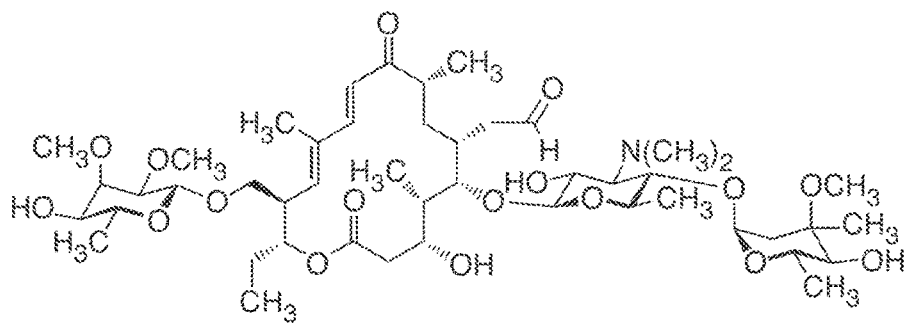

The macrolides specifically described herein include 14-membered ketolides, 14-membered azaketolides, 15-membered azaketolides, and 16-membered azaketolides. Ketolides are typically connected between C8 and C10 with a ketone. Azaketolides feature an amine, or aminoalkylene fragment in place of the keto group.

In certain embodiments, the invention provides macrolides with modified sugars at the C5 position of the macrolide (e.g., desosamine or mycaminose analogs), wherein the sugar is modified at the C6 position of the sugar. In certain embodiments, the invention provides compounds of Formula (I):

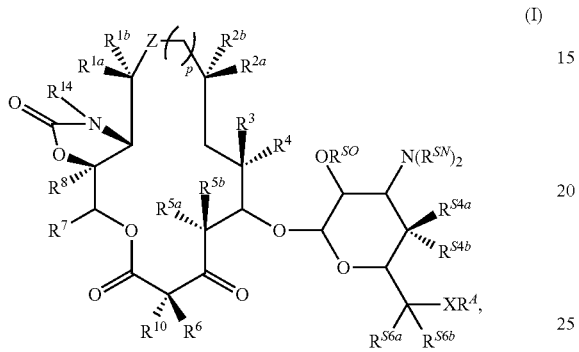

or pharmaceutically acceptable salt thereof, wherein:
Z is C(=O) or $NR^{Z2}$;
X is $-NR^B-$ or $-O-$, provided that X is $NR^B-$ when Z is $-C(=O)-$;
$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, acyl, or a nitrogen protecting group;
p is 0, 1, or 2, provided that p is 0 when Z is $-C(=O)-$;
$R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-C(=O)-L^{S2}-R^S$, $-C(=NR^{SN2})-L^{S2}-R^S$, $-S(=O)-L^{S2}-R^S$, $-S(=O)_2-L^{S2}-R^S$, a nitrogen protecting group when attached to a nitrogen atom, or an oxygen protectin group when attached to an oxygen atom, and $R^{SN2}$ is independently hydrogen, optionally substituted $C_1$-$C_6$ alkyl, or a nitrogen protecting group;
$R^B-$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
or $R^A$ and $R^B$ are taken together to form $=N_2$ or an optionally substituted heterocyclyl or heteroaryl ring;
$L^{S2}$ is a bond, $-NR^S-$, $-O-$, or $-S-$, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;
each $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ groups attached to the same nitrogen atom are joined to form an optionally substituted heterocyclyl or heteroaryl ring;
each of $R^{S4a}$ and $R^{S4b}$ is independently hydrogen, halogen, optionally substituted $C_1$-$C_6$ alkyl, or $-OR^{SO4}$;
each of $R^{S6a}$ and $R^{S6b}$ is independently hydrogen, halogen, or optionally substituted $C_1$-$C_6$ alkyl;
each $R^{SN}$ is independently hydrogen, optionally substituted $C_1$-$C_6$ alkyl, or a nitrogen protecting group, or two $R^{SN}$ groups attached to the same nitrogen atom are joined to form an optionally substituted heterocyclyl or heteroaryl ring;
each of $R^{SO}$ and $R^{SO4}$ is independently hydrogen, optionally substituted $C_1$-$C_6$ alkyl, a carbohydrate, or an oxygen protecting group;
each of $R^{1a}$ and $R^{1b}$ is independently hydrogen, halogen, acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
each of $R^{2a}$ and $R^{2b}$ is independently hydrogen, halogen, optionally substituted alkyl, or optionally substituted alkenyl;
each of $R^3$ and $R^4$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or $-OR^{3a}$;
each $R^{3a}$ is independently hydrogen, optionally substituted alkyl, optionally substituted alkenyl, optionally substituted alkynyl, an oxygen protecting group, or of formula:

each $L^{C3}$ is independently a bond, or is a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;
each $A^3$ is independently optionally substituted carbocyclyl, optionally substituted heterocyclyl, optionally substituted aryl, or optionally substituted heteroaryl;
each of $R^{5a}$ and $R^{5b}$ is independently hydrogen, halogen, optionally substituted alkyl, optionally substituted carbocyclyl, or optionally substituted heterocyclyl;
$R^6$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

R¹⁰ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

R⁷ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

R⁸ is hydrogen, halogen, or optionally substituted C₁-C₆ alkyl.

R¹⁴ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or of formula:

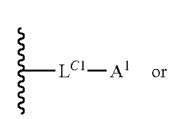
(L^{C1}-ii)

or

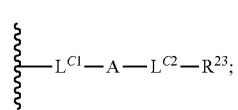
(L^{C1}-iii)

$L^{C1}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

A¹ is a leaving group (LG), —SH, —OH, —NH₂, —NH—NH₂, —N₂, —N₃, —O—NH₂, —CCH, —OC(=O)R^{Z8}, —C(=O)OR^{Z8}, or of formula:

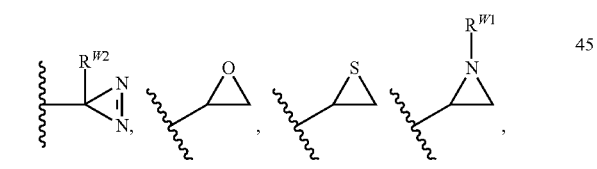

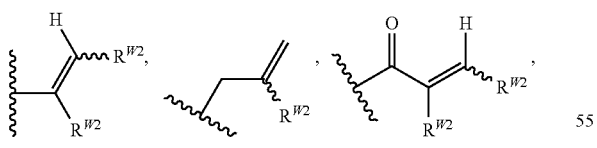

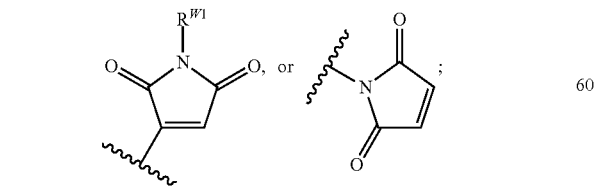

A is —NH—, —NH—NH—, —NH—O—, —O—NH—, —S—, —SS—, —O—, or of formula:

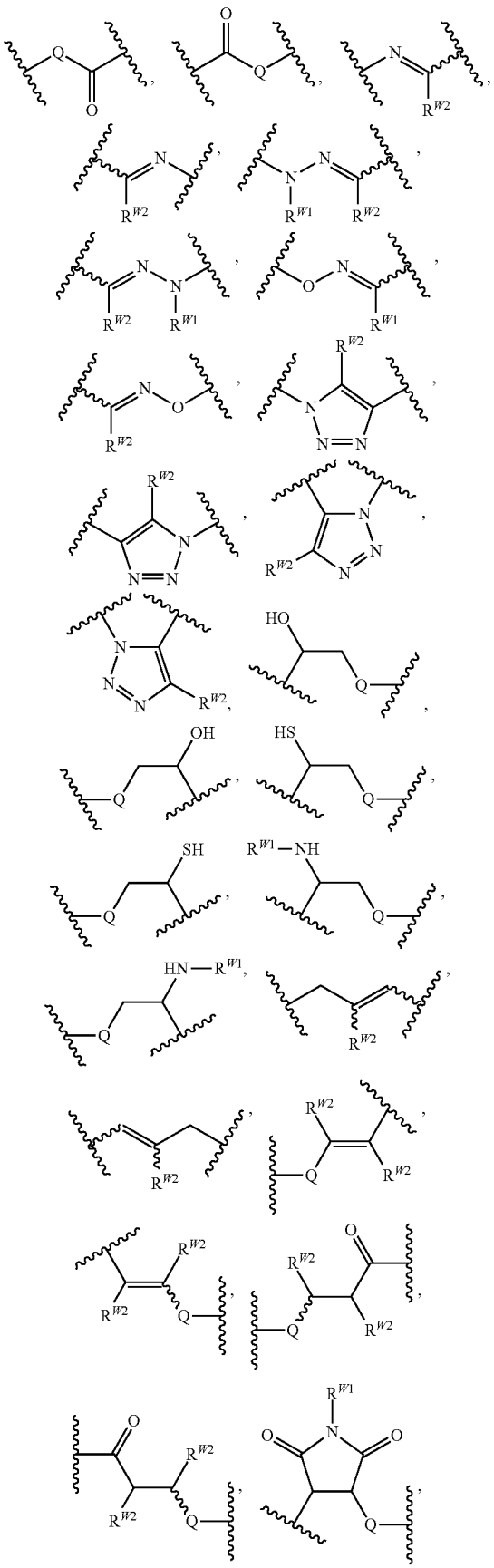

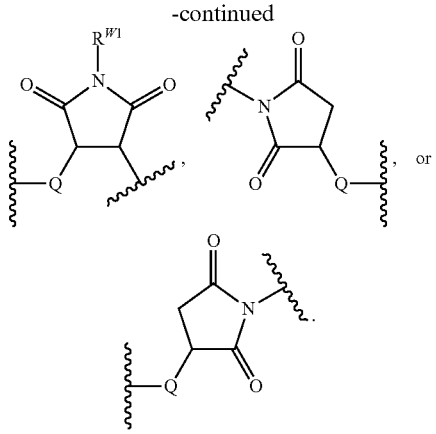

Q is —NH—, —NH—NH—, —O—NH—, —NH—O—, —S—, or —O—;

$L^{C2}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

$R^{W1}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each $R^{W2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two $R^{W2}$ groups are joined to form an optionally substituted cyclic moiety;

$R^{23}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups attached to the same nitrogen atom are joined to form an optionally substituted heterocyclyl or optionally substituted heteroaryl ring.

In certain embodiments, the compound of Formula (I) is not of the formula:

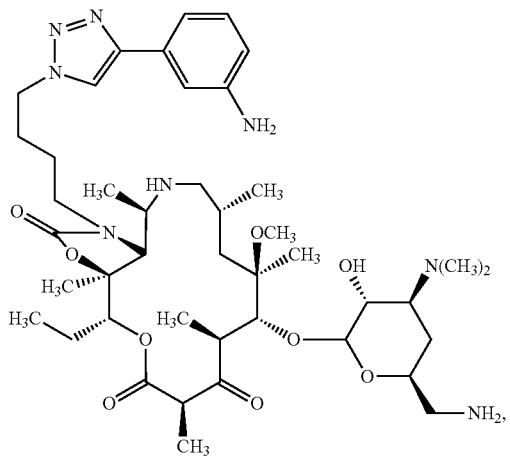

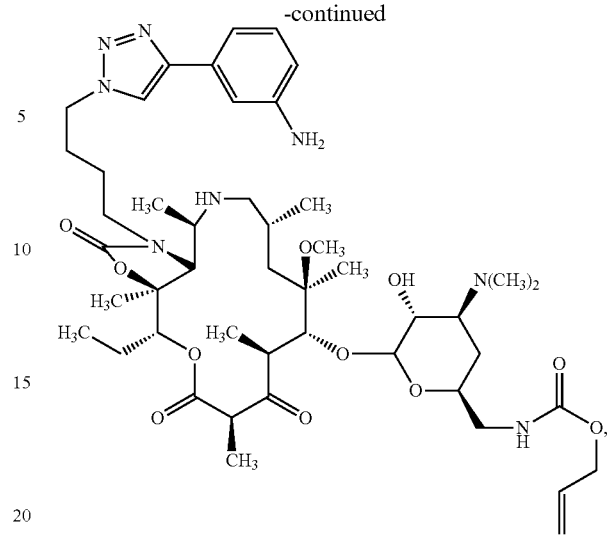

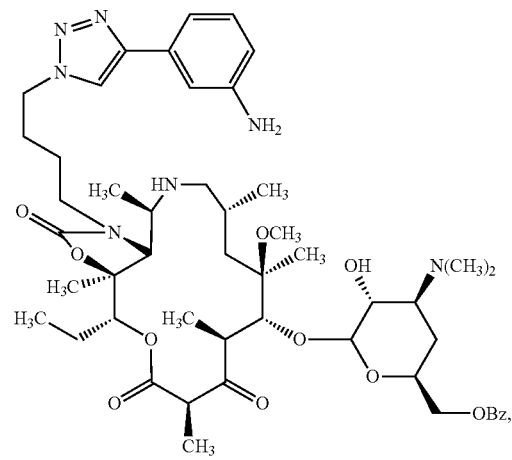

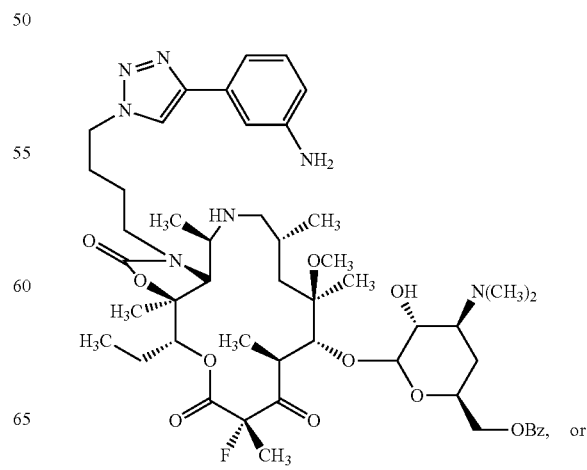

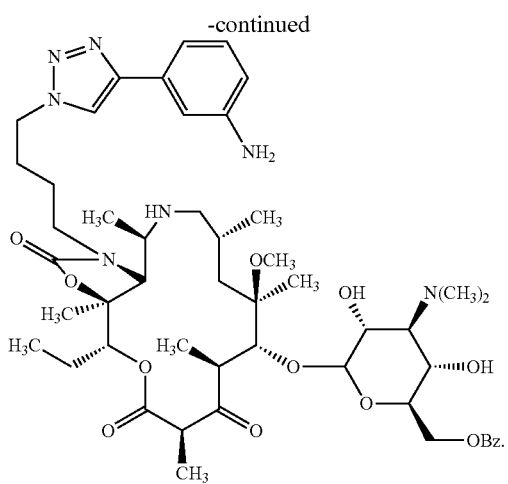

In certain embodiments, for a compound of any formulae described herein, when X is N, $R^A$ is a non-hydrogen group. In certain embodiments, for a compound of any formulae described herein, when X is N and $R^A$ is —(C=O)$OR^S$, $R^S$ is not alkenyl.

Unless otherwise stated, any formulae described herein are also meant to include salts, solvates, hydrates, polymorphs, co-crystals, tautomers, stereoisomers, and isotopically labeled derivatives thereof. In certain embodiments, the provided compound is a salt of any of the formulae described herein. In certain embodiments, the provided compound is a pharmaceutically acceptable salt of any of the formulae described herein. In certain embodiments, the provided compound is a solvate of any of the formulae described herein. In certain embodiments, the provided compound is a hydrate of any of the formulae described herein. In certain embodiments, the provided compound is a polymorph of any of the formulae described herein. In certain embodiments, the provided compound is a co-crystal of any of the formulae described herein. In certain embodiments, the provided compound is a tautomer of any of the formulae described herein. In certain embodiments, the provided compound is a stereoisomer of any of the formulae described herein. In certain embodiments, the provided compound is of an isotopically labeled form of any of the formulae described herein. For example, compounds having the present structures except for the replacement of hydrogen by deuterium or tritium, replacement of $^{19}$F with $^{18}$F, or the replacement of a $^{12}$C by a $^{13}$C or $^{14}$C are within the scope of the disclosure. In certain embodiments, the provided compound is a deuterated form of any of the formulae described herein.

In certain embodiments, the compound of Formula (I) is a compound of Formula (I-a):

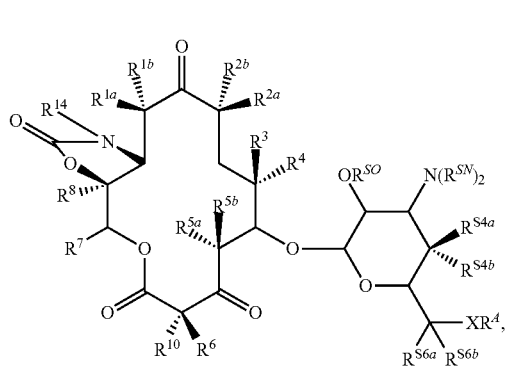

(I-a)

wherein $R^{1a}$, $R^{1b}$, $R^{2a}$, $R^{2b}$, $R^3$, $R^4$, $R^{5a}$, $R^{5b}$, $R^6$, $R^7$, $R^8$, $R^{10}$, $R^{14}$, X, $R^A$, $R^{S4a}$, $R^{S4b}$, $R^{S6a}$, $R^{S6b}$, $R^{SN}$, and $R^{SO}$ are as described herein.

In certain embodiments, the compound of Formula (I) is a compound of Formula (I-b):

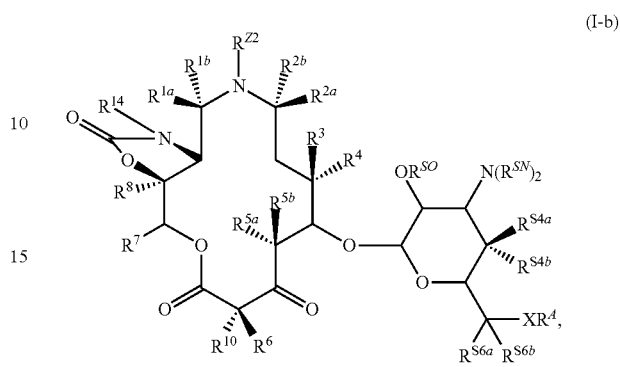

(I-b)

wherein $R^{1a}$, $R^{1b}$, $R^{2a}$, $R^{2b}$, $R^3$, $R^4$, $R^{5a}$, $R^{5b}$, $R^6$, $R^7$, $R^8$, $R^{10}$, $R^{14}$, X, $R^A$, $R^{S4a}$, $R^{S4b}$, $R^{S6a}$, $R^{S6b}$, $R^{SN}$, $R^{SO}$, and $R^{Z2}$ are as described herein.

In certain embodiments, the compound of Formula (I) is a compound of Formula (I-c):

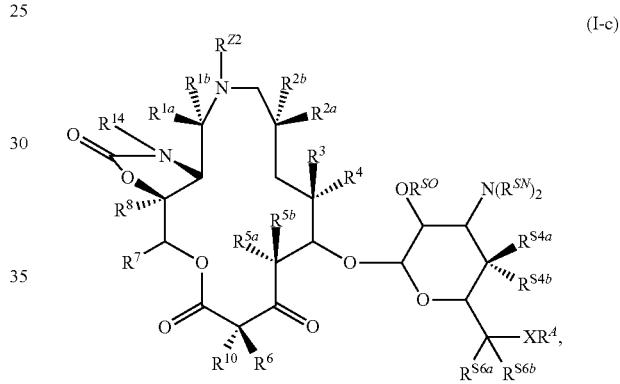

(I-c)

wherein $R^{1a}$, $R^{1b}$, $R^{2a}$, $R^{2b}$, $R^3$, $R^4$, $R^{5a}$, $R^{5b}$, $R^6$, $R^7$, $R^8$, $R^{10}$, $R^{14}$, X, $R^A$, $R^{S4a}$, $R^{S4b}$, $R^{S6a}$, $R^{S6b}$, $R^{SN}$, $R^{SO}$, and $R^{Z2}$ are as described herein.

In certain embodiments, the compound of Formula (I) is a compound of Formula (I-d):

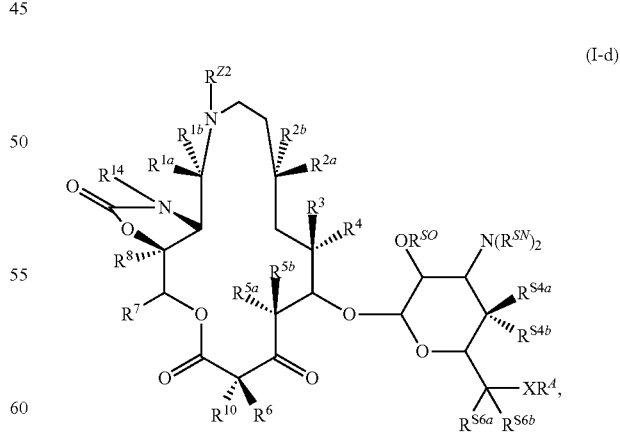

(I-d)

wherein $R^{1a}$, $R^{1b}$, $R^{2a}$, $R^{2b}$, $R^3$, $R^4$, $R^{5a}$, $R^{5b}$, $R^6$, $R^7$, $R^8$, $R^{10}$, $R^{14}$, X, $R^A$, $R^{S4a}$, $R^{S4b}$, $R^{S6a}$, $R^{S6b}$, $R^{SN}$, $R^{SO}$, and $R^{Z2}$ are as described herein.

In certain embodiments, the compound of Formula (I) is a compound of Formula (I-e):

(I-e)

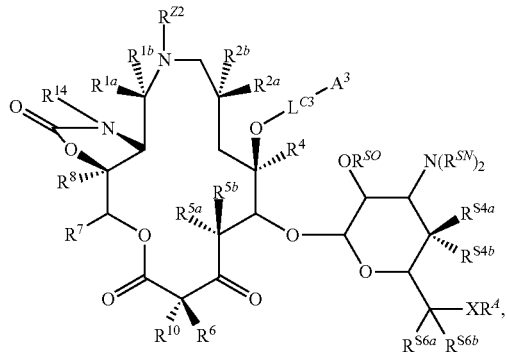

wherein $R^{1a}$, $R^{1b}$, $R^{2a}$, $R^{2b}$, $R^4$, $R^{5a}$, $R^{5b}$, $R^6$, $R^7$, $R^8$, $R^{10}$, $R^{14a}$, X, $R^A$, $R^{S4a}$, $R^{S4b}$, $R^{S6a}$, $R^{S6b}$, $R^{SN}$, $R^{SO}$, $R^{Z2}$, $L^{C3}$, and $A^3$ are as described herein.

In certain embodiments, the compound of Formula (I) is a compound of Formula (II-a):

(II-a)

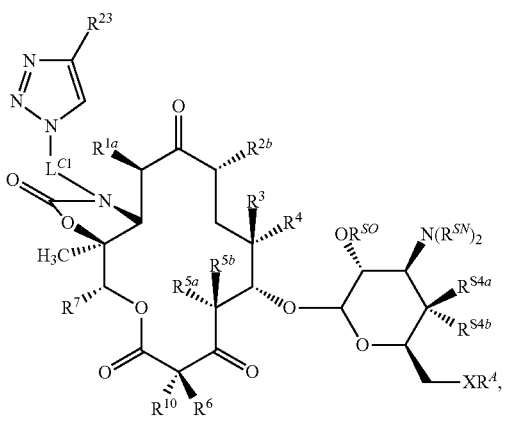

wherein $R^{1a}$, $R^{2b}$, $R^3$, $R^4$, $R^{5a}$, $R^{5b}$, $R^6$, $R^7$, $R^{10}$, $L^{C1}$, $R^{23}$, X, $R^A$, $R^{S4a}$, $R^{S4b}$, $R^{SN}$, and $R^{SO}$ are as described herein.

In certain embodiments, the compound of Formula (I) is a compound of Formula (II-b):

(II-b)

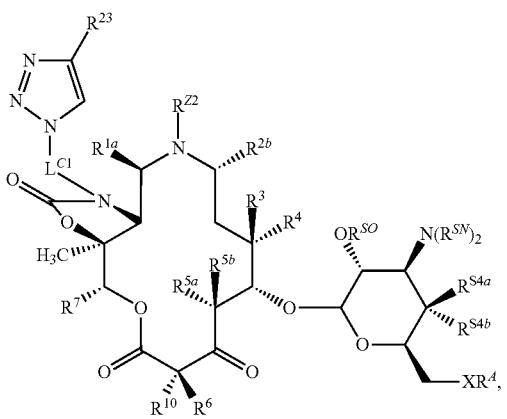

wherein $R^{1a}$, $R^{2b}$, $R^3$, $R^4$, $R^{5a}$, $R^{5b}$, $R^6$, $R^7$, $R^{10}$, $L^{C1}$, $R^{23}$, X, $R^A$, $R^{S4a}$, $R^{S4b}$, $R^{SN}$, $R^{SO}$, and $R^{Z2}$ are as described herein.

In certain embodiments, the compound of Formula (I) is a compound of Formula (II-c):

(II-c)

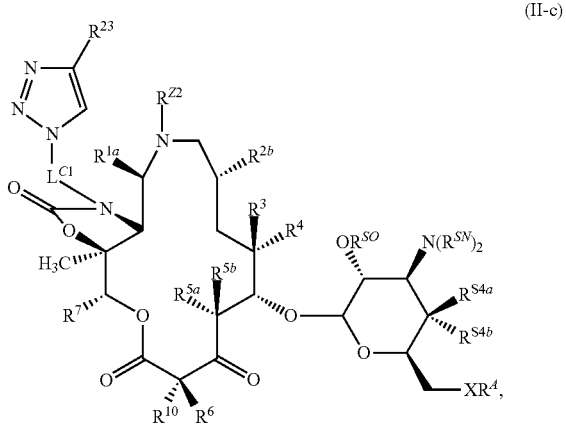

wherein $R^{1a}$, $R^{2b}$, $R^3$, $R^4$, $R^{5a}$, $R^{5b}$, $R^6$, $R^7$, $R^{10}$, $L^{C1}$, $R^{23}$, X, $R^A$, $R^{S4a}$, $R^{S4b}$, $R^{SN}$, $R^{SO}$, and $R^{Z2}$ are as described herein.

In certain embodiments, the compound of Formula (I) is a compound of Formula (II-d):

(II-d)

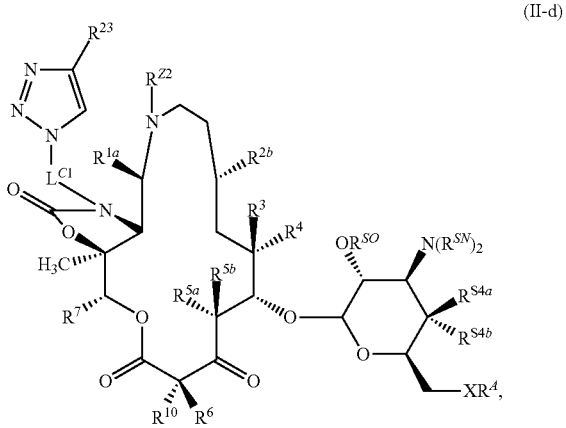

wherein $R^{1a}$, $R^{2b}$, $R^3$, $R^4$, $R^{5a}$, $R^6$, $R^7$, $R^{10}$, $L^{C1}$, $R^{23}$, X, $R^A$, $R^{S4a}$, $R^{S4b}$, $R^{SN}$, $R^{SO}$, and $R^{Z2}$ are as described herein.

In certain embodiments, the compound of Formula (I) is a compound of Formula (II-e):

(II-e)

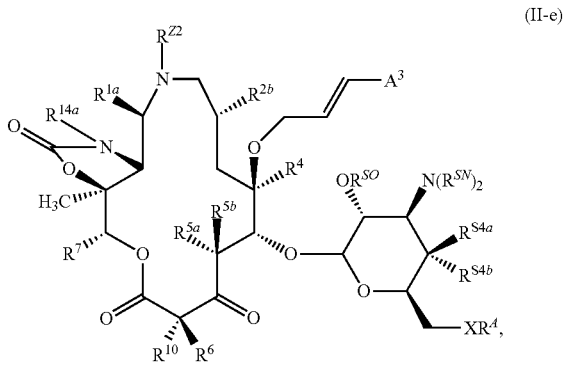

wherein $R^{1a}$, $R^{2b}$, $R^4$, $R^{5a}$, $R^{5b}$, $R^6$, $R^7$, $R^{10}$, $R^{14a}$, X, $R^A$, $R^{S4a}$, $R^{S4b}$, $R^{SN}$, $R^{SO}$, $R^{Z2}$, and $A^3$ are as described herein.

In certain embodiments, the compound of Formula (I) is a compound of Formula (III-a):

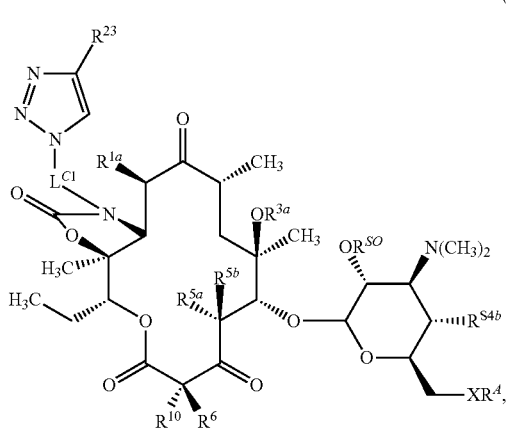

(III-a)

wherein $R^{1a}$, $R^{3a}$, $R^{5a}$, $R^{5b}$, $R^6$, $R^{10}$, $L^{C1}$, $R^{23}$, X, $R^A$, $R^{S4b}$, and $R^{SO}$ are as described herein.

In certain embodiments, the compound of Formula (I) is a compound of Formula (III-b):

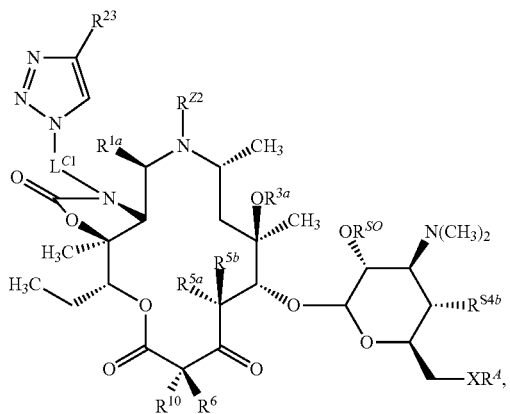

(III-b)

wherein $R^{1a}$, $R^{3a}$, $R^{5a}$, $R^{5b}$, $R^6$, $R^{10}$, $L^{C1}$, $R^{23}$, X, $R^A$, $R^{S4b}$, $R^{SO}$, and $R^{Z2}$ are as described herein.

In certain embodiments, the compound of Formula (I) is a compound of Formula (III-c):

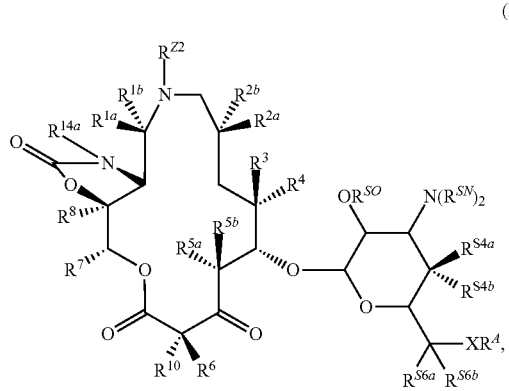

(III-c)

wherein $R^{1a}$, $R^{3a}$, $R^{5a}$, $R^{5b}$, $R^6$, $R^{10}$, $L^{C1}$, $R^{23}$, X, $R^A$, $R^{S4b}$, $R^{SO}$, and $R^{Z2}$ are as described herein.

In certain embodiments, the compound of Formula (I) is a compound of Formula (III-d):

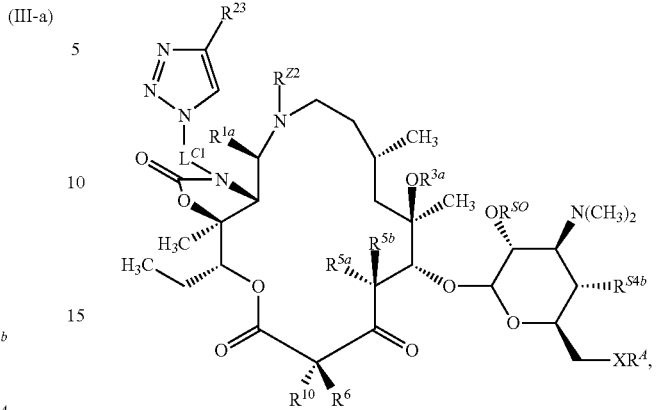

(III-d)

wherein $R^{1a}$, $R^3$, $R^5$, $R^{5b}$, $R^6$, $R^{10}$, $L^{C1}$, $R^{23}$, X, $R^A$, $R^{S4b}$, $R^{SO}$, and $R^{Z2}$ are as described herein.

In certain embodiments, the compound of Formula (I) is a compound of Formula (III-e):

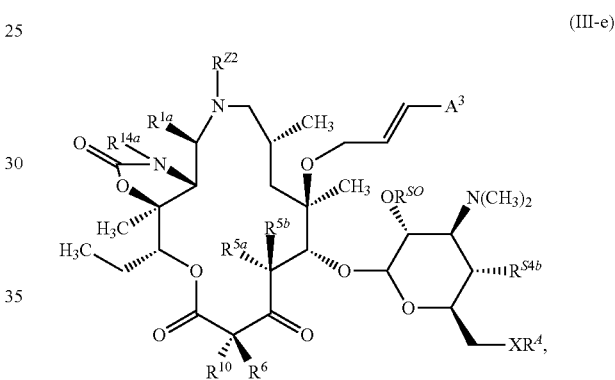

(III-e)

wherein $R^{1a}$, $R^{5a}$, $R^{5b}$, $R^6$, $R^{10}$, $R^{14a}$, X, $R^A$, $R^{S4b}$, $R^{S6a}$, $R^{4b}$, $R^{SO}$, $R^{Z2}$, and $A^3$ are as described herein.

In another aspect, the present invention provides macrolides comprising sugars (e.g., desosamine or mycaminose analogs), wherein the sugar is modified at the C3 position of the sugar (e.g., the dimethylamino moiety of desosamine or mycaminose). In certain embodiments, the invention provides macrolides which are compounds of Formula (I-N):

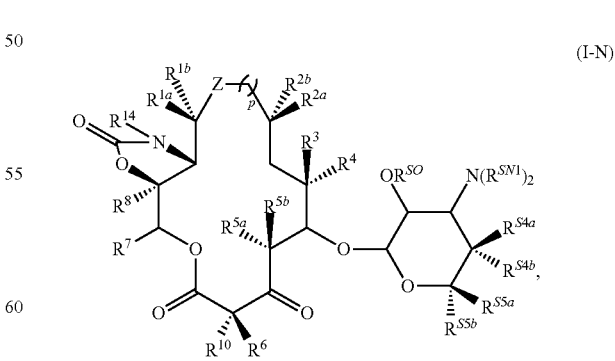

(I-N)

or pharmaceutically acceptable salts thereof, wherein:

Z is —C(=O)— or —$NR^{Z2}$—;

X is —$NR^B$— or —O—, provided that X is —$NR^B$— when Z is —C(=O)—;

$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, acyl, or a nitrogen protecting group;

p is 0, 1, or 2, provided that p is 0 when Z is —C(=O)—;

$R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)-$L^{S2}$-$R^S$, —C(=$NR^{SN2}$)-$L^{S2}$-$R^S$, —S(=O)-$L^{S2}$-$R^S$—, —S(=O)$_2$-$L^{S2}$-$R^S$, a nitrogen protecting group when attached to a nitrogen atom, or an oxygen protectin group when attached to an oxygen atom, and $R^{SN2}$ is independently hydrogen, optionally substituted $C_1$-$C_6$ alkyl, or a nitrogen protecting group;

$R^B$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

or $R^A$ and $R^B$ are taken together to form =$N_2$ or an optionally substituted heterocyclyl or heteroaryl ring;

$L^{S2}$ is a bond, —$NR^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;

each $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ groups attached to the same nitrogen atom are joined to form an optionally substituted heterocyclyl or heteroaryl ring;

each of $R^{S4a}$ and $R^{S4b}$ is independently hydrogen, halogen, optionally substituted $C_1$-$C_6$ alkyl, or —$OR^{SO4}$;

each instance of $R^{S5a}$ and $R^{S5b}$ is independently hydrogen, halogen, optionally substituted $C_1$-$C_6$ alkyl, —$OR^{SO5}$, or of the formula:

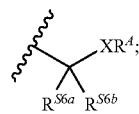

each instance of $R^{S6a}$ and $R^{S6b}$ is independently hydrogen, halogen, or optionally substituted $C_1$-$C_6$ alkyl;

each $R^{SN1}$ is independently hydrogen, optionally substituted $C_1$-$C_6$ alkyl, optionally substituted carbocyclyl, optionally substituted aryl, optionally substituted heterocyclyl, optionally substituted heteroaryl, optionally substituted acyl, or a nitrogen protecting group, or optionally two $R^{SN1}$ groups are joined to form an optionally substituted heterocyclyl or heteroaryl ring;

each of $R^{SO}$, $R^{S4}$, and $R^{SO5}$ is independently hydrogen, optionally substituted $C_1$-$C_6$ alkyl, a carbohydrate, or an oxygen protecting group;

each of $R^{1a}$ and $R^{1b}$ is independently hydrogen, halogen, acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each of $R^{2a}$ and $R^{2b}$ is independently hydrogen, halogen, optionally substituted alkyl, or optionally substituted alkenyl;

each of $R^3$ and $R^4$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or —$OR^{3a}$;

each $R^{3a}$ is independently hydrogen, optionally substituted alkyl, optionally substituted alkenyl, optionally substituted alkynyl, an oxygen protecting group, or of formula:

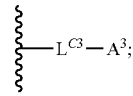

(L$^{C3}$-ii)

each $L^{C3}$ is independently a bond, or is a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

each $A^3$ is independently optionally substituted carbocyclyl, optionally substituted heterocyclyl, optionally substituted aryl, or optionally substituted heteroaryl;

each of $R^{5a}$ and $R^{5b}$ is independently hydrogen, halogen, optionally substituted alkyl, optionally substituted carbocyclyl, or optionally substituted heterocyclyl;

$R^6$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

$R^{10}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

$R^7$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^8$ is hydrogen, halogen, or optionally substituted $C_1$-$C_6$ alkyl.

$R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or of formula:

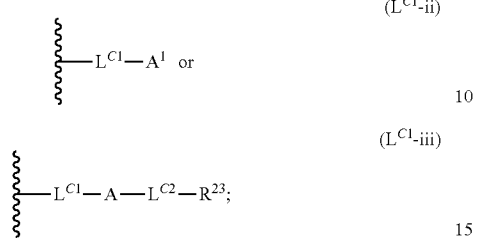

$L^{C1}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

$A^1$ is a leaving group (LG), —SH, —OH, —NH$_2$, —NH—NH$_2$, —N$_2$, —N$_3$, —O—NH$_2$, —CCH, —OC(=O)R$^{Z8}$, —C(=O)OR$^{Z8}$, or of formula:

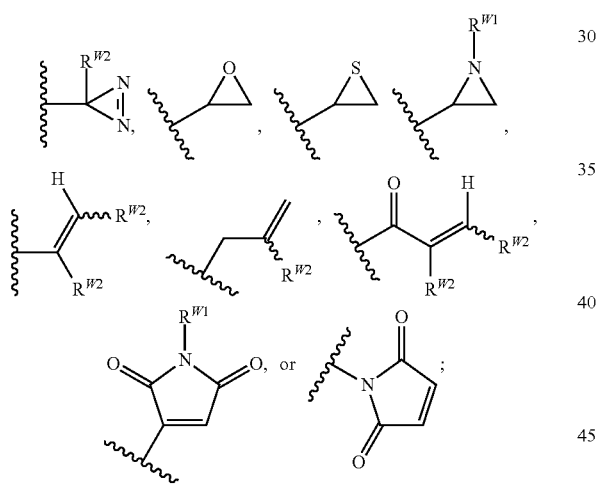

A is —NH—, —NH—NH—, —NH—O—, —O—NH—, —S—, —SS—, —O—, or of formula:

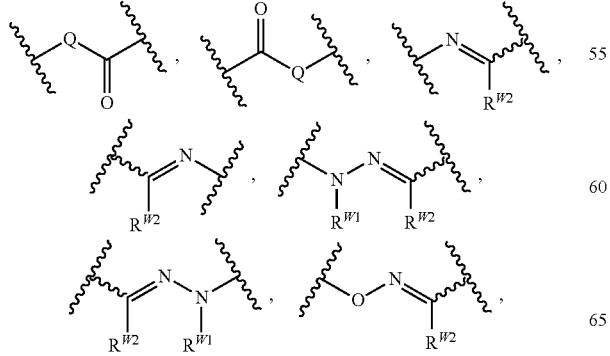

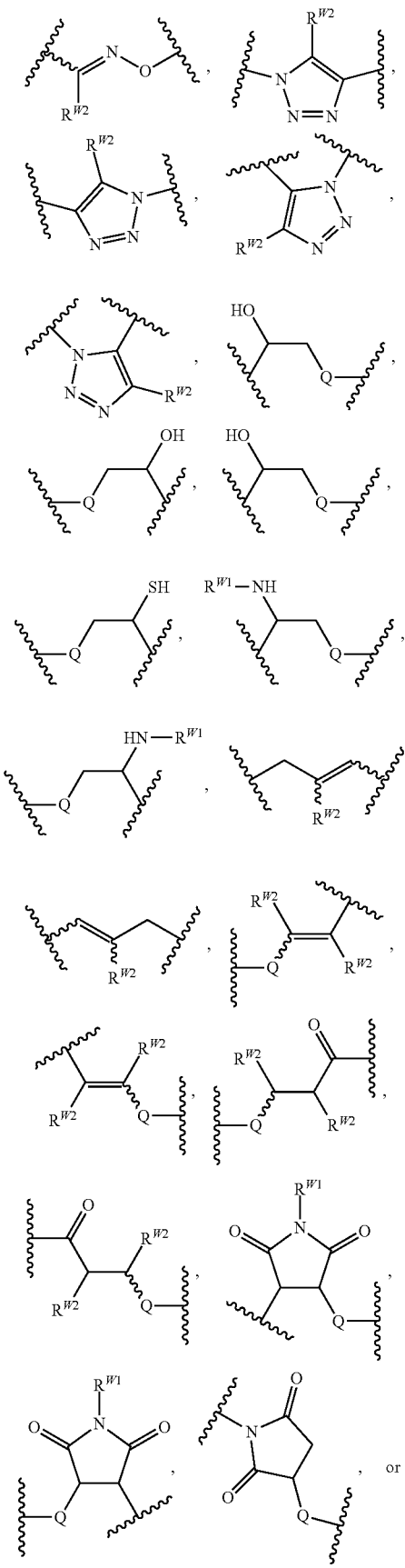

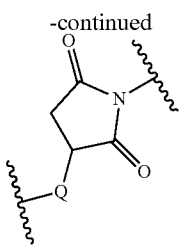

Q is —NH—, —NH—NH—, —O—NH—, —NH—O—, —S—, or —O—;

$L^{C2}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

$R^{W1}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each $R^{W2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two $R^{W2}$ groups are joined to form an optionally substituted cyclic moiety;

$R^{Z3}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z2}$ groups attached to the same nitrogen atom are joined to form an optionally substituted heterocyclyl or optionally substituted heteroaryl ring;

provided that at least one instance of $R^{SN1}$ is not methyl. In certain embodiments of Formula (I-N), at least one instance of $R^{SN1}$ is not methyl. In certain embodiments, both instances of $R^{SN1}$ are not methyl. In certain embodiments, one instance of $R^{SN1}$ is not methyl. In certain embodiments, at least one instance of $R^{SN1}$ is not unsubstituted $C_1$-$C_3$ alkyl. In certain embodiments, both instances of $R^{SN1}$ are not unsubstituted $C_1$-$C_3$ alkyl. In certain embodiments, at least one instance of $R^{SN1}$ is not unsubstituted $C_1$-$C_6$ alkyl. In certain embodiments, both instances of $R^{SN1}$ are not unsubstituted $C_1$-$C_6$ alkyl. In certain embodiments, at least one instance of $R^{SN1}$ is not hydrogen. In certain embodiments, both instances of $R^{SN1}$ are not hydrogen.

In certain embodiments of Formula (I-N), at least one of $R^{SN1}$ is not benzyl (—CH$_2$-phenyl). In certain embodiments, both $R^{SN1}$ are not benzyl (—CH$_2$-phenyl). In certain embodiments, at least one instance of $R^{SN1}$ is not tert-butyloxycarbonyl. In certain embodiments, if one instance of $R^{SN1}$ is tert-butyloxycarbonyl (Boc), the other instance is not hydrogen. In certain embodiments, if one instance of $R^{SN1}$ is hydrogen, the other instance is not tert-butyloxycarbonyl (Boc). In certain embodiments, one instance of $R^{SN1}$ is not tert-butyloxycarbonyl (Boc), and the other instance is not hydrogen.

In certain embodiments, the compound of Formula (I-N) is a compound of Formula (I-a-N):

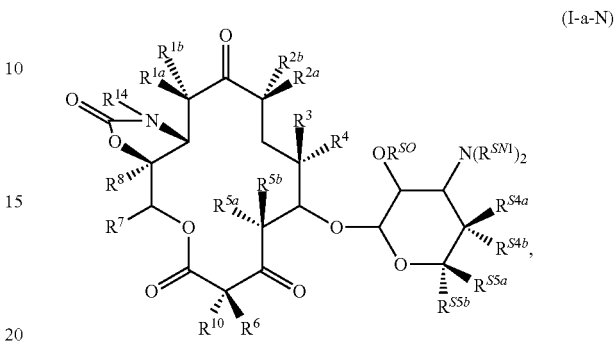

(I-a-N)

wherein $R^{1a}$, $R^{1b}$, $R^{2a}$, $R^{2b}$, $R^3$, $R^4$, $R^{5a}$, $R^{5b}$, $R^6$, $R^7$, $R^8$, $R^{10}$, $R^{14}$, $R^{S4a}$, $R^{S4b}$, $R^{S5a}$, $R^{S5b}$, $R^{SN1}$, and $R^{SO}$ are as described herein.

In certain embodiments, the compound of Formula (I-N) is a compound of Formula (I-b-N):

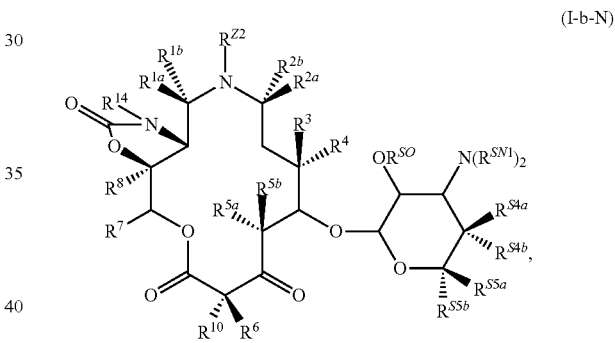

(I-b-N)

wherein $R^{1a}$, $R^{1b}$, $R^{2a}$, $R^{2b}$, $R^3$, $R^4$, $R^{5a}$, $R^{5b}$, $R^6$, $R^7$, $R^8$, $R^{10}$, $R^{14}$, $R^{S4a}$, $R^{S4b}$, $R^{S5a}$, $R^{S5b}$, $R^{SN1}$, $R^{SO}$, and $R^{Z2}$ are as described herein.

In certain embodiments, the compound of Formula (I-N) is a compound of Formula (I-c-N):

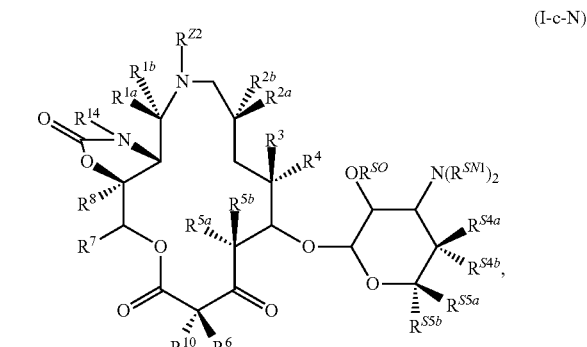

(I-c-N)

wherein $R^{1a}$, $R^{1b}$, $R^{2b}$, $R^3$, $R^4$, $R^{5a}$, $R^{5b}$, $R^6$, $R^7$, $R^8$, $R^{10}$, $R^{14}$, $R^{S4a}$, $R^{S4b}$, $R^{S5a}$, $R^{S5b}$, $R^{SN1}$, $R^{SO}$, and $R^{Z2}$ are as described herein.

In certain embodiments, the compound of Formula (I-N) is a compound of Formula (I-d-N):

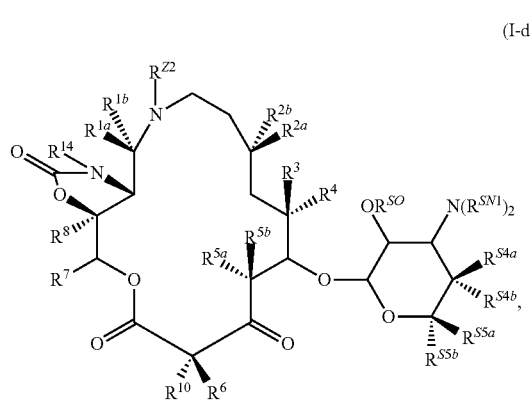

(I-d-N)

wherein $R^{1a}$, $R^{1b}$, $R^{2a}$, $R^{2b}$, $R^3$, $R^4$, $R^{5a}$, $R^{5b}$, $R^6$, $R^7$, $R^8$, $R^{10}$, $R^{14}$, $R^{S4a}$, $R^{S4b}$, $R^{S5a}$, $R^{S5b}$, $R^{SN1}$, $R^{SO}$, and $R^{Z2}$ are as described herein.

In certain embodiments, the compound of Formula (I-N) is a compound of Formula (I-e-N):

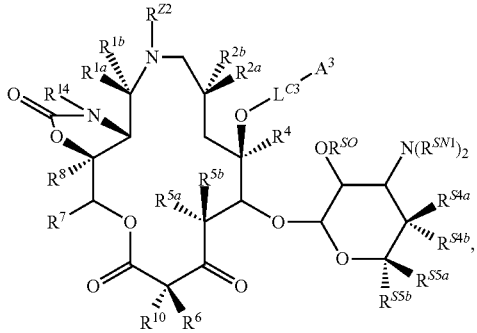

(I-e-N)

wherein $R^{1a}$, $R^{1b}$, $R^{2a}$, $R^{2b}$, $R^4$, $R^{5a}$, $R^{5b}$, $R^6$, $R^7$, $R^8$, $R^{10}$, $R^{14a}$, $R^{S4a}$, $R^{S4b}$, $R^{S5a}$, $R^{S5b}$, $R^{SN1}$, $R^{SO}$, $R^{Z2}$, $L^3$, and $A^3$ are as described herein.

In certain embodiments, the compound of Formula (I-N) is a compound of Formula (II-a-N):

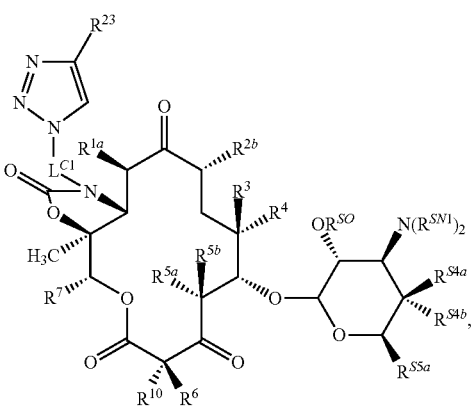

(II-a-N)

wherein $R^{1a}$, $R^{2b}$, $R^3$, $R^4$, $R^{5a}$, $R^{5b}$, $R^6$, $R^7$, $R^{10}$, $L^{C1}$, $R^{23}$, $R^{S4a}$, $R^{S4b}$, $R^{S5a}$, $R^{SN1}$, and $R^{SO}$ are as described herein.

In certain embodiments, the compound of Formula (I-N) is a compound of Formula (II-b-N):

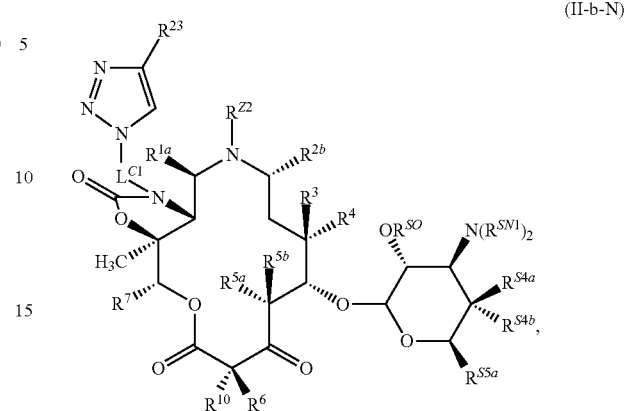

(II-b-N)

wherein $R^{1a}$, $R^{2b}$, $R^3$, $R^4$, $R^{5a}$, $R^{5b}$, $R^6$, $R^7$, $R^{10}$, $L^{C1}$, $R^{23}$, X, $R^A$, $R^{S4}$, $R^{S4b}$, $R^{Sa}$, $R^{SN1}$, $R^{SO}$, and $R^{Z2}$ are as described herein.

In certain embodiments, the compound of Formula (I-N) is a compound of Formula (II-c-N):

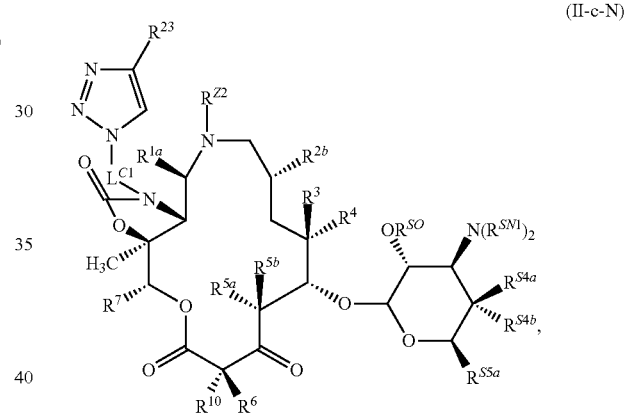

(II-c-N)

wherein $R^{1a}$, $R^{2b}$, $R^3$, $R^4$, $R^{5a}$, $R^{5b}$, $R^6$, $R^7$, $R^{10}$, $L^{C1}$, $R^{23}$, X, $R^A$, $R^{S4a}$, $R^{S4b}$, $R^{S5a}$, $R^{SN1}$, $R^{SO}$, and $R^{Z2}$ are as described herein.

In certain embodiments, the compound of Formula (I-N) is a compound of Formula (II-d-N):

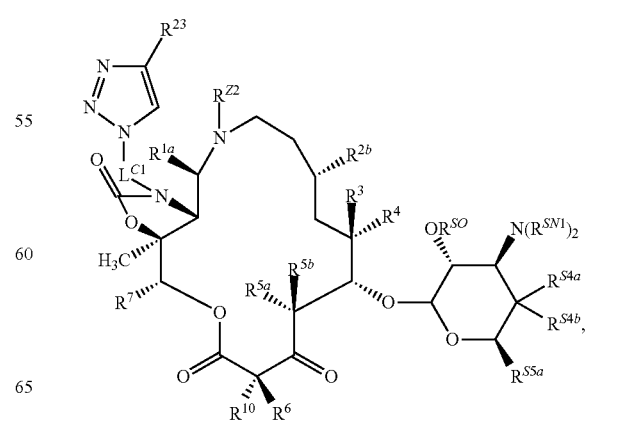

(II-d-N)

wherein $R^{1a}$, $R^{2b}$, $R^3$, $R^4$, $R^{5a}$, $R^{5b}$, $R^6$, $R^7$, $R^{10}$, $L^{C1}$, $R^{23}$, X, $R^A$, $R^{S4a}$, $R^{S4b}$, $R^{S5a}$, $R^{SN1}$, $R^{SO}$, and $R^{Z2}$ are as described herein.

In certain embodiments, the compound of Formula (I-N) is a compound of Formula (I-e-N):

(II-e-N)

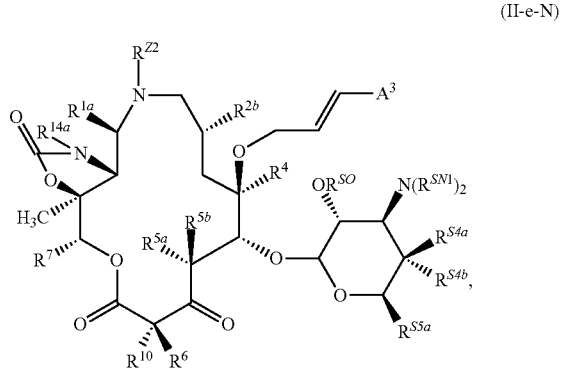

wherein $R^{1a}$, $R^{2b}$, $R^4$, $R^{5a}$, $R^{5b}$, $R^6$, $R^7$, $R^{10}$, $R^{14a}$, X, $R^A$, $R^{S4a}$, $R^{S4b}$, $R^{S5a}$, $R^{SN1}$, $R^{SO}$, $R^{Z2}$, and $A^3$ are as described herein.

In certain embodiments, the compound of Formula (I-N) is a compound of Formula (III-a-N):

(III-a-N)

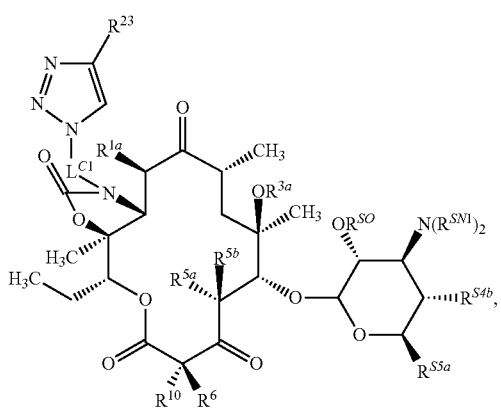

wherein $R^{1a}$, $R^{3a}$, $R^{5a}$, $R^{5b}$, $R^6$, $R^{10}$, $L^{C1}$, $R^{23}$, X, $R^A$, $R^{S4b}$, $R^{S5a}$, $R^{SN1}$, and $R^{SO}$ are as described herein.

In certain embodiments, the compound of Formula (I-N) is a compound of Formula (III-b-N):

(III-b-N)

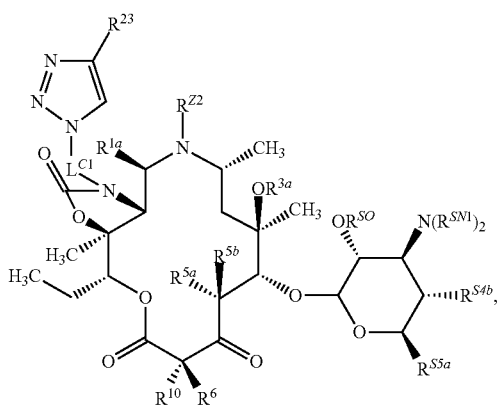

wherein $R^{1a}$, $R^{3a}$, $R^{5a}$, $R^{5b}$, $R^6$, $R^{10}$, $L^{C1}$, $R^{23}$, X, $R^A$, $R^{S4b}$, $R^{S5a}$, $R^{SO}$, $R^{SN1}$, and $R^{Z2}$ are as described herein.

In certain embodiments, the compound of Formula (I-N) is a compound of Formula (III-c-N):

(III-c-N)

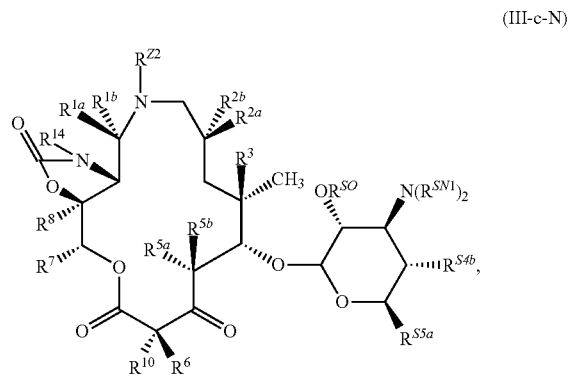

wherein $R^{1a}$, $R^{3a}$, $R^{5a}$, $R^{5b}$, $R^6$, $R^{10}$, $L^{C1}$, $R^{23}$, X, $R^A$, $R^{S4b}$, $R^{SO}$, and $R^{Z2}$ are as described herein.

In certain embodiments, the compound of Formula (I-N) is a compound of Formula (III-d-N):

(III-d-N)

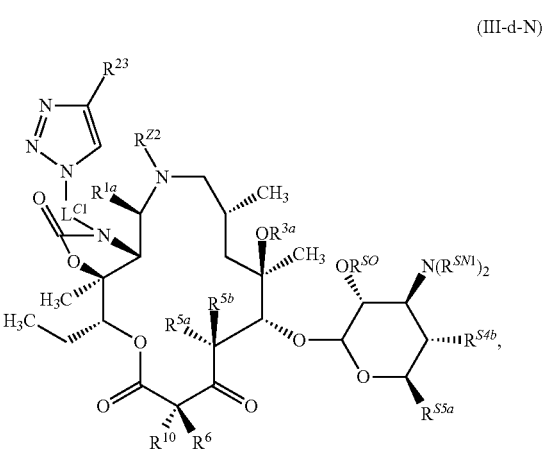

wherein $R^{1a}$, $R^{3a}$, $R^{5a}$, $R^{5b}$, $R^6$, $R^{10}$, $L^{C1}$, $R^2$, X, $R^A$, $R^{S4b}$, $R^{S5a}$, $R^{SO}$, $R^{SN1}$, and $R^{Z2}$ are as described herein.

In certain embodiments, the compound of Formula (I-N) is a compound of Formula (III-d-N-2):

(III-d-N-2)

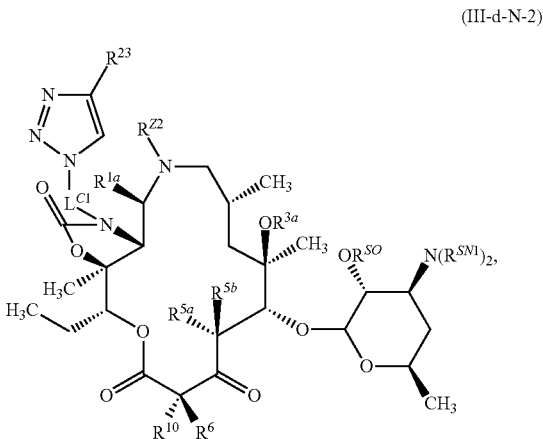

wherein $R^{1a}$, $R^{3a}$, $R^{5a}$, $R^{5b}$, $R^6$, $R^{10}$, $L^{C1}$, $R^{23}$, X, $R^A$, $R^{S4b}$, $R^{S5a}$, $R^{SO}$, $R^{SN1}$, and $R^{Z2}$ are as described herein.

In certain embodiments, the compound of Formula (I-N) is a compound of Formula (III-e-N):

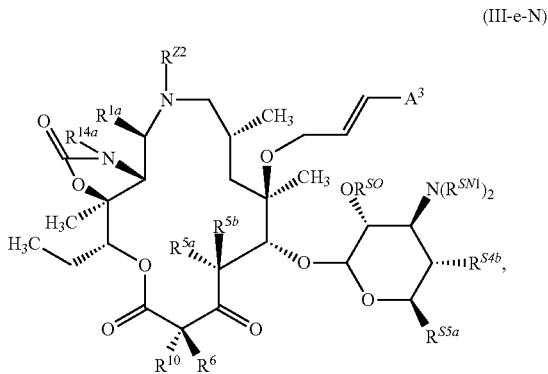

(III-e-N)

wherein $R^{1a}$, $R^{5a}$, $R^{5b}$, $R^6$, $R^{10}$, $R^{14a}$, X, $R^A$, $R^{S4b}$, $R^{S6a}$, $R^{S4b}$, $R^{S5b}$, $R^{SO}$, $R^{Z2}$, and A areas described herein.

Group Z

As generally defined herein, Z may be —C(=O)— or —$NR^{Z2}$—. Attached to group Z is a methylene (i.e., —$CH_2$—) group, which may be repeated 0, 1, or 2 times, according to variable p. In certain embodiments, Z is —C(=O)—, and p is 0, e.g., to give a 14-membered ketolide. In certain embodiments, Z is —C(=O)—, and p is 1 or 2. In certain embodiments, Z is —$NR^{Z2}$—, and p is 0, e.g., to give a 14-membered azaketolide. In certain embodiments, Z is —$NR^{Z2}$—, and p is 1, e.g., to give a 15-membered azaketolide. In certain embodiments, Z is —$NR^{Z2}$—, and p is 2, e.g., to give a 16-membered azaketolide. In certain embodiments, Z is —NH—, and p is 0. In certain embodiments, Z is —NH—, and p is 1. In certain embodiments, Z is —NH—, and p is 2.

$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, acyl, or a nitrogen protecting group. In certain embodiments, $R^{Z2}$ is hydrogen.

In certain embodiments, $R^{Z2}$ is acyl. In certain embodiments, $R^{Z2}$ is an aldehyde (—CHO). In certain embodiments $R^{Z2}$ is a nitrogen protecting group.

In certain embodiments, $R^{Z2}$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, $R^{Z2}$ is —$CH_3$. In certain embodiments, $R^{Z2}$ is alkyl substituted with one or more halogen atoms, e.g., optionally substituted haloalkyl; e.g., —$CF_3$, —$CF_2CF_3$, or —$CF_2H$. In certain embodiments, $R^{Z2}$ is —$CH_2CHO$.

In certain embodiments, $R^{Z2}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl. In certain embodiments, $R^{Z2}$ is optionally substituted heterocylyl, e.g., optionally substituted 3-6 membered heterocyclyl. In certain embodiments, $R^{Z2}$ is optionally substituted aryl, e.g., optionally substituted phenyl. In certain embodiments, $R^{Z2}$ is optionally substituted heteroaryl, e.g., optionally substituted 5- to 6-membered heteroaryl.

Groups X, $R^A$, and $R^B$

As generally defined herein, X may be —$NR^B$— or —O—. In certain embodiments, when Z is —C(=O)—, X is —$NR^B$—. In certain embodiments, X is —$NR^B$—. In some embodiments, X is —NH—. In certain embodiments, X is —O—.

As generally defined herein, $R^A$ may be hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)-$L^{S2}$-$R^S$, —C(=$NR^S$)-$L^{S2}$-$R^S$—, —S(=O)-$L^{S2}$-$R^S$, —S(=O)$_2$-$L^{S2}$-$R^S$, a nitrogen protecting group when attached to a nitrogen atom, or an oxygen protectin group when attached to an oxygen atom. As generally defined herein, $R^B$ may be hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or nitrogen protecting group. $R^A$ and $R^B$ may also be taken together to form =$N_2$, a heterocyclyl ring, or a heteroaryl ring.

In certain embodiments, when X is —$NR^B$—, $R^A$ is optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)-$L^{S2}$-$R^S$, —C(=$NR^S$)-$L^{S2}$-$R^S$, —S(=O)-$L^{S2}$-$R^S$, —S(=O)$_2$-$L^{S2}$-$R^S$, or a nitrogen protecting group; provided that when $R^A$ is —C(=O)—O—$R^S$, $R^S$ is hydrogen, optionally substituted alkyl, optionally substituted alkynyl, optionally substituted carbocyclyl, optionally substituted heterocyclyl, optionally substituted aryl, optionally substituted heteroaryl, or an oxygen protecting group.

In certain embodiments, when X is —$NR^B$—, $R^A$ is hydrogen, optionally substituted alkyl, optionally substituted alkenyl, —C(=O)-$L^{S2}$-$R^S$, —C(=$NR^{SN2}$)-$L^{S2}$-$R^S$—, S(=O)-$L^{S2}$-$R^S$, —S(=O)$_2$-$L^{S2}$-$R^S$, or a nitrogen protecting group. In some embodiments, $R^A$ is hydrogen. In some embodiments, $R^A$ is optionally substituted alkyl. In some embodiments, $R^A$ is optionally substituted $C_1$-$C_6$ alkyl. In some embodiments, $R^A$ is $C_1$-$C_6$ alkyl. In some embodiments, $R^A$ is optionally substituted alkenyl, e.g., $C_2$-$C_6$ alkenyl. In some embodiments, $R^A$ is methyl. In some embodiments, $R^A$ is ethyl, propyl, or butyl. In some embodiments, $R^A$ is optionally substituted alkenyl. In some embodiments, $R^A$ is optionally substituted alkynyl. In some embodiments, $R^A$ is optionally substituted carbocyclyl. In some embodiments, $R^A$ is optionally substituted heterocyclyl. In some embodiments, $R^A$ is optionally substituted aryl. In some embodiments, $R^A$ is optionally substituted heteroaryl. In some embodiments, $R^A$ is a nitrogen protecting group.

In certain embodiments, when X is —$NR^B$—, $R^A$ is —C(=O)-$L^{S2}$-$R^S$, —C(=$NR^{SN2}$)-$L^{S2}$-$R^S$—, —S(=O)-$L^{S2}$-$R^S$, or —S(=O)$_2$-$L^{S2}$-$R^S$. In certain embodiments, $R^A$ is —C(=O)-$L^{S2}$-$R^S$. In some embodiments, $R^A$ is —C(=O)$R^S$, —C(=O)$OR^S$, or —C(=O)$N(R^S)_2$. In certain embodiments, $R^A$ is —C(=$NR^{SN2}$)-$L^{S2}$-$R^S$. In some embodiments, $R^A$ is C(=$NR^{SN2}$)$R^S$, —C(=$NR^{SN2}$)$OR^S$, or —C(=$NR^{SN2}$)N($R^S$)$_2$. In certain embodiments, $R^A$ is —S(=O)-$L^{S2}$-$R^S$. In certain embodiments, $R^A$ is —S(=O)$_2$-$L^{S2}$-$R^S$. In some embodiments, $R^A$ is —S(=O)$_2R^S$. $R^{SN2}$ may be hydrogen, optionally substituted $C_1$-$C_6$ alkyl, or a nitrogen protecting group. In some embodiments, $R^{SN2}$ is hydrogen. In some embodiments, $R^{SN2}$ is optionally substituted $C_1$-$C_6$ alkyl. In some embodiments, $R^{SN2}$ is $C_1$-$C_6$ alkyl. In some embodiments, $R^{SN2}$ is methyl. In some embodiments, $R^{SN2}$ is ethyl, propyl, or butyl. In some embodiments, $R^{SN2}$ is a nitrogen protecting group.

In certain embodiments, when X is —O—, $R^A$ is hydrogen, optionally substituted alkyl, optionally substituted alkenyl, —C(=O)-$L^{S2}$-$R^S$, —C(=$NR^{SN2}$)-$L^{S2}$-$R^S$, —S(=O)-$L^{S2}$-$R^S$—, —S(=O)$_2$-$L^{S2}$-$R^S$, or an oxygen protectin group. In some embodiments, $R^A$ is hydrogen. In some embodiments, $R^A$ is optionally substituted alkyl. In some embodiments, $R^A$ is optionally substituted $C_1$-$C_6$ alkyl. In some embodiments, $R^A$ is $C_1$-$C_6$ alkyl. In some embodiments, $R^A$ is optionally substituted alkenyl, e.g., $C_2$-$C_6$ alkenyl. In some embodiments, $R^A$ is methyl. In some embodiments, $R^A$ is ethyl, propyl, or butyl. In some embodiments, $R^A$ is optionally substituted alkenyl. In some embodiments, $R^A$ is optionally substituted alkynyl. In some embodiments, $R^A$ is optionally substituted carbocyclyl. In some embodiments, $R^A$ is optionally substituted heterocyclyl. In some embodiments, $R^A$ is optionally substituted aryl. In some embodiments, $R^A$ is optionally substituted heteroaryl. In some embodiments, $R^A$ is an oxygen protecting group.

In certain embodiments, when X is —O—, $R^A$ is —C(=O)-$L^{S2}$-$R^S$, —C(=$NR^{SN2}$)-$L^{S2}$-$R^S$—, —S(=O)-$L^{S2}$-$R^S$, or —S(=O)$_2$-$L^{S2}$-$R^S$. In certain embodiments, $R^A$ is —C(=O)-$L^{S2}$-$R^S$. In some embodiments, $R^A$ is —C(=O) $R^S$, —C(=O)$OR^S$, or —C(=O)N($R^S$)$_2$. In certain embodiments, $R^A$ is —C(=$NR^{SN2}$)-$L^{S2}$-$R^S$. In some embodiments, $R^A$ is C(=$NR^S$M)$R^S$, —C(=$NR^{SN2}$)$R^S$, or C(=$NR^{SN2}$)N($R^S$)$_2$. In certain embodiments, $R^A$ is —S(=O)-$L^{S2}$-$R^S$. In certain embodiments, $R^A$ is —S(=O)$_2$-$L^{S2}$-$R^S$. In some embodiments, $R^A$ is —S(=O)$_2R^S$. $R^{SN2}$ may be hydrogen, optionally substituted $C_1$-$C_6$ alkyl, or a nitrogen protecting group. In some embodiments, $R^S$m is hydrogen. In some embodiments, $R^{SN2}$ is optionally substituted $C_1$-$C_6$ alkyl. In some embodiments, $R^{SN2}$ is $C_1$-$C_6$ alkyl. In some embodiments, $R^{SN2}$ is methyl. In some embodiments, $R^{SN2}$ is ethyl, propyl, or butyl. In some embodiments, $R^{SN2}$ is a nitrogen protecting group.

$R^A$ may include $L^{S2}$. $L^{S2}$ may be a bond, —$NR^S$—, —O—, or —S—, or a linking group selected from optionally substituted alkylene, optionally substituted alkenylene, optionally substituted alkynylene, optionally substituted heteroalkylene, optionally substituted heteroalkenylene, optionally substituted heteroalkynylene, and combinations thereof. In certain embodiments, $L^{S2}$ is absent, —$NR^S$—, —O—, or —S—. In some embodiments, $L^{S2}$ is a bond. In some embodiments, $L^{S2}$ is —$NR^S$—. In some embodiments, $L^{S2}$ is —O—. In some embodiments, $L^{S2}$ is —S—. In some embodiments, $L^{S2}$ is optionally substituted alkylene. In some embodiments, $L^{S2}$ is optionally substituted alkenylene. In some embodiments, $L^{S2}$ is optionally substituted alkynylene. In some embodiments, $L^{S2}$ is optionally substituted heteroalkylene. In some embodiments, $L^{S2}$ is —CH$_2$NH—, —CH$_2$NMe-, —CH$_2$O—, —CH$_2$CH$_2$NH—, —CH$_2$CH$_2$NMe-, or —CH$_2$CH$_2$O—. In some embodiments, $L^{S2}$ is optionally substituted heteroalkenylene. In some embodiments, $L^{S2}$ is optionally substituted heteroalkynylene.

$R^A$ may include one or more $R^S$. $R^S$ may be independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ groups attached to the same nitrogen atom may be joined to form an optionally substituted heterocyclyl or heteroaryl ring. In certain embodiments, $R^S$ is hydrogen, optionally substituted alkyl, optionally substituted carbocyclyl, optionally substituted heterocyclyl, optionally substituted aryl, optionally substituted heteroaryl, or a nitrogen, oxygen, or sulfur protecting group. In some embodiments, $R^S$ is hydrogen. In some embodiments, $R^S$ is optionally substituted alkyl. In some embodiments, $R^S$ is optionally substituted $C_1$-$C_6$ alkyl. In some embodiments, $R^S$ is $C_1$-$C_6$ alkyl. In some embodiments, $R^A$ is methyl. In some embodiments, $R^A$ is ethyl, propyl, or butyl. In some embodiments, $R^S$ is optionally substituted alkenyl. In some embodiments, $R^S$ is optionally substituted alkynyl. In some embodiments, $R^S$ is optionally substituted carbocyclyl. In some embodiments, $R^S$ is optionally substituted heterocyclyl. In some embodiments, $R^S$ is optionally substituted aryl. In some embodiments, $R^S$ is optionally substituted heteroaryl. In some embodiments, $R^S$ is a nitrogen protecting group. In some embodiments, $R^S$ is an oxygen protecting group. In some embodiments, $R^S$ is a sulfur protecting group. In some embodiments, two $R^S$ are joined to form a heterocyclyl ring. In some embodiments, two $R^S$ are joined to form a heteroaryl ring.

In certain embodiments, $R^B$ is hydrogen, optionally substituted alkyl, or a nitrogen protecting group. In some embodiments, $R^B$ is hydrogen. In some embodiments, $R^B$ is optionally substituted alkyl. In some embodiments, $R^B$ is optionally substituted $C_1$-$C_6$ alkyl. In some embodiments, $R^B$ is $C_1$-$C_6$ alkyl. In some embodiments, $R^B$ is methyl. In some embodiments, $R^B$ is ethyl, propyl, or butyl. In some embodiments, $R^B$ is optionally substituted alkenyl. In some embodiments, $R^B$ is optionally substituted alkynyl. In some embodiments, $R^B$ is optionally substituted carbocyclyl. In some embodiments, $R^B$ is optionally substituted heterocyclyl. In some embodiments, $R^B$ is optionally substituted aryl. In some embodiments, $R^B$ is optionally substituted heteroaryl. In some embodiments, $R^B$ is a nitrogen protecting group.

In certain embodiments, X is —O—, and $R^A$ is hydrogen, optionally substituted alkyl, or an oxygen protecting group. In certain embodiments, substituent —$XR^A$ is:

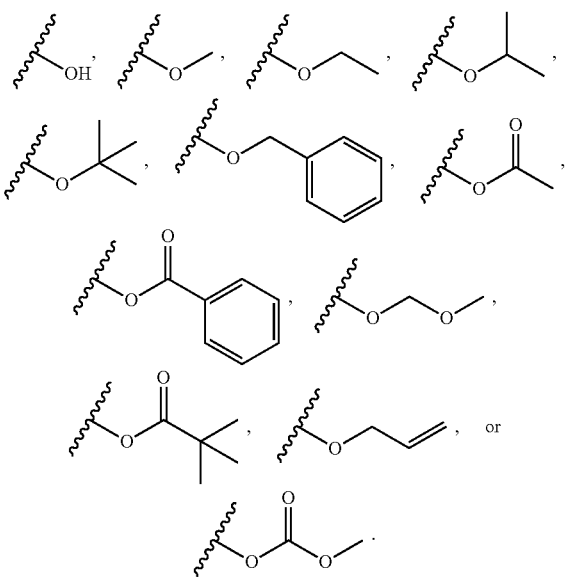

In certain embodiments, X is —NR$^B$—, and each of R$^A$ and R$^B$ is independently hydrogen, optionally substituted alkyl, or a nitrogen protecting group. In certain embodiments, substituent —XR$^A$ is:

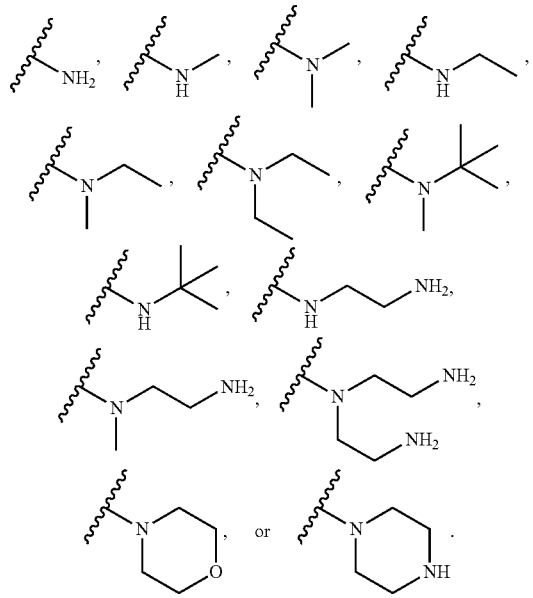

In certain embodiments, substituent —XR$^A$ is —NHC(=O)R$^S$, —NHC(=O)OR$^S$, or —NHC(=O)N(R$^S$)$_2$. In certain embodiments, substituent —XR$^A$ is:

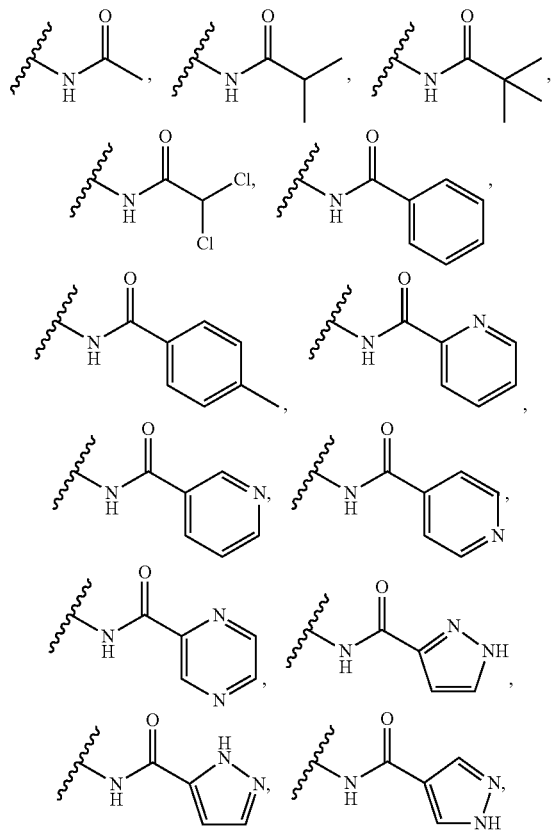

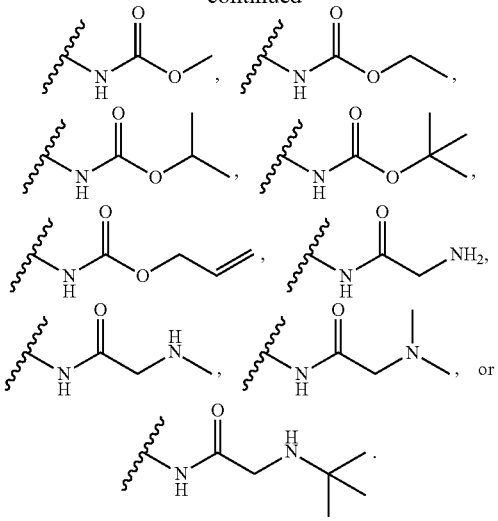

In certain embodiments, substituent —XR$^A$ is —NHC(=NR$^{SN2}$)R$^S$, —NHC(=NR$^{SN2}$)OR$^S$, or —NHC(=NR$^{SN2}$)N(R)$_2$. In certain embodiments, substituent —XR$^A$ is:

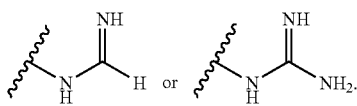

In certain embodiments, substituent —XR$^A$ is —NHS(=O)$_2$R$^S$. In certain embodiments, substituent —XR$^A$ is:

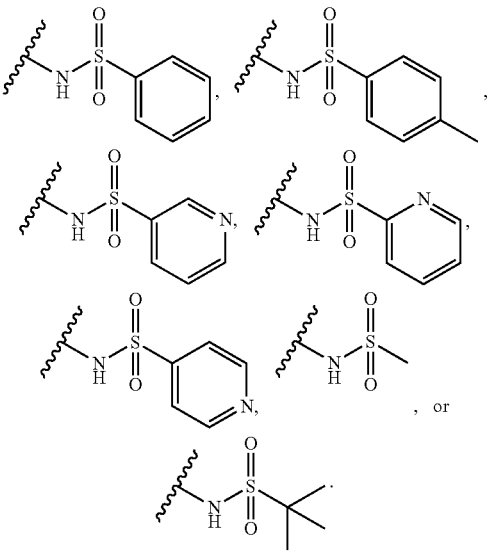

In certain embodiments, X is —NR$^B$— and, R$^A$ and R are taken together to form =N$_2$ or an optionally substituted heterocyclyl or heteroaryl ring. In certain embodiments, X is —NR$^B$— and, R$^A$ and R$^B$ are taken together to form =N$_2$, i.e., the substituent —XR$^A$ is —N$_3$. In certain embodiments, R$^A$ and R$^B$ are taken together to form an optionally substituted heterocyclyl ring e.g., optionally substituted 3-6 membered heterocyclyl. In certain embodiments, X is —NR$^B$— and, $R^A$ and $R^B$ are taken together to form an optionally substituted heteroaryl ring, e.g., optionally substituted 5- to 6-membered heteroaryl. In some embodiments, X is —$NR^B$— and, $R^A$ and $R^B$ are taken together to form an optionally substituted 5-membered heteroaryl. In some embodiments, X is —$NR^B$— and, $R^A$ and $R^B$ are taken together to form an optionally substituted triazole. In some embodiments, the substituent —$XR^A$ is of formula:

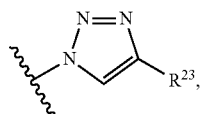

wherein $R^{23}$ is as defined herein. For example, $R^A$ is selected from any one of the following aryl or heteroaryl ring systems:

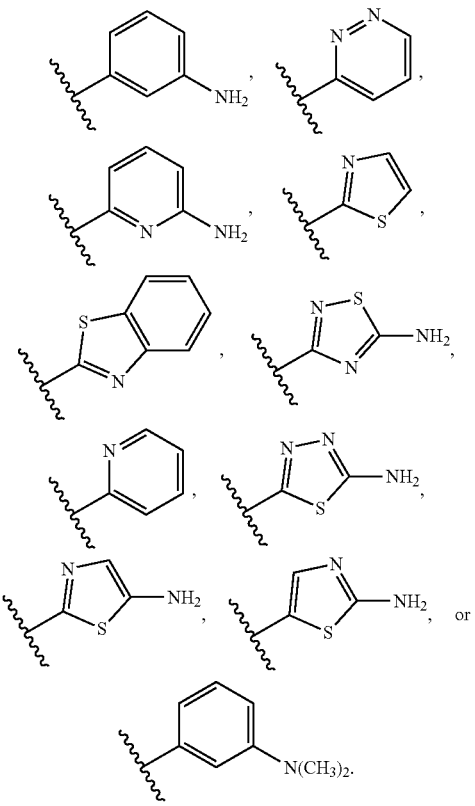

Groups $R^{S6a}$ and $R^{S6b}$

As generally defined herein, $R^{S6a}$ and $R^{S6b}$ may independently be hydrogen, halogen, or optionally substituted $C_1$-$C_6$ alkyl. In certain embodiments, $R^{S6a}$ and $R^{S6b}$ are hydrogen. In certain embodiments, $R^{S6a}$ and $R^{S6b}$ are halogen. In certain embodiments, $R^{S6a}$ and $R^{S6b}$ are optionally substituted $C_1$-$C_6$ alkyl. In certain embodiments, $R^{S6a}$ and $R^{S6b}$ are $C_1$-$C_6$ alkyl. In certain embodiments, $R^{S6a}$ is hydrogen, and $R^{S6b}$ is halogen. In certain embodiments, $R^{S6a}$ is hydrogen, and $R^{S6b}$ optionally substituted $C_1$-$C_6$ alkyl. In certain embodiments, $R^{S6a}$ is hydrogen, and $R^{S6b}$ $C_1$-$C_6$ alkyl. In some embodiments, $R^{S6a}$ is hydrogen. In some embodiments, $R^{S6a}$ is —F. In some embodiments, $R^{S6a}$ is —Cl, —Br, or —I. In some embodiments, $R^{S6a}$ is optionally substituted alkyl. In some embodiments, $R^{S6a}$ is optionally substituted $C_1$-$C_6$ alkyl. In some embodiments, $R^{S6a}$ is $C_1$-$C_6$ alkyl. In some embodiments, $R^{S6a}$ is methyl. In some embodiments, $R^{S6a}$ is ethyl, propyl, or butyl. In some embodiments, $R^{S6b}$ is hydrogen. In some embodiments, $R^{S6b}$ is —F. In some embodiments, $R^{S6b}$ is —Cl, —Br, or —I. In some embodiments, $R^{S6b}$ is optionally substituted alkyl. In some embodiments, $R^{S6b}$ is optionally substituted $C_1$-$C_6$ alkyl. In some embodiments, $R^{S6b}$ is $C_1$-$C_6$ alkyl. In some embodiments, $R^{S6b}$ is methyl. In some embodiments, $R^{S6b}$ is ethyl, propyl, or butyl. In certain embodiments, $R^{S6a}$ is methyl, and $R^{S6b}$ is hydrogen. In certain embodiments, $R^{S6b}$ is methyl, and $R^{S6a}$ is hydrogen. In certain embodiments, the carbon to which $R^{S6a}$ and $R^{S6b}$ are attached is a stereocenter of the (R)-configuration. In certain embodiments, the carbon to which $R^{S6a}$ and $R^{S6b}$ are attached is a stereocenter of the (S)-configuration.

Groups $R^{S4a}$ and $R^{S4b}$

As generally defined herein, each of $R^{S4a}$ and $R^{S4b}$ may independently be hydrogen, halogen, optionally substituted $C_1$-$C_6$ alkyl, or —$OR^{SO4}$. In certain embodiments, $R^{S4a}$ and $R^{S4b}$ are hydrogen. In certain embodiments, $R^{S4a}$ and $R^{S4b}$ are halogen. In certain embodiments, $R^{S4a}$ and $R^{S4b}$ are optionally substituted $C_1$-$C_6$ alkyl. In certain embodiments, $R^{S4a}$ and $R^{S4b}$ are $C_1$-$C_6$ alkyl. In certain embodiments, $R^{S4a}$ is hydrogen, and $R^{S4b}$ is halogen. In certain embodiments, $R^{S4a}$ is hydrogen, and $R^{S4b}$ is optionally substituted $C_1$-$C_6$ alkyl. In certain embodiments, $R^{S4a}$ is hydrogen, and $R^{S4b}$ is $C_1$-$C_6$ alkyl. In certain embodiments, $R^{S4a}$ is hydrogen, and $R^{S4b}$ is —$OR^{SO4}$. In certain embodiments, $R^{S4b}$ is hydrogen, and $R^{S4a}$ is halogen. In certain embodiments, $R^{S4b}$ is hydrogen, and $R^{S4a}$ is optionally substituted $C_1$-$C_6$ alkyl. In certain embodiments, $R^{S4b}$ is hydrogen, and $R^{S4a}$ is $C_1$-$C_6$ alkyl. In certain embodiments, $R^{S4b}$ is hydrogen, and $R^{S4a}$ is —$OR^4$.

In some embodiments, $R^{S4A}$ is hydrogen. In some embodiments, $R^{S4A}$ is —F. In some embodiments, $R^{S4a}$ is —Cl, —Br, or —I. In some embodiments, $R^{S4a}$ is optionally substituted alkyl. In some embodiments, $R^{S4a}$ is optionally substituted $C_1$-$C_6$ alkyl. In some embodiments, $R^{S4a}$ is $C_1$-$C_6$ alkyl. In some embodiments, $R^{S4a}$ is methyl. In some embodiments, $R^{S4a}$ is ethyl, propyl, or butyl. In certain embodiments, $R^{S4a}$ is —$OR^{SO4}$. In certain embodiments, $R^{S4a}$ is —OH. In certain embodiments, $R^{S4a}$ is —$OR^{SO4}$, and $R^{SO4}$ is optionally substituted $C_1$-$C_6$ alkyl. In certain embodiments, $R^{S4a}$ is —$OR^{SO4}$, and $R^{SO4}$ is a carbohydrate. In certain embodiments, $R^{S4a}$ is —$OR^4$, and $R^{SO4}$ is a monosaccharide. In certain embodiments, $R^{S4a}$ is —$OR^{SO4}$, and $R^{SO4}$ is an oxygen protecting group. In some embodiments, $R^{S4b}$ is hydrogen. In some embodiments, $R^{S4b}$ is —F. In some embodiments, $R^{S4b}$ is —Cl, —Br, or —I. In some embodiments, $R^{S4b}$ is optionally substituted alkyl. In some embodiments, $R^{S4b}$ is optionally substituted $C_1$-$C_6$ alkyl. In some embodiments, $R^{S4b}$ is $C_1$-$C_6$ alkyl. In some embodiments, $R^{S4b}$ is methyl. In some embodiments, $R^{S4b}$ is ethyl, propyl, or butyl. In certain embodiments, $R^{S4b}$ is —$OR^{SO4}$. In certain embodiments, $R^{S4b}$ is —OH. In certain embodiments, $R^{S4b}$ is —$OR^4$, and $R^{SO4}$ is optionally substituted $C_1$-$C_6$ alkyl. In certain embodiments, $R^{S4b}$ is —$OR^4$, and $R^{SO4}$ is a carbohydrate.

Groups $R^{S5a}$ and $R^{S5b}$

As generally defined herein, each of $R^{S5a}$ and $R^{S5b}$ are independently hydrogen, halogen, optionally substituted $C_1$-$C_6$ alkyl, —$OR^{SO5}$, or of the formula:

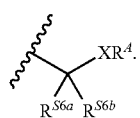

In certain embodiments, $R^{S55}$ is hydrogen, and $R^{S5a}$ is optionally substituted $C_1$-$C_6$ alkyl. In certain embodiments, $R^{S5b}$ is hydrogen, and $R^{S5a}$ is unsubstituted $C_1$-$C_6$ alkyl. In certain embodiments, $R^{S5b}$ is hydrogen, and $R^{S5a}$ is optionally substituted $C_1$-$C_3$ alkyl. In certain embodiments, $R^{S5b}$ is hydrogen, and $R^{S5a}$ is unsubstituted $C_1$-$C_3$ alkyl. In certain embodiments, $R^{S5b}$ is hydrogen, and $R^{S5a}$ is ethyl, n-propyl, iso-propyl, n-butyl, sec-butyl, or tert-butyl. In certain embodiments, $R^{S5b}$ is hydrogen, and $R^{S5a}$ is methyl.

In certain embodiments, $R^{S5a}$ is hydrogen, and $R^{S5b}$ is optionally substituted $C_1$-$C_6$ alkyl. In certain embodiments, $R^{S5a}$ is hydrogen, and $R^{S5b}$ is unsubstituted $C_1$-$C_6$ alkyl. In certain embodiments, $R^{S5a}$ is hydrogen, and $R^{S5b}$ is optionally substituted $C_1$-$C_3$ alkyl. In certain embodiments, $R^{S5a}$ is hydrogen, and $R^{S5b}$ is unsubstituted $C_1$-$C_3$ alkyl. In certain embodiments, $R^{S5a}$ is hydrogen, and $R^{S5b}$ is ethyl, n-propyl, iso-propyl, n-butyl, sec-butyl, or tert-butyl. In certain embodiments, $R^{S5a}$ is hydrogen, and $R^{S5b}$ is methyl.

In certain embodiments, $R^{S5a}$ and $R^{S5b}$ are hydrogen. In certain embodiments, $R^{S5a}$ and $R^{S5b}$ are halogen. In certain embodiments, $R^{S5a}$ and $R^{S5b}$ are optionally substituted $C_1$-$C_6$ alkyl. In certain embodiments, $R^{S5a}$ and $R^{S5b}$ are unsubstituted $C_1$-$C_6$ alkyl. In certain embodiments, $R^{S5a}$ and $R^{S5b}$ are optionally substituted $C_1$-$C_3$ alkyl. In certain embodiments, $R^{S5a}$ and $R^{S5b}$ are unsubstituted $C_1$-$C_3$ alkyl. In certain embodiments, $R^{S5a}$ and $R^{S5b}$ are each independently methyl, ethyl, n-propyl, iso-propyl, n-butyl, sec-butyl, or tert-butyl.

In some embodiments, $R^{S5a}$ is optionally substituted alkyl. In some embodiments, $R^{S5a}$ is optionally substituted $C_1$-$C_6$ alkyl. In some embodiments, $R^{S5a}$ is unsubstituted $C_1$-$C_6$ alkyl. In some embodiments, $R^{S5a}$ is optionally substituted $C_1$-$C_3$ alkyl. In some embodiments, $R^{S5a}$ is unsubstituted $C_1$-$C_3$ alkyl. In some embodiments, $R^{S5a}$ is methyl. In some embodiments, $R^{S5a}$ is ethyl, n-propyl, iso-propyl, n-butyl, sec-butyl, or tert-butyl.

In some embodiments, $R^{S5a}$ is hydrogen. In some embodiments, $R^{S5a}$ is halogen. In some embodiments, $R^{S5a}$ is —F. In some embodiments, $R^{S5a}$ is —Cl, —Br, or —I. In certain embodiments, $R^{S5a}$ is —$OR^{SO5}$. In certain embodiments, $R^{S5a}$ is —OH. In certain embodiments, $R^{S5a}$ is —$OR^{S}$, and $R^{SO5}$ is optionally substituted $C_1$-$C_6$ alkyl. In certain embodiments, $R^{S5a}$ is —$OR^{SO5}$, and $R^{SO5}$ is a carbohydrate. In certain embodiments, $R^{S5a}$ is —$OR^{SO5}$, and $R^{SO5}$ is a monosaccharide. In certain embodiments, $R^{S5a}$ is —$OR^{SO5}$, and $R^{SO5}$ is an oxygen protecting group.

In some embodiments, $R^{S5b}$ is optionally substituted alkyl. In some embodiments, $R^{S5b}$ is optionally substituted $C_1$-$C_6$ alkyl. In some embodiments, $R^{S5b}$ is unsubstituted $C_1$-$C_6$ alkyl. In some embodiments, $R^{S5b}$ is optionally substituted $C_1$-$C_3$ alkyl. In some embodiments, $R^{S5b}$ is unsubstituted $C_1$-$C_3$ alkyl. In some embodiments, $R^{S}$ is methyl. In some embodiments, $R^{S5b}$ is ethyl, n-propyl, iso-propyl, n-butyl, sec-butyl, or tert-butyl.

In some embodiments, $R^{S5b}$ is hydrogen. In some embodiments, $R^{S5b}$ is halogen. In some embodiments, $R^{S5b}$ is —F. In some embodiments, $R^{S5b}$ is —Cl, —Br, or —I. In certain embodiments, $R^{S5b}$ is —$OR^{SO5}$. In certain embodiments, $R^{S5b}$ is —OH. In certain embodiments, $R^{S5b}$ is —$OR^{SO5}$, and $R^{SO5}$ is optionally substituted $C_1$-$C_6$ alkyl. In certain embodiments, $R^{S5b}$ is —$OR^{SO5}$, and $R^{SO5}$ is a carbohydrate.

As generally defined herein, each instance of $R^{SO5}$ is independently hydrogen, optionally substituted $C_1$-$C_6$ alkyl, a carbohydrate, or an oxygen protecting group. In certain embodiments, $R^{SO5}$ is hydrogen. In certain embodiments, $R^{SO5}$ is optionally substituted $C_1$-$C_6$ alkyl. In certain embodiments, $R^{SO5}$ is a carbohydrate. In certain embodiments, $R^{SO5}$ is an oxygen protecting group.

In certain embodiments, $R^{S5a}$ is of the formula:

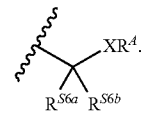

In certain embodiments, $R^{S5b}$ is of the formula:

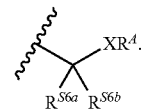

In certain embodiments, $R^{S5a}$ is of the formula:

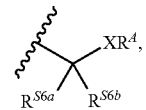

and $R^{S5b}$ is hydrogen. In certain embodiments, $R^{S5a}$ is of the formula:

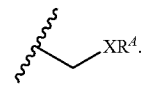

certain embodiments, $R^{S5b}$ is of the formula:

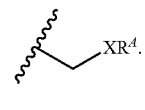

In certain embodiments, $R^{S5a}$ is of the formula:

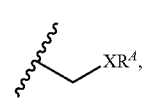

and $R^{S5b}$ is hydrogen.

Group $R^{SN}$

As generally defined herein, each $R^{SN}$ of the sugar substituent —$N(R^{SN})_2$ may independently be hydrogen, optionally substituted $C_1$-$C_6$ alkyl, or a nitrogen protecting group, or two $R^{SN}$ may be joined to form an optionally substituted heterocyclyl or heteroaryl ring. In certain embodiments, at least one $R^{SN}$ is hydrogen. In certain embodiments, both $R^{SN}$ are joined to form an optionally substituted heterocyclyl ring. In certain embodiments, both $R^{SN}$ are joined to form an optionally substituted heteroaryl ring. In certain embodiments, both $R^{SN}$ are $C_1$-$C_6$ alkyl. In certain embodiments, both $R^{SN}$ are $C_1$-$C_6$ alkyl. In certain embodiments, both $R^{SN}$ are methyl. In certain embodiments, both $R^{SN}$ are both ethyl, both propyl, or both butyl. In certain embodiments, both $R^{SN}$ are independently methyl, propyl, or butyl. In certain embodiments, both $R^{SN}$ are nitrogen protecting groups. In certain embodiments, both $R^{SN}$ are identical nitrogen protecting groups. In certain embodiments, one $R^{SN}$ is hydrogen, and the other $R^{SN}$ is optionally substituted $C_1$-$C_6$ alkyl. In certain embodiments, one $R^{SN}$ is hydrogen, and the other $R^{SN}$ is $C_1$-$C_6$ alkyl. In certain embodiments, one $R^{SN}$ is hydrogen, and the other $R^{SN}$ is methyl. In certain embodiments, one $R^{SN}$ is hydrogen, and the other $R^{SN}$ is ethyl, propyl, or butyl. In certain embodiments, $R^{SN}$ is hydrogen, and the other $R^{SN}$ is a nitrogen protecting group. In certain embodiments, one $R^{SN}$ is hydrogen, and the other $R^{SN}$ is benzyl. In certain embodiments, both $R^{SN}$ are benzyl. In certain embodiments, one $R^{SN}$ is hydrogen, and the other $R^{SN}$ is alkoxycarbonyl (e.g., methoxycarbonyl, tert-butylcarbonyl). In certain embodiments, $R^{SN}$ is hydrogen, and the other $R^{SN}$ is carbobenzyloxy, fluorophenylmethyloxycarbonyl, acetyl, benzoyl, p-toluenesulfonyl, p-bromobenzenesulfonyl, 2-nitrobenzenesulfonyl, 4-nitrobenzenesulfonyl, methanesulfonyl, or trifluoromethanesulfonyl.

Group $R^{SN1}$

As generally defined herein, each $R^{SN1}$ of the sugar substituent —N($R^{SN1}$)$_2$ is independently hydrogen, optionally substituted $C_1$-$C_6$ alkyl, optionally substituted carbocyclyl, optionally substituted heterocyclyl, optionally substituted aryl, optionally substituted heteroaryl, optionally substituted acyl, or a nitrogen protecting group, or optionally two $R^{SN1}$ are joined to form an optionally substituted heterocyclyl or optionally substituted heteroaryl ring. As described herein, at least one instance of $R^{SN1}$ is not methyl. In certain embodiments, at least one $R^{SN1}$ is hydrogen. In certain embodiments, at least one $R^{SN1}$ is optionally substituted $C_1$-$C_6$ alkyl. In certain embodiments, at least one $R^{SN1}$ is optionally substituted carbocyclyl. In certain embodiments, at least one $R^{SN1}$ is optionally substituted aryl. In certain embodiments, at least one $R^{SN1}$ is optionally substituted heterocyclyl. In certain embodiments, at least one $R^{SN1}$ is optionally substituted heteroaryl. In certain embodiments, at least one $R^{SN1}$ is optionally substituted acyl. In certain embodiments, at least one $R^{SN1}$ is a nitrogen protecting group. In certain embodiments, two $R^{SN1}$ are joined to form an optionally substituted heterocyclyl or optionally substituted heteroaryl ring.

In certain embodiments, at least one $R^{SN1}$ is optionally substituted $C_1$-$C_6$ alkyl. In certain embodiments, at least one $R^{SN1}$ is substituted $C_1$-$C_6$ alkyl. In certain embodiments, at least one $R^{SN1}$ is unsubstituted $C_1$-$C_6$ alkyl. In certain embodiments, at least one $R^{SN1}$ is optionally substituted $C_1$-$C_3$ alkyl. In certain embodiments, at least one $R^{SN1}$ is unsubstituted $C_1$-$C_3$ alkyl. In certain embodiments, at least one $R^{SN1}$ is selected from the group consisting of methyl, ethyl, n-propyl, iso-propyl, n-butyl, iso-butyl, sec-butyl, and tert-butyl. In certain embodiments, at least one $R^{SN1}$ is selected from the group consisting of ethyl, n-propyl, iso-propyl, n-butyl, iso-butyl, sec-butyl, and tert-butyl. In certain embodiments, one $R^{SN1}$ is methyl. In certain embodiments, at least one $R^{SN1}$ is —$C_1$-$C_6$ alkyl-aryl. In certain embodiments, at least one $R^{SN1}$ is —$C_1$-$C_3$ alkyl-aryl. In certain embodiments, at least one $R^{SN1}$ is —$C_1$-$C_3$ alkyl-phenyl. In certain embodiments, at least one $R^{SN1}$ is —$C_1$-$C_6$ alkyl-carbocyclyl. In certain embodiments, at least one $R^{SN1}$ is —$C_1$-$C_6$ alkyl-heterocyclyl. In certain embodiments, at least one $R^{SN1}$ is —$C_1$-$C_6$ alkyl-heteroaryl. In certain embodiments, at least one $R^{SN1}$ is —$C_1$-$C_3$ alkyl-heteroaryl. In certain embodiments, at least one $R^{SN1}$ is —$C_1$-$C_3$ alkyl-pyridyl. In certain embodiments, at least one $R^{SN1}$ is —$CH_2$-pyridyl. In certain embodiments, at least one $R^{SN1}$ is —$C_1$-$C_6$ alkyl-$CO_2H$. In certain embodiments, at least one $R^{SN}$ is —$C_1$-$C_3$ alkyl-$CO_2H$. In certain embodiments, at least one $R^{SN1}$ is —$C_1$-$C_6$ alkyl-CN. In certain embodiments, at least one $R^{SN1}$ is —$C_1$-$C_3$ alkyl-CN. In certain embodiments, at least one $R^{SN1}$ is —$C_1$-$C_6$ alkyl-OH. In certain embodiments, at least one $R^{SN1}$ is —$C_1$-$C_3$ alkyl-OH. In certain embodiments, at least one $R^{SN1}$ is —$C_1$-$C_6$ alkyl-$SO_2$—$C_1$-$C_3$ alkyl. In certain embodiments, at least one $R^{SN1}$ is —$C_1$-$C_6$ alkyl-$SO_2$—$C_1$-$C_3$ alkyl. In certain embodiments, at least one $R^{SN1}$ is —$C_1$-$C_3$ alkyl-$SO_2$—$C_1$-$C_3$ alkyl. In certain embodiments, at least one $R^{SN1}$ is —$C_1$-$C_3$ alkyl-$SO_2$—$C_1$-$C_3$ alkyl. In certain embodiments, at least one $R^{SN1}$ is selected from the group consisting of:

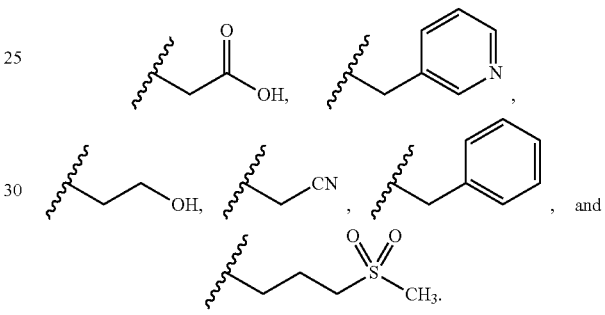

In certain embodiments, at least one $R^{SN1}$ is optionally substituted heteroaryl. In certain embodiments, at least one $R^{SN1}$ is optionally substituted 5- to 6-membered heteroaryl. In certain embodiments, at least one $R^{SN1}$ is optionally substituted 6-membered heteroaryl. In certain embodiments, at least one $R^{SN1}$ is optionally substituted 6-membered heteroaryl comprising 1 or 2 nitrogen atoms. In certain embodiments, at least one $R^{SN1}$ is optionally substituted 6-membered heteroaryl comprising 2 nitrogen atoms. In certain embodiments, at least one $R^{SN1}$ is optionally substituted pyridinyl, optionally substituted pyrazinyl, optionally substituted pyrimidinyl, or optionally substituted pyridazinyl. In certain embodiments, at least one $R^{SN1}$ is optionally substituted pyrazinyl. In certain embodiments, at least one $R^{SN1}$ is unsubstituted pyrazinyl. In certain embodiments, at least one $R^{SN1}$ is of the formula:

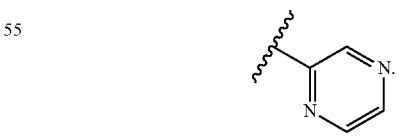

In certain embodiments, two $R^{SN1}$ are joined to form an optionally substituted heterocyclyl or heteroaryl ring. In certain embodiments, two $R^{SN1}$ are joined together to form optionally substituted heteroaryl. In certain embodiments, two $R^{SN1}$ are joined together to form optionally substituted 5-membered heteroaryl. In certain embodiments, two $R^{SN1}$ are joined together to form an optionally substituted pyrrol ring. In certain embodiments, two $R^{SN1}$ are joined together to form an optionally substituted imizazole ring. In certain embodiments, two $R^{SN1}$ are joined together to form an unsubstituted pyrrol ring. In certain embodiments, two $R^{SN1}$ are joined together to form an unsubstituted imizazole ring.

In certain embodiments, two $R^{SN1}$ are joined together to form optionally substituted heterocyclyl. In certain embodiments, two $R^{SN1}$ are joined together to form optionally substituted 3- to 6-membered heterocyclyl. In certain embodiments, two $R^{SN1}$ are joined together to form optionally substituted 5-membered heterocyclyl. In certain embodiments, two $R^{SN1}$ are joined together to form optionally substituted 6-membered heterocyclyl. In certain embodiments, two $R^{SN1}$ are joined together to form an optionally substituted pyrrolidine ring. In certain embodiments, two $R^{SN1}$ are joined together to form an unsubstituted pyrrolidine ring. In certain embodiments, two $R^{SN1}$ are joined together to form a pyrrolidine ring substituted with one instance of —OH. In certain embodiments, two $R^{SN1}$ are joined together to form a 5-membered heterocyclic ring comprising two heteroatoms selected from O and N. In certain embodiments, two $R^{SN1}$ are joined together to form an optionally substituted oxazoline ring. In certain embodiments, two $R^{SN1}$ are joined together to form an oxazoline ring substituted with one instance of —CH$_2$OH. In certain embodiments, two $R^{SN1}$ are joined together to form a 6-membered heterocyclic ring comprising two heteroatoms selected from O and N. In certain embodiments, two $R^{SN1}$ are joined together to form an optionally substituted morpholino ring. In certain embodiments, two $R^{SN1}$ are joined together to form an unsubstituted morpholino ring. In certain embodiments, two $R^{SN1}$ are joined together to form one of the following:

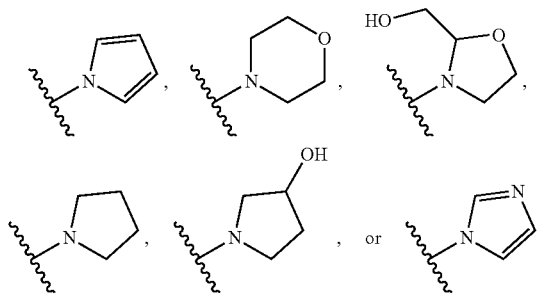

In certain embodiments, two $R^{SN1}$ are joined together to form one of the following:

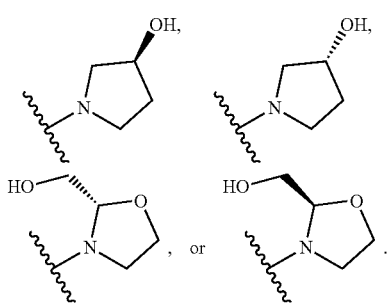

In certain embodiments, at least one of $R^{SN1}$ is a nitrogen protecting group. In certain embodiments, at least one of $R^{SN1}$ is tert-butyloxycarbonyl (Boc). In certain embodiments, at least one of $R^{SN1}$ is benzyl (—CH$_2$-phenyl). In certain embodiments, both $R^{SN1}$ are benzyl.

In certain embodiments, the moiety represented by the formula —N($R^{SN1}$)$_2$ is of one of the following formulae:

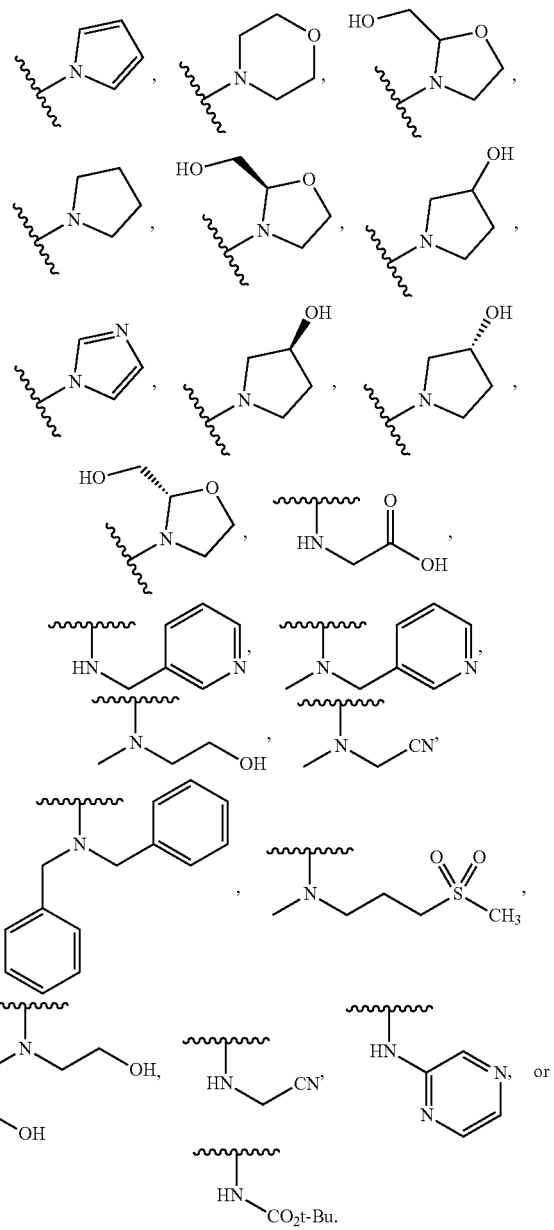

In certain embodiments, the moiety represented by the formula —N($R^{SN1}$)$_2$ is not:

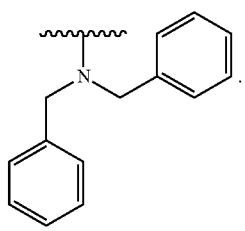 [SMILES: *N(Cc1ccccc1)Cc1ccccc1]

In certain embodiments, the moiety represented by the formula —N(R$^{SN1}$)$_2$ is not:

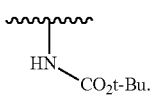

In certain embodiments, the moiety represented by the formula —N(R$^{SN1}$)$_2$ is not:

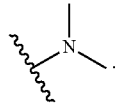 [SMILES: *N(C)C]

In certain embodiments, the moiety represented by the formula —N(R$^{SN1}$)$_2$ is not:

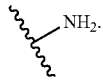

Group R$^{SO}$

As generally defined herein, each R$^{SO}$ may independently be hydrogen, optionally substituted C$_1$-C$_6$ alkyl, a carbohydrate, or an oxygen protecting group. In some embodiments, R$^{SO}$ is hydrogen. In some embodiments, R$^{SO}$ is optionally substituted C$_1$-C$_6$ alkyl. In some embodiments, R$^{SO}$ is C$_1$-C$_6$ alkyl. In some embodiments, R$^{SO}$ is methyl. In some embodiments, R$^{SO}$ is ethyl, propyl, or butyl. In certain embodiments, R$^{SO}$ is an oxygen protecting group. In some embodiments, R$^{SO}$ is alkoxycarbonyl. In some embodiments, R$^{SO}$ is methoxycarbonyl. In some embodiments, R$^{SO}$ is acetyl, benzoyl, benzyl, methoxymethyl ether, p-methoxybenzyl ether, methylthiomethylether, pivaloyl, tetrahydropyranyl, tetrahydrofuranyl, triphenylmethyl, or silyl (e.g., trimethyl silyl, tert-butyldimethylsilyl, triisopropylsilyloxymethyl, triisopropylsilyl). In some embodiments, R$^{SO}$ is a carbohydrate. In some embodiments, R$^{SO}$ is a monosaccharide.

Groups R$^{1a}$ and R$^{1b}$

As generally defined herein, each of R$^{1a}$ and R$^{1b}$ is independently hydrogen, halogen, acyl, optionally substituted alkyl, optionally substituted alkenyl, optionally substituted alkynyl, optionally substituted carbocyclyl, optionally substituted heterocylyl, optionally substituted aryl, optionally substituted heteroaryl. In certain embodiments, the carbon to which R$^{1a}$ and R$^{1b}$ are attached is a stereocenter of the (R)-configuration. In certain embodiments, the carbon to which R$^{1a}$ and R$^{1b}$ are attached is a stereocenter of the (S)-configuration.

In certain embodiments, at least one of R$^{1a}$ and R$^{1b}$ is hydrogen. In certain embodiments, both R$^{1a}$ and R$^{1b}$ are hydrogen. In certain embodiments, at least one of R$^{1a}$ and R$^{1b}$ is halogen; e.g. —F, —Cl, —Br, or I. In certain embodiments, both R$^{1a}$ and R$^{1b}$ are halogen; e.g. —F, —Cl, —Br, or I.

In certain embodiments, at least one of R$^{1a}$ and R$^{1b}$ is acyl. In certain embodiments, at least one of R$^{1a}$ and R$^{1b}$ is a carboxylic acid. In certain embodiments, at least one of R$^{1a}$ and R$^{1b}$ is a ketone. In certain embodiments, at least one of R$^{1a}$ and R$^{1b}$ is an aldehyde (—CHO).

In certain embodiments, at least one instance of R$^{1a}$ and R$^{1b}$ is optionally substituted alkyl, e.g., optionally substituted C$_1$-C$_6$alkyl optionally substituted C$_1$-C$_2$alkyl, optionally substituted C$_{2-3}$alkyl, optionally substituted C$_{3-4}$alkyl, optionally substituted C$_{4-5}$ alkyl, or optionally substituted C$_{5-6}$alkyl. In certain embodiments, at least one instance of R$^{1a}$ and R$^{1b}$ is —CH$_3$. In certain embodiments, both instances of R$^{1a}$ and R$^{1b}$ are —CH$_3$. In certain embodiments, at least one instance of R$^{1a}$ and R$^{1b}$ is alkyl substituted with one or more halogen atoms, e.g., optionally substituted haloalkyl; e.g., —CF$_3$, —CF$_2$CF$_3$, or —CF$_2$H. In certain embodiments, at least one of R$^{1a}$ and R$^{1b}$ is —CH$_2$CHO.

In certain embodiments, at least one instance of R$^{1a}$ and R$^{1b}$ is optionally substituted alkenyl, e.g., optionally substituted C$_{2-6}$alkenyl, optionally substituted C$_{2-3}$alkenyl, optionally substituted C$_{3-4}$alkenyl, optionally substituted C$_{4-5}$alkenyl, or optionally substituted C$_{5-6}$alkenyl. In certain embodiments, at least one instance of R$^{1a}$ and R$^{1b}$ is vinyl, allyl, or prenyl.

In certain embodiments, at least one instance of R$^{1a}$ and R$^{1b}$ is optionally substituted carbocyclyl, e.g., optionally substituted C$_{3-6}$carbocyclyl, optionally substituted C$_{3-4}$ carbocyclyl, optionally substituted C$_{4-5}$ carbocyclyl, or optionally substituted C$_{5-6}$ carbocyclyl. In certain embodiments, at least one instance of R$^{1a}$ and R$^{1b}$ is optionally substituted heterocylyl, e.g., optionally substituted 3-6 membered heterocyclyl. In certain embodiments, at least one instance of R$^{1a}$ and R$^{1b}$ is optionally substituted aryl, e.g., optionally substituted phenyl. In certain embodiments, at least one instance of R$^{1a}$ and R$^{1b}$ is optionally substituted heteroaryl, e.g., optionally substituted 5- to 6-membered heteroaryl.

In certain embodiments, at least one of R$^{1a}$ and R$^{1b}$ is:

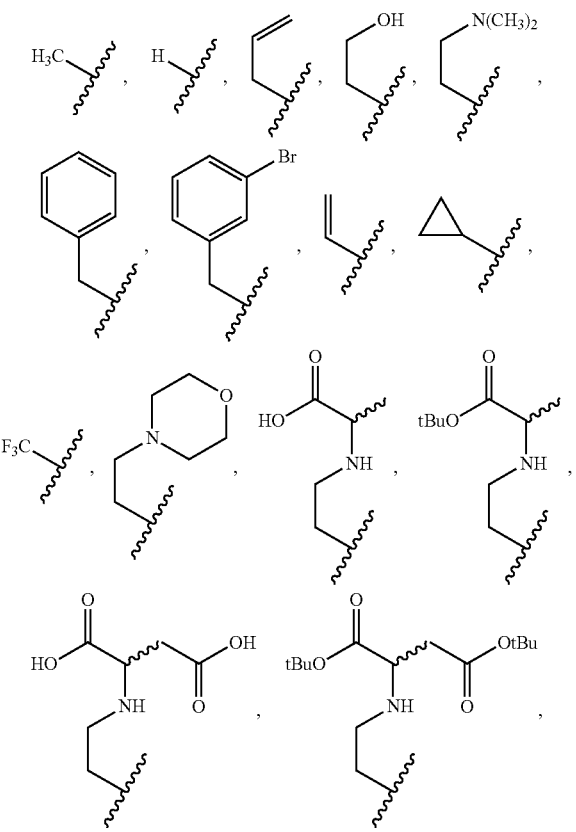

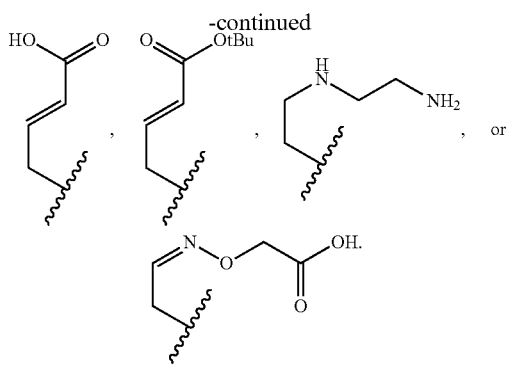

Groups $R^{2a}$ and $R^{2b}$

As generally defined herein, each of $R^{2a}$ and $R^{2b}$ is independently hydrogen, halogen, optionally substituted alkyl, or optionally substituted alkenyl. In certain embodiments, the carbon to which $R^{2a}$ and $R^{2b}$ are attached is a stereocenter of the (R)-configuration. In certain embodiments, the carbon to which $R^{2a}$ and $R^{2b}$ are attached is a stereocenter of the (S)-configuration.

In certain embodiments, at least one instance of $R^{2a}$ and $R^{2b}$ is hydrogen. In certain embodiments, both $R^{2a}$ and $R^{2b}$ are hydrogen. In certain embodiments, at least one of $R^{2a}$ and $R^{2b}$ is halogen; e.g. —F, —Cl, —Br, or I. In certain embodiments, both $R^{2a}$ and $R^{2b}$ are halogen; e.g. —F, —Cl, —Br, or I.

In certain embodiments, at least one instance of $R^{2a}$ and $R^{2b}$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$ alkyl, or optionally substituted $C_{5-6}$alkyl. In certain embodiments, at least one instance of $R^{2a}$ and $R^{2b}$ is —CH$_3$. In certain embodiments, both instances of $R^{2a}$ and $R^{2b}$ are —CH$_3$. In certain embodiments, at least one instance of $R^{2a}$ and $R^{2b}$ is alkyl optionally substituted with one or more halogen atoms, e.g., optionally substituted haloalkyl; e.g., —CF$_3$, —CF$_2$CF$_3$, or —CF$_2$H. In certain embodiments, at least one of $R^{2a}$ and $R^{2b}$ is —CH$_2$CHO.

Groups $R^3$ and $R^4$

As generally defined herein, each of $R^3$ and $R^4$ hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or —OR$^{3a}$. In certain embodiments, the carbon to which $R^3$ and $R^4$ are attached is a stereocenter of the (R)-configuration. In certain embodiments, the carbon to which $R^3$ and $R^4$ are attached is a stereocenter of the (S)-configuration.

In certain embodiments, at least one of $R^3$ and $R^4$ is hydrogen. In certain embodiments, both $R^3$ and $R^4$ are hydrogen. In certain embodiments, at least one of $R^3$ and $R^4$ is halogen; e.g., —F, —Cl, —Br, or I. In certain embodiments, both $R^3$ and $R^4$ are halogen; e.g. —F, —Cl, —Br, or I.

In certain embodiments, at least one instance of $R^3$ and $R^4$ is optionally substituted alkyl, e.g., optionally substituted $C_{1-6}$alkyl. In certain embodiments, at least one instance of $R^3$ and $R^4$ is —CH$_3$. In certain embodiments, both instances of $R^3$ and $R^4$ are —CH$_3$.

In certain embodiments, at least one instance of $R^3$ and $R^4$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$ alkenyl. In certain embodiments, at least one instance of $R^3$ and $R^4$ is vinyl, allyl, or prenyl.

In certain embodiments, at least one instance of $R^3$ and $R^4$ is —OR$^{3a}$. In certain embodiments, at least one instance of $R^3$ and $R^4$ is —OH. In certain embodiments, at least one instance of $R^3$ and $R^4$ is —OMe. In certain embodiments, $R^3$ is methyl, and $R^4$ is —OMe. In certain embodiments, at $R^3$ is —OMe, and $R^4$ is methyl. In certain embodiments, at least one instance of $R^3$ and $R^4$ is —OR$^{3a}$. Each instance of $R^{3a}$ is independently hydrogen, optionally substituted alkyl, optionally substituted alkenyl, optionally substituted alkynyl, an oxygen protecting group, or of formula:

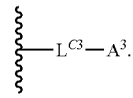   (L$^{C3}$-ii)

In certain embodiments, $R^{3a}$ is hydrogen. In certain embodiments, $R^{3a}$ is optionally substituted alkyl, e.g., optionally substituted $C_{1-6}$alkyl. In certain embodiments, $R^{3a}$ is —CH$_3$. In certain embodiments, $R^{3a}$ is optionally substituted alkenyl, e.g., optionally substituted $C_{2-6}$alkenyl. In certain embodiments, $R^{3a}$ is vinyl, allyl, or prenyl. In certain embodiments, $R^{3a}$ is an oxygen protecting group.

In certain embodiments, $R^{3a}$ is of formula:

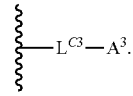   (L$^{C3}$-ii)

Each L$^{C3}$ is independently a bond, or is a linking group selected from optionally substituted alkylene, optionally substituted alkenylene, optionally substituted alkynylene; optionally substituted heteroalkylene, optionally substituted heteroalkenylene, and optionally substituted heteroalkynylene, or combinations thereof. In certain embodiments, L$^{C3}$ is a bond.

In certain embodiments, L$^{C3}$ is optionally substituted alkylene, e.g., substituted or unsubstituted $C_{1-6}$alkylene. In certain embodiments, L$^{C3}$ is of the formula —(CH$_2$)$_n$—, wherein n is 1, 2, 3, 4, 5, 6, 7, 8, 9, or 10. In certain embodiments, L$^{C3}$ is substituted or unsubstituted alkenylene, e.g., substituted or unsubstituted $C_{2-6}$alkenylene. In certain embodiments, L$^{C3}$ is substituted or unsubstituted alkynylene, e.g., substituted or unsubstituted $C_{2-6}$alkynylene.

Each A$^3$ is independently optionally substituted carbocyclyl, optionally substituted heterocyclyl, optionally substituted aryl, or optionally substituted heteroaryl. In certain embodiments, A$^3$ is optionally substituted carbocyclyl, e.g., optionally substituted $C_{3-6}$carbocyclyl. In certain embodiments, A$^3$ is optionally substituted heterocyclyl, e.g., optionally substituted 3-6 membered heterocyclyl. In certain embodiments, A$^3$ is optionally substituted aryl, e.g., optionally substituted monocyclic aryl, optionally substituted 5,6-fused bicyclic aryl, or optionally substituted 6,6-fused aryl. In certain embodiments, A$^3$ is optionally substituted heteroaryl, e.g., e.g., optionally substituted 5-6 membered heteroaryl, optionally substituted 5,6 fused-bicyclic heteroaryl, or optionally substituted 6,6 fused-bicyclic heteroaryl.
In certain embodiments, $A^3$ is selected from any one of the following aryl or heteroaryl ring systems:
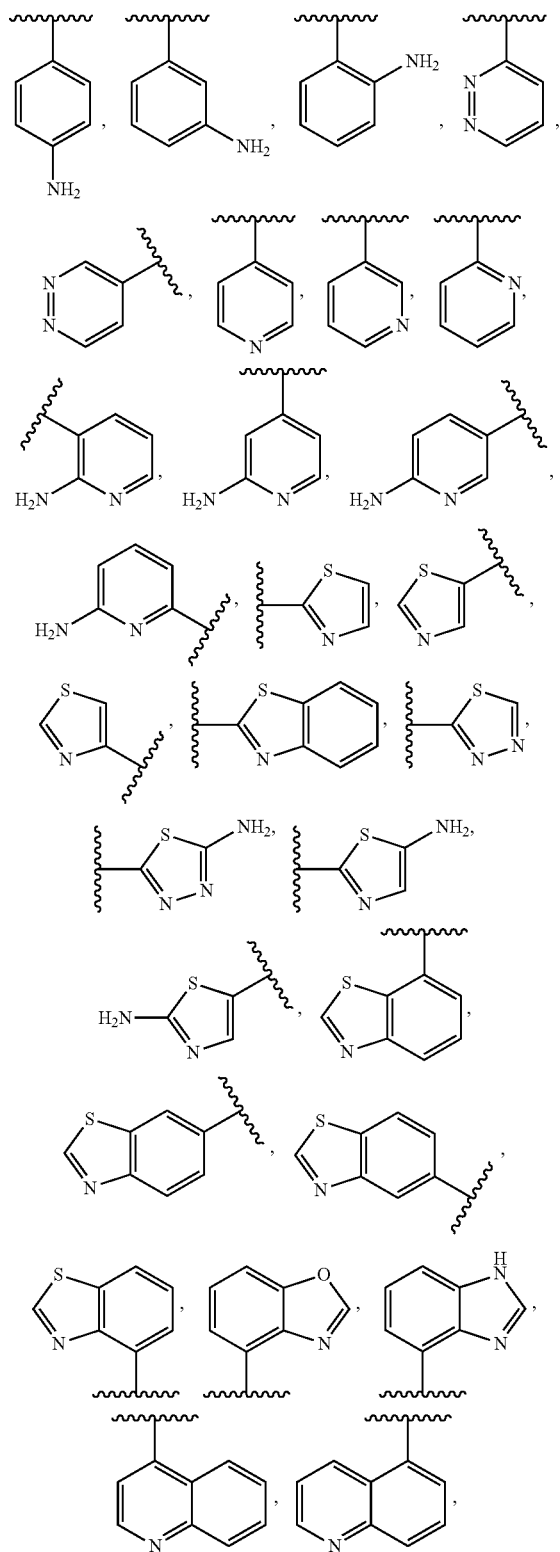
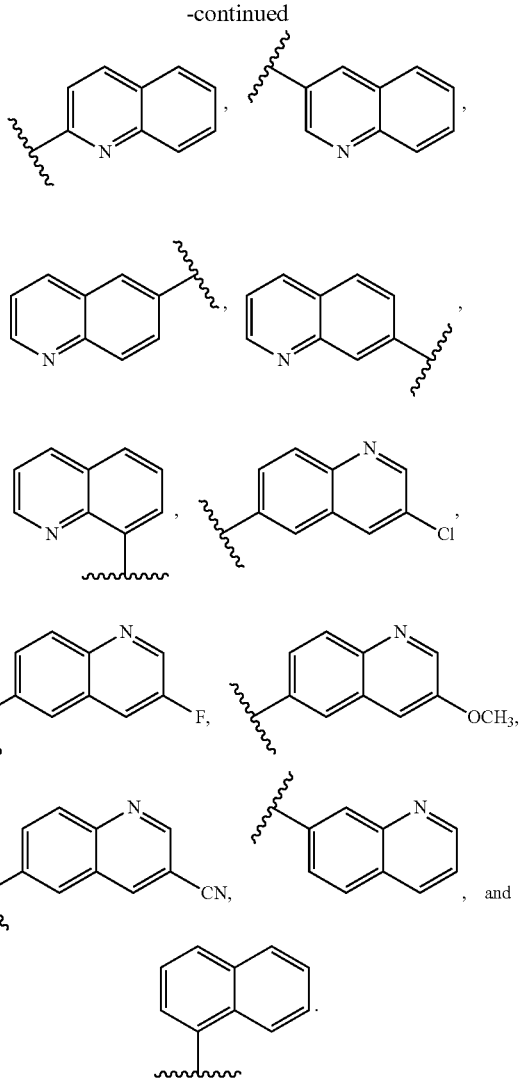
In certain embodiments, $R^3$ is —$OR^{3a}$, wherein —$O^{R3a}$ is:
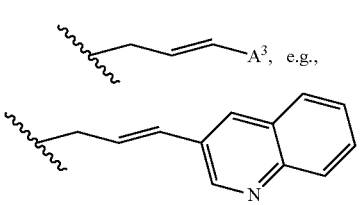
In certain embodiments, $R^4$ is —$OR^{3a}$, wherein —$O^{R3a}$, is:
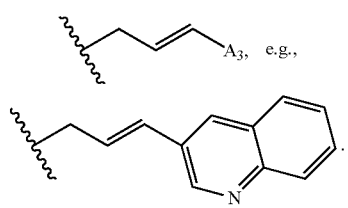

In certain embodiments, at least one of $R^3$ and $R^4$ is:

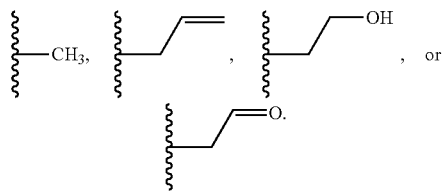

Groups $R^{5a}$ and $R^{5b}$

As generally defined herein, each instance of $R^{5a}$ and $R^{5b}$ is independently hydrogen, halogen, optionally substituted alkyl, optionally substituted carbocyclyl, or optionally substituted heterocyclyl. In certain embodiments, one instance of $R^{5a}$ and $R^{5b}$ is hydrogen, and the other of $R^{5a}$ and $R^{5b}$ is a non-hydrogen group. In certain embodiments, each instance of $R^{5a}$ and $R^{5b}$ is hydrogen. In certain embodiments, each instance of $R^{5a}$ and $R^{5b}$ is a non-hydrogen group. In certain embodiments, the carbon to which $R^{5a}$ and $R^{5b}$ is attached are a stereocenter of the (R)-configuration. In certain embodiments, the carbon to which $R^{5a}$ and $R^{5b}$ are attached is a stereocenter of the (S)-configuration.

In certain embodiments, at least one instance of $R^{5a}$ and $R^{5b}$ is optionally substituted alkyl, e.g., optionally substituted $C_{1-6}$alkyl, optionally substituted $C_{1-2}$alkyl, optionally substituted $C_{2-3}$alkyl optionally substituted $C_{3-4}$alkyl, optionally substituted $C_{4-5}$ alkyl, or optionally substituted $C_{5-6}$alkyl. In certain embodiments, at least one instance of $R^{5a}$ and $R^{5b}$ is —$CH_3$. In certain embodiments, both instances of $R^{5a}$ and $R^{5b}$ are —$CH_3$.

Groups $R^6$ and $R^{10}$

As generally defined herein, $R^6$ and/or $R^{10}$ is hydrogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, optionally substituted heteroaralkyl. In certain embodiments, $R^6$ is hydrogen. In certain embodiments, $R^{10}$ is hydrogen. In certain embodiments, $R^6$ is hydrogen and $R^{10}$ is hydrogen. In certain embodiments, both of $R^6$ and $R^{10}$ are non-hydrogen groups. In certain embodiments, the carbon to which $R^6$ and $R^{10}$ are attached is a stereocenter of the (R)-configuration. In certain embodiments, the carbon to which $R^6$ and $R^{10}$ are attached is a stereocenter of the (S)-configuration.

In certain embodiments, at least one instance of $R^6$ and $R^0$ is optionally substituted alkyl; e.g., optionally substituted $C_{1-6}$alkyl. In certain embodiments, at least one instance of $R^6$ and $R^{10}$ is —$CH_3$. In certain embodiments, at least one instance of $R^6$ and $R^{10}$ is —$CH_2CN$. In certain embodiments, at least one instance of $R^6$ and $R^{10}$ is —$CH_2C(=O)OR^{32}$, wherein $R^{32}$ is hydrogen, optionally substituted alkyl, optionally substituted alkenyl, optionally substituted alkynyl, optionally substituted carbocycyl, optionally substituted heterocyclyl, optionally substituted aryl, optionally substituted heteroaryl.

In certain embodiments, at least one instance of $R^6$ and $R^{10}$ is optionally substituted alkenyl, e.g., optionally substituted $C_{2-6}$alkenyl. In certain embodiments, at least one instance of $R^6$ and $R^{10}$ is optionally substituted alkynyl, e.g., optionally substituted $C_{2-6}$alkynyl.

In certain embodiments, at least one instance of $R^6$ and $R^{10}$ is optionally substituted carbocyclyl, e.g., optionally substituted $C_{3-6}$carbocyclyl. In certain embodiments, at least one instance of $R^6$ and $R^{10}$ is optionally substituted heterocyclyl, e.g., optionally substituted 3-6 membered heterocyclyl. In certain embodiments, at least one instance of $R^6$ and $R^{10}$ is optionally substituted aryl; e.g., optionally substituted phenyl. In certain embodiments, at least one instance of $R^6$ and $R^{10}$ is optionally substituted aralkyl, e.g., optionally substituted benzyl. In certain embodiments, at least one instance of $R^6$ and $R^{10}$ is optionally substituted heteroaryl, e.g., optionally substituted 5- to 6-membered heteroaryl. In certain embodiments, at least one instance of $R^6$ and $R^{10}$ is optionally substituted heteroaralkyl; e.g., optionally substituted pyrazolylalkyl, imidazolylalkyl, thiazolylalkyl, oxazolylalkyl, pyridinylalkyl, pyrimidinylalkyl, or pyrazinylalkyl.

In certain embodiments, at least one instance of $R^6$ and $R^{10}$ is halogen, e.g., fluoro, bromo, chloro, or iodo. In some embodiments, $R^6$ is fluoro. In some embodiments, $R^{10}$ is fluoro. In certain embodiments, $R^6$ is fluoro, and $R^{10}$ is methyl. In certain embodiments, $R^6$ is methyl, and $R^{10}$ is fluoro.

In certain embodiments, $R^6$ is:

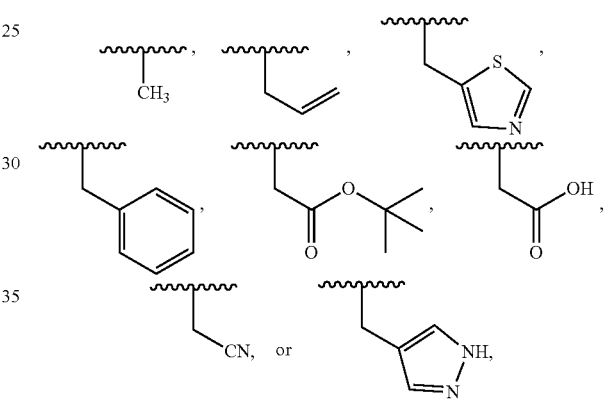

and $R^{10}$ is hydrogen or fluoro.

Group $R^7$

As generally defined herein, $R^7$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl. In certain embodiments, $R^7$ is hydrogen. However, in certain embodiments, $R^7$ is a non-hydrogen group, and the carbon to which $R^7$ is attached is a stereocenter of the (R)-configuration. In certain embodiments, $R^7$ is a non-hydrogen group, and the carbon to which $R^7$ is attached is a stereocenter of the (S)-configuration.

In certain embodiments, $R^7$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$alkyl, or optionally substituted $C_{5-6}$alkyl. In certain embodiments, $R^7$ is —$CH_3$ or —$CH_2CH_3$.

Group $R^8$

As generally defined herein, $R^8$ is hydrogen, halogen, or optionally substituted $C_1$-$C_6$ alkyl. In certain embodiments, $R^8$ is hydrogen. In certain embodiments, $R^8$ is optionally substituted alkyl, e.g., optionally substituted $C_{1-6}$alkyl, optionally substituted $C_{1-2}$alkyl, optionally substituted $C_{2-3}$alkyl, optionally substituted $C_{3-4}$alkyl, optionally substituted $C_{4-5}$ alkyl, or optionally substituted $C_{5-6}$alkyl. In certain embodiments, $R^8$ is —$CH_3$ or —$CH_2CH_3$. In certain embodiments, $R^8$ is halogen, e.g., fluoro, bromo, chloro, or iodo.

Group $R^{14}$

As defined generally herein, $R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or of formula:

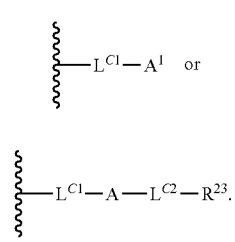

Groups of formula ($L^{C1}$-ii) are, in certain embodiments, a precursor to groups of ($L^{C1}$-iii). Transformations of group 14 have been described in detail in PCT publication WO2014/165792, which is incorporated herein in its entirety by reference. The present invention includes all possible embodiments of $R^{14}$, $L^{C1}$, $L^{C2}$, A, $A^1$, and $R^{23}$ described in WO2014/165792.

In certain embodiments, $R^{14}$ is hydrogen. In certain embodiments, $R^{14}$ is optionally substituted alkyl, e.g., optionally substituted $C_{1-6}$alkyl optionally substituted $C_{1-2}$alkyl, optionally substituted $C_{2-3}$alkyl, optionally substituted $C_{3-4}$alkyl, optionally substituted $C_{4-5}$ alkyl, or optionally substituted $C_{5-6}$alkyl. In certain embodiments, $R^{14}$ is —$CH_3$ or —$CH_2CH_3$.

In certain embodiments, $R^{14}$ is optionally substituted alkenyl, e.g., optionally substituted $C_{2-6}$alkenyl, optionally substituted $C_{2-3}$alkenyl, optionally substituted $C_{3-4}$alkenyl, optionally substituted $C_{4-5}$alkenyl, or optionally substituted $C_{5-6}$alkenyl. In certain embodiments, $R^{14}$ is vinyl, allyl, or prenyl. In certain embodiments, $R^{14}$ is optionally substituted alkynyl, e.g., optionally substituted $C_{2-6}$alkynyl, optionally substituted $C_{2-3}$alkynyl, optionally substituted $C_{3-4}$alkynyl, optionally substituted $C_{4-5}$alkynyl, or optionally substituted $C_{5-6}$alkynyl.

In certain embodiments, $R^{14}$ is optionally substituted carbocyclyl, e.g., optionally substituted $C_{3-6}$carbocyclyl, optionally substituted $C_{3-4}$carbocyclyl, optionally substituted $C_{4-5}$ carbocyclyl, or optionally substituted $C_{5-6}$ carbocyclyl. In certain embodiments, $R^{14}$ is optionally substituted heterocyclyl, e.g., optionally substituted 3-6 membered heterocyclyl. In certain embodiments, $R^{14}$ is optionally substituted aryl; e.g., optionally substituted phenyl. In certain embodiments, $R^{14}$ is optionally substituted heteroaryl, e.g., optionally substituted 5- to 6-membered heteroaryl.

Group A

In certain embodiments, A is optionally substituted heteroaryl, e.g., 5- to 6-membered optionally substituted heteroaryl. In certain embodiments, wherein A is 5-membered heteroaryl, $R^{14}$ is of the formula ($L^{C1}$-viii):

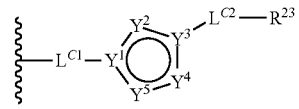

wherein each instance of $Y^1$, $Y^2$, $Y^3$, $Y^4$, and $Y^5$ is independently $CR^Y$, O, S, N, or $NR^Y$, wherein $R^Y$ is hydrogen or optionally substituted alkyl. In certain embodiments, wherein A is 5-membered heteroaryl, $R^{14}$ is of formula:

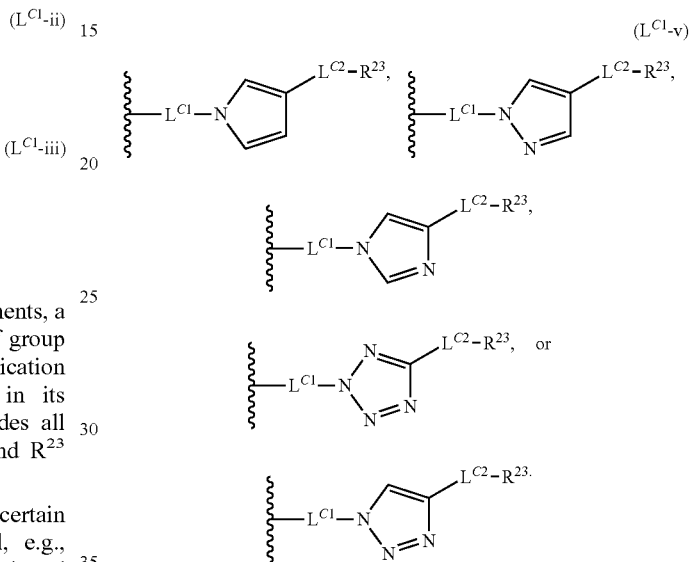

Groups $L^{C1}$ and $L^{C2}$

As generally defined herein, each instance of $L^{C1}$ and $L^{C2}$ is independently a bond, or a linking group selected from the group consisting of optionally substituted alkylene, optionally substituted alkenylene, optionally substituted alkynylene; optionally substituted heteroalkylene, optionally substituted heteroalkenylene, optionally substituted heteroalkynylene, and combinations thereof.

In certain embodiments, $L^{C1}$ is a bond. It is generally understood that if $L^{C1}$ is a bond, then the group -LG, -$A^1$, or -A-$L^{C2}$-$R^{23}$, as described herein, is directly attached to the parent moiety, e.g., the macrolide or intermediate compounds. Furthermore, in certain embodiments, $L^{C2}$ is a bond. It is generally understood that if $L^{C2}$ is a bond, then the group $R^{23}$ is directly attached to A, as described herein.

In certain embodiments, $L^{C1}$ and $L^{C2}$ are each optionally and independently linking groups comprising at least one instance of optionally substituted alkylene, e.g., substituted or unsubstituted $C_{1-6}$alkylene. In certain embodiments, $L^{C1}$ and $L^{C2}$ are each optionally and independently an alkylene linking group of the formula —$(CH_2)_n$—, wherein n is 1, 2, 3, 4, 5, 6, 7, 8, 9, or 10. In certain embodiments, $L^{C1}$ and $L^{C2}$ are each optionally and independently linking groups comprising at least one instance of substituted or unsubstituted alkenylene, e.g., substituted or unsubstituted $C_{2-6}$alkenylene. In certain embodiments, $L^{C1}$ and $L^{C2}$ are each optionally and independently linking groups comprising at least one instance of substituted or unsubstituted alkynylene, e.g., substituted or unsubstituted $C_{2-6}$alkynylene.

In certain embodiments, $L^{C1}$ is:

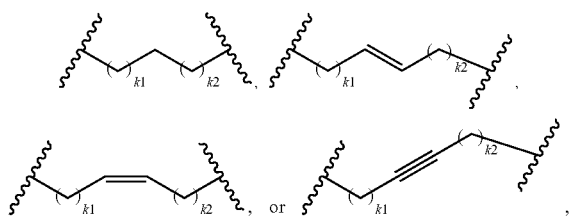

wherein each of k1 and k2 are independently 0, 1, 2, 3, or 4.

In certain embodiments, $L^{C1}$ is:

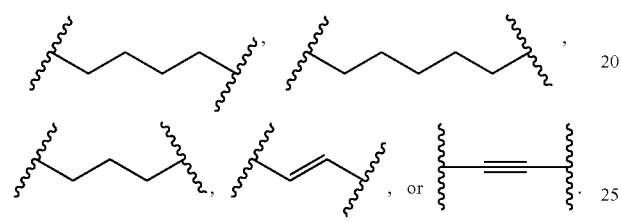

Group $R^{23}$

As generally defined herein, each $R^{23}$ is independently optionally substituted carbocyclyl, optionally substituted heterocyclyl, optionally substituted aryl, or optionally substituted heteroaryl. In certain embodiments, $R^{23}$ is optionally substituted carbocyclyl, e.g., optionally substituted $C_{3-6}$carbocyclyl. In certain embodiments, $R^{23}$ is optionally substituted heterocyclyl, e.g., optionally substituted 3-6 membered heterocyclyl. In certain embodiments, $R^{23}$ is optionally substituted aryl, e.g., optionally substituted monocyclic aryl, optionally substituted 5,6-fused bicyclic aryl, or optionally substituted 6,6-fused aryl. In certain embodiments, $R^{23}$ is optionally substituted phenyl. In certain embodiments, $R^{23}$ is optionally substituted napthyl. In certain embodiments, $R^{23}$ is optionally substituted heteroaryl, e.g., optionally substituted monocyclic heteoaryl or optionally substituted bicyclic heteroaryl, e.g., optionally substituted 5-6 membered heteroaryl, optionally substituted 5,6 fused-bicyclic heteroaryl, or optionally substituted 6,6 fused-bicyclic heteroaryl. In certain embodiments, $R^{23}$ is amino substituted aryl, e.g., aminophenyl, or amino substituted heteroaryl, e.g., aminothiazole, or aminodithiazole.

In certain embodiments, $R^{23}$ is selected from any one of the following aryl or heteroaryl ring systems:

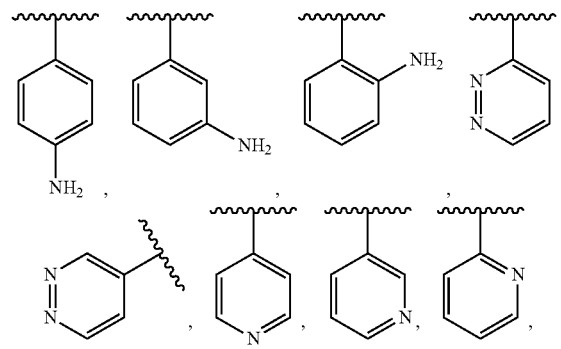

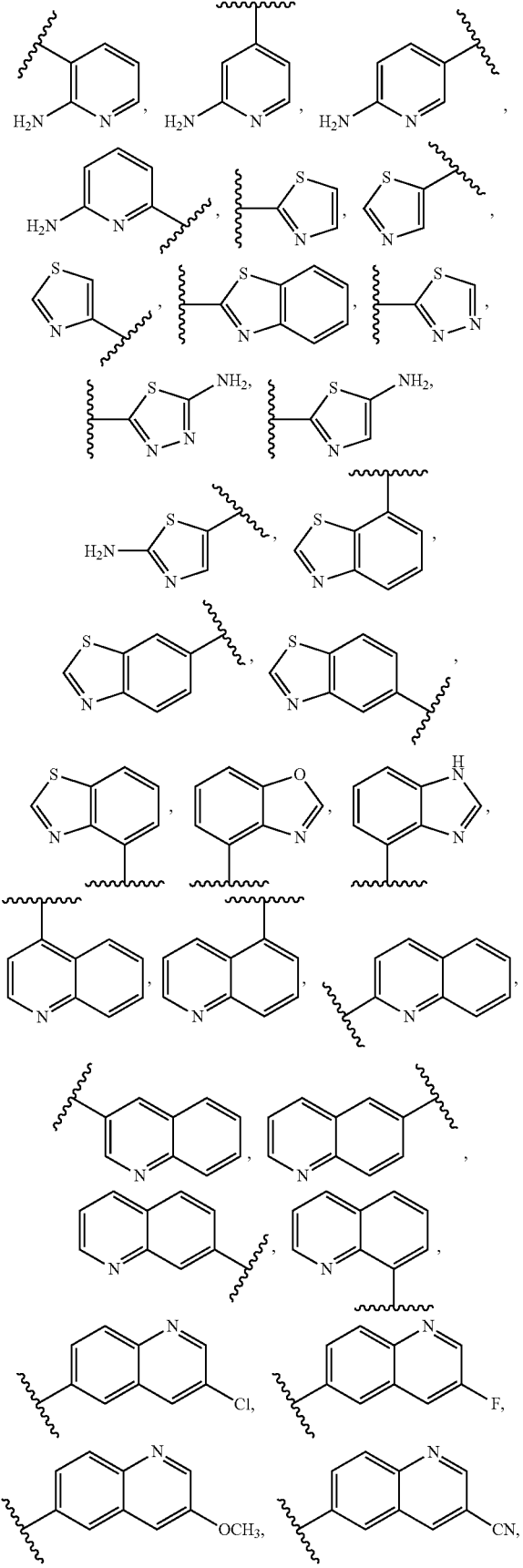

-continued
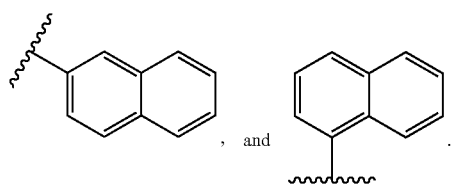, and
In certain embodiments, $R^{23}$ is:
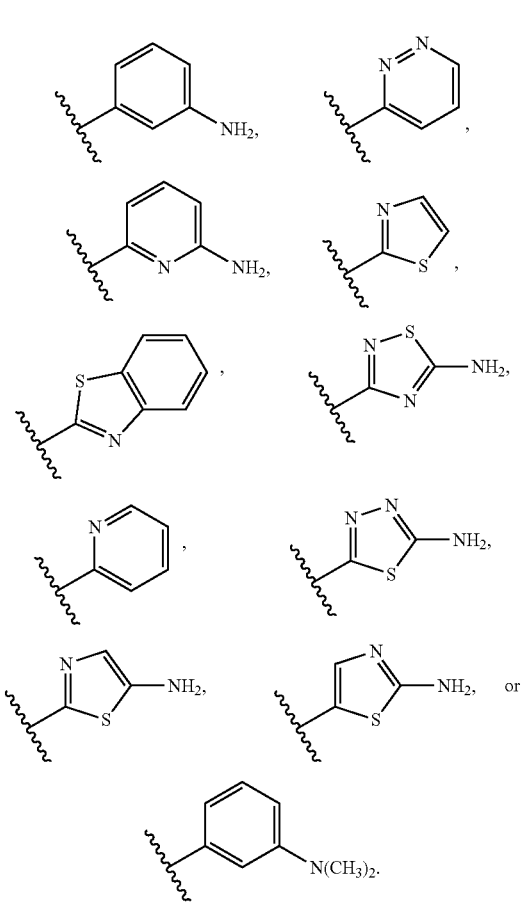
In certain embodiments, $R^{14}$ is of formula ($L^{C1}$-v):
$$(L^{C1}\text{-v})$$
wherein:
 $L^{C1}$ is:
-continued
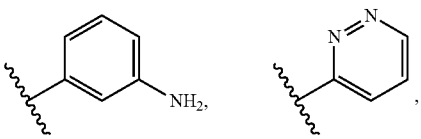, , or ;
$L^{C2}$ is a bond; and
$R^{23}$ is:
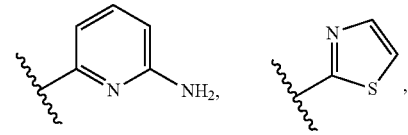
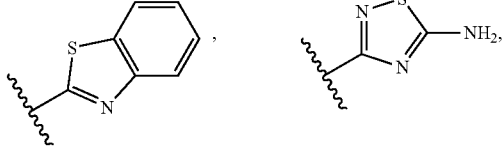
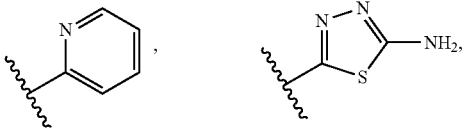
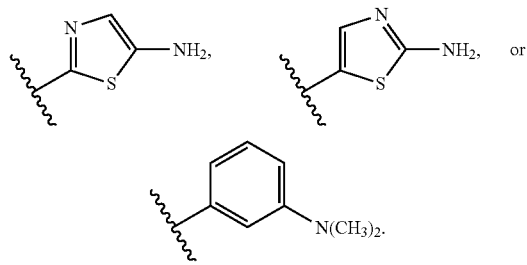
In certain embodiments, $R^{14}$ is of formula ($L^{C1}$-ii):
$$(L^{C1}\text{-ii})$$
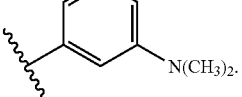
wherein $A^1$ is —$N_3$ and $L^{C1}$ is of formula:
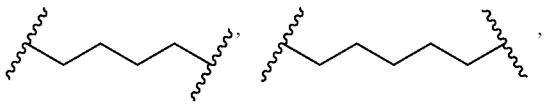
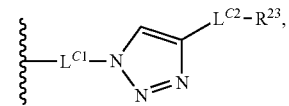
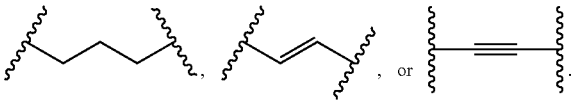
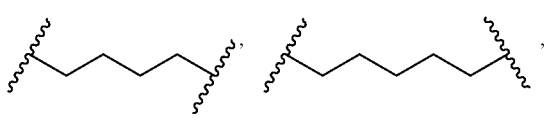

Exemplary Macrolides and Sugars

Compounds of Formula (I) comprise a macrolide unit and a sugar unit. The macrolide unit may be described as fragment (A), and the sugar unit as fragment (B), as depicted below. The point of attachment between unit (A) and unit (B) is indicated with "B" in unit (A), and "A" in unit (B), i.e., the sugar unit is attached to the C5 position of the macrolide by a single carbon-oxygen bond.

Compounds of Formula (I-N) also comprise a macrolide unit and a sugar unit; the macrolide unit may be described as fragment (A), and the sugar unit as fragment (B-N), as depicted below. The point of attachment between unit (A) and unit (B-N) is indicated with "B" in unit (A), and "A" in unit (B-N), i.e., the sugar unit is attached to the C5 position of the macrolide by a single carbon-oxygen bond.

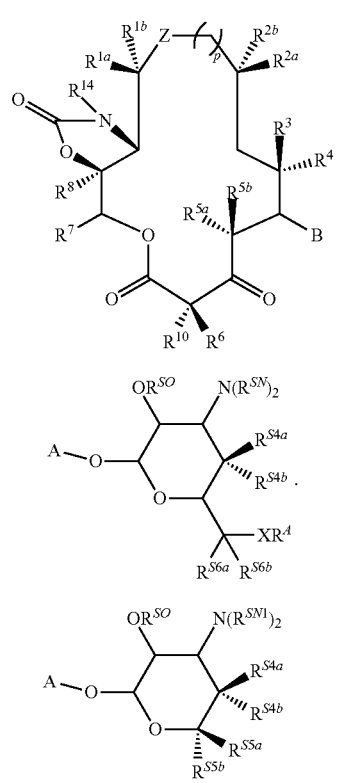

In certain embodiments, the sugar unit (B) is of formula:

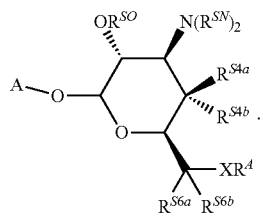

In certain embodiments, the sugar unit (B) is of formula:

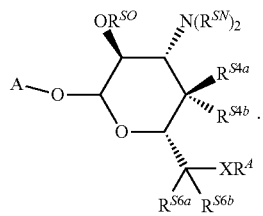

In certain embodiments, the sugar unit (B) is of formula:

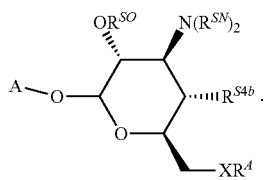

In certain embodiments, the sugar unit (B) is of formula:

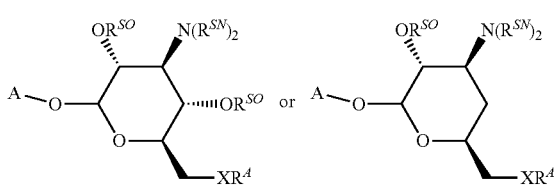

In certain embodiments, the sugar unit (B) is of formula:

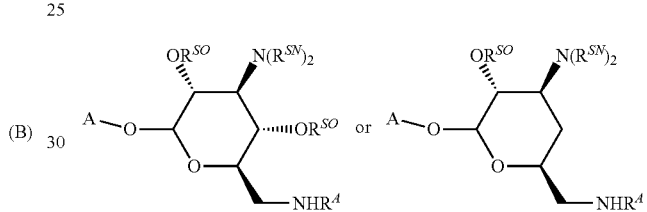

In certain embodiments, the sugar unit (B) is of formula:

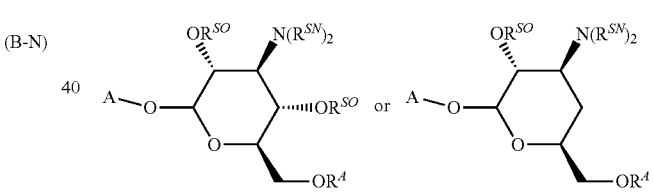

In certain embodiments, the sugar unit (B) is of formula:

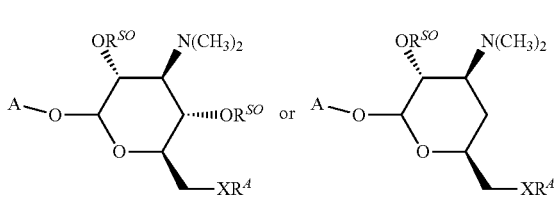

In certain embodiments, the sugar unit (B) is of formula:

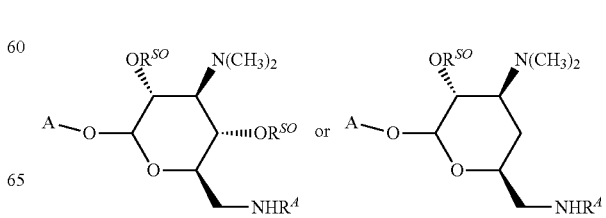

In certain embodiments, the sugar unit (B) is of formula:

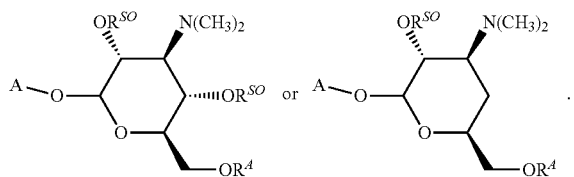

In certain embodiments, the sugar unit (B) is of formula:

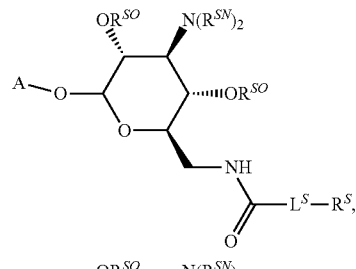

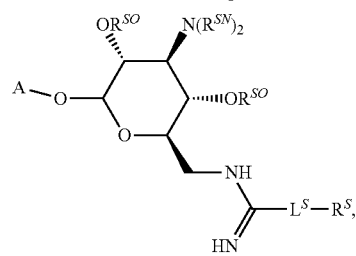

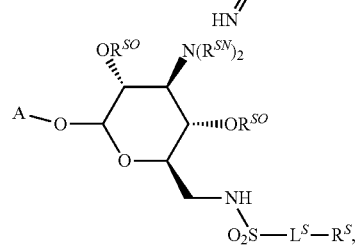

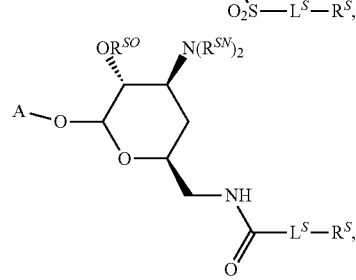

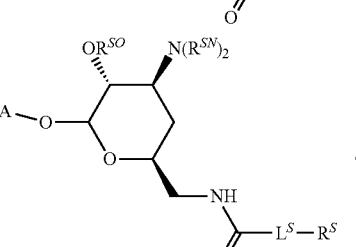

or

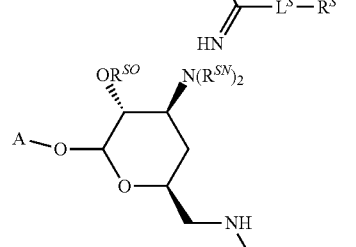

In certain embodiments, the sugar unit (B) is of formula:

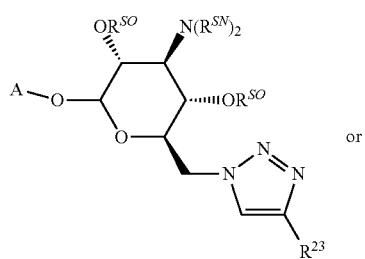

or

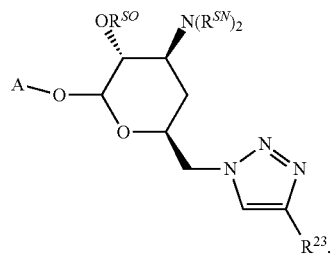

In certain embodiments, the sugar unit (B-N) is of formula:

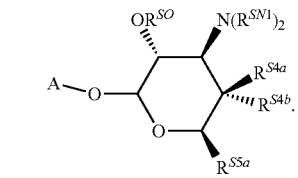

In certain embodiments, the sugar unit (B-N) is of formula:

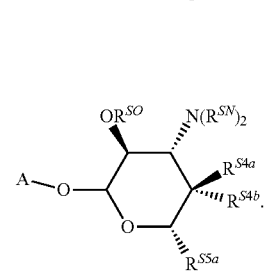

In certain embodiments, the sugar unit (B-N) is of formula:

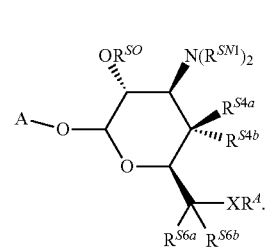

In certain embodiments, the sugar unit (B-N) is of formula:

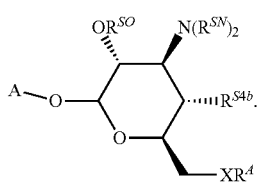

In certain embodiments, the sugar unit (B-N) is of formula:

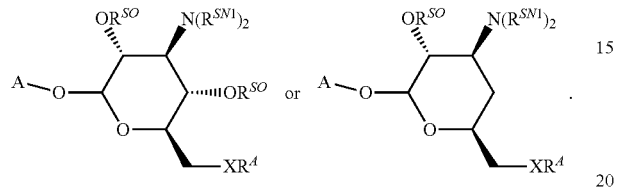

In certain embodiments, the sugar unit (B-N) is of formula:

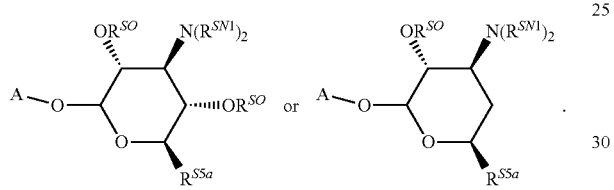

In certain embodiments, the sugar unit (B-N) is of formula:

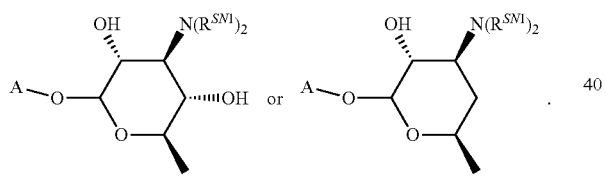

Exemplary fragment units for macrolide unit (A) and sugar unit (B) are depicted in Tables 1A and 1B, respectively. Exemplary fragment units for macrolide unit (B-N) are depicted in Table 1B-N. In certain embodiments, the compound of Formula (I) comprises a macrolide unit (A) selected from Table 1A. In certain embodiments, the compound of Formula (I) comprises a sugar unit (B) selected from Table 1B. In certain embodiments, the compound of Formula (I) comprises a macrolide unit selected from Table 1A, and sugar unit selected from Table 1B. In certain embodiments, the compound of Formula (I-N) comprises a macrolide unit (A) selected from Table 1A. In certain embodiments, the compound of Formula (I-N) comprises a sugar unit (B-N) selected from Table 1B-N. In certain embodiments, the compound of Formula (I-N) comprises a macrolide unit selected from Table 1A, and sugar unit selected from Table 1B-N. The invention contemplates all possible combinations of macrolide and sugar units listed in Tables 1A and 1B, but neither the macrolide unit nor sugar unit is in any way limited to those listed in Tables 1A and 1B. The invention also contemplates all possible combinations of macrolide and sugar units listed in Tables 1A and 1B-N, but neither the macrolide unit nor sugar unit is in any way limited to those listed in Tables 1A and 1B-N. In certain embodiments, the macrolide is a compound listed in Table E1. In other specific embodiments, the macrolide is a compound listed in Table E1-N.

TABLE 1A

Examples of macrolide unit (A).

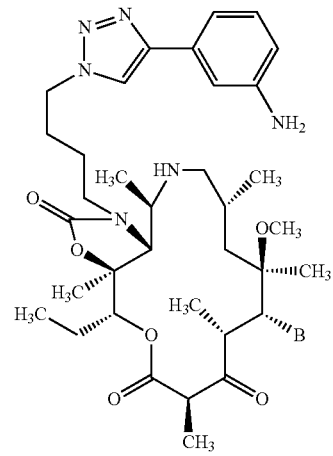

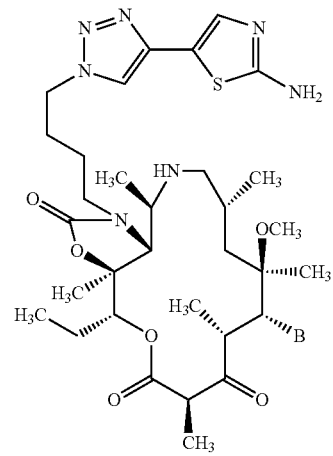

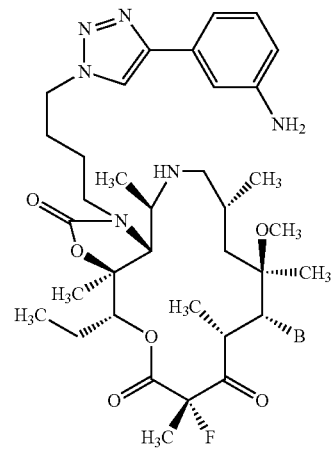

TABLE 1A-continued
Examples of macrolide unit (A).

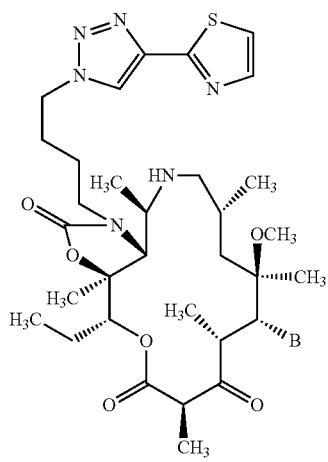
TABLE 1A-continued
Examples of macrolide unit (A).
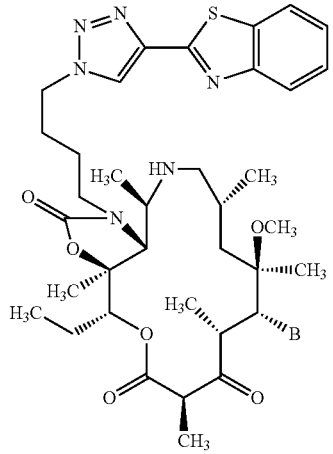
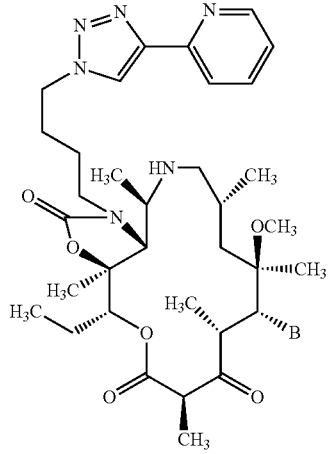
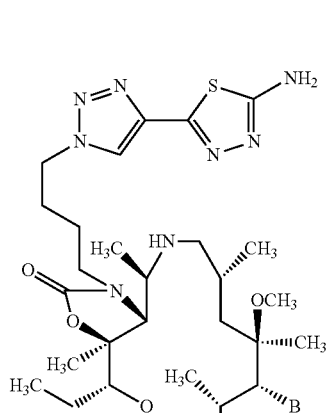

TABLE 1A-continued
Examples of macrolide unit (A).
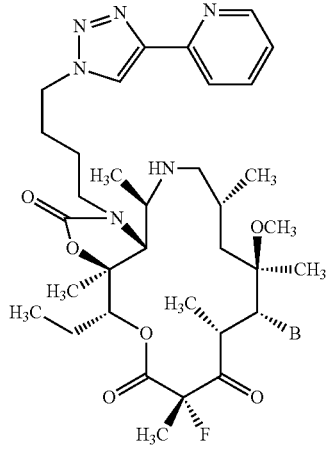
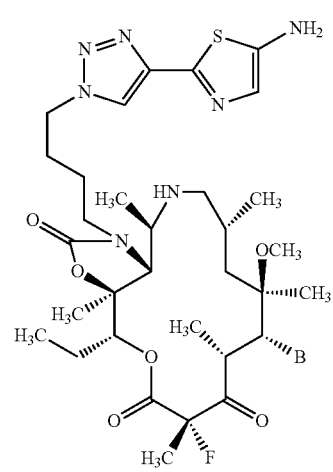
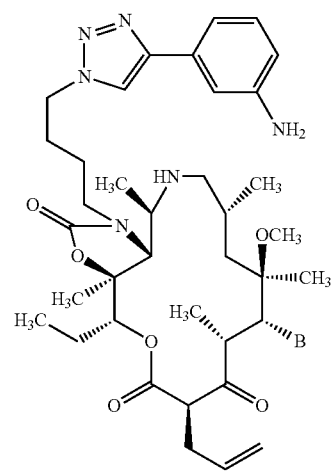
TABLE 1A-continued
Examples of macrolide unit (A).
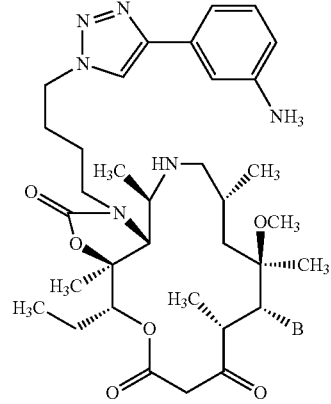
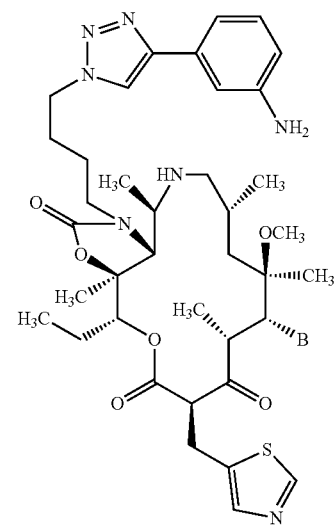
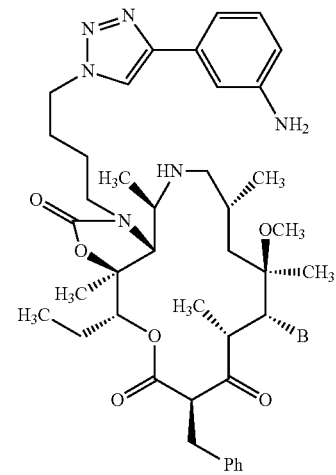

TABLE 1A-continued
Examples of macrolide unit (A).
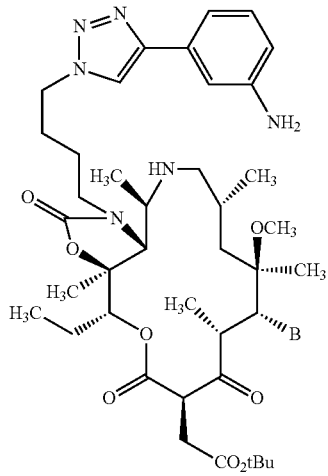
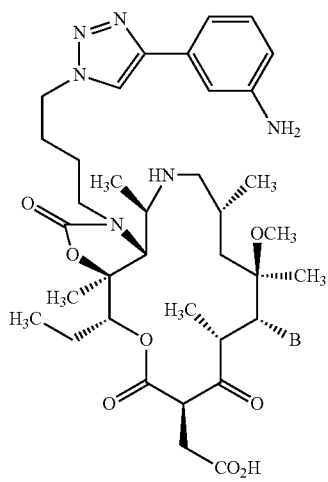
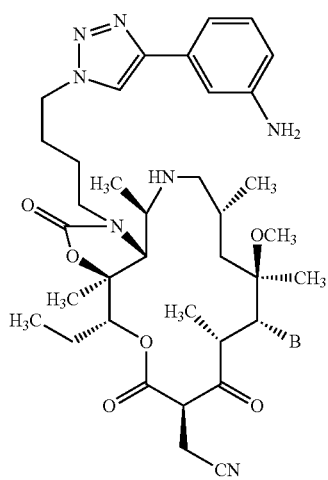
TABLE 1A-continued
Examples of macrolide unit (A).
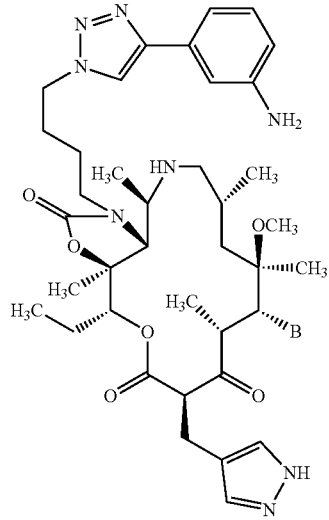
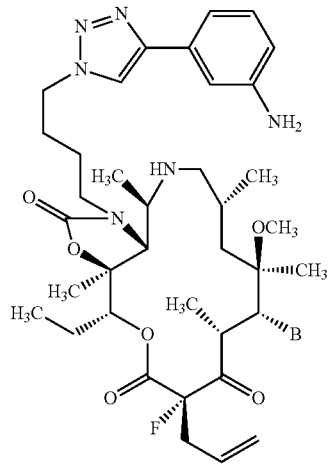
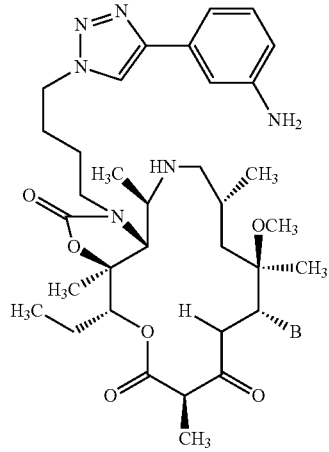

TABLE 1A-continued
Examples of macrolide unit (A).
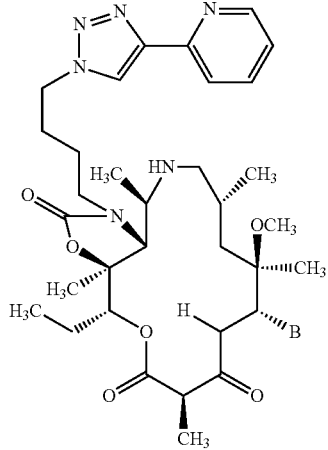
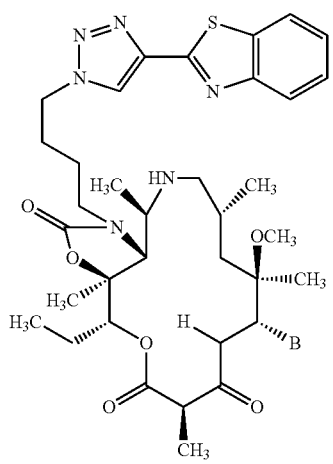
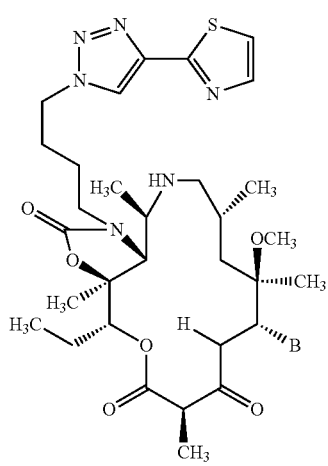
TABLE 1A-continued
Examples of macrolide unit (A).
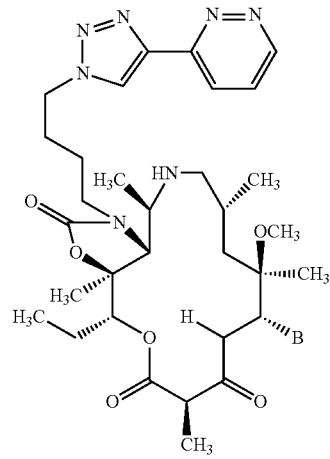
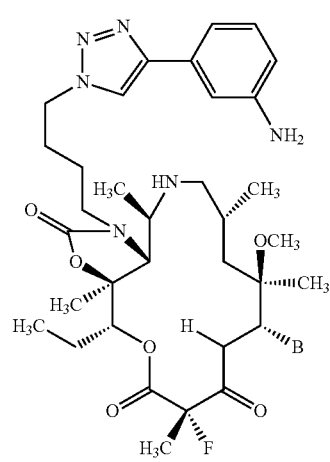
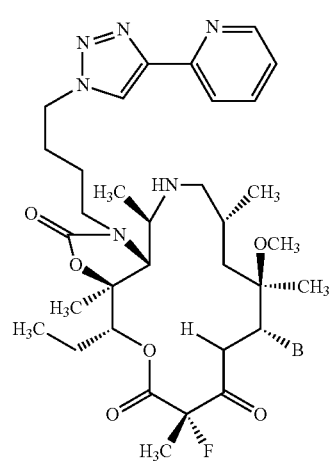

TABLE 1A-continued
Examples of macrolide unit (A).
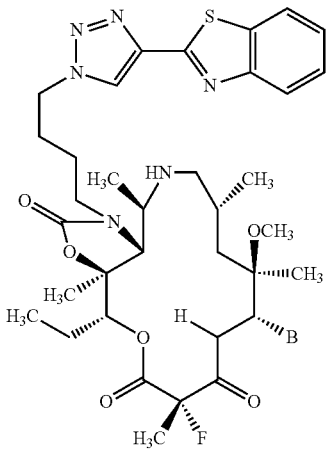
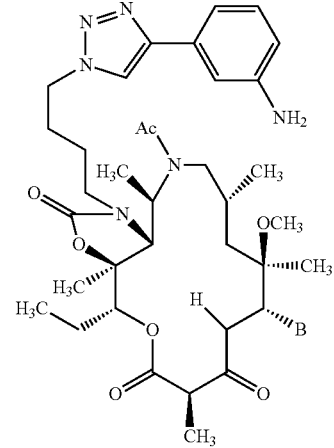
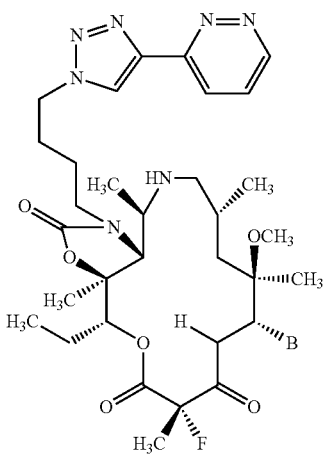
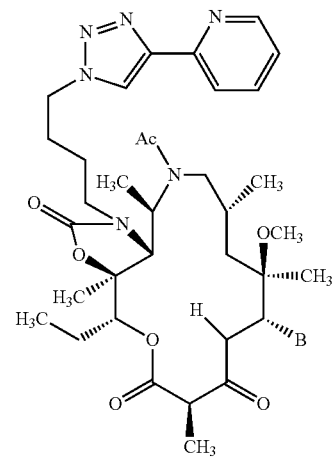
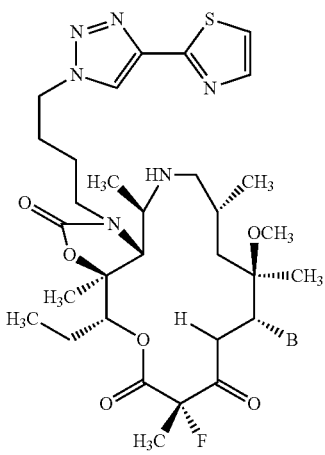
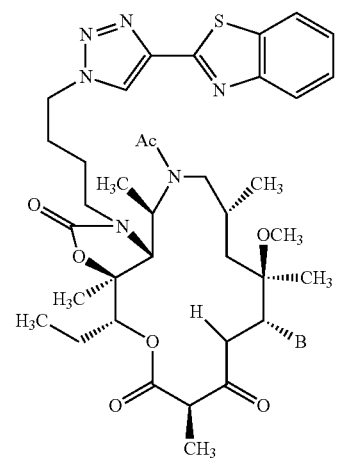

TABLE 1A-continued
Examples of macrolide unit (A).
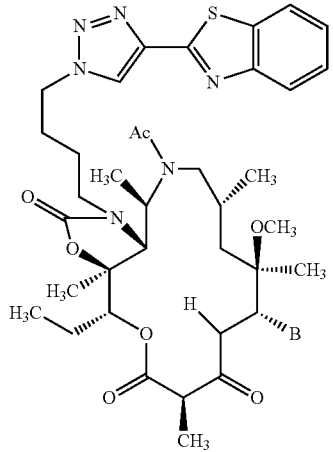
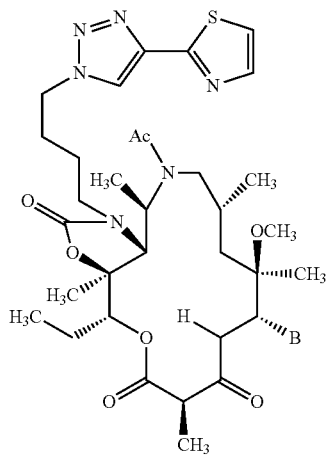
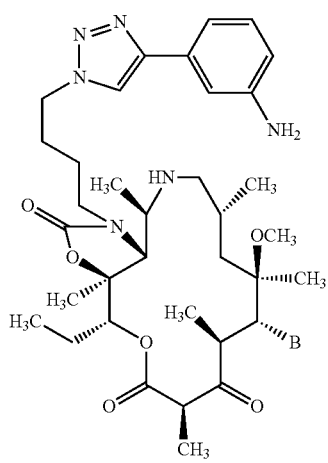
TABLE 1A-continued
Examples of macrolide unit (A).
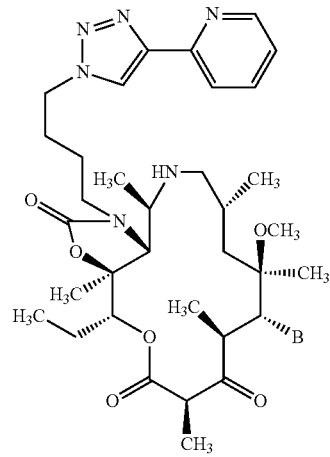
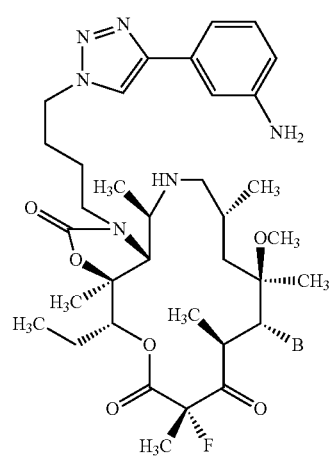
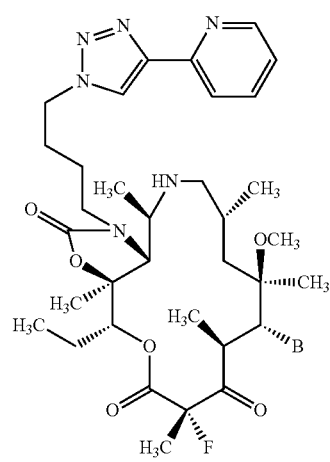

TABLE 1A-continued
Examples of macrolide unit (A).
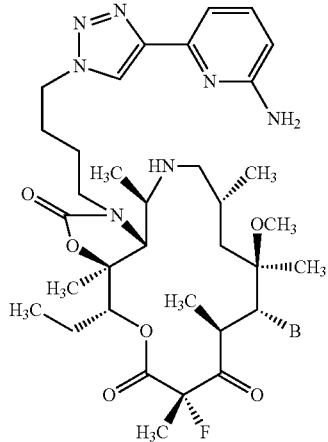
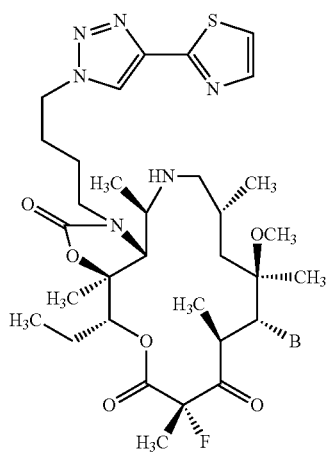
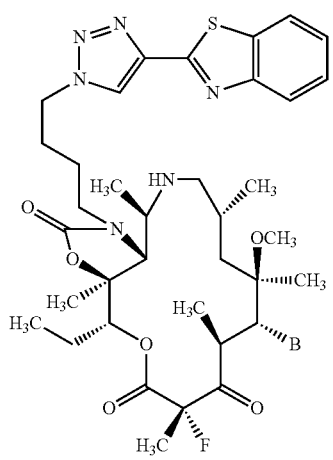
TABLE 1A-continued
Examples of macrolide unit (A).
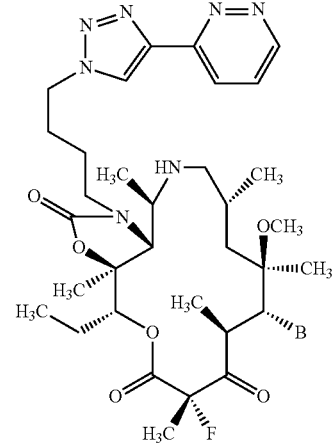
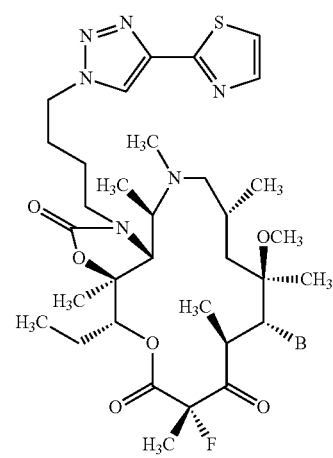
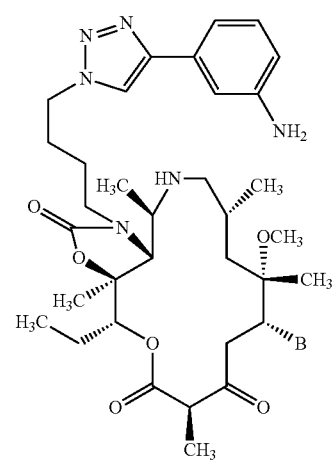

TABLE 1A-continued
Examples of macrolide unit (A).
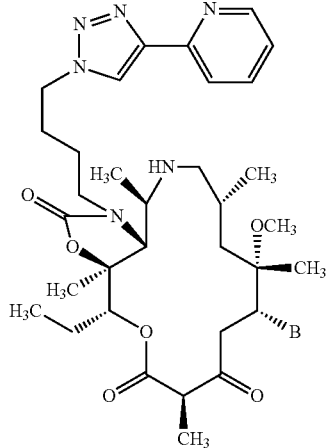
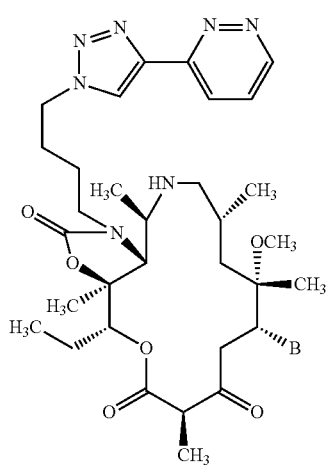
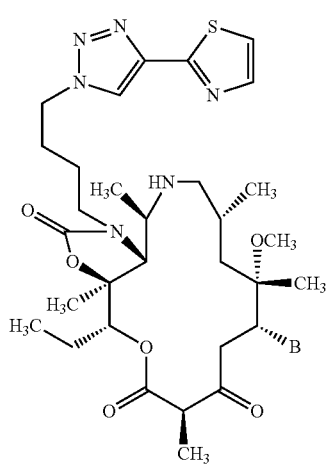
TABLE 1A-continued
Examples of macrolide unit (A).
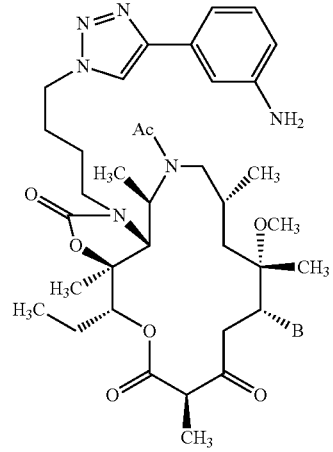
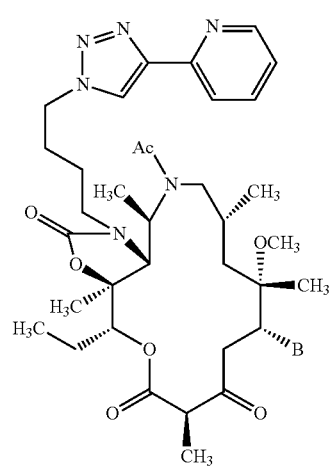
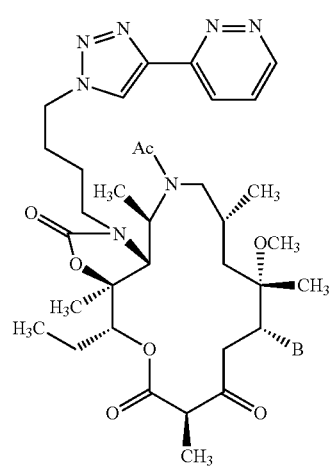

TABLE 1A-continued
Examples of macrolide unit (A).
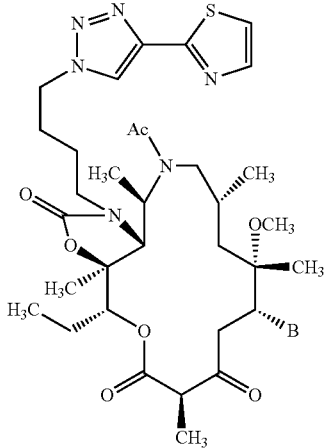
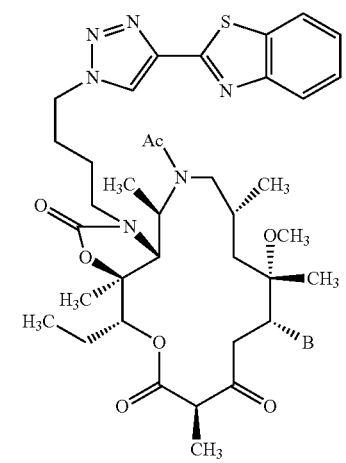
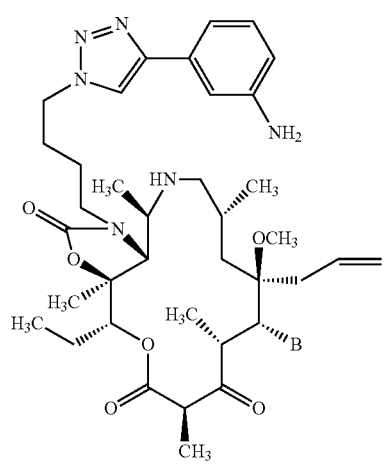
TABLE 1A-continued
Examples of macrolide unit (A).
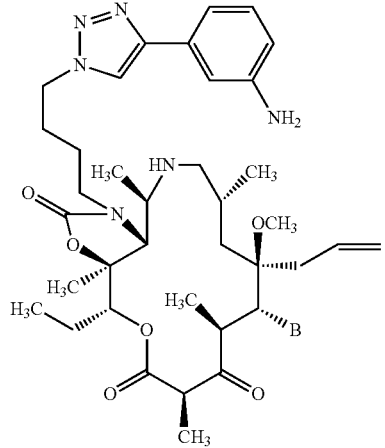
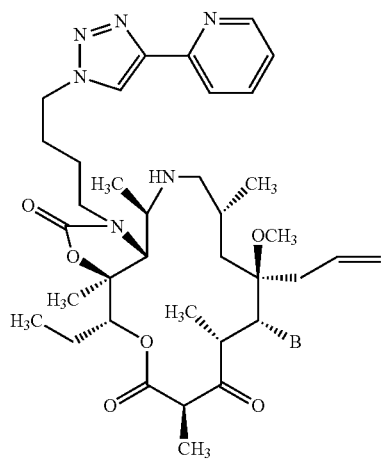
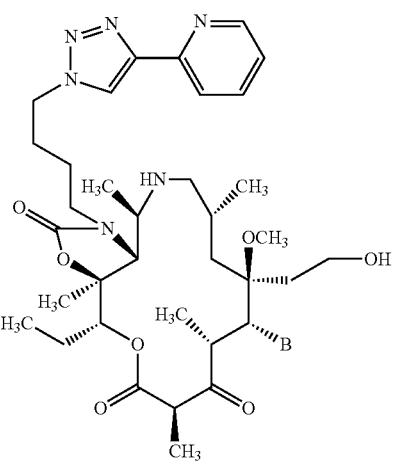

TABLE 1A-continued
Examples of macrolide unit (A).
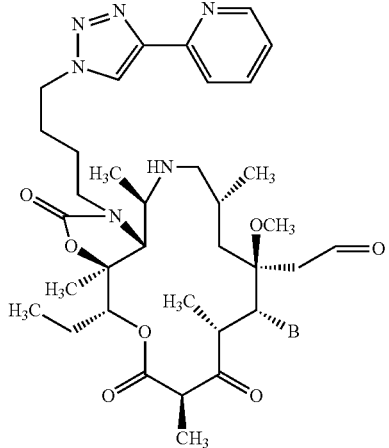
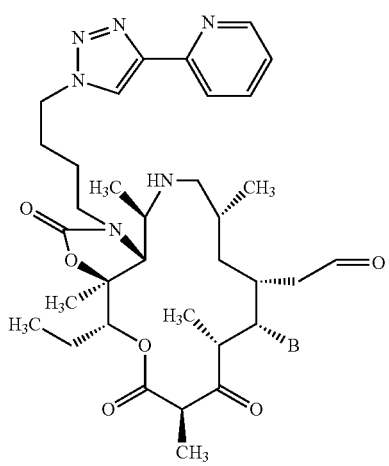
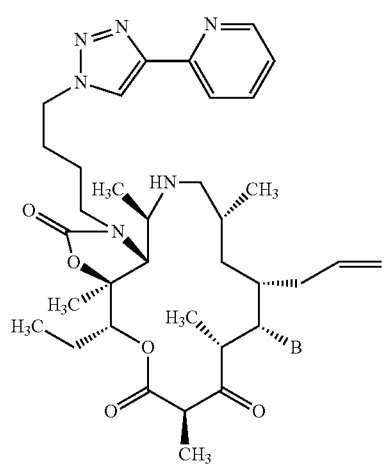
TABLE 1A-continued
Examples of macrolide unit (A).
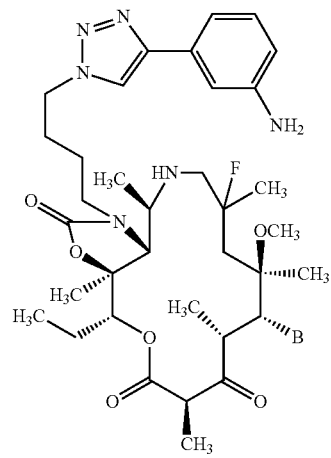
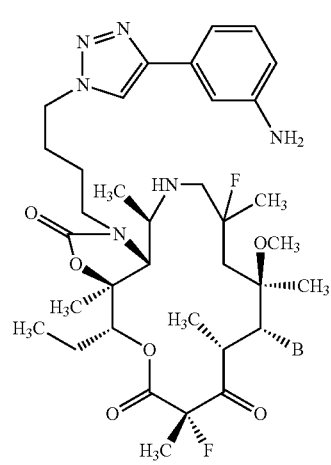
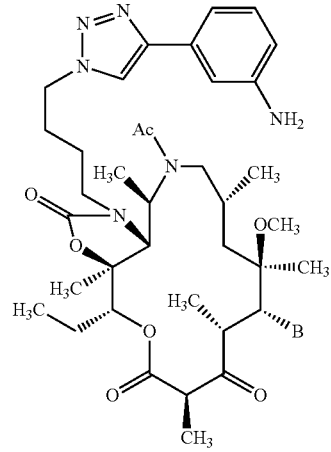

TABLE 1A-continued
Examples of macrolide unit (A).
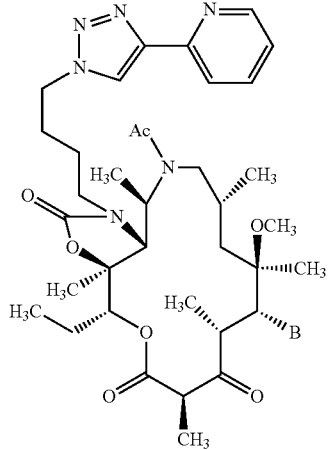
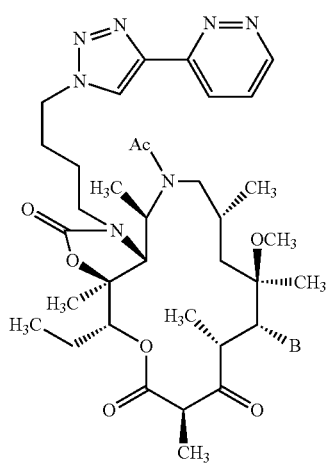
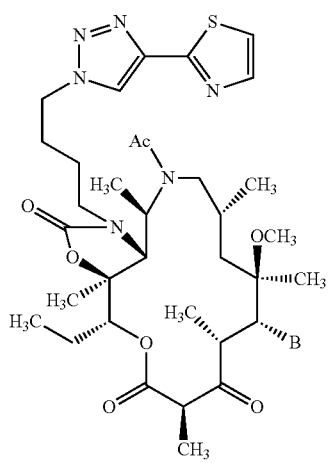
TABLE 1A-continued
Examples of macrolide unit (A).
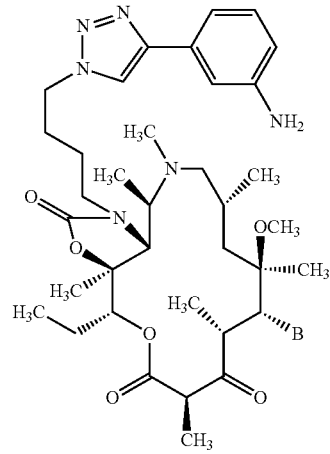
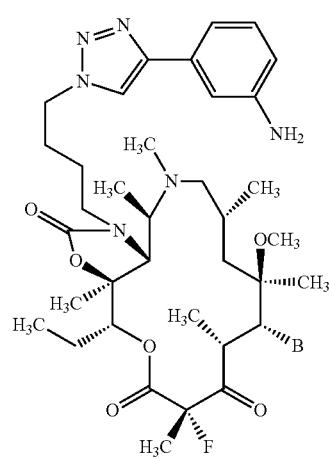
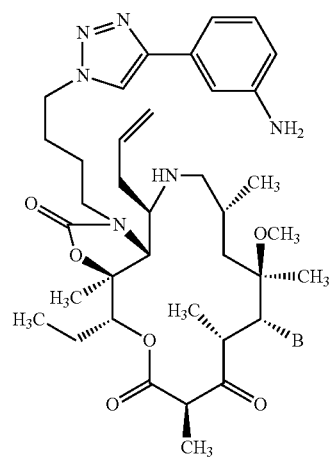

TABLE 1A-continued
Examples of macrolide unit (A).
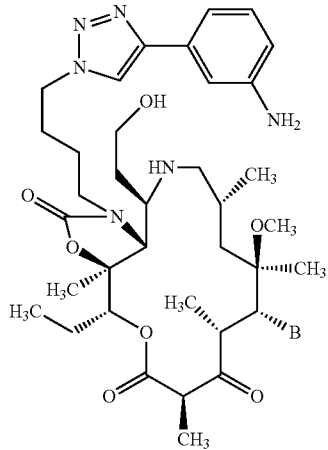
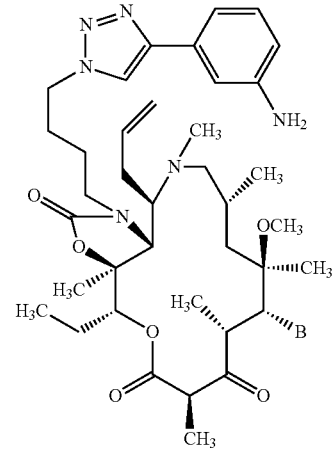
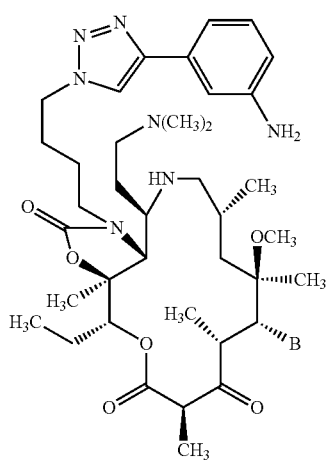
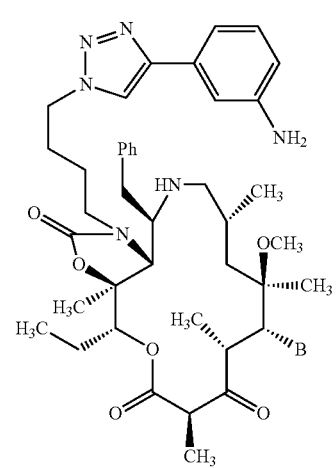
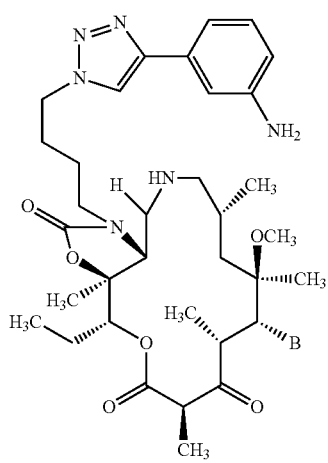
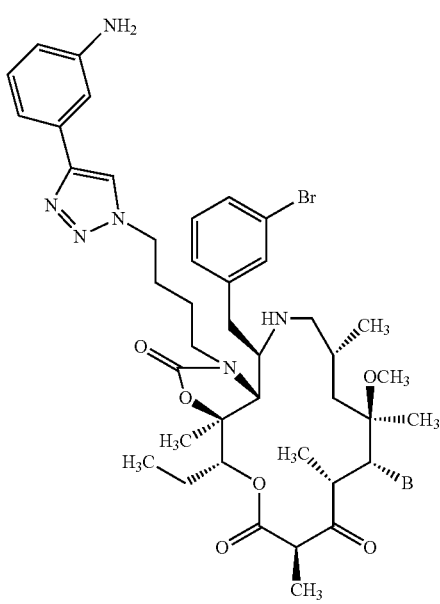

TABLE 1A-continued
Examples of macrolide unit (A).
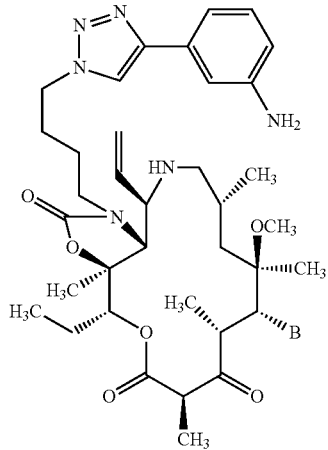
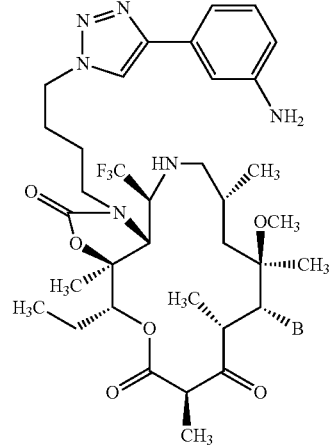
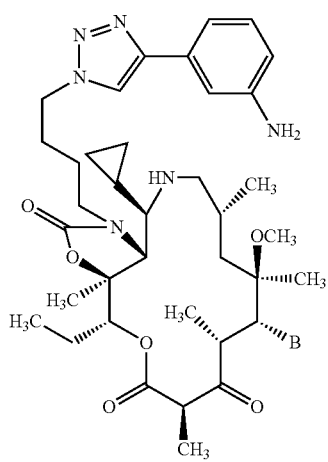
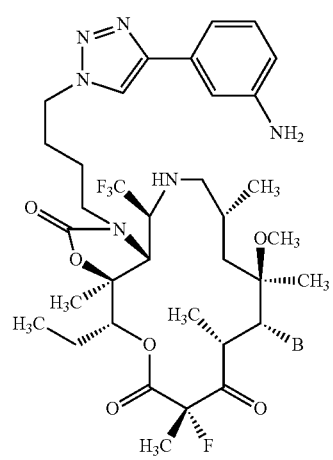
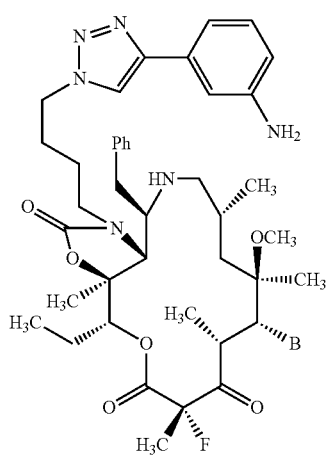
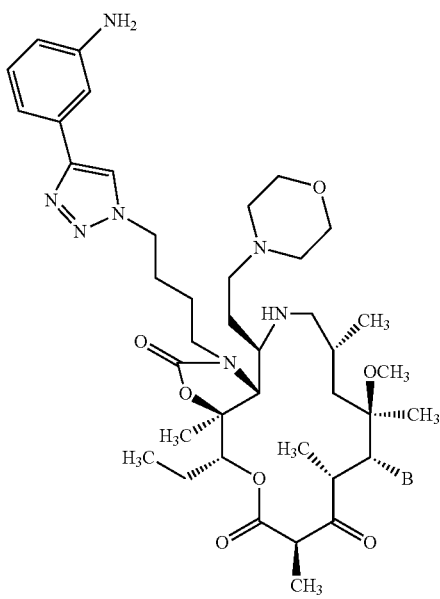

TABLE 1A-continued
Examples of macrolide unit (A).
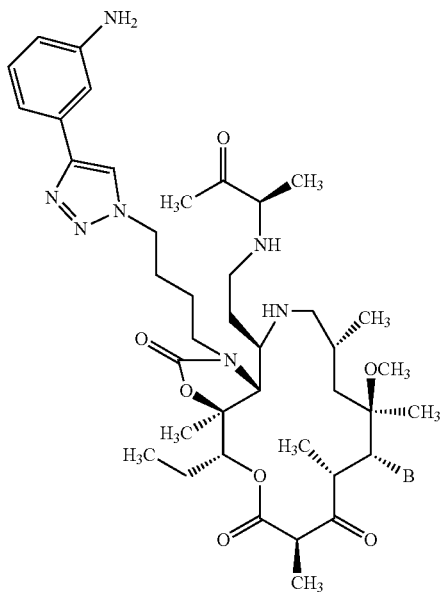
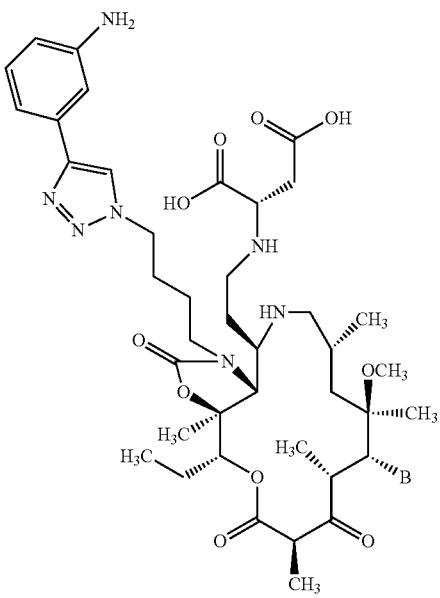
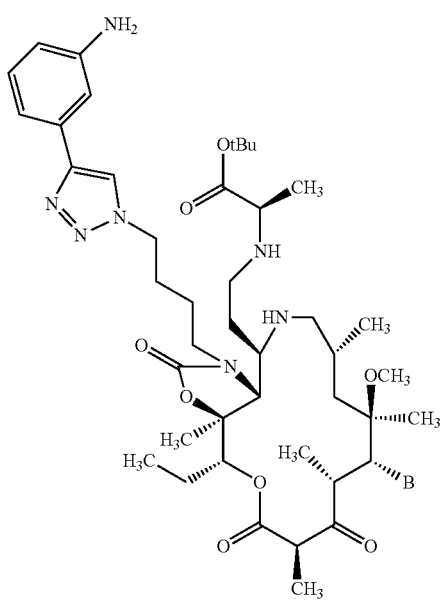
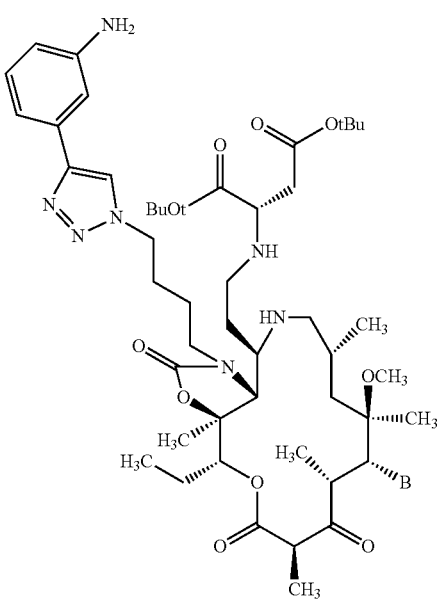

91
TABLE 1A-continued
Examples of macrolide unit (A).
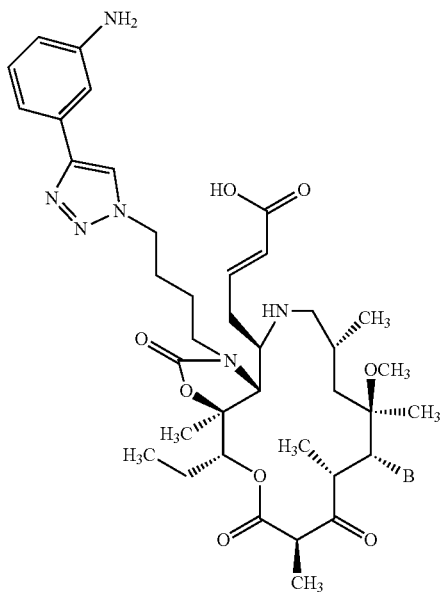
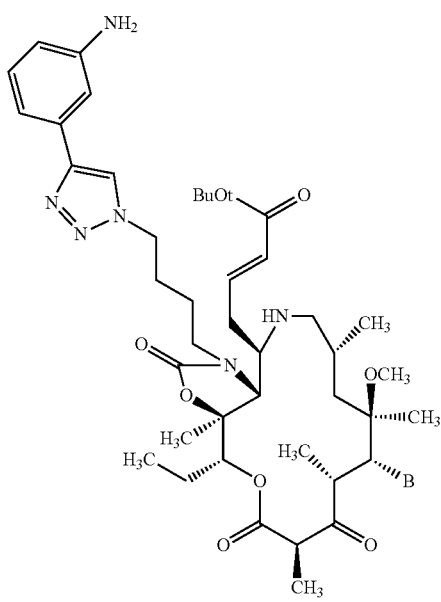
92
TABLE 1A-continued
Examples of macrolide unit (A).
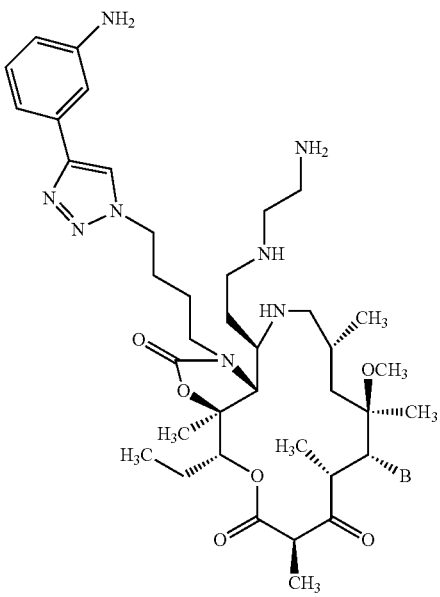
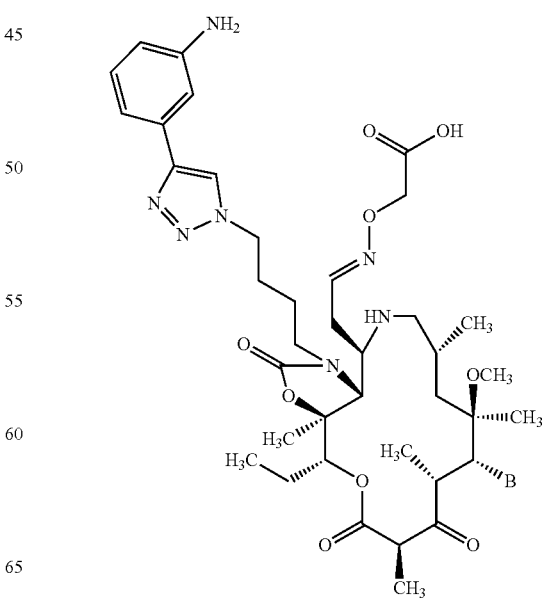

TABLE 1A-continued
Examples of macrolide unit (A).
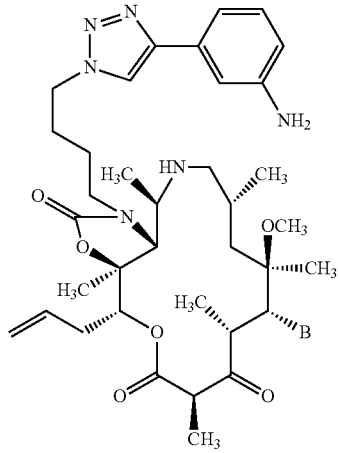
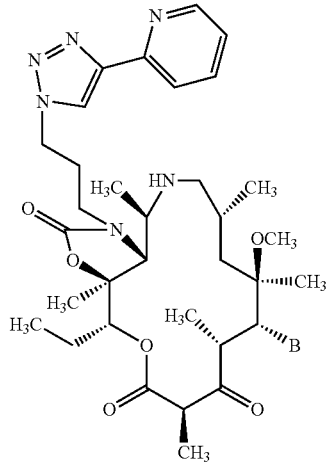
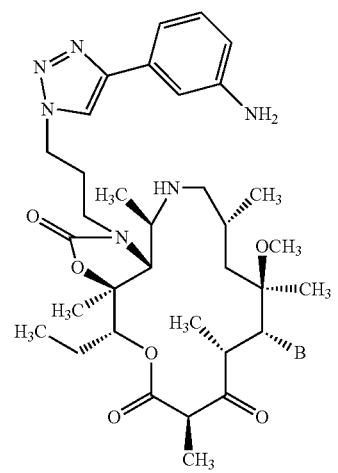
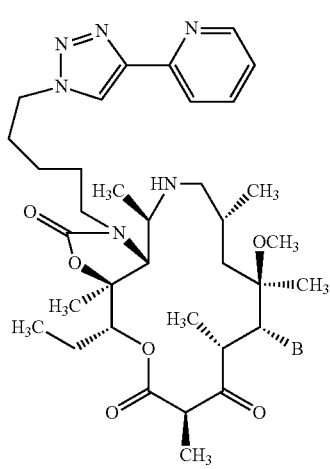
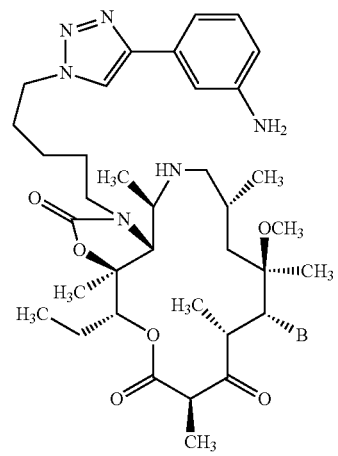
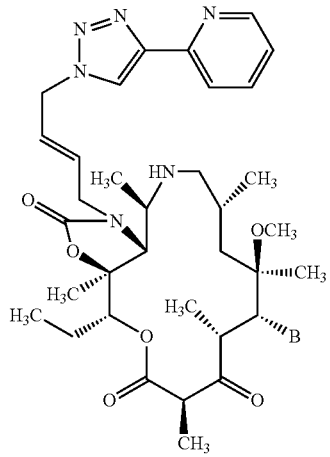

TABLE 1A-continued
Examples of macrolide unit (A).
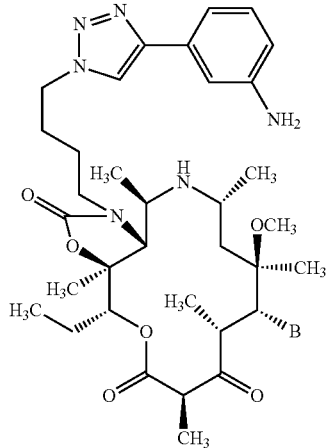
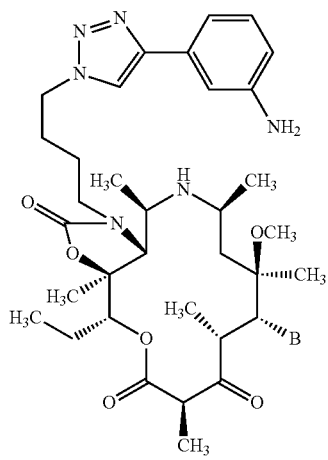
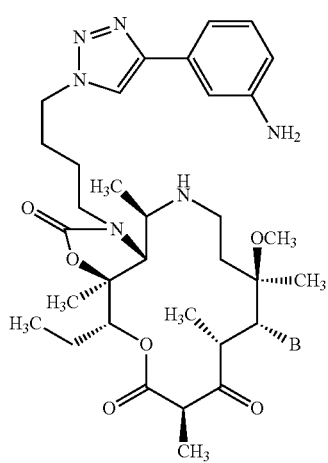
TABLE 1A-continued
Examples of macrolide unit (A).
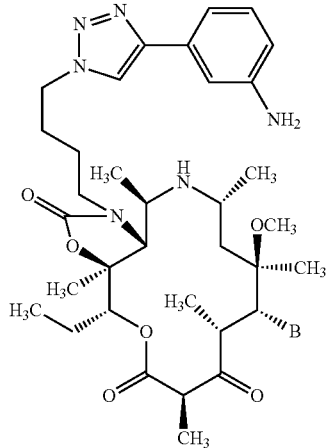
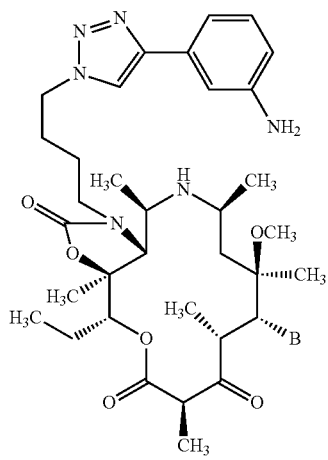
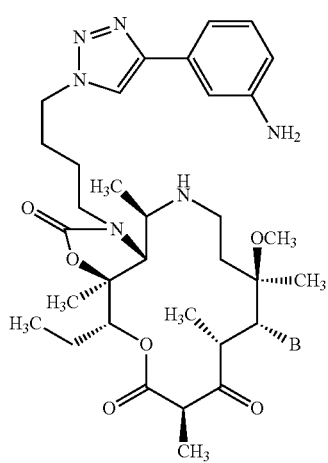

TABLE 1A-continued
Examples of macrolide unit (A).
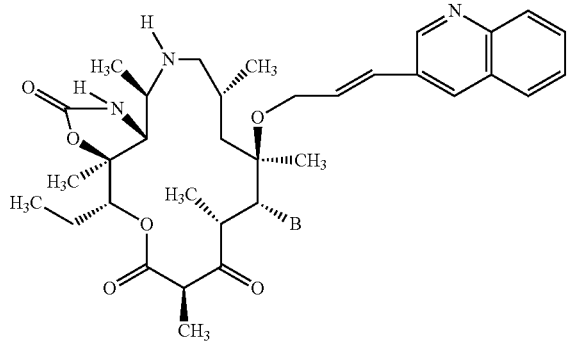
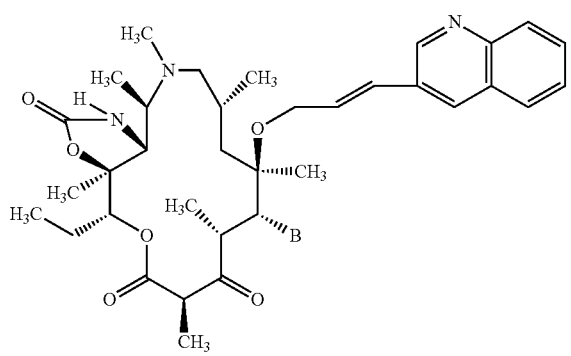
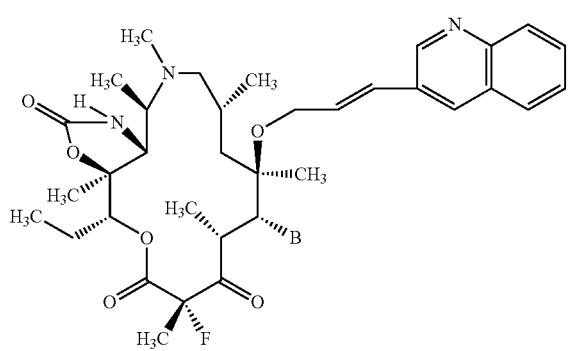
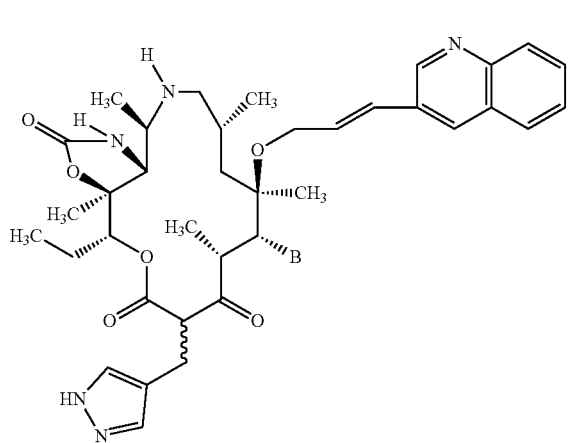
TABLE 1A-continued
Examples of macrolide unit (A).
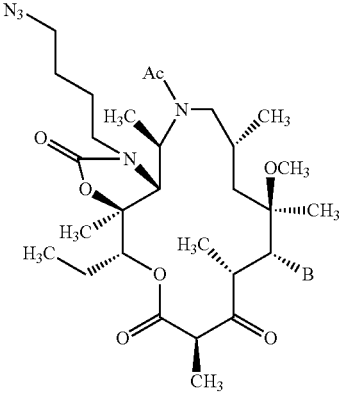
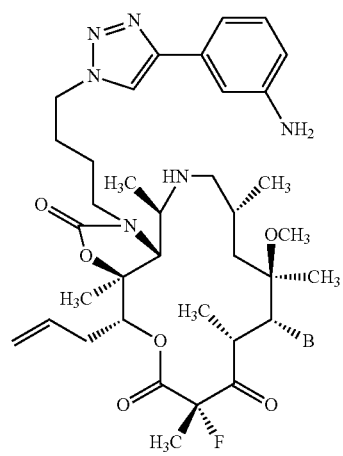
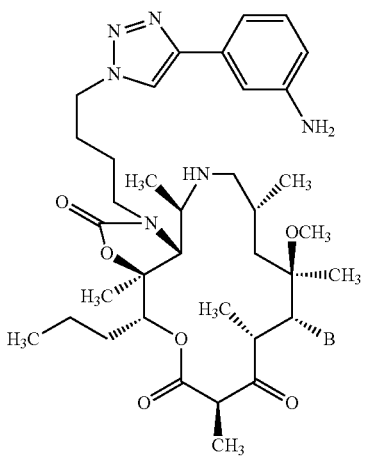

TABLE 1A-continued
Examples of macrolide unit (A).
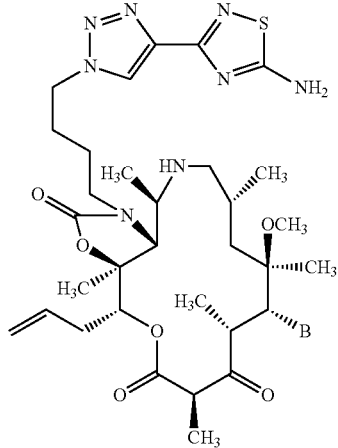
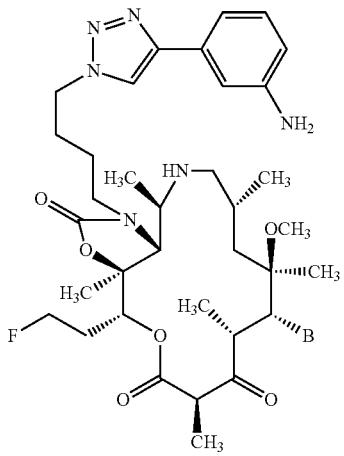
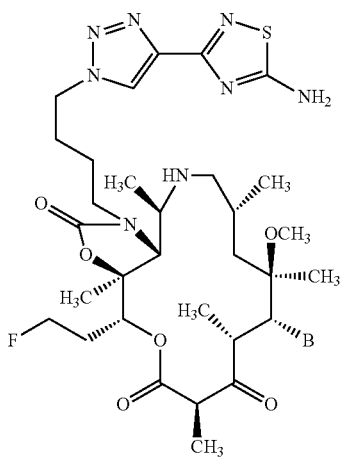
TABLE 1A-continued
Examples of macrolide unit (A).
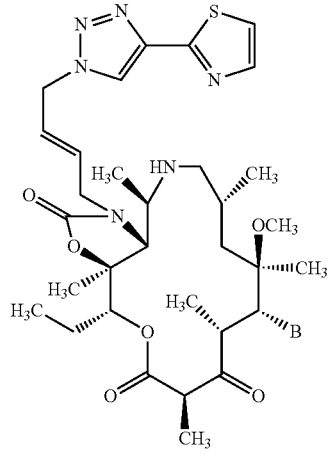
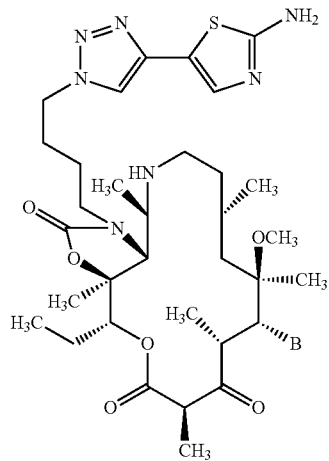
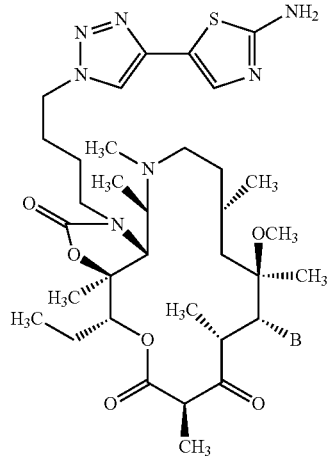

TABLE 1A-continued
Examples of macrolide unit (A).
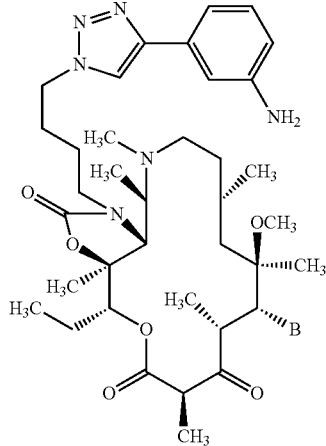
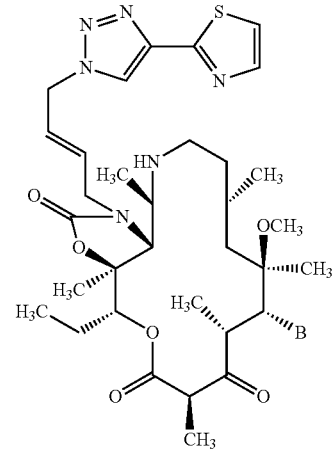
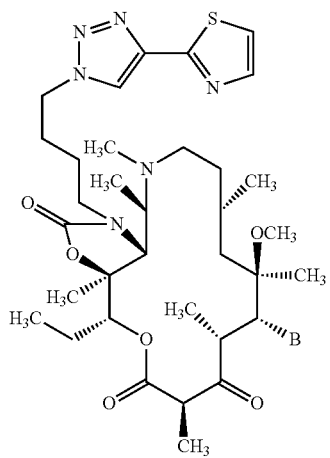
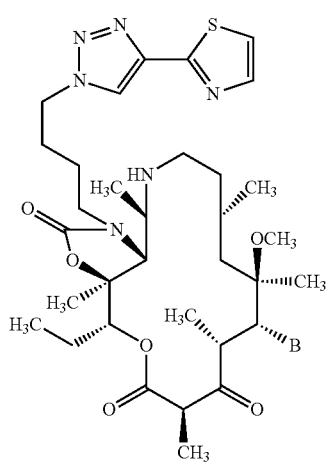
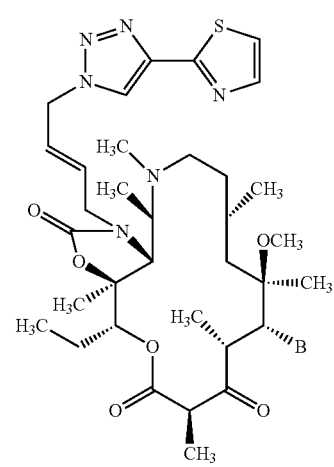

TABLE 1A-continued
Examples of macrolide unit (A).
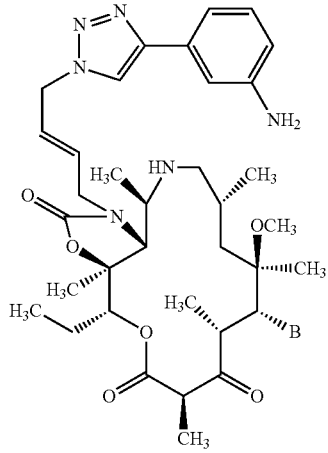
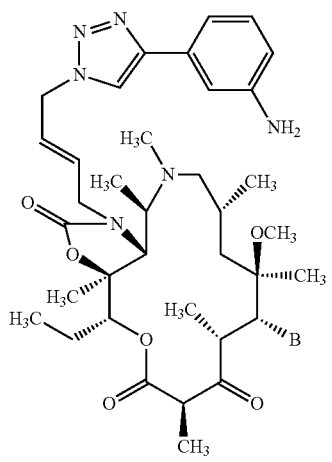
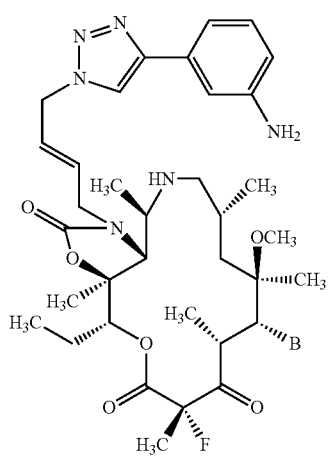
TABLE 1A-continued
Examples of macrolide unit (A).
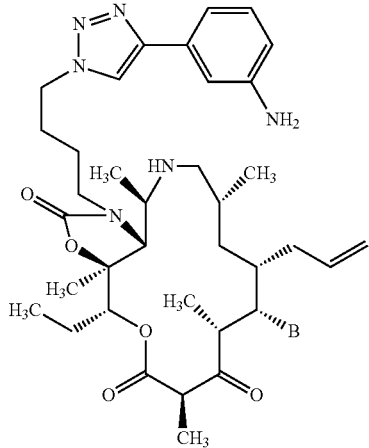
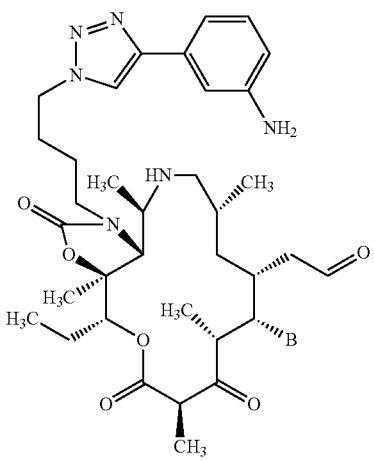
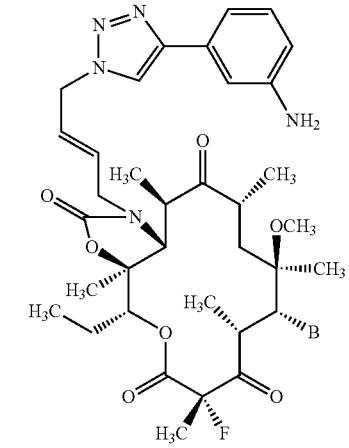

TABLE 1A-continued
Examples of macrolide unit (A).
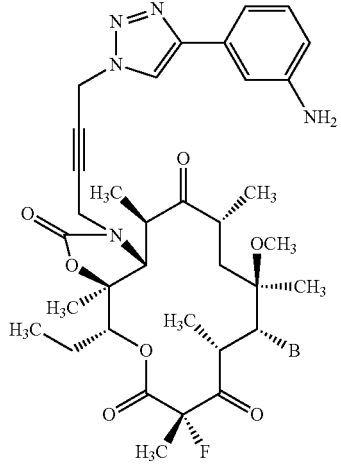
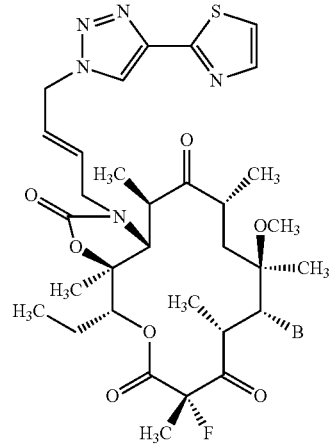
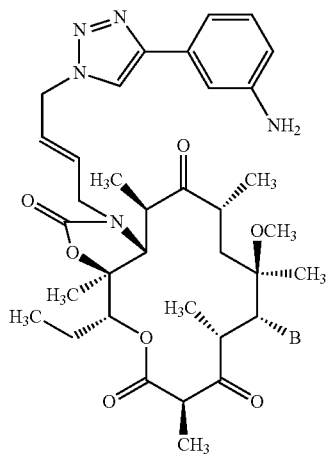
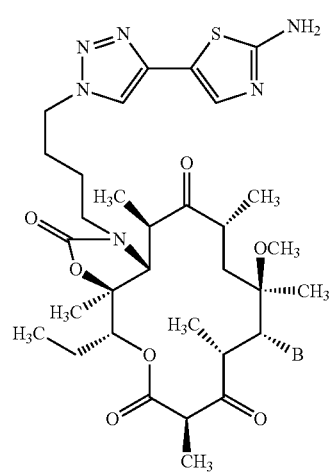
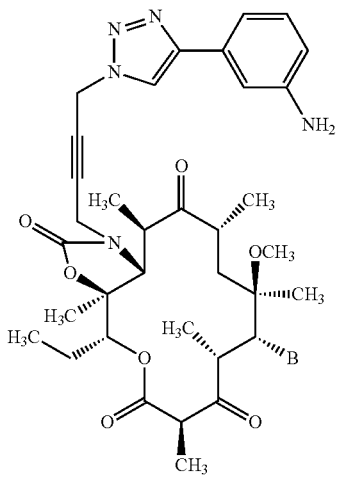

TABLE 1A-continued
Examples of macrolide unit (A).
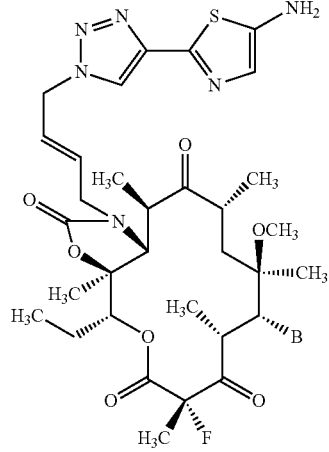
TABLE 1B
Examples of desosamine unit (B).
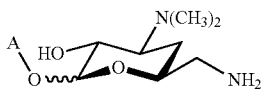
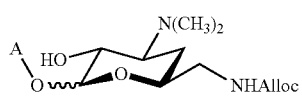
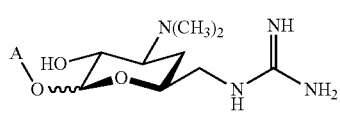
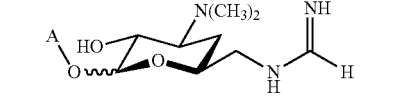
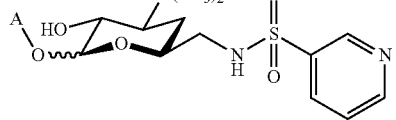
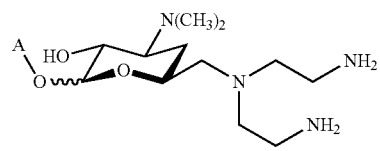
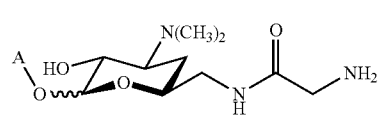
TABLE 1B-continued
Examples of desosamine unit (B).
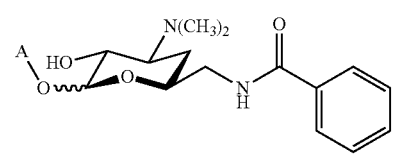
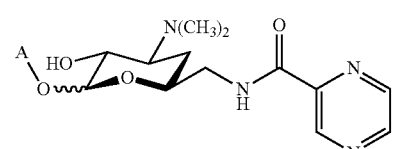
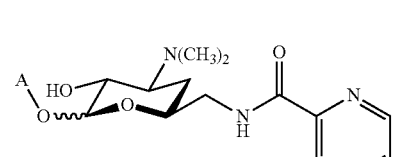
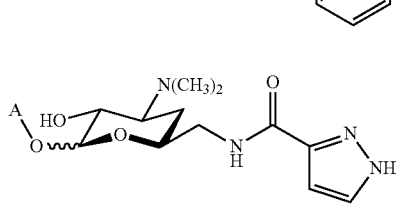
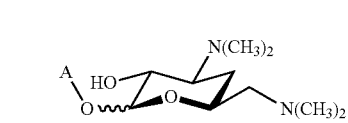
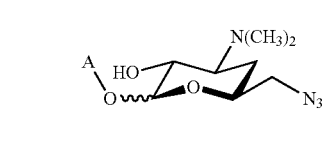
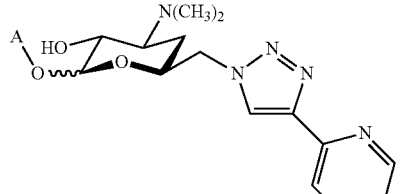
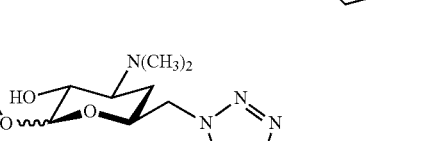
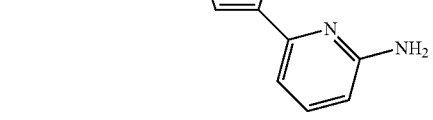

TABLE 1B-continued

Examples of desosamine unit (B).

TABLE 1B-N

Examples of sugar unit (B-N).

TABLE 1B-N-continued

Examples of sugar unit (B-N).

TABLE 1B-N-continued

Examples of sugar unit (B-N).

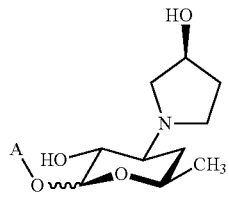

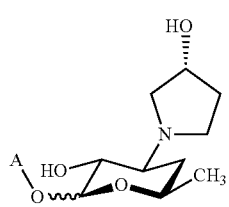

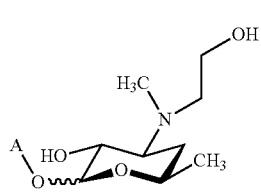

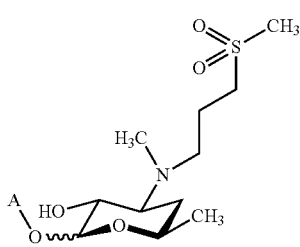

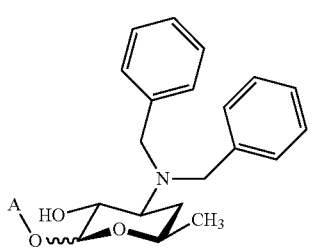

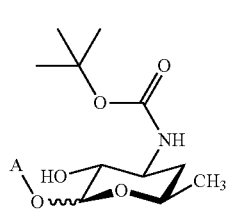

In certain embodiments, the sugar unit represented by (B-N) is not of the formula:

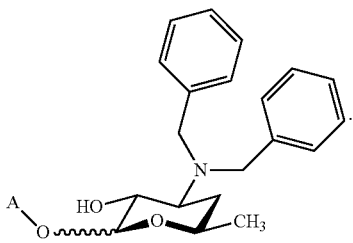

In certain embodiments, the sugar unit represented by (B-N) is not of the formula:

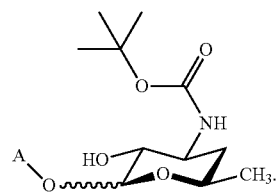

In certain embodiments, the sugar unit represented by (B-N) is not of the formula:

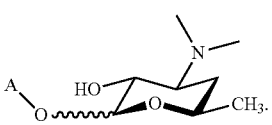

In certain embodiments, the sugar moiety of a compound of Formula (I-N) is not of the formula:

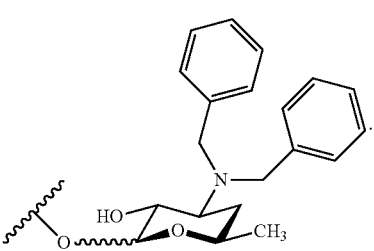

In certain embodiments, the sugar moiety of a compound of Formula (I-N) is not of the formula:

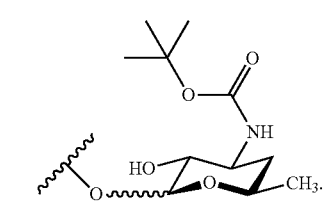

In certain embodiments, the sugar moiety of a compound of Formula (I-N) is not of the formula:

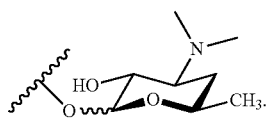

Additional Formulae

Provided herein are certain intermediates that may be prepared during the preparation of a macrolide described herein. Such intermediates include the eastern half of a macrolide prior to coupling and uncyclized precursors prior to macrolactonization.

In one aspect, the present invention provides a macrolide eastern half intermediate of Formula (E):

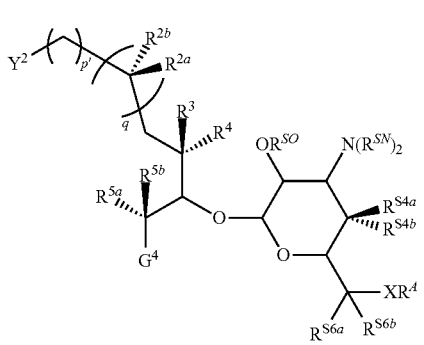

or salt thereof, wherein:

$R^{2a}$, $R^{2b}$, $R^3$, $R^4$, $R^{5a}$, $R^{5b}$, $R^6$, $R^A$, $R^B$, $R^{S4a}$, $R^{S4b}$, $R^{S6a}$, $R^{SN}$, $R^{SO}$, and $R^{Z2}$ are as described herein;

p' is 0, 1, or 2;

q is 0 or 1;

$Y^2$ is —$Z^4$H, —$CH_2NO_2$, -LG, —C(=O)$R^{Z3}$, —C(=O)OR$^{Z3}$, —C(=O)LG, —C(=O)CH=P($R^{P1}$)($R^{P1}$)($R^{P3}$), or —C(=O)$CH_2$P(=O)(OR$^{P2}$)(OR$^{P3}$);

LG is a leaving group;

$Z^4$ is —O—, —S—, or —NR$^{Z2}$—;

$R^{Z3}$ is hydrogen, halogen, optionally substituted alkyl, optionally substituted alkenyl, optionally substituted alkynyl, optionally substituted carbocyclyl, optionally substituted heterocylyl, optionally substituted aryl, or optionally substituted heteroaryl;

each of $R^{P1}$, $R^{P2}$, and $R^{P3}$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl;

$G^4$ is of formula:

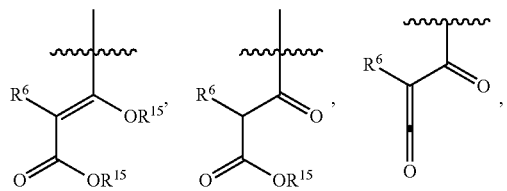

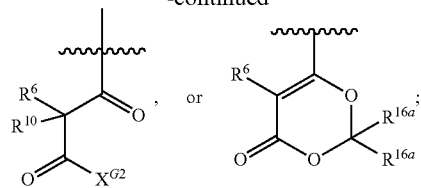

each instance of $X^{G2}$ is —OR$^{15}$, —SR$^{15}$, or —N(R$^{15}$)$_2$;

each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{15}$ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In another aspect, the present invention provides an uncyclized macrolide intermediate of Formula (N):

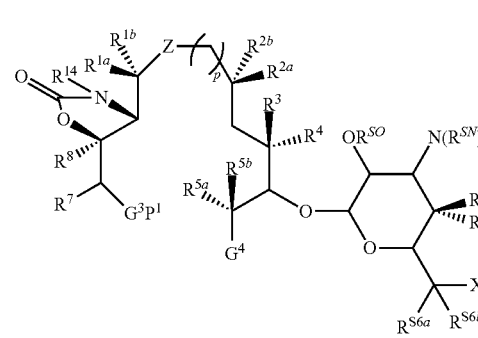

or salt thereof, wherein:

Z, p, $R^{1a}$, $R^{1b}$, $R^{2a}$, $R^{2b}$, $R^3$, $R^4$, $R^{5a}$, $R^{5b}$, $R^6$, $R^7$, $R^8$, $R^{14}$, $R^A$, $R^B$, $R^{S4a}$, $R^{S4b}$, $R^{S6a}$, $R^{S6b}$, $R^{SN}$, $R^{SO}$, and $R^{Z2}$ are as described herein;

$P^1$ is hydrogen, silyl, optionally substituted alkyl, or optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

$G^3$ is —O—, —S—, or —N(R$^{G1}$)—, wherein $R^{G1}$ is hydrogen, optionally substituted alkyl, or a nitrogen protecting group;

$G^4$ is of formula:

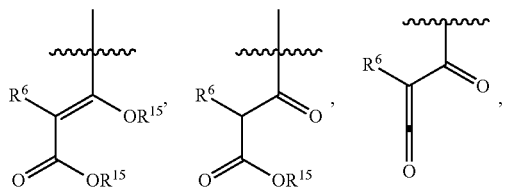

-continued

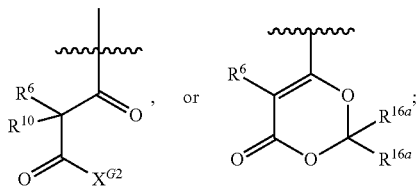

each instance of $X^{G2}$ is —$OR^{15}$, —$SR^{15}$, or —$N(R^{15})_2$;

each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{15}$ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In yet another aspect, the present invention provides an uncyclized ketolide intermediate of Formula (M-2):

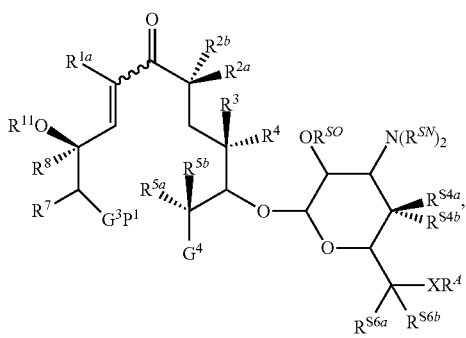

(M-2)

or salt thereof, wherein:

$R^{1a}$, $R^{2a}$, $R^{2b}$, $R^3$, $R^4$, $R^{5a}$, $R^{5b}$, $R^6$, $R^7$, $R^8$, $R^{14}$, $R^A$, $R^B$, $R^{S4a}$, $R^{S4b}$, $R^{S6a}$, $R^{S6b}$, $R^{SN}$, and $R^{SO}$ are as described herein;

$R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$P^1$ is hydrogen, silyl, optionally substituted alkyl, or optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

$G^3$ is —O—, —S—, or —N($R^{G1}$)—, wherein $R^{G1}$ is hydrogen, optionally substituted alkyl, or a nitrogen protecting group;

$G^4$ is of formula:

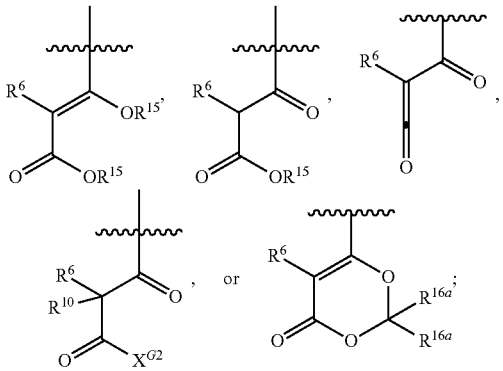

each instance of $X^{G2}$ is —$OR^{15}$, —$SR^{15}$, or —$N(R^{15})_2$;

each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{15}$ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In another aspect, the present invention provides a macrolide eastern half intermediate of Formula (E-N):

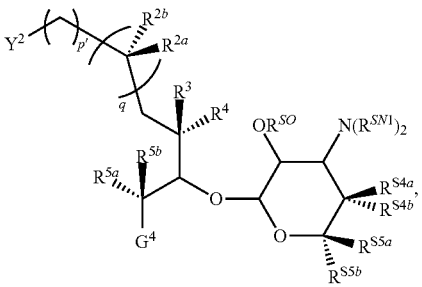

(E-N)

or salt thereof, wherein:

$R^{2a}$, $R^{2b}$, $R^3$, $R^4$, $R^{5a}$, $R^{5b}$, $R^6$, $R^B$, $R^{S4a}$, $R^{S4b}$, $R^{S5a}$, $R^{S5b}$, $R^{SN1}$, $R^{SO}$, and $R^{Z2}$ are as described herein;

p' is 0, 1, or 2;

q is 0 or 1;

$Y^2$ is —$Z^4$H, —$CH_2NO_2$, -LG, —$C(=O)R^{Z3}$, —$C(=O)OR^{Z3}$, —$C(=O)LG$, —$C(=O)CH=P(R^{P1})(R^{P2})(R^{P3})$, or —$C(=O)CH_2P(=O)(OR^{P2})(OR^{P3})$;

LG is a leaving group;

$Z^4$ is —O—, —S—, or —$NR^{Z2}$—;

$R^{Z3}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each of $R^{P1}$, $R^{P2}$, and $R^{P3}$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl;

G⁴ is of formula:

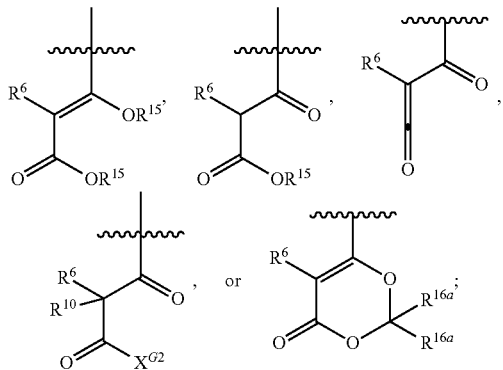

each instance of $X^{G2}$ is —OR¹⁵, —SR¹⁵, or —N(R¹⁵)₂;

each instance of R¹⁵ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R¹⁵ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In another aspect, the present invention provides an uncyclized macrolide intermediate of Formula (N-N):

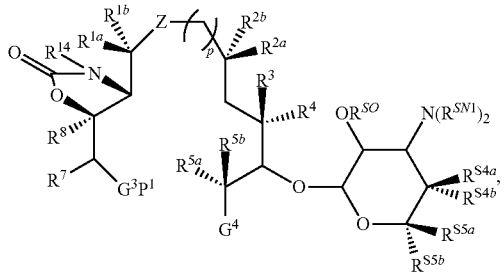

(N-N)

or salt thereof, wherein:

Z, p, $R^{1a}$, $R^{1b}$, $R^{2a}$, $R^{2b}$, $R^3$, $R^4$, $R^{5a}$, $R^{5b}$, $R^6$, $R^7$, $R^8$, $R^{14}$, $R^A$, $R^B$, $R^{S4a}$, $R^{S4b}$, $R^{S5a}$, $R^{S5b}$, $R^{SN1}$, $R^{SO}$, and $R^{Z2}$ are as described herein;

P¹ is hydrogen, silyl, optionally substituted alkyl, or optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

G³ is —O—, —S—, or —N(R^{G1})—, wherein $R^{G1}$ is hydrogen, optionally substituted alkyl, or a nitrogen protecting group;

G⁴ is of formula:

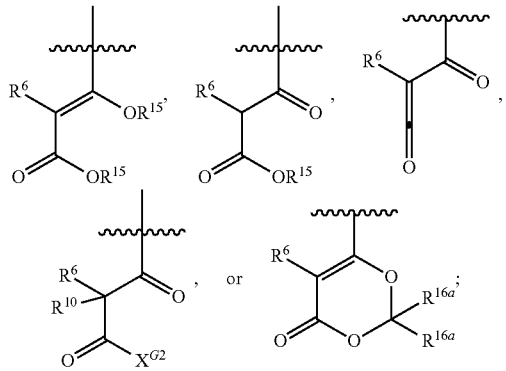

each instance of $X^{G2}$ is —OR¹⁵, —SR¹⁵, or —N(R¹⁵)₂;

each instance of R¹⁵ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two R¹⁵ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In yet another aspect, the present invention provides an uncyclized ketolide intermediate of Formula (M-2-N):

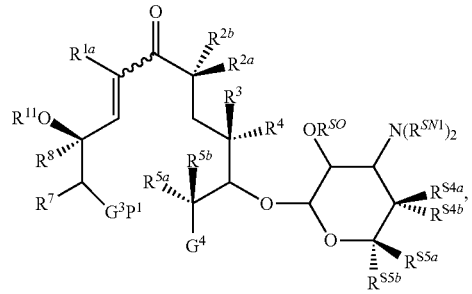

(M-2-N)

or salt thereof, wherein:

$R^{1a}$, $R^{2a}$, $R^{2b}$, $R^3$, $R^4$, $R^{5a}$, $R^{5b}$, $R^6$, $R^7$, $R^8$, $R^{14}$, $R^A$, $R^B$, $R^{S4a}$, $R^{S4b}$, $R^{S5a}$, $R^{S5b}$, $R^{SN1}$, and $R^{SO}$ are as described herein;

R¹¹ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

P¹ is hydrogen, silyl, optionally substituted alkyl, or optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

$G^3$ is —O—, —S—, or —N($R^{G1}$)—, wherein $R^{G1}$ is hydrogen, optionally substituted alkyl, or a nitrogen protecting group;

$G^4$ is of formula:

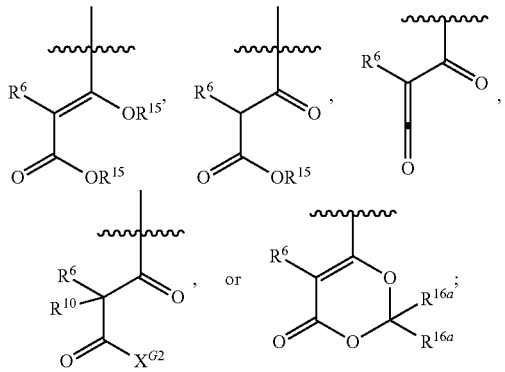

each instance of $X^{G2}$ is —$OR^{15}$, —$SR^{15}$, or —N($R^{15}$)$_2$;

each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{15}$ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

Preparation by Coupling and Macrolactonization

In certain embodiments, macrolides of the present invention are prepared by coupling an eastern half of Formula (E) and a western half of Formula (W) to provide an uncyclized macrolide precursor of Formula (N) as depicted in Scheme 1, and the precursor of Formula (N) is cyclized to give a macrolide of Formula (I) as depicted in Scheme 2.

In other embodiments, macrolides of the present invention are prepared by coupling an eastern half of Formula (E-N) and a western half of Formula (W) to provide an uncyclized macrolide precursor of Formula (N-N) as depicted in Scheme 1-N, and the precursor of Formula (N-N) is cyclized to give a macrolide of Formula (I-N) as depicted in Scheme 2-N.

Exemplary methods that may be used in the preparation of a macrolide of the present disclosure are described below, and are not to be construed as limiting. Further description of the methods for preparation of the eastern and western halves, coupling of the halves, macrocyclization, and other methods for various steps in the preparation of the macrolides herein are described in PCT publication WO2014/165792, which is incorporated herein in its entirety by reference. The macrolides herein may be prepared by other methods of synthesis known in the art, and the procedures described herein may be modified or combined with other known methods.

Scheme 1.

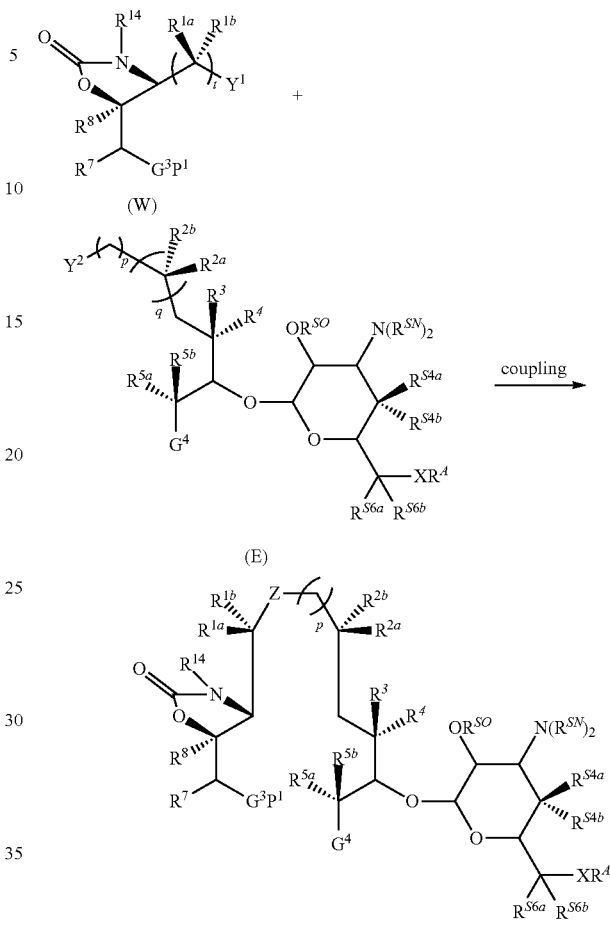

Scheme 2.

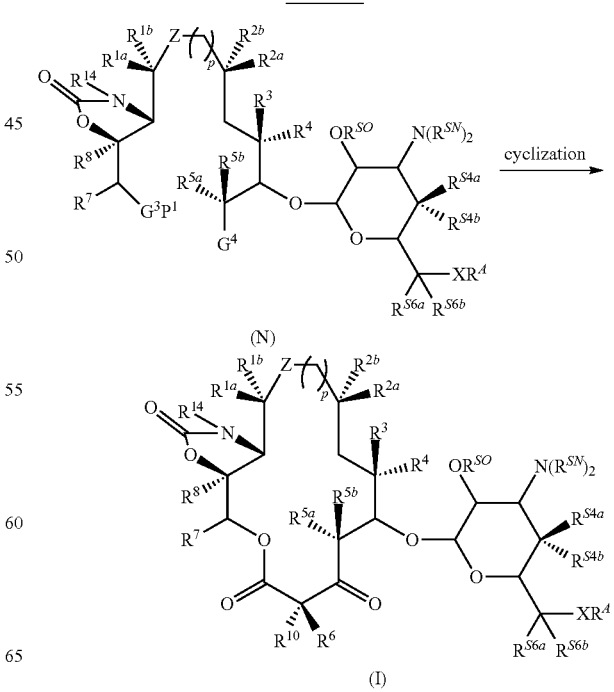

Scheme 1-N.

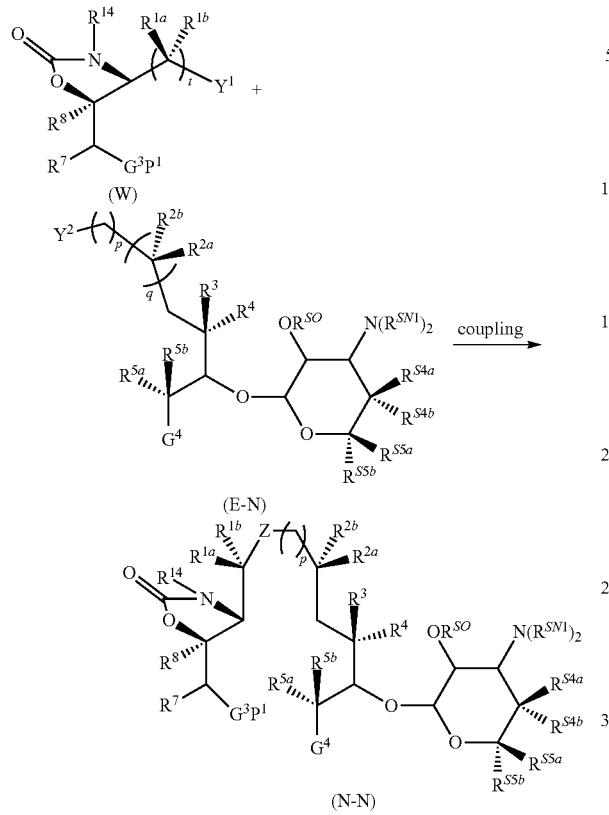

Scheme 2-N.

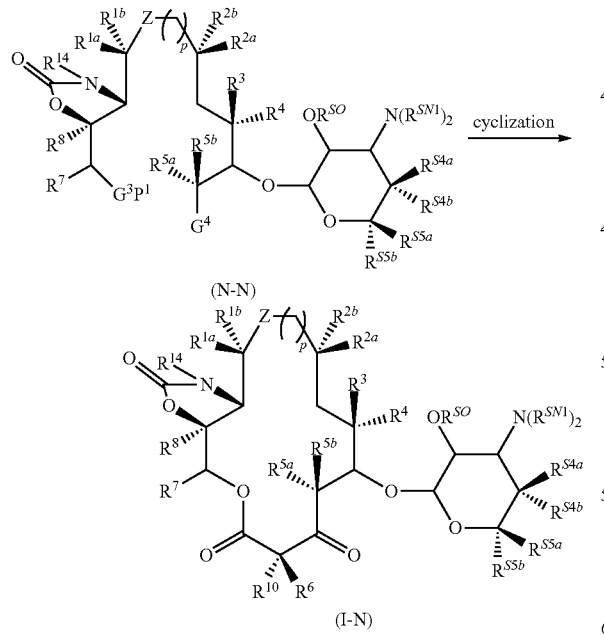

For all intermediates and precursors, Z, p, $R^{1a}$, $R^{1b}$, $R^{2a}$, $R^{2b}$, $R^3$, $R^4$, $R^{5a}$, $R^{5b}$, $R^6$, $R^7$, $R^8$, $R^{10}$, $R^{14}$, $R^A$, $R^B$, $R^{S4a}$, $R^{S4b}$, $R^{S6a}$, $R^{S6b}$, $R^{S5a}$, $R^{S5b}$, $R^{SN}$, $R^{SN1}$, $R^{SO}$, and $R^{Z2}$ are as defined herein for a compound of Formula (I) or Formula (I-N), unless otherwise stated.

Other variables depicted for intermediates and precursors are defined as follows:

p' is 0, 1, or 2;
q is 0 or 1;
t is 0 or 1;
Y is —$Z^4$H, —$CH_2NO_2$, -LG, —C(=O)$R^{Z3}$, —C(=O)O$R^{Z3}$, —C(=O)LG, or of formula:

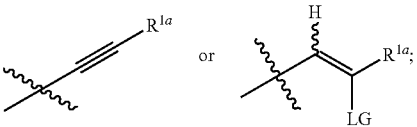

$Y^2$ is —$Z^4$H, —$CH_2NO_2$, -LG, —C(=O)$R^{Z3}$, —C(=O)O$R^{Z3}$, —C(=O)LG, —C(=O)CH=P($R^{P1}$)($R^{P2}$)($R^{P3}$), or —C(=O)$CH_2$P(=O)(O$R^{P2}$)(O$R^{P3}$);
LG is a leaving group;
$Z^4$ is —O—, —S—, or —N$R^{Z2}$—;
$R^{Z3}$ is hydrogen, halogen, optionally substituted alkyl, optionally substituted alkenyl, optionally substituted alkynyl, optionally substituted carbocyclyl, optionally substituted heterocylyl, optionally substituted aryl, or optionally substituted heteroaryl;
each of $R^{P1}$, $R^{P2}$, and $R^{P3}$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl;
$P^1$ is hydrogen, silyl, optionally substituted alkyl, or optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;
$G^3$ is —O—, —S—, or —N($R^{G1}$)—, wherein $R^{G1}$ is hydrogen, optionally substituted alkyl, or a nitrogen protecting group;
$G^4$ is of formula:

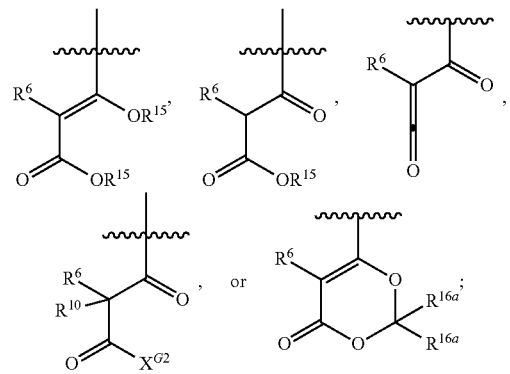

each instance of $X^{G2}$ is —O$R^{15}$, —S$R^{15}$, or —N($R^{15}$)$_2$;
each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{15}$ groups are joined to form an optionally substituted heterocyclyl or heteroaryl ring; and
each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, the coupling of the eastern and western halves is as depicted in Scheme 3, Scheme 3.

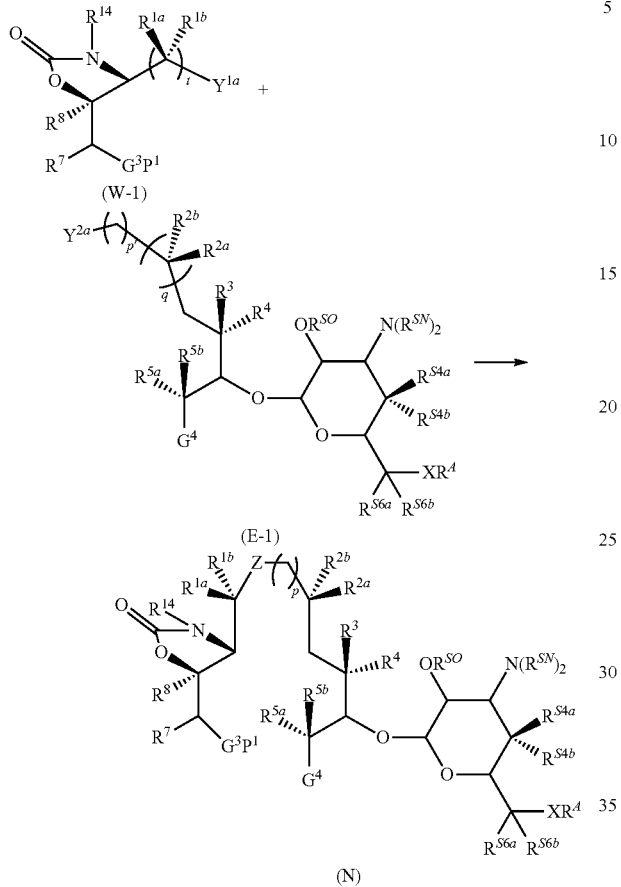

wherein the western half is a compound of Formula (W-1) and the eastern half is a compound of Formula (E-1), and wherein:

p' is 0, 1, or 2;
q is 0 or 1;
t is 0 or 1;
$Y^{1a}$ is —NHR$^{Z2}$, —CH$_2$NO$_2$, -LG, or —C(═O)R$^{Z3}$;
$Y^{2a}$ is —NHR$^{Z2}$, —CH$_2$NO$_2$, -LG, or —C(═O)R$^{Z3}$
LG is a leaving group;
R$^{Z3}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, the coupling of the eastern and western halves is as depicted in Scheme 3-N, Scheme 3-N.

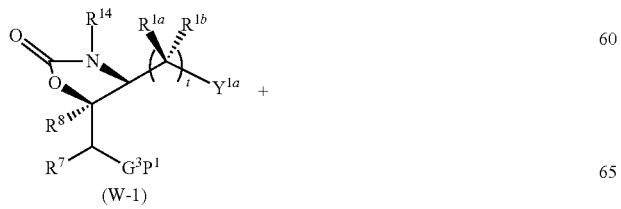

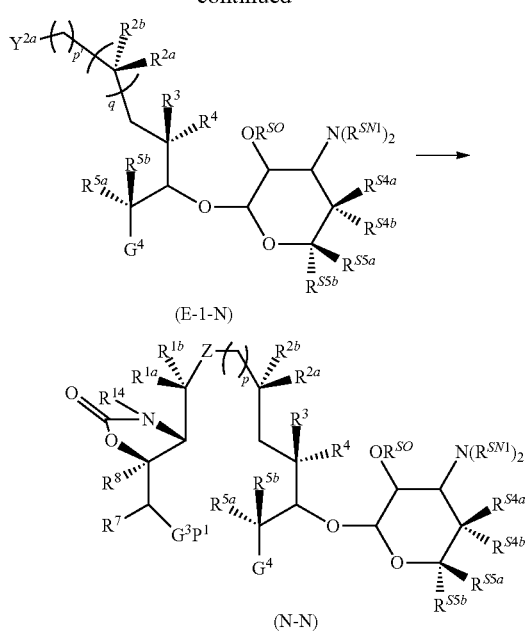

wherein the western half is a compound of Formula (W-1) and the eastern half is a compound of Formula (E-1-N), and wherein:

p' is 0, 1, or 2;
q is 0 or 1;
t is 0 or 1;
$Y^{1a}$ is —NHR$^{Z2}$, —CH$_2$NO$_2$, -LG, or —C(═O)R$^3$;
$Y^2a$ is —NHR$^{Z2}$, —CH$_2$NO$_2$, -LG, or —C(═O)R$^{Z3}$; LG is a leaving group;

R$^{Z3}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

Scheme 4.

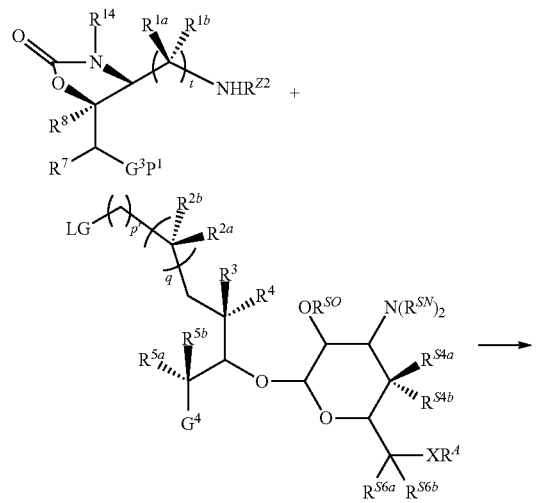

125
-continued

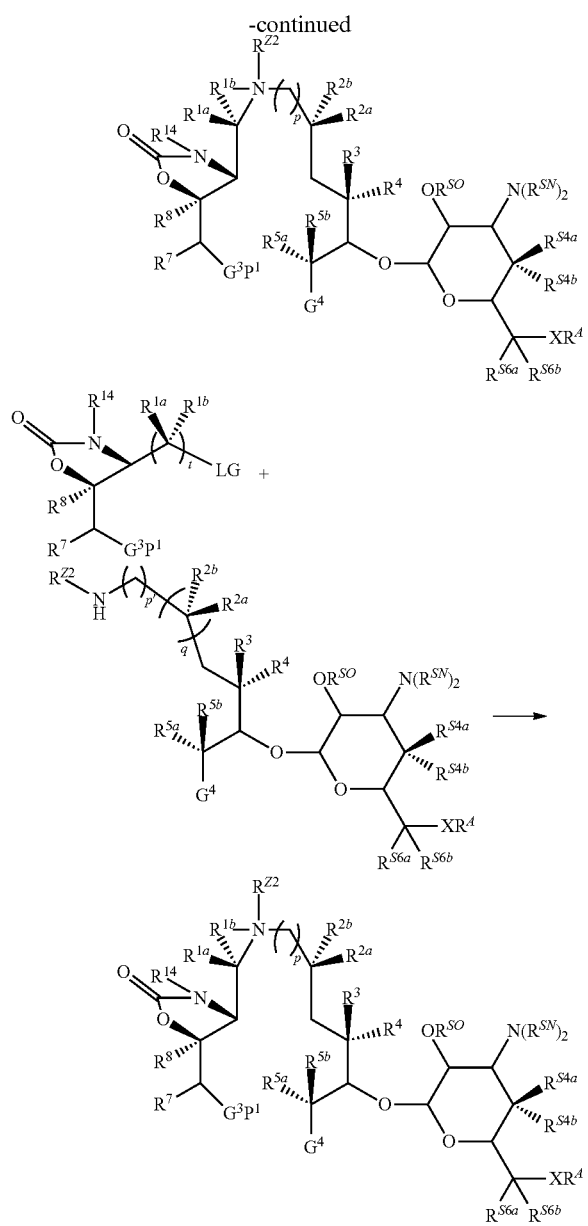

126
-continued

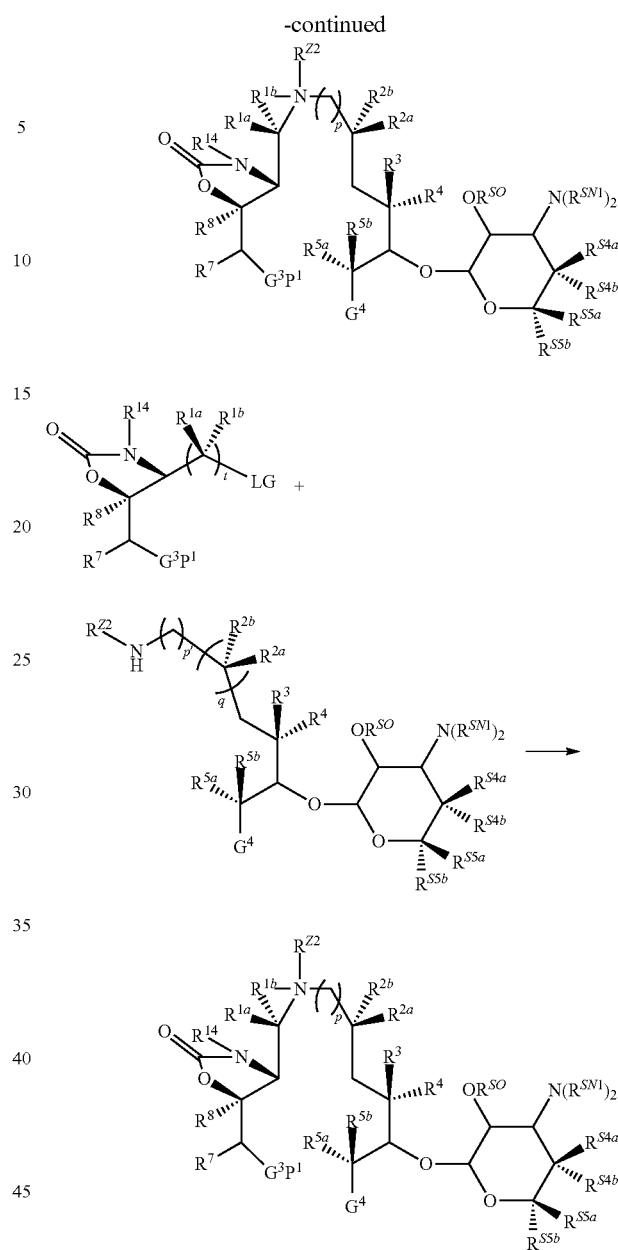

Scheme 4-N.

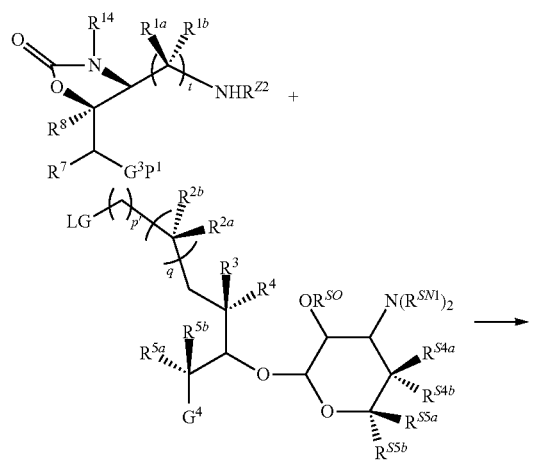

For example, as depicted in Scheme 4, in certain embodiments, when $Y^{1a}$ is —$NHR^{Z2}$ and $Y^{2a}$ is a leaving group (LG), or when $Y^{2a}$ is —$NHR^{Z2}$ and $Y^1$a is a leaving group (LG), the coupling of the eastern and western halves by nucleophilic displacement (nucleophilic substitution), optionally in the presence of a base, provides an uncyclized macrolide precursor of formula (N), wherein Z is —$NR^{Z2}$—, and wherein $R^{Z2}$ is a hydrogen or non-hydrogen group. Exemplary bases include, but are not limited to, organic bases (e.g., pyridine, DMAP, Hunig's base) and inorganic bases (e.g., sodium bicarbonate, sodium carbonate). Exemplary leaving groups include bromine, chlorine, iodine, tosylate, triflate, mesylate, and besylate. Analogous routes to uncyclized macrolide precursors of Formula (N-N), wherein Z is —$NR^{Z2}$—, and wherein $R^{Z2}$ is a hydrogen or non-hydrogen group, are shown in Scheme 4-N.

Scheme 5.
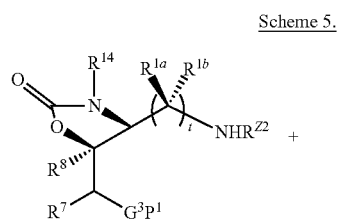
Scheme 5N.

As depicted in Scheme 5, in certain embodiments, when $Y^{1a}$ is —$NH_2$ or —$NHR^{Z2}$, and $Y^{2a}$ is —C(=O)$R^{Z3}$, or when $Y^{2a}$ is —$NH_2$ or —$NHR^{Z2}$ and $Y^{1a}$ is —C(=O)$R^{Z3}$, the coupling of the eastern and western halves by reductive amination, optionally followed by protection of the amine group by a non-hydrogen $R^{Z2}$, provides a compound of Formula (N), wherein Z is —$NR^{Z2}$—, wherein $R^{Z2}$ is hydrogen or a non-hydrogen group. Exemplary reductive amination conditions include, but are not limited to, use of $B_{10}H_{14}$, $InCl_3$/$Et_3SiH$, $NaBH_4$, $NaBH_4$/$H_3BO_3$, $NaBH_3CN$ or $NaBH(OAc)_3$, optionally in the prescence of an acid (e.g., AcOH, TFA) or protic solvent (e.g., MeOH). In certain embodiments, $R^2$ is hydrogen. In certain embodiments, $R^{Z2}$ is methyl. In certain embodiments, $R^{Z2}$ is a nitrogen protecting group. Analagous routes to uncyclized macrolide precursors of Formula (N-N), wherein Z is —$NR^{Z2}$—, and wherein $R^{Z2}$ is hydrogen or a non-hydrogen group, are shown in Scheme 5-N.

Scheme 6a.

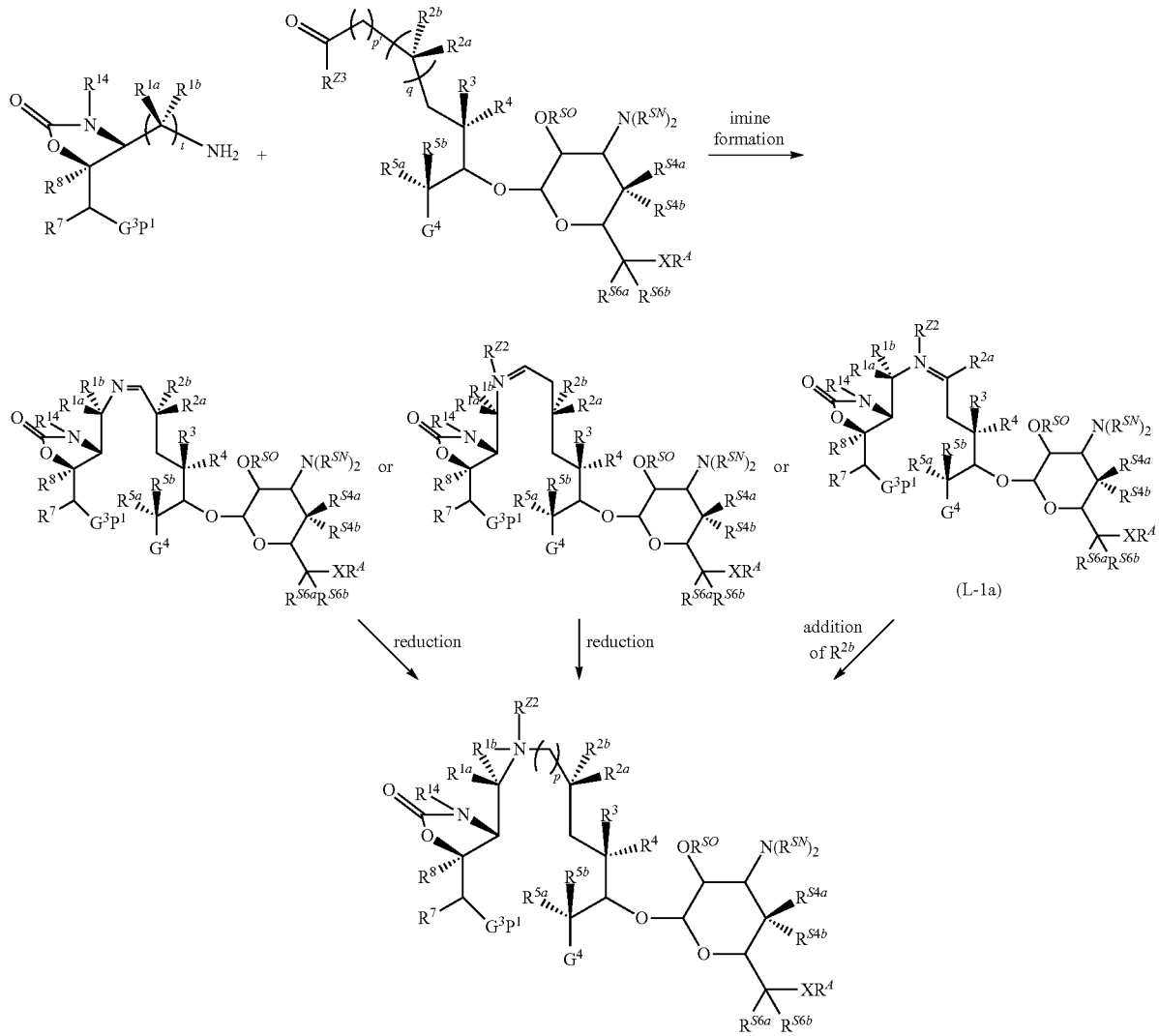

Scheme 6a-N.

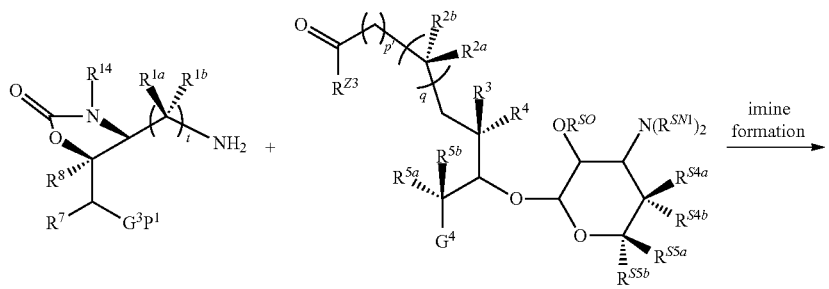

-continued

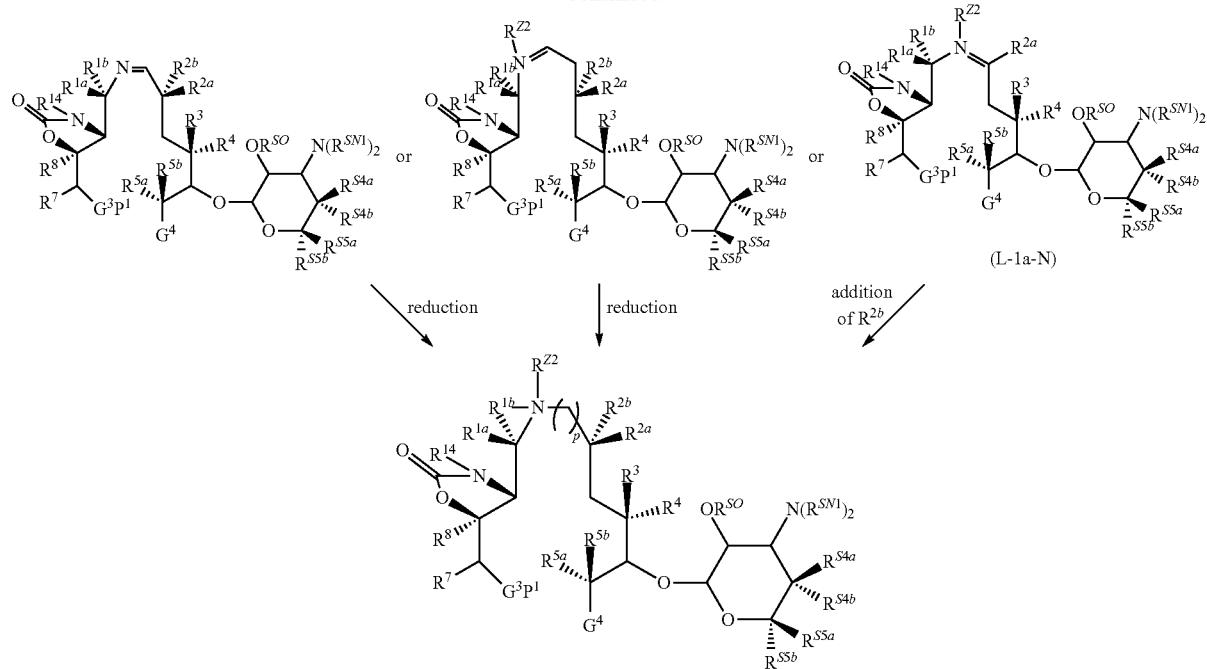

In certain embodiments, wherein $Y^{1a}$ is —NH$_2$, and $Y^{2}a$ is —C(=O)R$^Z$, coupling of the eastern and western halves by imine formation provides an imine, optionally followed by protection of the amine group by a non-hydrogen R$^{Z2}$, provides an imine according to Scheme 6a. In the case where q is 1 and p is 0 or 1, the imine may be reduced to give a compound of Formula (N), wherein Z is —NR$^{Z2}$—. In the case where q is 0 and p is 0, a compound of Formula (L-1a) is formed, wherein R$^{Z3}$ from the eastern half becomes R$^{2a}$. Addition of group R$^{2b}$ to this imine of Formula (L-1a) generates a compound of Formula (N), wherein Z is —NR$^{Z2}$. In certain embodiments, R$^{Z2}$ is hydrogen. In certain embodiments, R$^{Z2}$ is protected as methyl or a nitrogen protecting group. Analogous routes to compounds of Formula (N-N), wherein Z is —NR$^{Z2}$—, are shown below in Scheme 6a-N.

Scheme 6b.

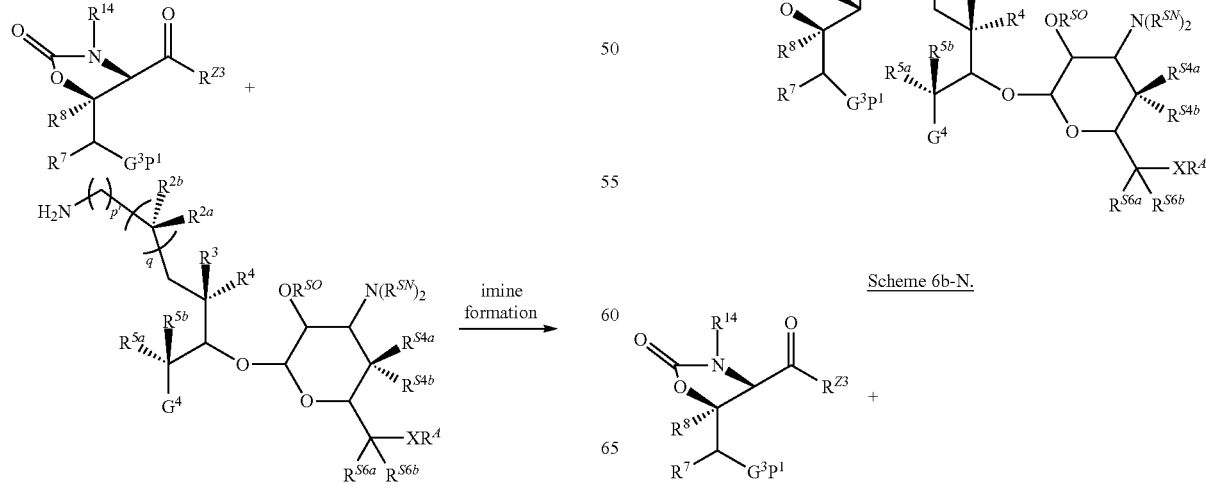

-continued

Scheme 6b-N.

133
-continued

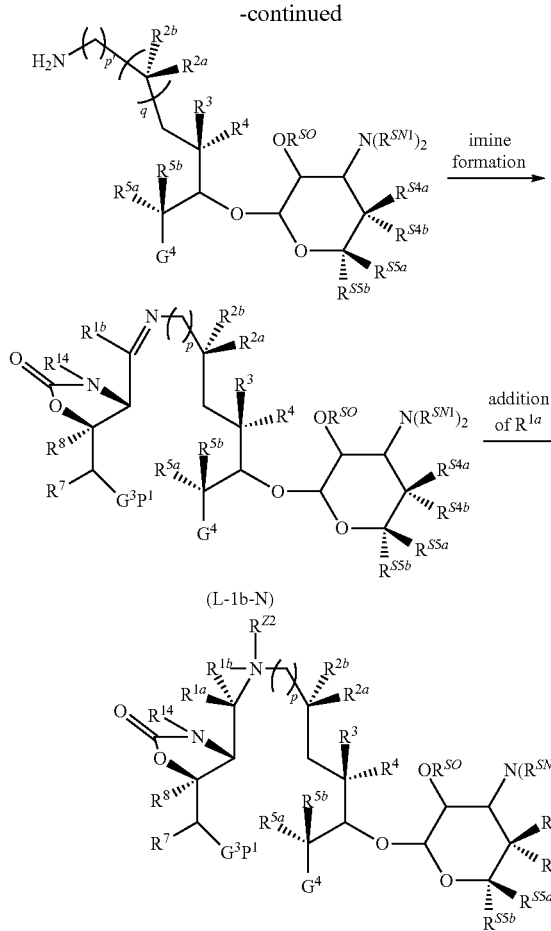

(L-1b-N)

Alternatively, in certain embodiments, wherein $Y^{2a}$ is —NH$_2$, and $Y^{1a}$ is —C(=O)R$^{Z3}$, coupling of the eastern and western halves by imine formation, optionally followed by protection of the amine group by a non-hydrogen $R^{Z2}$, provides an imine of Formula (L-1b) according to Scheme 6b. Addition of group $R^{1a}$ to this imine generates a compound of Formula (N), wherein Z is —NR$^{Z2}$—. In certain embodiments, $R^{Z2}$ is hydrogen. In certain embodiments, $R^{Z2}$ is protected as methyl or a nitrogen protecting group. An analogous route to compounds of Formula (N-N), wherein Z is —NR$^{Z2}$—, is shown in Scheme 6b-N.

Further contemplated are nitro-aldol reaction (Henry reaction) coupling products, and oxidized, reduced, and/or addition products formed therefrom. The nitro aldol reaction may be catalyzed or promoted by many different sets of conditions, e.g., use of an organic base, inorganic base, quaternary ammonium salt, and/or a catalyst; and use of protic or aprotic solvents and/or use of solventless conditions. See, e.g., Luzzio *Tetrahedron* (2001) 915-945, for a review of various conditions employed in a nitro aldol reaction.

Scheme 7a.

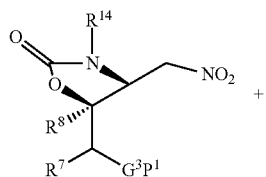 +

134
-continued

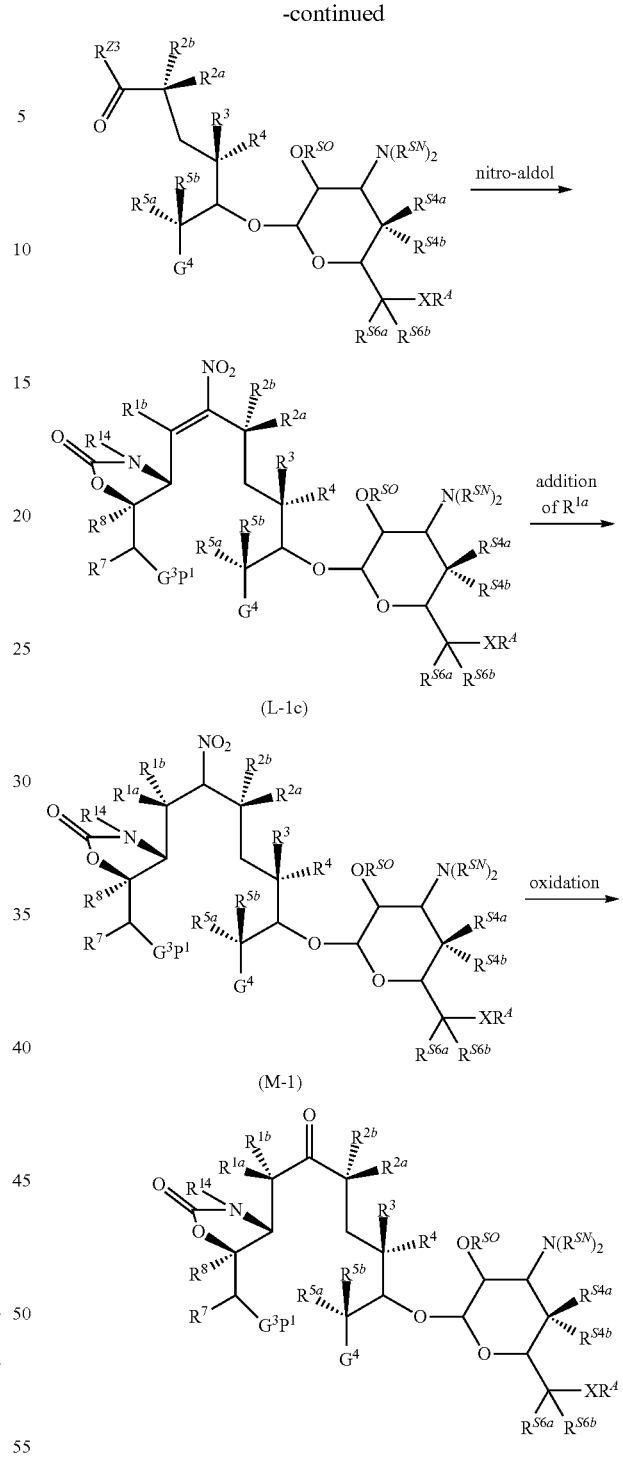

(M-1)

Scheme 7a-N.

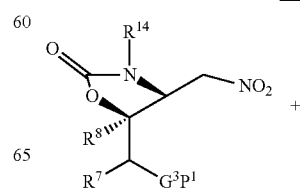 +

135

-continued

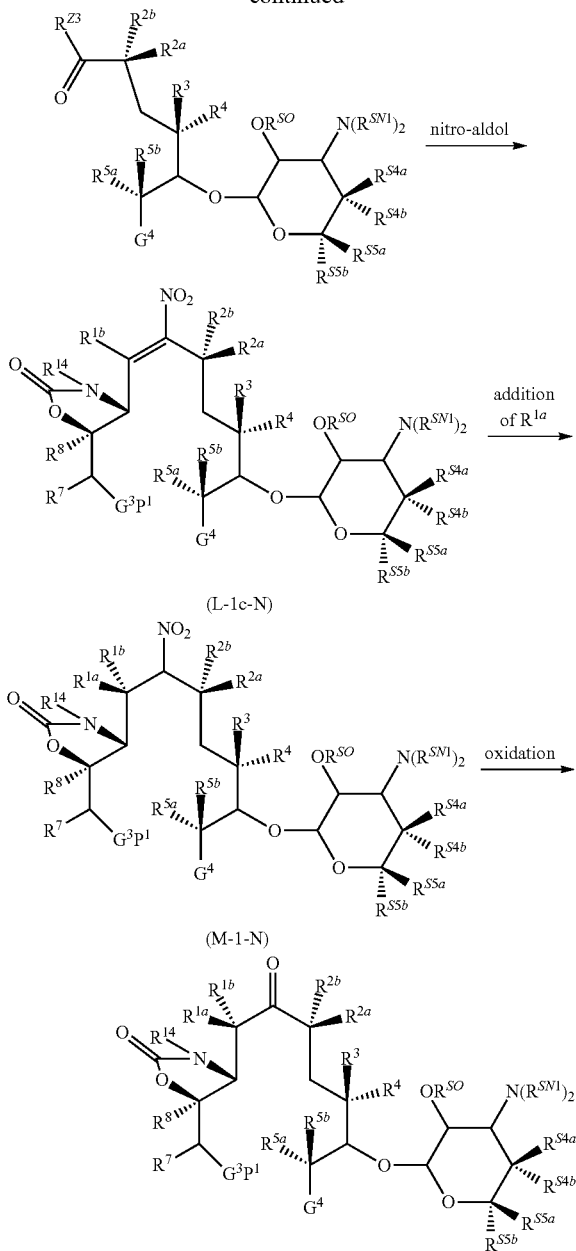

For example, in certain embodiments, wherein $Y^{1a}$ is —$CH_2NO_2$, and $Y^{2a}$ is —C(=O)$R^{Z3}$, coupling of the eastern and western halves provides a nitro alkene of Formula (L-1c) according to Scheme 7a. Addition of $R^{1a}$ to the alkene of Formula (L-1c), provides a nitro compound of Formula (M-1). Oxidation of the nitro group to a ketone yields a compound of Formula (N) wherein Z is —C(=O)—. An analogous route to compounds of Formula (N-N), wherein Z is —C(=O)—, is shown in Scheme 7a-N.

Scheme 7b.

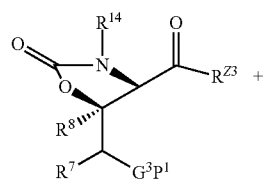

136

-continued

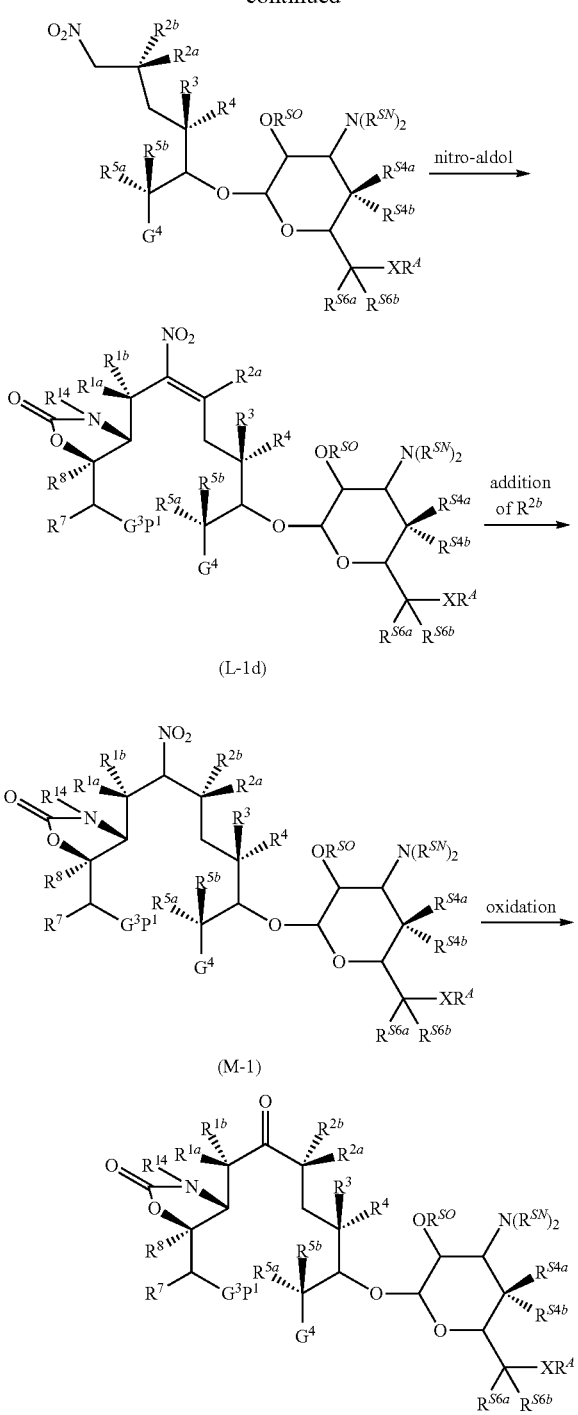

Scheme 7b-N.

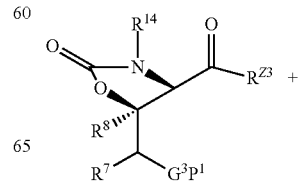

-continued

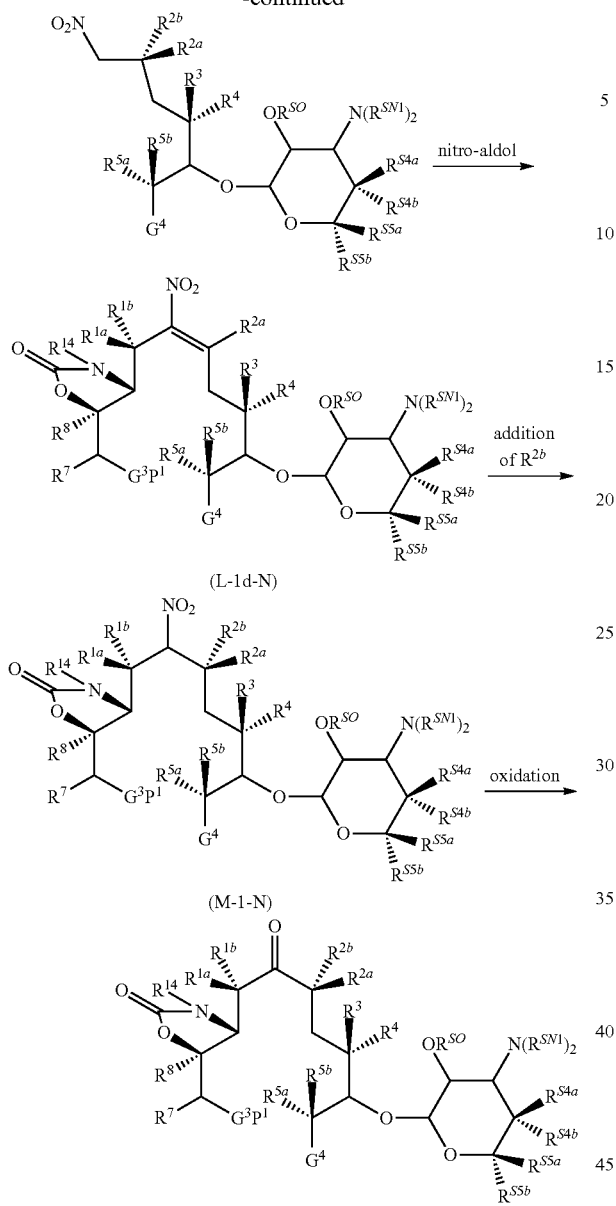

(L-1d-N)

(M-1-N)

Alternatively, in certain embodiments, wherein $Y^{2a}$ is —CH$_2$NO$_2$, and $Y^{1a}$ is —C(═O)R$^3$, coupling of the eastern and western halves provides a nitro alkene of Formula (L-1d) according to Scheme 7b. Addition of R$^{1a}$ to the alkene of Formula (L-1d), provides a nitro compound of Formula (M-1). Oxidation of the nitro group to a ketone yields a compound of Formula (N) wherein Z is —C(═O)—. An analogous route to compounds of Formula (N-N), wherein Z is —C(═O)—, is shown in Scheme 7b-N.

In certain embodiments, the coupling of the eastern and western halves is as depicted in Scheme 8, Scheme 8.

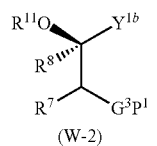

(W-2)

-continued

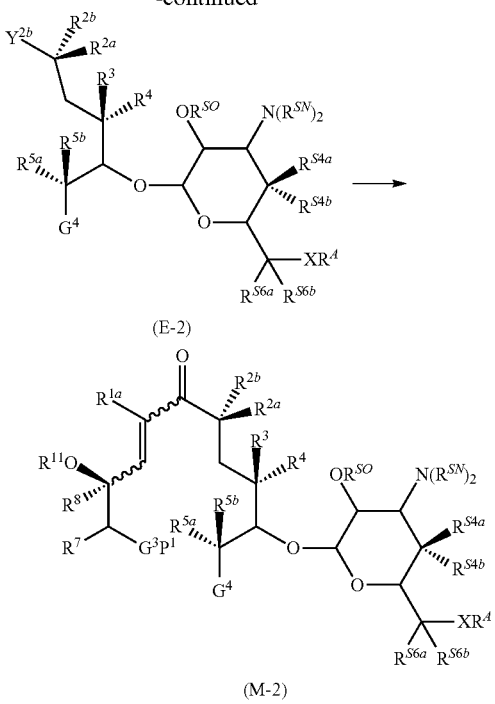

(E-2)

(M-2)

wherein the western half is a compound of Formula (W-2) and the eastern half is a compound of Formula (E-2), and wherein:

R$^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;

$Y^{1b}$ is —C(═O)R$^{Z3}$;

$Y^{2b}$ is —C(═O)CH═P(R$^{P1}$)(R$^{P2}$)(R$^{P3}$) or —C(═O)CH$_2$P(═O)(OR$^{P2}$)(OR$^{P3}$);

R$^{Z3}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each of R$^{P1}$, R$^{P2}$, and R$^{P3}$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl.

In certain embodiments, the coupling of the eastern and western halves is as depicted in Scheme 8-N, Scheme 8-N.

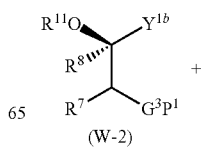

(W-2)

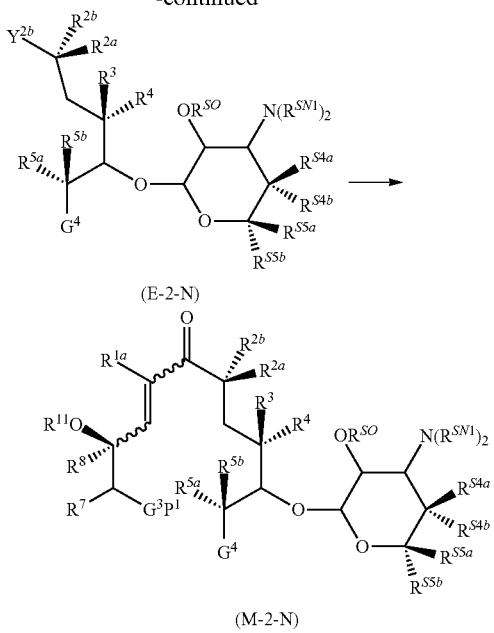

(E-2-N)

(M-2-N)

wherein the western half is a compound of Formula (W-2) and the eastern half is a compound of Formula (E-2-N), and wherein:

- $R^{11}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen protecting group;
- $Y^{1b}$ is —C(=O)R$^{Z3}$;
- $Y^{2b}$ is —C(=O)CH=P(R$^{P1}$)(R$^{P2}$)(R$^{P3}$) or —C(=O)CH$_2$P(=O)(OR$^{P2}$)(OR$^{P3}$);
- $R^{Z3}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;
- each of $R^{P1}$, $R^{P2}$, and $R^{P3}$ is independently optionally substituted alkyl, optionally substituted alkenyl, optionally substituted alkynyl, optionally substituted carbocyclyl, optionally substituted heterocyclyl, optionally substituted aryl, or optionally substituted heteroaryl.

Scheme 9.

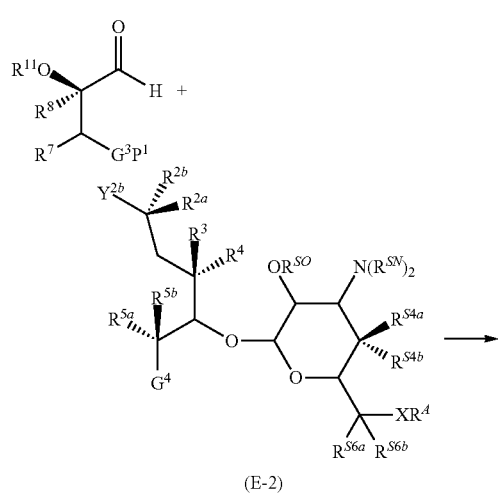

(E-2)

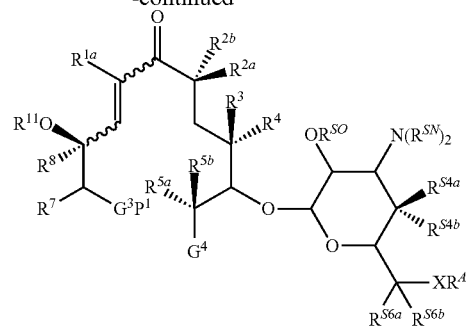

(M-2)

Scheme 9-N.

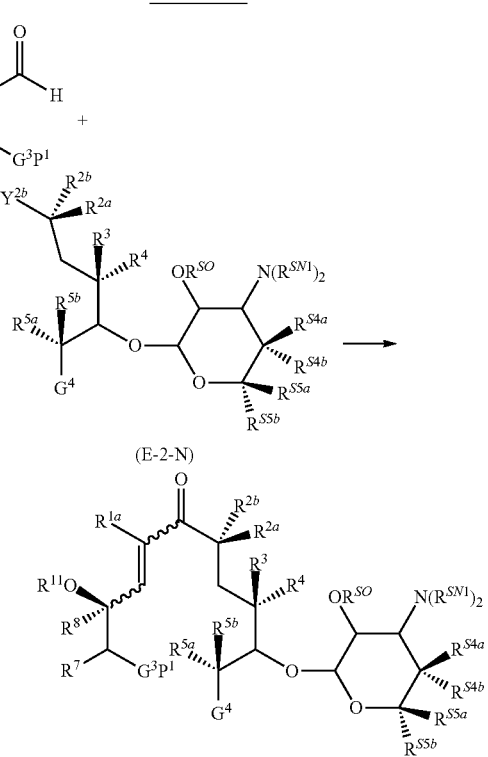

(E-2-N)

(M-2-N)

For example, in certain embodiments, when $Y^{1b}$ is —C(=O)R$^{Z3}$ and R$^{Z3}$ is hydrogen (i.e., wherein $Y^{1b}$ is —CHO) and $Y^{2b}$ is —C(=O)—CH=P(R$^{P1}$)(R$^{P2}$)(R$^{P3}$) or —C(=O)—CH$_2$—P(O)(OR$^{P2}$)(OR$^{P3}$), coupling of the eastern and western halves via a Wittig or Horner-Emmons reaction forms the moiety —CH=CH—C(=O)—, and provides an α,β-unsaturated ketone according to Scheme 9. In certain embodiments, the C=C double bond of the α,β-unsaturated ketone is provided in the cis-configuration. In certain embodiments, the C=C double bond of the α,β-unsaturated ketone is provided in the trans-configuration. An analogous route to compounds of Formula (M-2-N) is shown in Scheme 9-N.

The cyclic carbamate, installed prior to macrocyclization (see, e.g., Scheme 10a or Scheme 10a-N) or after macrocyclization (See, e.g., Scheme 10b or Scheme 10b-N), may be formed via Michael addition of the amine NH$_2$R$^{14}$ to the α,β-unsaturated keto moiety, followed by reaction of the attached amino group —NHR$^{14}$ and vicinal hydroxyl group (i.e., R$^{11}$ is hydrogen) with reagent LG-C(=O)-LG, wherein each LG is a leaving group as defined herein (e.g., chloro), substituted hydroxyl (e.g., to provide a carbonate ester), substituted thiol, substituted amino (e.g., imidazolyl). In certain embodiments, the free hydroxyl group is first treated with reagent LG-C(=O)-LG, following which an amine of $NH_2R^{14}$ is added, leading to initial formation of an acyclic carbamate prior to conjugate addition of the intermediate —$NHR^{14}$ group to the unsaturated ketone.

Scheme 10a.

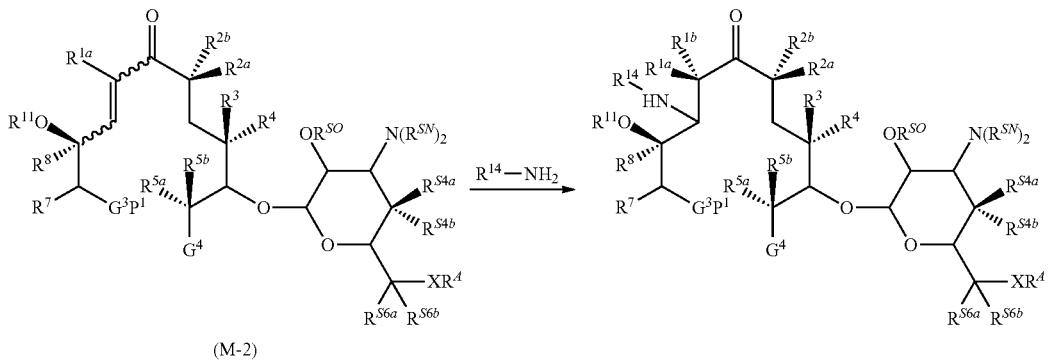

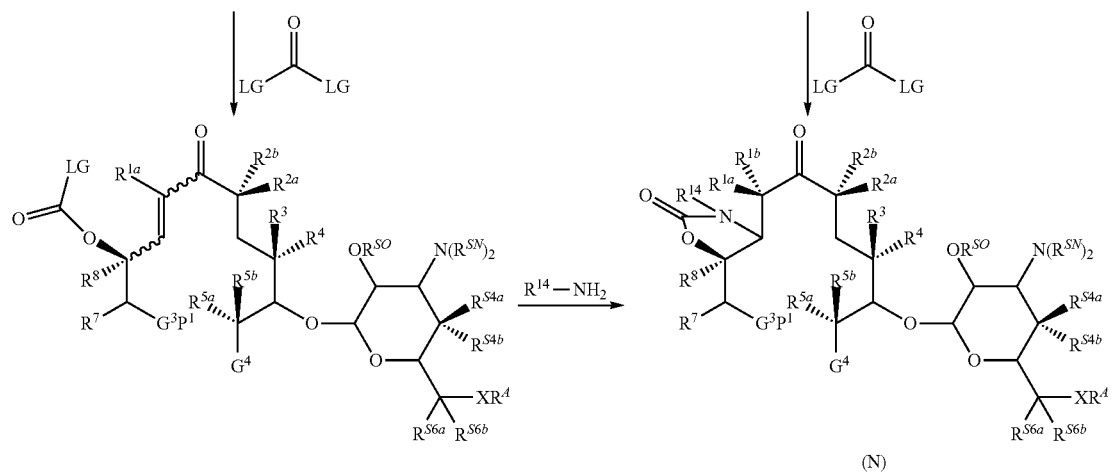

Scheme 10a-N.

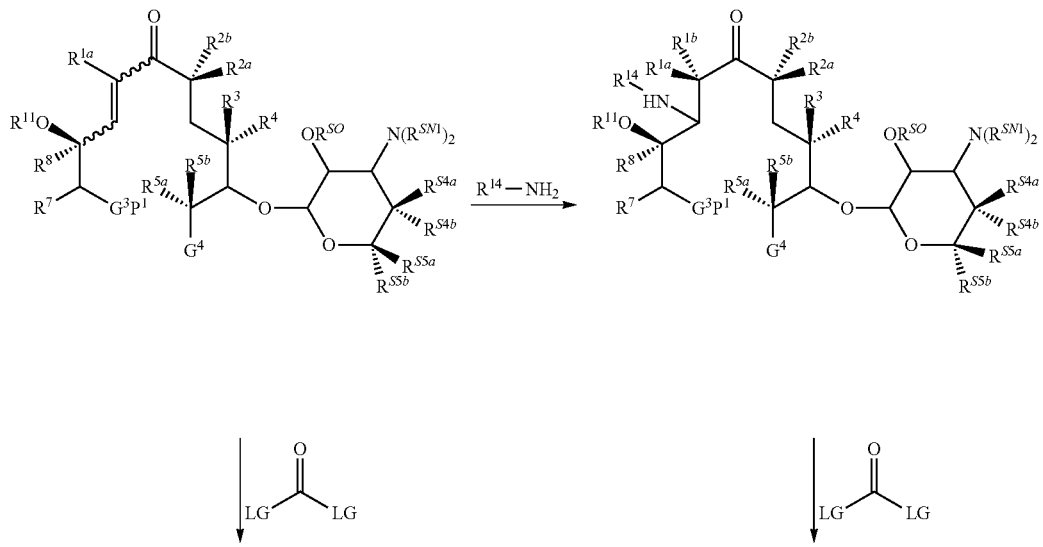

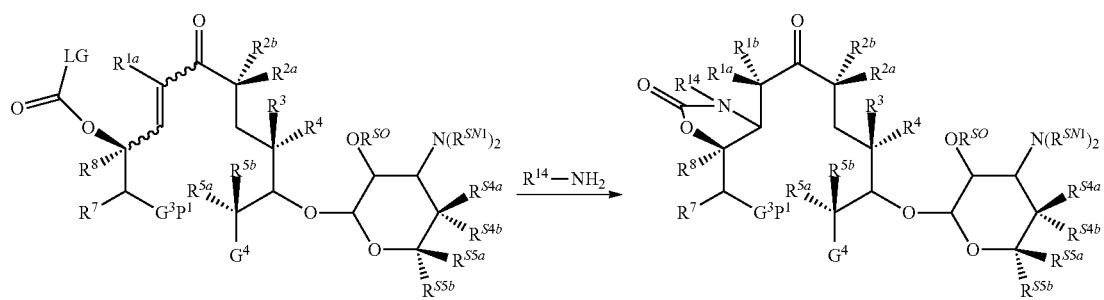
Scheme 10b.
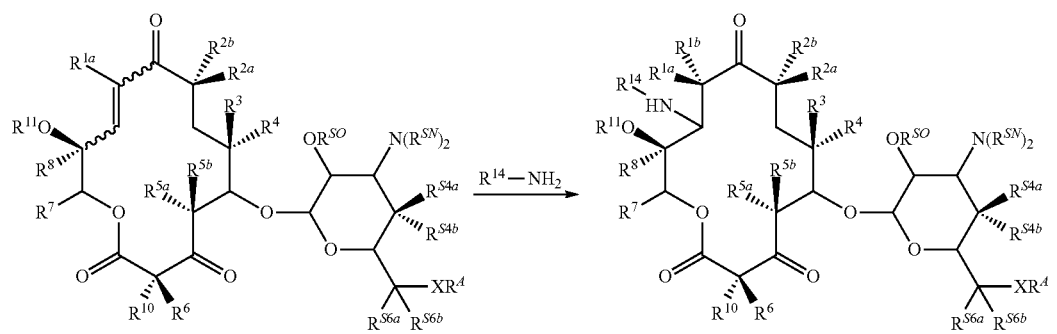
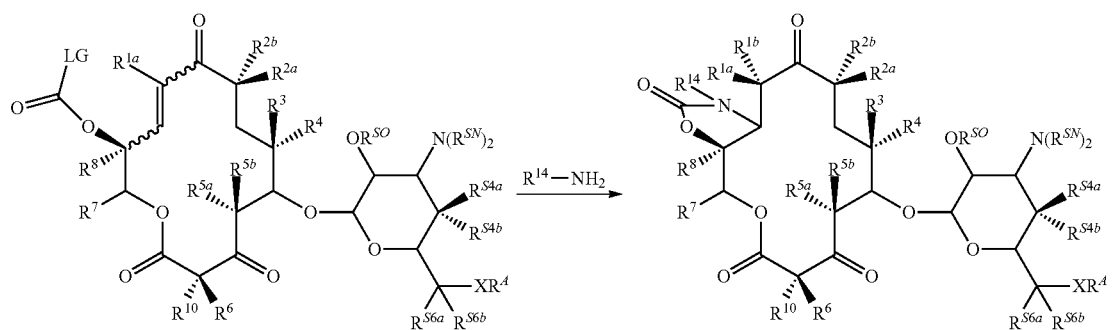

Scheme 10b-N.

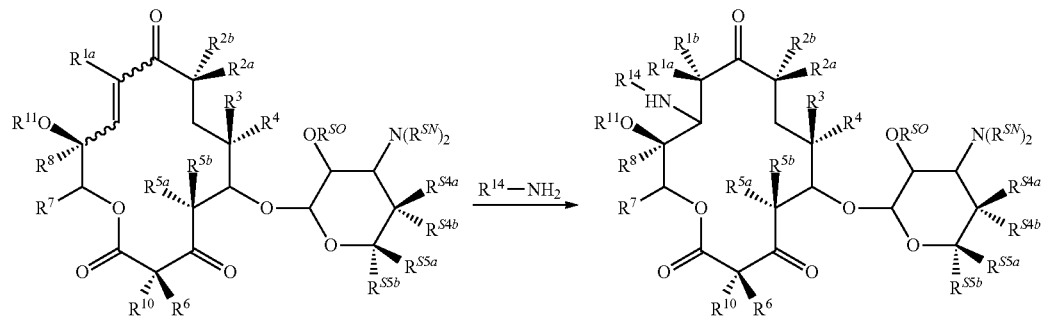

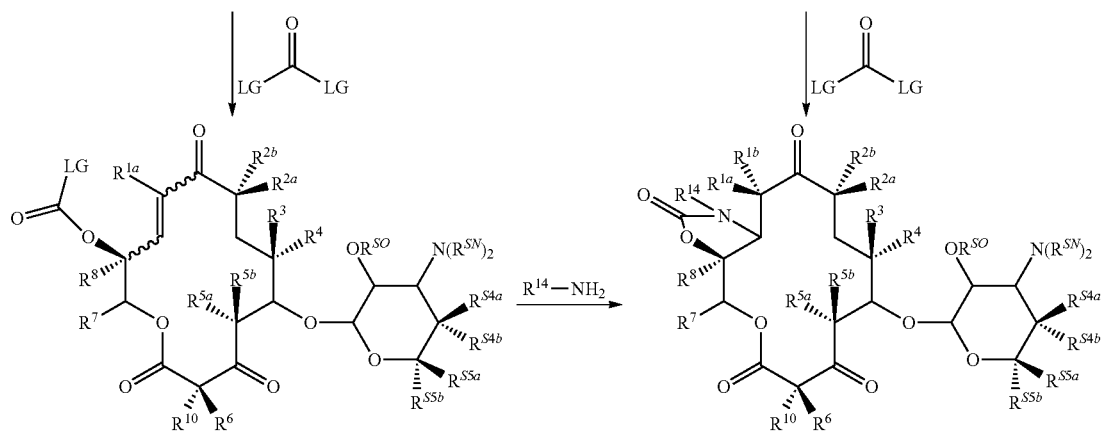

Alternatively, the cyclic carbamate, installed prior to macrocyclization (see, e.g., Scheme 11a or Scheme 11a-N) or after macrocyclization (see, e.g., Scheme 11b or Scheme 11b-N), may be formed via reaction of the free hydroxyl group (i.e., $R^{11}$ is hydrogen) with an isocyanate reagent O=C=N—$R^{14}$ or amide LG-C(=O)NH—$R^{14}$, followed by conjugate addition of the intermediate —$NHR^{14}$ group to the unsaturated ketone. In certain embodiments, the isocyanate reacts with the free hydroxyl group and —$NHR^{14}$ undergoes the conjugate addition reaction in a single step. In certain embodiments, the intermediate acyclic carbamate is isolated. In certain embodiments, base is added to the isolated acyclic carbamate to promote the conjugate addition reaction.

-continued

Scheme 11a

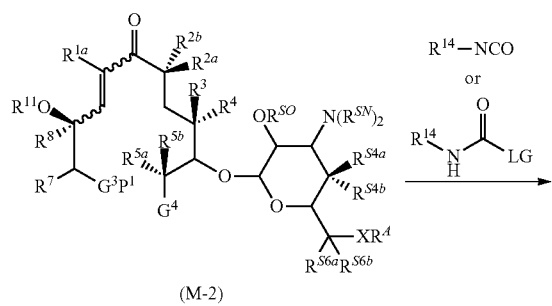

Scheme 11a-N

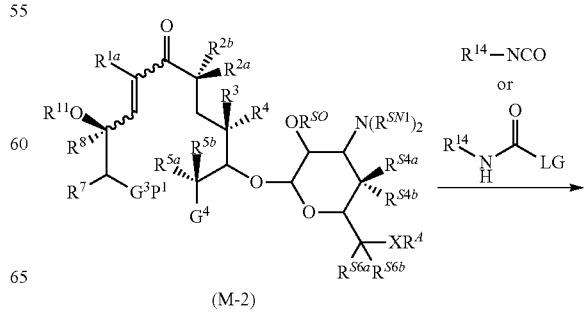

-continued

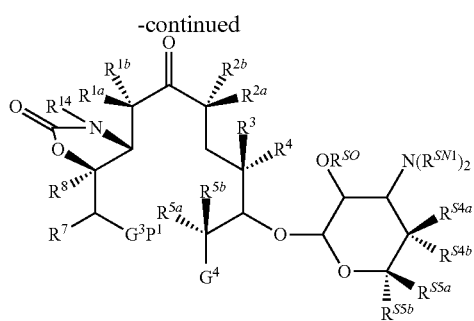

Scheme 11b

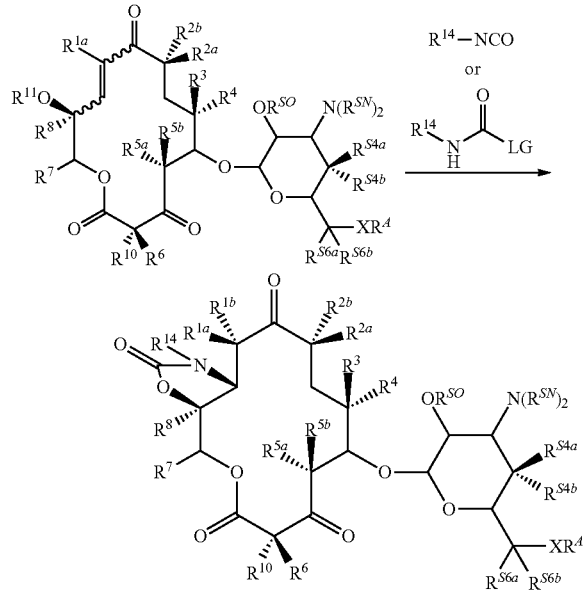

Scheme 11b-N

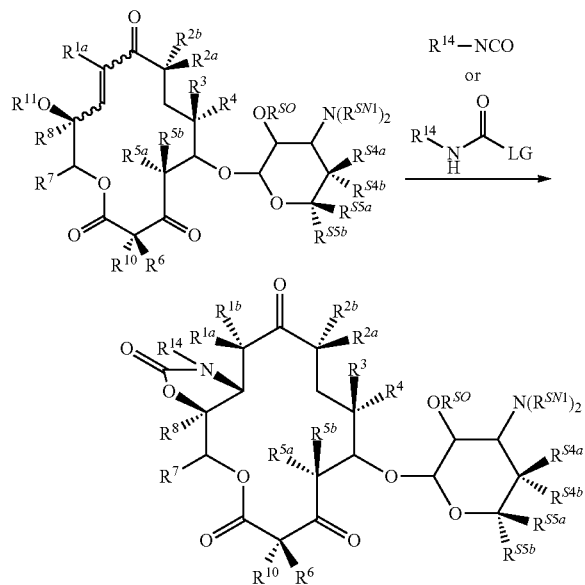

Various macrolides may be accessed from these coupled products of Formula (N) and Formula (N-N), depending upon the nature of the group $G^4$, upon macrocyclization. For example, as depicted in Scheme 12, when $G^2$ is a group of formula:

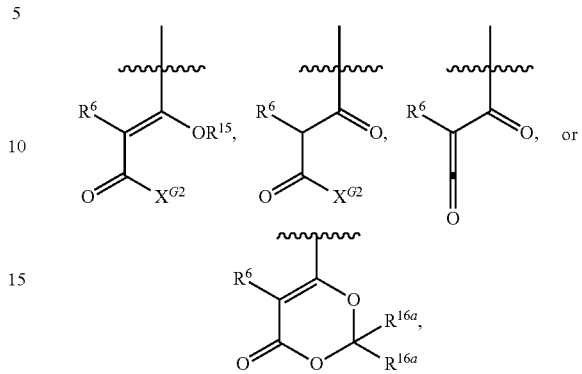

and $R^6$ is a hydrogen or non-hydrogen group, macrocyclization of the compound of Formula (N), e.g., wherein $P^1$ is hydrogen, provides a macrolide with one hydrogen substituent at C2. Enolization of the macrolide, followed by addition of a non-hydrogen group $R^{10}$ (e.g., with a base and an $R^{10}$ alkylating agent, e.g., $R^{10}$-LG, or with a halogenating agent if $R^{10}$ is halogen), provides a macrolide of Formula (I), wherein $R^{10}$ is a non-hydrogen group.

In other embodiments, as depicted in Scheme 12b, when $G^2$ is a group of formula:

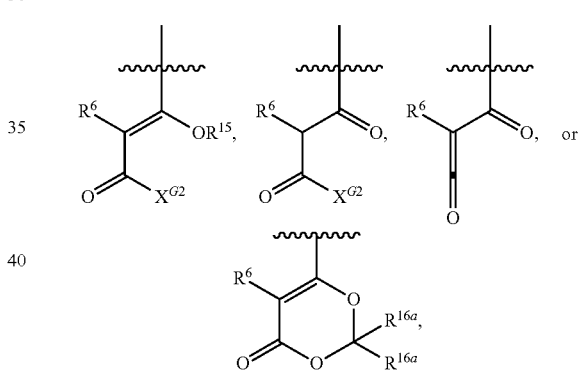

and $R^6$ is a hydrogen or non-hydrogen group, macrocyclization of the compound of Formula (N-N), e.g., wherein $P^1$ is hydrogen, provides a macrolide with one hydrogen substituent at C2. Enolization of the macrolide, followed by addition of a non-hydrogen group $R^{10}$ (e.g., with a base and an $R^{10}$ alkylating agent, e.g., $R^{10}$-LG, or with a halogenating agent if $R^{10}$ is halogen), provides a macrolide of Formula (I-N), wherein $R^{10}$ is a non-hydrogen group.

Scheme 12.

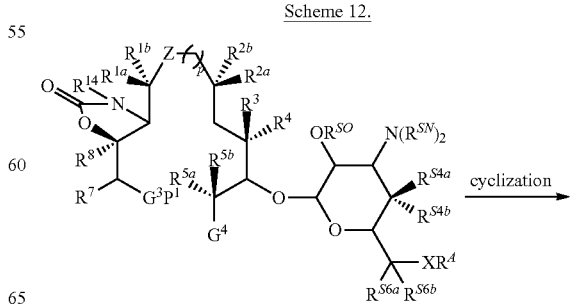

(N)

-continued

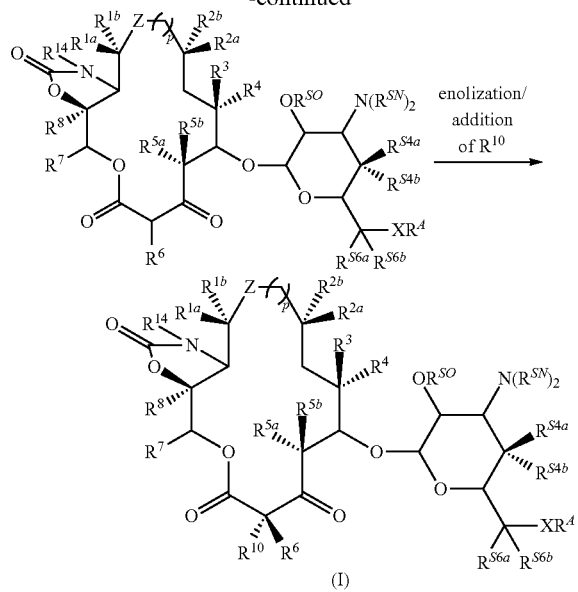

Scheme 12-N.

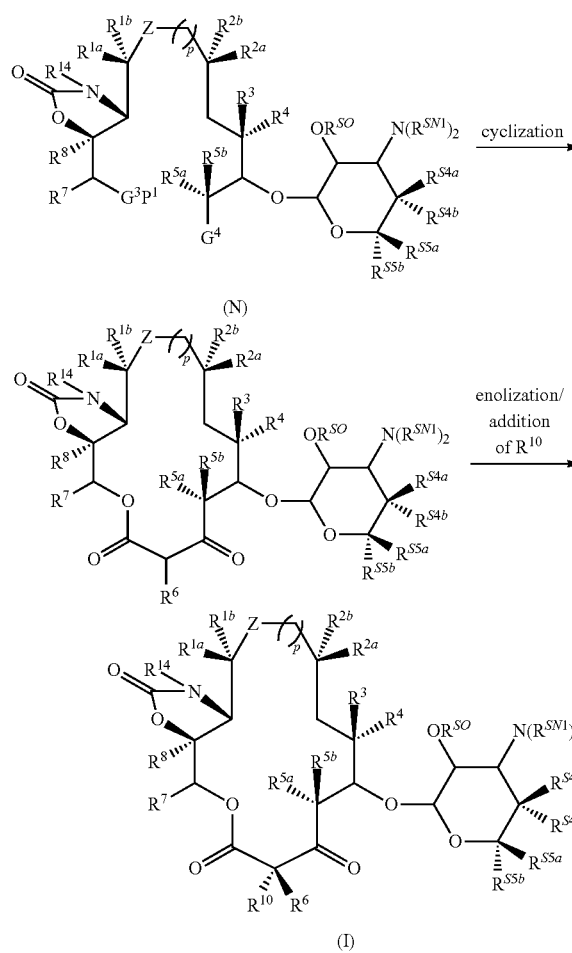

Alternatively, as depicted in Scheme 13, when G² is a group of formula:

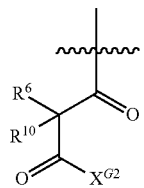

and wherein each of $R^6$ and $R^{10}$ is a hydrogen or non-hydrogen group, macrocyclization of the compound of Formula (N) e.g., wherein $P^1$ is hydrogen, provides a macrolide of Formula (I).

Scheme 13.

In other embodiments, as depicted in Scheme 13-N, when G² is a group of formula:

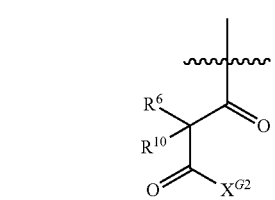

and wherein each of $R^6$ and $R^{10}$ is a hydrogen or non-hydrogen group, macrocyclization of the compound of Formula (N-N) e.g., wherein $P^1$ is hydrogen, provides a macrolide of Formula (I-N).

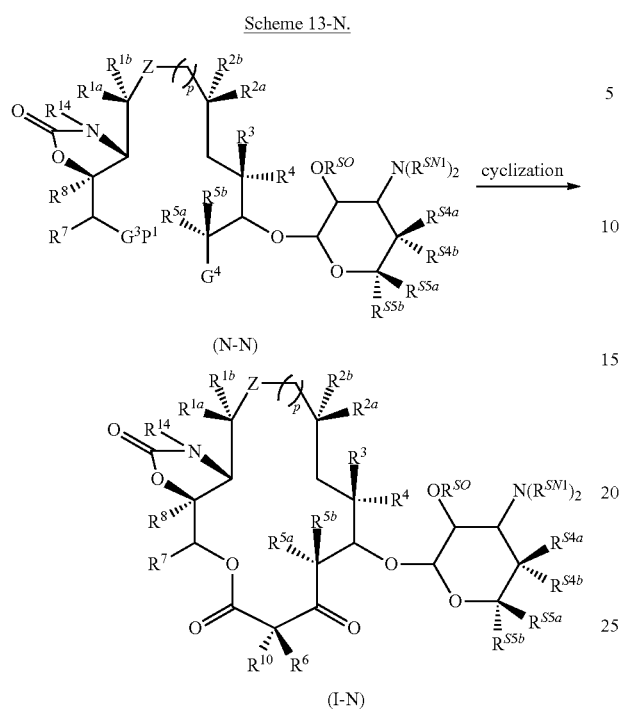

Scheme 13-N.

(N-N)

(I-N)

The modified sugar is typically attached to the macrolide framework during synthesis of the eastern half, but may also be attached at other stages of the preparation. The sugar may be attached by a glycosylation reaction between the hydroxyl group at the C5 position and a suitable glycosyl donor as exemplified in Scheme 14. Typical glycosyl donors have a leaving group attached to the anomeric carbon. Exemplary groups for the anomeric leaving group include halogens, thioethers, acetamidates, acetate, phosphates, and O-pentenyl. A thioglycoside is sugar with a thioether group at the anomeric carbon of the sugar. In certain embodiments, the modified sugar moiety is attached to the macrolide framework as a thioglycoside. In certain embodiments, substituents of the sugar may be modified after glycosylation of the macrolide or macrolide precursor (e.g., eastern half). In certain embodiments, the sugar is not further modified after glycosylation of the macrolide or macrolide precursor.

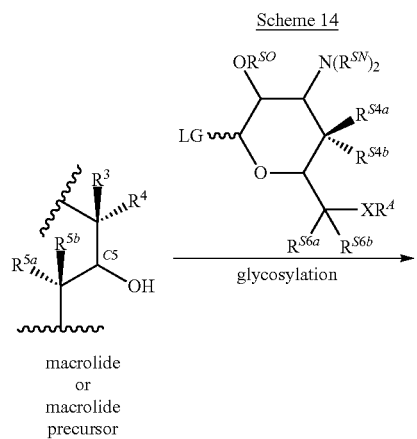

Scheme 14 macrolide or macrolide precursor

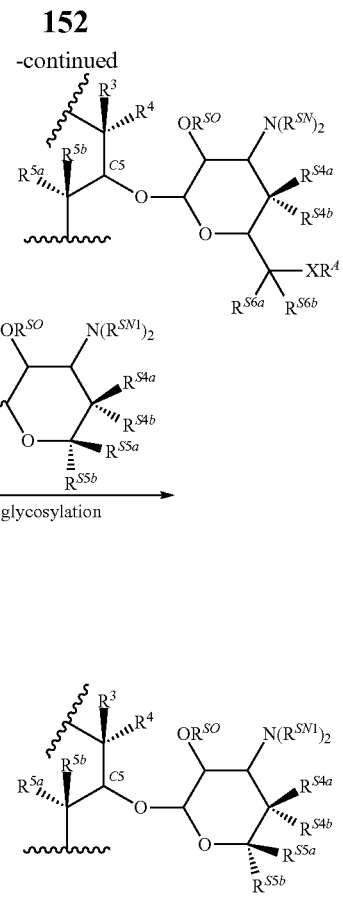

macrolide or macrolide precursor

Pharmaceutical Compositions and Administration

The present invention provides pharmaceutical compositions comprising a macrolide as described herein, or a pharmaceutically acceptable salt thereof, and a pharmaceutically acceptable excipient.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy,* 21st Edition (Lippincott Williams & Wilkins, 2005).

Pharmaceutical compositions described herein can be prepared by any method known in the art of pharmacology. In general, such preparatory methods include the steps of bringing the macrolide of the present invention into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the macrolide of the present invention. The amount of the macrolide is generally equal to the dosage of the macrolide which would be administered to a subject and/or a convenient fraction of such a dosage such as, for example, one-half or one-third of such a dosage.

Relative amounts of the macrolide, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) macrolide.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Liquid dosage forms for oral and parenteral administration include pharmaceutically acceptable emulsions, microemulsions, solutions, suspensions, syrups and elixirs. In addition to the macrolides, the liquid dosage forms may comprise inert diluents commonly used in the art such as, for example, water or other solvents, solubilizing agents, and emulsifiers, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium.

Solid dosage forms for oral administration include capsules, tablets, pills, powders, and granules. In such solid dosage forms, the macrolide is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Dosage forms for topical and/or transdermal administration of a macrolide of this invention may include ointments, pastes, creams, lotions, gels, powders, solutions, sprays, inhalants and/or patches. Generally, the macrolide is admixed under sterile conditions with a pharmaceutically acceptable carrier and/or any needed preservatives and/or buffers as can be required.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Macrolides provided herein are typically formulated in dosage unit form for ease of administration and uniformity of dosage. It will be understood, however, that the total daily amount of the macrolide will be decided by the attending physician within the scope of sound medical judgment. The specific therapeutically effective dose level for any particular subject will depend upon a variety of factors including the disease, disorder, or condition being treated and the severity of the disorder; the activity of the specific macrolide employed; the specific composition employed; the age, body weight, general health, sex and diet of the subject; the time of administration, route of administration, and rate of excretion of the specific macrolide employed; the duration of the treatment; drugs used in combination or coincidental with the specific macrolide employed; and like factors well known in the medical arts.

The macrolides and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. In general the most appropriate route of administration will depend upon a variety of factors including the nature of the agent, the therapeutic regimen, and/or the condition of the subject. Oral administration is the preferred mode of administration. However, in certain embodiments, the subject may not be in a condition to tolerate oral administration, and thus intravenous, intramuscular, and/or rectal administration are also preferred alternative modes of administration.

An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein.

It will be also appreciated that a macrolide or composition, as described herein, can be administered in combination with one or more additional therapeutically active agents. The macrolide or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive macrolide with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutically agent is an antibiotic. Exemplary antibiotics include, but are not limited to, penicillins (e.g., penicillin, amoxicillin), cephalosporins (e.g., cephalexin), macrolides (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, and quinupristin/dalfoprisin (Syndercid™).

Also encompassed by the invention are kits (e.g., pharmaceutical packs). The kits provided may comprise an inventive pharmaceutical composition or macrolide and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or macrolide. In some embodiments, the inventive pharmaceutical composition or macrolide provided in the container and the second container are combined to form one unit dosage form.

Methods of Treatment and Uses

The present invention contemplates using macrolides of the present invention for the treatment of infectious diseases, for example, fungal, bacterial, viral, or parasitic infections, and for the treatment of inflammatory conditions. Ketolides are known to exhibit anti-bacterial activity as well as anti-parasitic activity. See, for example, Clark et al., *Bioorganic & Medicinal Chemistry Letters* (2000) 10:815-819 (anti-bacterial activity); and Lee et al., *J. Med. Chem.* (2011) 54:2792-2804 (anti-bacterial and anti-parasitic activity). Ketolides are also known to exhibit an anti-inflammatory effect. See, for example, Amsden, *Journal of Antimicrobial Chemotherapy* (2005) 55:10-21 (chronic pulmonary inflammatory syndromes).

Thus, as generally described herein, provided is a method of treating a infectious disease comprising administering an effective amount of a macrolide of the present invention, or a pharmaceutically acceptable salt thereof, to a subject in need thereof. Such a method can be conducted in vivo (i.e., by administration to a subject) or in vitro (e.g., upon contact with the pathogen, tissue, or cell culture). Treating, as used herein, encompasses therapeutic treatment and prophylactic treatment.

In certain embodiments, the effective amount is a therapeutically effective amount. For example, in certain embodiments, the method slows the progress of an infectious disease in the subject. In certain embodiments, the method improves the condition of the subject suffering from an infectious disease. In certain embodiments, the subject has a suspected or confirmed infectious disease.

In certain embodiments, the effective amount is a prophylatically effective amount. For example, in certain embodiments, the method prevents or reduces the likelihood of an infectious disease, e.g., in certain embodiments, the method comprises administering a macrolide of the present invention to a subject in need thereof in an amount sufficient to prevent or reduce the likelihood of an infectious disease. In certain embodiments, the subject is at risk of an infectious disease (e.g., has been exposed to another subject who has a suspected or confirmed infectious disease or has been exposed or thought to be exposed to a pathogen).

In another aspect, provided is an in vitro method of inhibiting pathogenic growth comprising contacting an effective amount of the macrolide of the present invention with a pathogen (e.g., a bacteria, virus, fungus, or parasite) in a cell culture.

As used herein, "infectious disease" and "microbial infection" are used interchangeably, and refer to an infection with a pathogen, such as a fungus, bacteria, virus, or a parasite. In certain embodiments, the infectious disease is caused by a pathogen resistant to other treatments. In certain embodiments, the infectious disease is caused by a pathogen that is multi-drug tolerant or resistant, e.g., the infectious disease is caused by a pathogen that neither grows nor dies in the presence of or as a result of other treatments.

In certain embodiments, the infectious disease is a bacterial infection. For example, in certain embodiments, provided is a method of treating a bacterial infection comprising administering an effective amount of a macrolide of the present invention, or a pharmaceutically acceptable salt thereof, to a subject in need thereof.

In certain embodiments, the macrolide has a mean inhibitory concentration (MIC), with respect to a particular bacteria, of less than 50 µg/mL, less than 25 µg/mL, less than 20 µg/mL, less than 10 µg/mL, less than 5 µg/mL, or less than 1 µg/mL.

In certain embodiments, the bacteria is susceptible (e.g., responds to) or resistant to known commercial macrolides, such as azithromycin, clindamycin, telithromycin, erythromycin, spiramycin, and the like. In certain embodiments, the bacteria is resistant to a known macrolide. For example, in certain embodiments, the bacteria is erythromycin resistant (ER).

In certain embodiments, the bacterial infection is resistant to other antibiotics (e.g., non-macrolide) therapy. For example, in certain embodiments, the pathogen is vancomycin resistant (VR). In certain embodiments, the pathogen is a methicillin-resistant (MR), e.g., in certain embodiments, the bacterial infection is an methicillin-resistant *S. aureus* infection (a MRSA infection).

In certain embodiments, the bacteria has an efflux (e.g., mef, msr) genotype. In certain embodiments, the bacteria has a methylase (e.g., erm) genotype. In certain embodiments, the bacteria has a constitutive genotype. In certain embodiments, the bacteria has an inducible genotype.

Exemplary bacterial infections include, but are not limited to, infections with a Gram positive bacteria (e.g., of the phylum Actinobacteria, phylum Firmicutes, or phylum Tenericutes); Gram negative bacteria (e.g., of the phylum Aquificae, phylum Deinococcus-*Thermus*, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacterial infection is an infection with a Gram positive bacteria.

In certain embodiments, the Gram positive bacteria is a bacteria of the phylum Firmicutes.

In certain embodiments, the bacteria is a member of the phylum Firmicutes and the genus *Enterococcus*, i.e., the bacterial infection is an *Enterococcus* infection. Exemplary Enterococci bacteria include, but are not limited to, *E. avium, E. durans, E. faecalis, E. faecium, E. gallinarum, E. solitarius, E. casseliflavus,* and *E. raffinosus*.

In certain embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri,* and *S. xylosus*. In certain embodiments, the *Staphylococcus* infection is an *S. aureus* infection. In certain embodiments, the *S. aureus* has an efflux (e.g., mef, msr) genotype. In certain embodiments, the *S. aureus* has a methylase (e.g., erm) genotype.

In certain embodiments, the bacteria is a member of the phylum Firmicutes and the genus *Bacillus*, i.e., the bacterial infection is a *Bacillus* infection. Exemplary *Bacillus* bacteria include, but are not limited to, *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulans, B. coagulans, B. firmus, B. flavothermus, B. fusiformis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis,* and *B. weihenstephanensis*. In certain embodiments, the *Bacillus* infection is a *B. subtilis* infection. In certain embodiments, the *B. subtilis* has an efflux (e.g., mef, msr) genotype. In certain embodiments, the *B. subtilis* has a methylase (e.g., erm) genotype.

In certain embodiments, the bacteria is a member of the phylum Firmicutes and the genus Strepococcus, i.e., the bacterial infection is a Strepococcus infection. Exemplary Strepococcus bacteria include, but are not limited to, *S. agalactiae, S. anginosus, S. bovis, S. canis, S. constellatus, S. dysgalactiae, S. equinus, S. iniae, S. intermedius, S. mitis, S. mutans, S. oralis, S. parasanguinis, S. peroris, S. pneumoniae, S. pyogenes, S. ratti, S. salivarius, S. thermophilus, S. sanguinis, S. sobrinus, S. suis, S. uberis, S. vestibularis, S. viridans,* and *S. zooepidemicus*. In certain embodiments, the Strepococcus infection is an *S. pyogenes* infection. In certain embodiments, the Strepococcus infection is an *S. pneumoniae* infection. In certain embodiments, the *S. pneumoniae* has an efflux (e.g., mef, msr) genotype. In certain embodiments, the *S. pneumoniae* has a methylase (e.g., erm) genotype.

In certain embodiments, the bacterial infection is an infection with a Gram negative bacteria.

In certain embodiments, the Gram negative bacteria is a bacteria of the phylum Proteobacteria and the genus *Escherichia*. i.e., the bacterial infection is an *Escherichia* infection. Exemplary *Escherichia* bacteria include, but are not limited to, *E. albertii, E. blattae, E. coli, E. fergusonii, E. hermannii,* and *E. vulneris*. In certain embodiments, the *Escherichia* infection is an *E. coli* infection.

In certain embodiments, the Gram negative bacteria is a bacteria of the phylum Proteobacteria and the genus *Haemophilus*. i.e., the bacterial infection is an *Haemophilus* infection. Exemplary *Haemophilus* bacteria include, but are not limited to, *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis,* and *H. somnus*. In certain embodiments, the *Escherichia* infection is an *H. influenzae* infection.

In certain embodiments, the bacteria is an atypical bacteria, i.e., are neither Gram positive nor Gram negative.

In certain embodiments, the infectious disease is an infection with a parasitic infection. Thus, in certain embodiments, provided is a method of treating a parasitic infection comprising administering an effective amount of a macrolide of the present invention, or a pharmaceutically acceptable salt thereof, to a subject in need thereof.

In certain embodiments, the macrolide has a $IC_{50}$ (uM) with respect to a particular parasite, of less than 50 uM, less than 25 uM, less than 20 uM, less than 10 uM, less than 5 uM, or less than 1 uM.

Exemplary parasites include, but are not limited to, *Trypanosoma* spp. (e.g., *Trypanosoma cruzi, Trypansosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp. (e.g., *P. flaciparum*),

*Crytosporidium* spp., *Isospora* spp., *Balantidium* spp., *Loa Loa*, *Ascaris lumbricoides*, *Dirofilaria immitis*, and *Toxoplasma* ssp. (e.g. *T. gondii*).

As generally described herein, the present invention further a method of treating an inflammatory condition comprising administering an effective amount of a macrolide of the present invention, or a pharmaceutically acceptable salt thereof, to a subject in need thereof. Such a method can be conducted in vivo (i.e., by administration to a subject) or in vitro (e.g., upon contact with the pathogen, tissue, or cell culture). Treating, as used herein, encompasses therapeutic treatment and prophylactic treatment.

In certain embodiments, the effective amount is a therapeutically effective amount. For example, in certain embodiments, the method slows the progress of an inflammatory condition in the subject. In certain embodiments, the method improves the condition of the subject suffering from an inflammatory condition. In certain embodiments, the subject has a suspected or confirmed inflammatory condition.

In certain embodiments, the effective amount is a prophylatically effective amount. For example, in certain embodiments, the method prevents or reduces the likelihood of an inflammatory condition, e.g., in certain embodiments, the method comprises administering a macrolide of the present invention to a subject in need thereof in an amount sufficient to prevent or reduce the likelihood of an inflammatory condition. In certain embodiments, the subject is at risk to an inflammatory condition.

In another aspect, provided is an in vitro method of treating an inflammatory condition comprising contacting an effective amount of the macrolide of the present invention with an inflammatory cell culture.

The term "inflammatory condition" refers to those diseases, disorders, or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent). Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory conditions include, but are not limited to, chronic pulmonary inflammatory syndromes (e.g., diffuse panbronchiolitis, cystic fibrosis, asthma, bronchiectasis, chronic obstructive pulmonary disease).

In certain embodiments, the inflammatory condition is an acute inflammatory condition (e.g., for example, inflammation resulting from an infection). In certain embodiments, the inflammatory condition is a chronic inflammatory condition. In certain embodiments, the inflammatory condition is inflammation associated with cancer.

Definitions

Chemical Terms

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

In a formula, ⁓ is a single bond where the stereochemistry of the moieties immediately attached thereto is not specified, - - - is absent or a single bond, and ═ or ≡ is a single or double bond.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, or the replacement of $^{12}$C with $^{13}$C or $^{14}$C are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). Examples of haloalkyl groups include —$CF_3$, —$CF_2CF_3$, —$CF_2CF_2CF_3$, —$CCl_3$, —$CFCl_2$, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$alkyl"). In some embodiments, a heteroalkyl group is a saturated group having 1 to 4 carbon atoms and 1 or 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C=C double bond for which the stereochemistry is not specified (e.g., —CH=CHCH_3 or

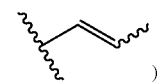

)

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("heteroC$_{2-7}$ alkenyl"). In some embodiments, a heteroalkenyl group has 2 to 6 carbon atoms, at least one double bond, and 1 or more heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and 1 or 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and 1 or 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" refers to a radical of a non-aromatic cyclic hydrocarbon group having from 3 to 14 ring carbon atoms ("C$_{3-14}$ carbocyclyl") and zero heteroatoms in the non-aromatic ring system. In some embodiments, a carbocyclyl group has 3 to 10 ring carbon atoms ("C$_{3-10}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 4 to 6 ring carbon atoms ("C$_{4-6}$ carbocyclyl"). In some embodiments, a carbocyclyl group has 5 to 6 ring carbon atoms ("C$_{5-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 n electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety. The invention is not intended to be limited in any manner by the exemplary substituents described herein.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$a, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$; each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ee}$)$_2$, —SO$_2$R$^{ee}$, —SO$_2$R$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C6-10 aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$ ($C_{1-6}$ alkyl), —NHC(=O)N($C_{1-6}$ alkyl)$_2$, —NHC(=O)NH ($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)$_2$($C_{1-6}$ alkyl), —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

The term "amino" refers to the group —NH$_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

The term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3^+$X$^-$ wherein R$^{bb}$ and X$^-$ are as defined herein.

The term "sulfonyl" refers to a group selected from —SO$_2$N(R$^{bb}$)$_2$, —SO$_2$R$^{aa}$, and —SO$_2$OR$^{aa}$, wherein R$^{aa}$ and R$^{bb}$ are as defined herein.

The term "sulfinyl" refers to the group —S(=O)R$^{aa}$, wherein R$^{aa}$ is as defined herein.

The term "acyl" refers to a group having the general formula —C(=O)R$^{X1}$, —C(=O)OR$^{X1}$, —C(=O)—O—C(=O)R$^{X1}$, —C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, —C(=NR$^{X1}$)OR$^{X1}$, —C(=NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "silyl" refers to the group —Si(R$^{aa}$)$_3$, wherein R$^{aa}$ is as defined herein.

The term "oxo" refers to the group =O, and the term "thiooxo" refers to the group =S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{cc}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), 3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, co-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), —$OR^{aa}$ (when the O atom is attached to a carbonyl group, wherein $R^{aa}$ is as defined herein), —$O(C=O)R^{LG}$, or —$O(SO)_2R^{LG}$ (e.g., tosyl, mesyl, besyl), wherein $R^{LG}$ is optionally substituted alkyl, optionally substituted aryl, or optionally substituted heteroaryl. In some cases, the leaving group is a halogen. In some embodiments, the leaving group is I.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

The term "carbohydrate" or "saccharide" refers to an aldehydic or ketonic derivative of polyhydric alcohols.

Carbohydrates include compounds with relatively small molecules (e.g., sugars) as well as macromolecular or polymeric substances (e.g., starch, glycogen, and cellulose polysaccharides). The term "sugar" refers to monosaccharides, disaccharides, or polysaccharides. Monosaccharides are the simplest carbohydrates in that they cannot be hydrolyzed to smaller carbohydrates. Most monosaccharides can be represented by the general formula $C_yH_{2y}O_y$ (e.g., $C_6H_{12}O_6$ (a hexose such as glucose)), wherein y is an integer equal to or greater than 3. Certain polyhydric alcohols not represented by the general formula described above may also be considered monosaccharides. For example, deoxyribose is of the formula $C_5H_{10}O_4$ and is a monosaccharide. Monosaccharides usually consist of five or six carbon atoms and are referred to as pentoses and hexoses, receptively. If the monosaccharide contains an aldehyde it is referred to as an aldose; and if it contains a ketone, it is referred to as a ketose. Monosaccharides may also consist of three, four, or seven carbon atoms in an aldose or ketose form and are referred to as trioses, tetroses, and heptoses, respectively. Glyceraldehyde and dihydroxyacetone are considered to be aldotriose and ketotriose sugars, respectively. Examples of aldotetrose sugars include erythrose and threose; and ketotetrose sugars include erythrulose. Aldopentose sugars include ribose, arabinose, xylose, and lyxose; and ketopentose sugars include ribulose, arabulose, xylulose, and lyxulose. Examples of aldohexose sugars include glucose (for example, dextrose), mannose, galactose, allose, altrose, talose, gulose, and idose; and ketohexose sugars include fructose, psicose, sorbose, and tagatose. Ketoheptose sugars include sedoheptulose. Each carbon atom of a monosaccharide bearing a hydroxyl group (—OH), with the exception of the first and last carbons, is asymmetric, making the carbon atom a stereocenter with two possible configurations (R or S). Because of this asymmetry, a number of isomers may exist for any given monosaccharide formula. The aldohexose D-glucose, for example, has the formula $C_6H_{12}O_6$, of which all but two of its six carbons atoms are stereogenic, making D-glucose one of the 16 (i.e., $2^4$) possible stereoisomers. The assignment of D or L is made according to the orientation of the asymmetric carbon furthest from the carbonyl group: in a standard Fischer projection if the hydroxyl group is on the right the molecule is a D sugar, otherwise it is an L sugar. The aldehyde or ketone group of a straight-chain monosaccharide will react reversibly with a hydroxyl group on a different carbon atom to form a hemiacetal or hemiketal, forming a heterocyclic ring with an oxygen bridge between two carbon atoms. Rings with five and six atoms are called furanose and pyranose forms, respectively, and exist in equilibrium with the straight-chain form. During the conversion from the straight-chain form to the cyclic form, the carbon atom containing the carbonyl oxygen, called the anomeric carbon, becomes a stereogenic center with two possible configurations: the oxygen atom may take a position either above or below the plane of the ring. The resulting possible pair of stereoisomers is called anomers. In an at anomer, the —OH substituent on the anomeric carbon rests on the opposite side (trans) of the ring from the —CH$_2$OH side branch. The alternative form, in which the —CH$_2$OH substituent and the anomeric hydroxyl are on the same side (cis) of the plane of the ring, is called a P anomer. A carbohydrate including two or more joined monosaccharide units is called a disaccharide or polysaccharide (e.g., a trisaccharide), respectively. The two or more monosaccharide units bound together by a covalent bond known as a glycosidic linkage formed via a dehydration reaction, resulting in the loss of a hydrogen atom from one monosaccharide and a hydroxyl group from another. Exemplary disaccharides include sucrose, lactulose, lactose, maltose, isomaltose, trehalose, cellobiose, xylobiose, laminaribiose, gentiobiose, mannobiose, melibiose, nigerose, or rutinose. Exemplary trisaccharides include, but are not limited to, isomaltotriose, nigerotriose, maltotriose, melezitose, maltotriulose, raffinose, and kestose. The term carbohydrate also includes other natural or synthetic stereoisomers of the carbohydrates described herein.

These and other exemplary substituents are described in more detail in the Detailed Description, Examples, and claims. The invention is not intended to be limited in any manner by the above exemplary listing of substituents.

Other Definitions

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}$ alkyl$)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R.x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R.0.5 $H_2O$)), and polyhydrates (x is a number greater than 1, e.g., dihydrates (R.2 $H_2O$) and hexahydrates (R.6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal "Disease," "disorder," and "condition" are used interchangeably herein.

The term "administer," "administering," or "administration" refers to implanting, absorbing, ingesting, injecting, inhaling, or otherwise introducing a compound described herein, or a composition thereof, in or on a subject.

As used herein, and unless otherwise specified, the terms "treat," "treating" and "treatment" contemplate an action that occurs while a subject is suffering from the specified infectious disease or inflammatory condition, which reduces the severity of the infectious disease or inflammatory condition, or retards or slows the progression of the infectious disease or inflammatory condition ("therapeutic treatment"), and also contemplates an action that occurs before a subject begins to suffer from the specified infectious disease or inflammatory condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of an infectious disease or inflammatory condition, or to delay or minimize one or more symptoms associated with the infectious disease or inflammatory condition. A therapeutically effective amount of a compound means an amount of therapeutic agent, alone or in combination with other therapies, which provides a therapeutic benefit in the treatment of the infectious disease or inflammatory condition. The term "therapeutically effective amount" can encompass an amount that improves overall therapy, reduces or avoids symptoms or causes of infectious disease or inflammatory condition, or enhances the therapeutic efficacy of another therapeutic agent.

As used herein, and unless otherwise specified, a "prophylactically effective amount" of a compound is an amount sufficient to prevent an infectious disease or inflammatory condition, or one or more symptoms associated with the infectious disease or inflammatory condition, or prevent its recurrence. A prophylactically effective amount of a compound means an amount of a therapeutic agent, alone or in combination with other agents, which provides a prophylactic benefit in the prevention of the infectious disease or inflammatory condition. The term "prophylactically effective amount" can encompass an amount that improves overall prophylaxis or enhances the prophylactic efficacy of another prophylactic agent.

The term "inflammatory disease" refers to a disease caused by, resulting from, or resulting in inflammation. The term "inflammatory disease" may also refer to a dysregulated inflammatory reaction that causes an exaggerated response by macrophages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyalgia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syndrome, giant cell arteritis, progressive systemic sclerosis (scleroderma), ankylosing spondylitis, polymyositis, dermatomyositis, pemphigus, pemphigoid, diabetes (e.g., Type I), myasthenia gravis, Hashimoto's thyroiditis, Graves' disease, Goodpasture's disease, mixed connective tissue disease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, talcosis, pneumoconiosis, sarcoidosis, desquamative interstitial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis *nodosa*), inflammatory dermatoses, hepatitis, delayed-type hypersensitivity reactions (e.g., poison ivy dermatitis), pneumonia, respiratory tract inflammation, Adult Respiratory Distress Syndrome (ARDS), encephalitis, immediate hypersensitivity reactions, asthma, hayfever, allergies, acute anaphylaxis, rheumatic fever, glomerulonephritis, pyelonephritis, cellulitis, cystitis, chronic cholecystitis, ischemia (ischemic injury), reperfusion injury, allograft rejection, host-versus-graft rejection, appendicitis, arteritis, blepharitis, bronchiolitis, bronchitis, cervicitis, cholangitis, chorioamnionitis, conjunctivitis, dacryoadenitis, dermatomyositis, endocarditis, endometritis, enteritis, enterocolitis, epicondylitis, epididymitis, fasciitis, fibrositis, gastritis, gastroenteritis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpingitis, sinusitis, stomatitis, synovitis, testitis, tonsillitis, urethritis, urocystitis, uveitis, vaginitis, vasculitis, vulvitis, vulvovaginitis, angitis, chronic bronchitis, osteomyelitis, optic neuritis, temporal arteritis, transverse myelitis, necrotizing fasciitis, and necrotizing enterocolitis. An ocular inflammatory disease includes, but is not limited to, postsurgical inflammation.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Macrolide Binding and Resistance

Figure 2:
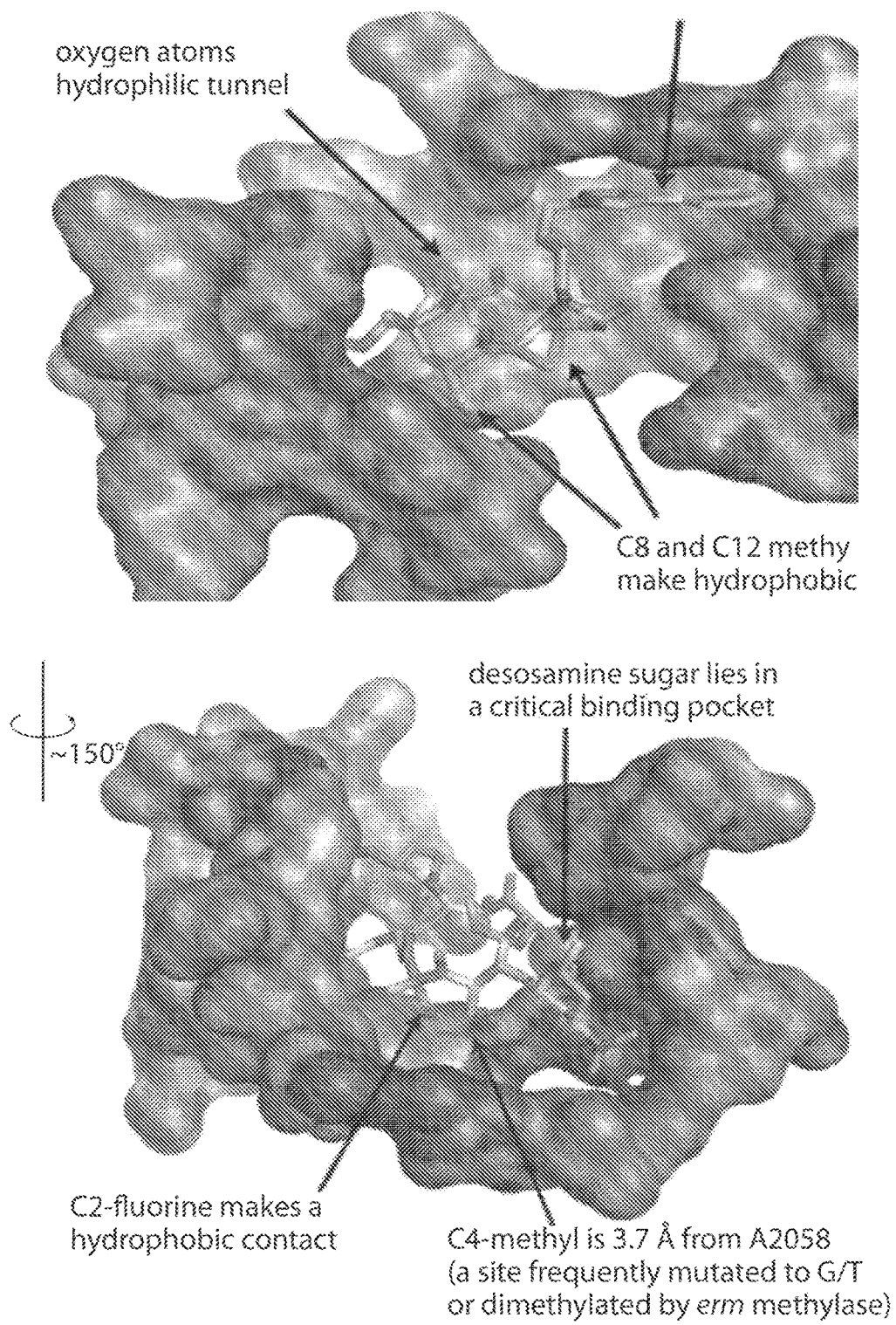
FIG. 2 depicts the crystal structure of solithromycin bound to a ribosome of *E. coli*. Residues in a 12-Å sphere generated using MacPyMol from PDB #3ORB. See, e.g., Llano-Sotelo *Antimicrob. Agents Chemother.* (2010) 54:4961-4970.

The macrolide antibiotics, as exemplified by the macrolides depicted in FIG. 1, inhibit peptide synthesis by hindering transit of the nascent peptide through the exit tunnel in the bacterial ribosome. All 13- to 16-membered macrolide antibiotics bind with almost identical macrolactone (or azalactone) conformations in which a hydrophobic face of the molecule (comprising several methyl groups and one ethyl group) is engaged with the wall of the peptidyl exit tunnel and a hydrophilic face of the molecule (comprising four C—O and C═O groups) is exposed to the hydrophobic interior of the tunnel (FIG. 2, 12 Å sphere around solithromycin depicted). See, e.g., Bulkley et al., *Proc. Natl. Acad. Sci. U.S.A* 2010, 107, 17158-17163; Tu et al., *Cell* (Cambridge, Mass., U. S.) 2005, 121, 257-270; Hansen et al., *J. Mol. Biol.* 2003, 330, 1061-1075; Llano-Sotelo et al., *Antimicrob. Agents Chemother.* 2010, 54, 4961-4970. Critical hydrogen-bonding interactions occur between the desosamine sugar and the ribosome, which is consistent with the view that this residue, which is present in all macrolides approved by the FDA for human use (but is modified in tylosin, a veterinary antibiotic) is important in binding. The sidechains of telithromycin and solithromycin are believed to engage in pi-stacking interactions with the A752-U2609 base pair, enhancing binding to the ribosome. See, e.g., Mankin, *Curr. Opin. Microbiol.* 2008, 11, 414-421; Douthwaite et al., *Mol. Microbiol.* 2000, 36, 183-192; Hansen et al., *Mol. Microbiol.* 1999, 31, 623-631. The 3-aminophenyl substituent of solithromycin has been shown by X-ray crystallography to make contacts with A752 and G748 through hydrogen bonding, which may account in part for the higher binding affinity of solithromycin relative to telithromycin. See, e.g., Llano-Sotelo et al., *Antimicrob. Agents Chemother.* 2010, 54, 4961-4970. The fluorine atom at position C2 of solithromycin makes a hydrophobic contact with C2611, and is believed to account for the 4- to 16-fold increase in activity versus the non-fluorinated molecule against panels of Gram-positive bacteria. See, e.g., Llano-Sotelo et al., *Antimicrob. Agents Chemother.* 2010, 54, 4961-4970.

Modification of the macrolide binding pocket is one of the primary forms of resistance among pathogenic bacteria. This can take the form of a base modification (e.g., A2058 dimethylation by erm genes), a base mutation (e.g., A2058G, A2059G, C2611G), or a more subtle alteration of the binding pocket caused by distal mutations in the ribosome (e.g., L4 ribosomal peptide modification). See, e.g., Leclercq et al., *Antimicrob. Agents Chemother.* 1991, 35, 1273-1276; Leclercq et al., *Antimicrob. Agents Chemother.* 1991, 35, 1267-1272; Weisblum, *Antimicrob. Agents Chemother.* 1995, 39, 577-585; Vester et al., *Antimicrob. Agents Chemother.* 2001, 45, 1-12; Tu et al., *Cell* (Cambridge, Mass., U. S.) 2005, 121, 257-270. Semi-synthetic modifications of macrolides, restricted to just a few positions, have led to greatly increased binding through additional contacts to the binding site. We believe that modifications to other positions yet unexplored provide great opportunity for further antibiotic development.

Convergent Synthetic Method

The method used to prepare fully synthetic macrolides has been described previously. See, e.g., PCT publication WO2014/165792, which is incorporated herein by reference in its entirety. In brief, the method comprises the synthesis of eastern half and western half precursors to the macrolide which are independently synthesized as fragments of similar complexity. The synthesis typically converges with coupling of the eastern and western halves, and macrolactonization to form the 14, 15, or 16 membered macrolide ring. A diverse range of substituents at various ring positions can be introduced during synthesis of the separate halves, after coupling but before lactonization, or after both coupling and lactonization, or a combination thereof. Herein we exemplify the synthesis for compounds of the present invention, wherein the desosamine sugar is modified (e.g., a desosamine or myaminose analog). Also provided are exemplary methods for preparation of the modified sugars which may be incorporated into preparation of a macrolide.

Preparation of macrolides with
6-triazolyl-D-desosamines

Synthesis of 6-azido-D-desosamine glycosyl donor ((2R,3R,4S,6S)-6-(azidomethyl)-4-(dimethylamino)-2-methoxytetrahydro-2H-pyran-3-yl methyl carbonate) (11)

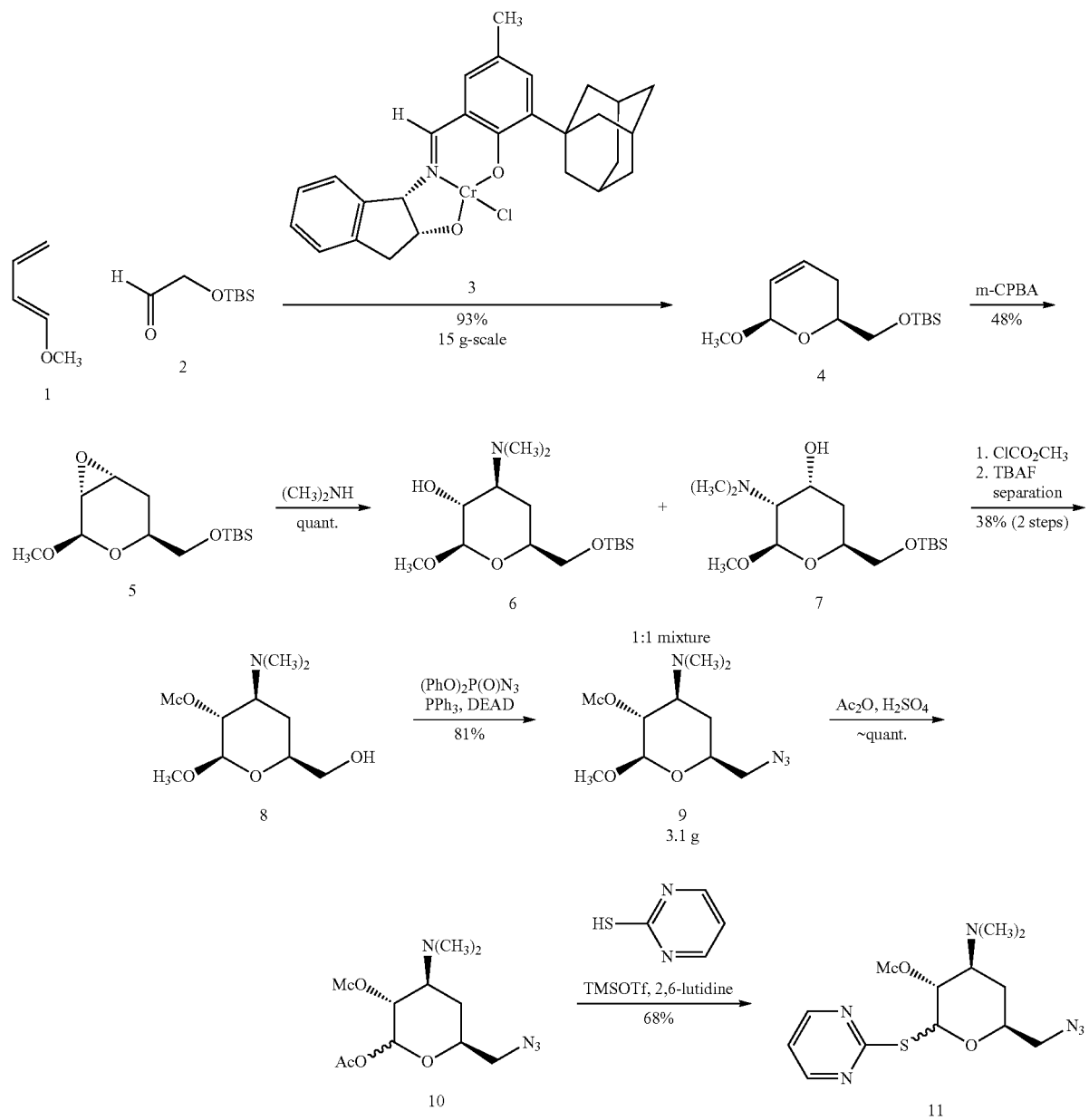

The synthesis of methyl 2-O-methoxycarbonyl-3,4-dideoxy-3-dimethylamino-β-D-xylo-hexopyranoside (8) was adapted from procedures described by Roy and co-workers. See, e.g., Giguere et al. *J. Org. Chem.* (2011) 76:9687-9698. Methoxycarbonyl chloride was used in place of acetic anhydride in the step of protecting the C2 hydroxyl position. From intermediate 8 a Mitsunobu reaction with diphenylphosphoryl azide (DPPA) yields the protected 6-azido D-desosamine derivative 9 in 81% yield. Deprotection of both hydroxyl groups would provide 6-azido D-desoamine.

Azido sugar 9 was converted to the protected thioglycoside in two additional steps. Treatment with acetic anhydride quantitatively converts the anomeric methoxy position to acetoxy. The acetoxy group of 10 is a suitable leaving group for thioglycosidation, which was carried out with mercaptopyrimidine, trimethylsilyl triflate and 2,6-lutidine to yield thioglycoside 11 in 68% yield.

Preparation of the Eastern Half of a
6-Azido-D-Desosamine Analog (15)

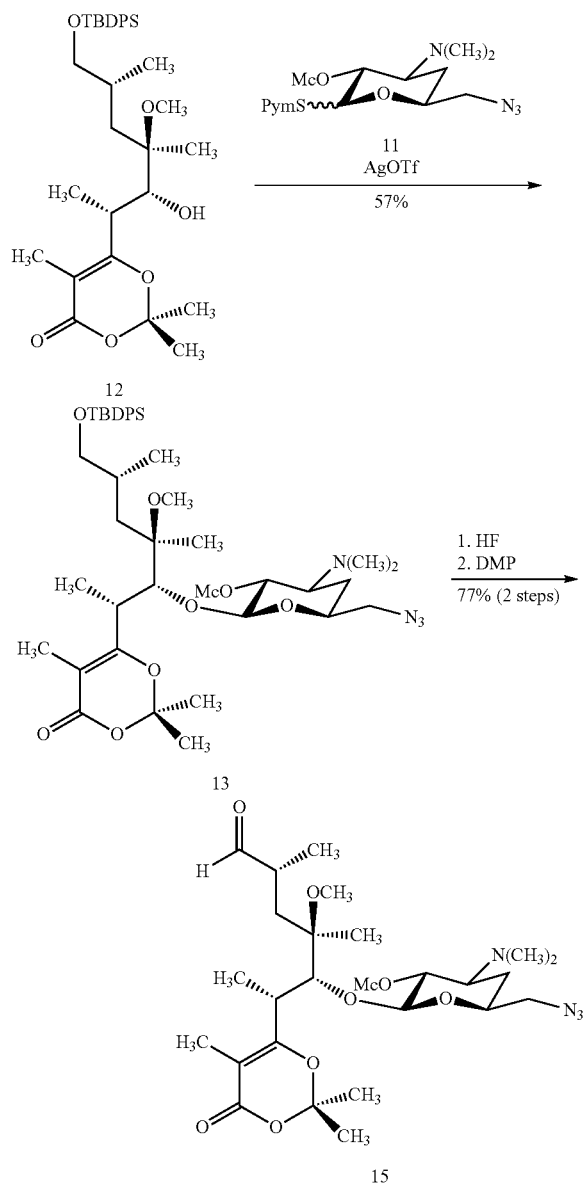

Eastern Half 13

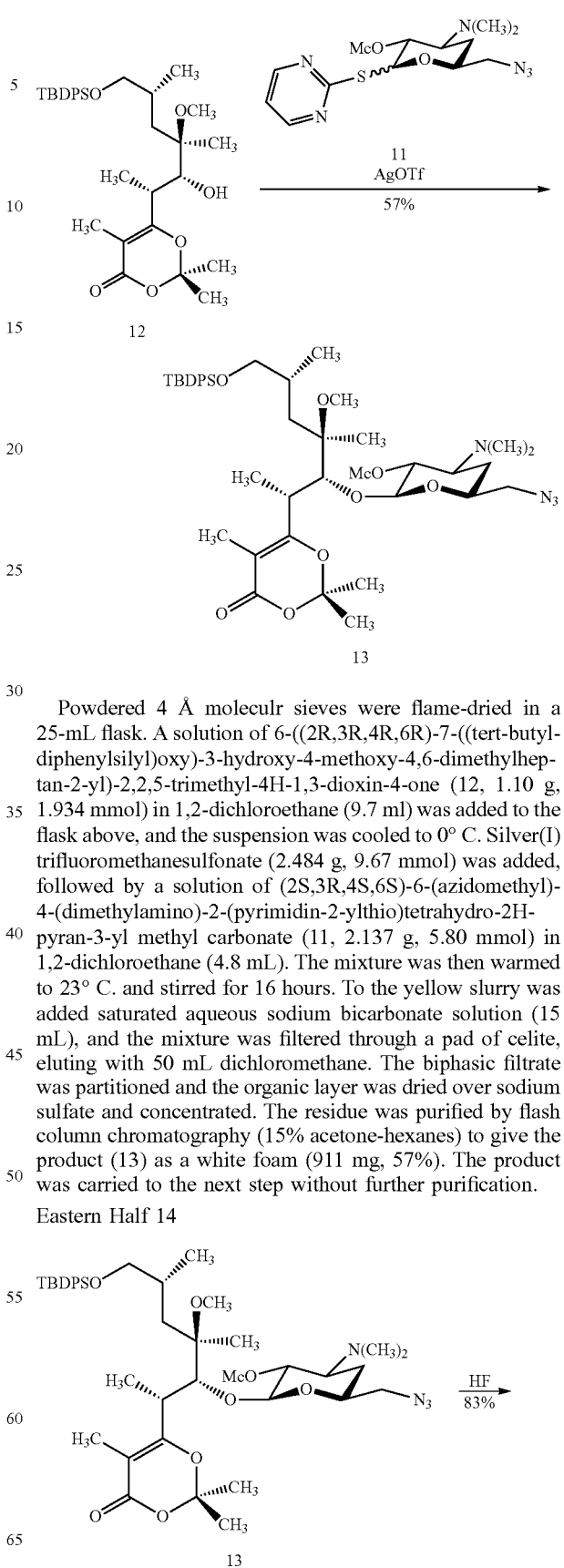

Powdered 4 Å moleculr sieves were flame-dried in a 25-mL flask. A solution of 6-((2R,3R,4R,6R)-7-((tert-butyldiphenylsilyl)oxy)-3-hydroxy-4-methoxy-4,6-dimethylheptan-2-yl)-2,2,5-trimethyl-4H-1,3-dioxin-4-one (12, 1.10 g, 1.934 mmol) in 1,2-dichloroethane (9.7 ml) was added to the flask above, and the suspension was cooled to 0° C. Silver(I) trifluoromethanesulfonate (2.484 g, 9.67 mmol) was added, followed by a solution of (2S,3R,4S,6S)-6-(azidomethyl)-4-(dimethylamino)-2-(pyrimidin-2-ylthio)tetrahydro-2H-pyran-3-yl methyl carbonate (11, 2.137 g, 5.80 mmol) in 1,2-dichloroethane (4.8 mL). The mixture was then warmed to 23° C. and stirred for 16 hours. To the yellow slurry was added saturated aqueous sodium bicarbonate solution (15 mL), and the mixture was filtered through a pad of celite, eluting with 50 mL dichloromethane. The biphasic filtrate was partitioned and the organic layer was dried over sodium sulfate and concentrated. The residue was purified by flash column chromatography (15% acetone-hexanes) to give the product (13) as a white foam (911 mg, 57%). The product was carried to the next step without further purification.

Eastern Half 14

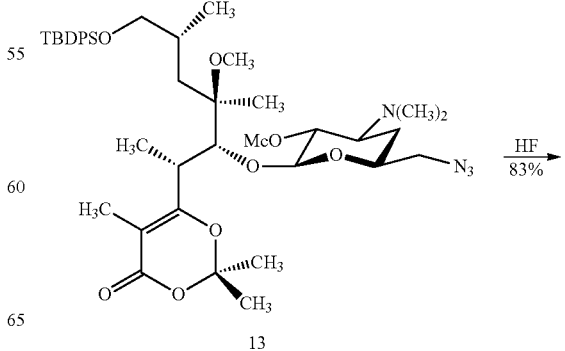

-continued

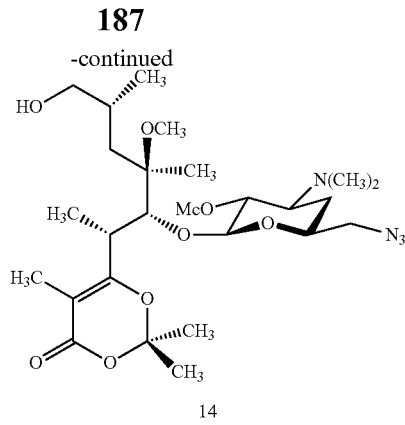

14

(2S,3R,4S,6S)-6-(azidomethyl)-2-(((2R,3R,4R,6R)-7-((tert-butyldiphenylsilyl)oxy)-4-methoxy-4,6-dimethyl-2-(2,2,5-trimethyl-4-oxo-4H-H-1,3-dioxin-6-yl)heptan-3-yl)oxy)-4-(dimethylamino)tetrahydro-2H-pyran-3-yl methyl carbonate (13, 911 mg, 1.104 mmol) was dissolved in acetonitrile (2208 μl). Hydrofluoric acid (793 μl, 22.08 mmol) was added. The mixture was stirred at 23° C. After 2 hours, LC-MS indicated full conversion. The reaction mixture was slowly added to 100 mL saturated aqueous sodium bicarbonate solution. The mixture was extracted with ether (3×20 mL). The combined ether layers were washed with brine, dried over magnesium sulfate, and concentrated. The residue was purified by flash column chromatography (20% acetone-hexanes) to give the product (14) as a white foam (540 mg, 83%).

1H NMR (500 MHz, CDCl$_3$) δ 4.68 (d, J=7.6 Hz, 1H), 4.61 (dd, J=10.6, 7.6 Hz, 1H), 4.02 (d, J=3.0 Hz, 1H), 3.76 (s, 3H), 3.60-3.52 (m, 2H), 3.52-3.45 (m, 1H), 3.45-3.37 (m, 2H), 3.31-3.22 (m, 1H), 3.12 (dd, J=13.1, 2.6 Hz, 1H), 3.08 (s, 3H), 2.81 (td, J=12.0, 4.4 Hz, 1H), 2.29 (s, 6H), 1.90-1.81 (m, 1H), 1.85 (s, 3H), 1.78-1.72 (m, 1H), 1.71 (s, 3H), 1.67 (s, 3H), 1.56 (dd, J=14.5, 2.8 Hz, 1H), 1.45 (dd, J=24.4, 12.2 Hz, 1H), 1.37 (dd, J=14.5, 9.5 Hz, 1H), 1.29 (s, 3H), 1.05 (d, J=7.4 Hz, 3H), 0.91 (d, J=6.9 Hz, 3H). $^{13}$C NMR (126 MHz, CDCl$_3$) δ 166.93, 162.65, 155.08, 104.53, 99.93, 99.63, 79.62, 75.78, 75.13, 73.33, 68.31, 62.56, 54.79, 54.44, 49.69, 40.58, 38.45, 33.73, 30.98, 26.30, 25.57, 24.47, 19.90, 19.55, 13.16, 9.85. FTIR (neat), cm$^{-1}$: 3427 (br), 2936 (m), 2098 (s), 1753 (s), 1720 (s), 1641 (s), 1278 (s), 1048 (s), 993 (s), 914 (s), 729 (s). HRMS (ESI): Calcd for (C$_{27}$H$_{46}$N$_4$O$_{10}$+H)$^+$: 587.3287; Found: 587.3305.

Eastern Half 15

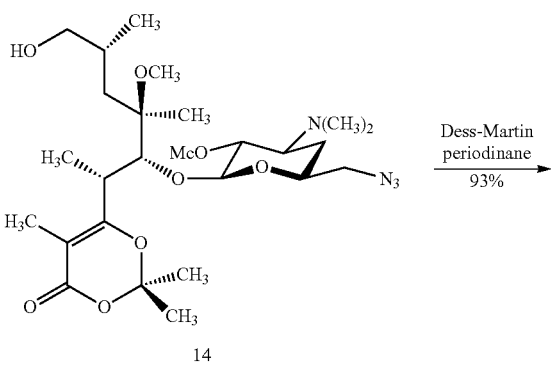

14

-continued

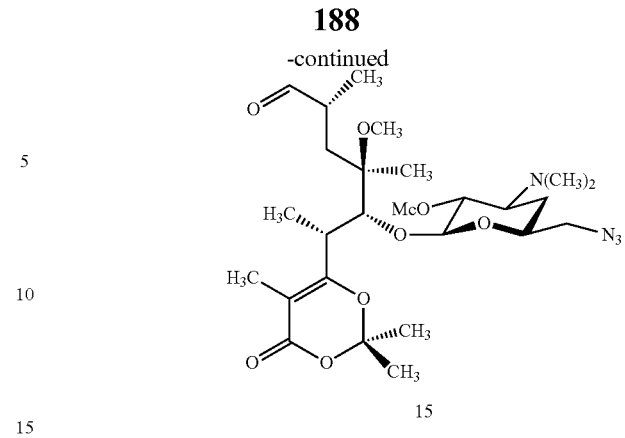

15

(2S,3R,4S,6S)-6-(azidomethyl)-4-(dimethylamino)-2-(((2R,3R,4R,6R)-7-hydroxy-4-methoxy-4,6-dimethyl-2-(2,2,5-trimethyl-4-oxo-4H-1,3-dioxin-6-yl)heptan-3-yl)oxy)tetrahydro-2H-pyran-3-yl methyl carbonate (14, 540 mg, 0.920 mmol) was dissolved in water-saturated CH2Cl2 (1841 μL). Dess-Martin periodinane (586 mg, 1.381 mmol) was added in one portion and the suspension was stirred at 23° C. After 1 hour, TLC (with ether/sodium bicarbonate extraction, 50% acetone-hexanes) indicated full conversion. To the reaction mixture was added ether (20 mL), saturated aqueous sodium bicarbonate solution (10 mL), saturated sodium thiosulfate solution (10 mL), and the mixture was stirred vigorously for 15 minutes. The layers were separated. The aqueous layer was extracted with ether (2×20 mL). The combined ether layers were washed with brine, dried over magnesium sulfate and concentrated to give the product (15) as a white foam (502 mg, 93%).

$^1$H NMR (500 MHz, CDCl$_3$) δ 9.35 (t, J=4.3 Hz, 1H), 4.65 (d, J=7.6 Hz, 1H), 4.59 (dd, J=10.5, 7.6 Hz, 1H), 3.96 (d, J=3.2 Hz, 1H), 3.77 (s, 3H), 3.56 (dd, J=10.7, 8.6 Hz, 1H), 3.45-3.36 (m, 2H), 3.13 (dd, J=13.1, 2.6 Hz, 1H), 2.94 (s, 3H), 2.81 (td, J=12.0, 4.4 Hz, 1H), 2.51-2.41 (m, 1H), 2.30 (s, 6H), 1.84 (s, 3H), 1.82-1.72 (m, 2H), 1.70 (s, 3H), 1.67 (s, 3H), 1.55 (dd, J=14.2, 3.2 Hz, 1H), 1.45 (dd, J=24.2, 12.0 Hz, 1H), 1.25 (s, 3H), 1.07 (d, J=7.3 Hz, 3H), 1.05 (d, J=7.0 Hz, 3H). $^{13}$C NMR (126 MHz, CDCl$_3$) δ 204.48, 166.95, 162.72, 155.12, 104.53, 99.88, 99.81, 78.27, 76.53, 75.11, 73.28, 62.67, 54.81, 54.44, 49.53, 41.77, 40.58, 37.32, 33.77, 26.19, 25.47, 24.56, 19.85, 15.59, 13.15, 9.76. FTIR (neat), cm$^{-1}$: 2936 (m), 2098 (s), 1753 (s), 1720 (s), 1641 (s), 1265 (s), 1049 (s), 993 (s), 912 (s), 729 (s). HRMS (ESI): Calcd for (C$_{27}$H$_{44}$N$_4$O$_{10}$+H)$^+$: 585.3130; Found: 585.3147.

Coupling of the Eastern and Western Halves of a 6-Azido-D-Desosamine Analog

Western Half 17

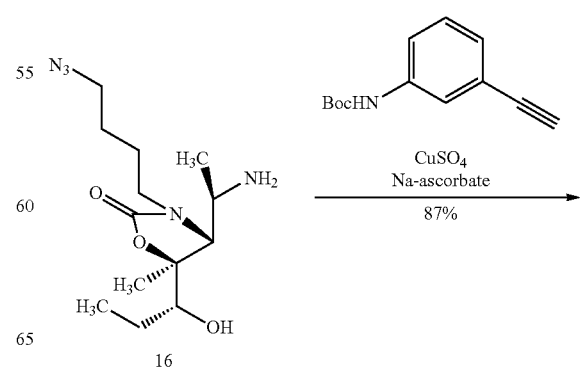

16

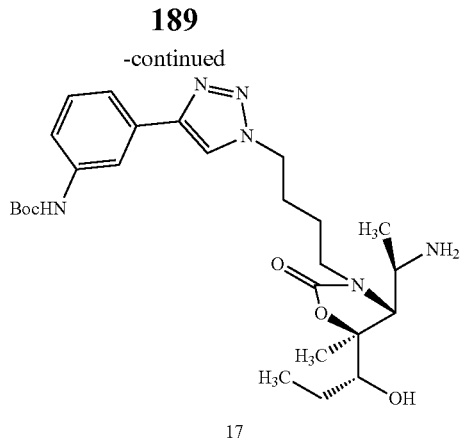

17

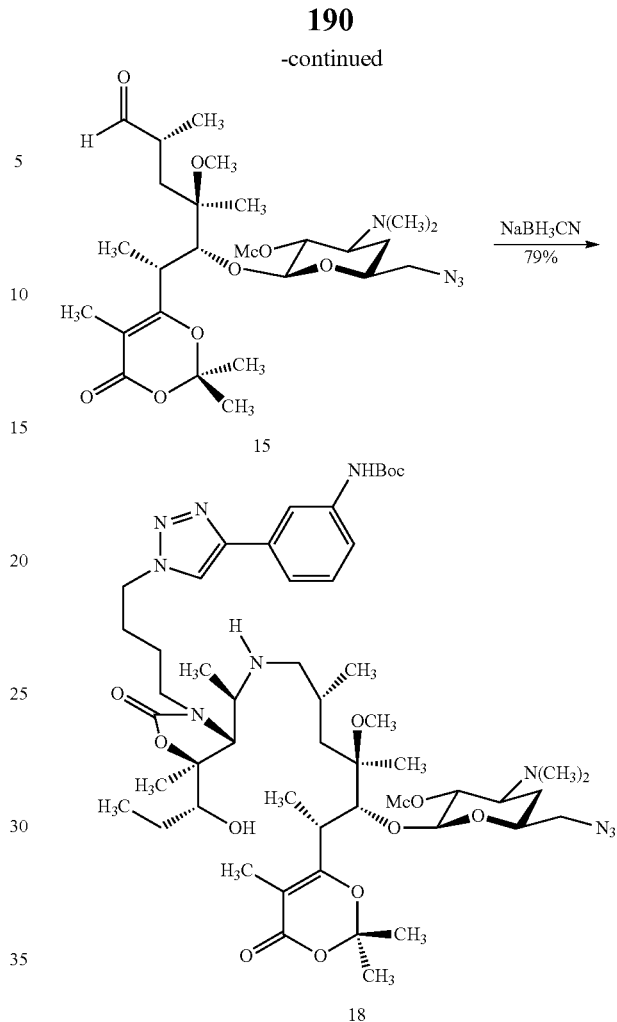

15

18

Tert-butyl (3-ethynylphenyl)carbamate (16, 29.0 mg, 0.134 mmol) and (4R,5S)-4-((R)-1-aminoethyl)-3-(4-azidobutyl)-5-((R)-1-hydroxypropyl)-5-methyloxazolidin-2-one (40 mg, 0.134 mmol) were dissolved in 5:1 tBuOH/H$_2$O (0.5 mL). Sodium ascorbate (0.1 M in water, 134 µl, 0.013 mmol) was added followed by copper(II) sulfate (0.1 M in water, 66.8 µl, 6.68 µmol). The yellow solution was stirred at 23° C. for 16 hours. The reaction mixture was diluted with 1 mL saturated sodium bicarbonate solution, and extracted with dichloromethane (3×5 mL). The combined organic layers were dried over sodium sulfate and concentrated. The residue was purified by column chromatography (3→5% methanol-dichloromethane+0.3→0.5% saturated aqueous ammonium hydroxide solution) to give the product (17) as a white solid (60 mg, 87%).

1H NMR (500 MHz, CDCl$_3$) δ 7.84 (s, 1H), 7.83 (s, 1H), 7.51-7.46 (m, 1H), 7.34-7.27 (m, 2H), 6.93 (s, 1H), 4.36 (qt, J=13.9, 6.9 Hz, 2H), 3.65 (d, J=2.2 Hz, 1H), 3.61 (dd, J=14.4, 7.5 Hz, 1H), 3.48-3.37 (m, 2H), 3.26 (qd, J=6.4, 2.0 Hz, 1H), 2.07-1.80 (m, 2H), 1.71-1.54 (m, 3H), 1.51 (s, 9H), 1.39-1.28 (m, 1H), 1.33 (s, 3H), 1.11 (d, J=6.5 Hz, 3H), 1.00 (t, J=7.3 Hz, 3H). $^{13}$C NMR (126 MHz, CDCl$_3$) δ 158.05, 152.83, 147.42, 138.94, 131.10, 129.49, 120.37, 120.19, 118.17, 115.48, 83.80, 80.55, 63.43, 49.71, 47.18, 42.49, 28.30, 26.87, 23.47, 23.38, 18.55, 15.50, 11.01. FTIR (neat), cm$^{-1}$: 3340 (br), 2960 (m), 2098 (m), 1717 (s), 1444 (s), 1265 (s), 1165 (s), 1051 (s), 729 (s). HRMS (ESI): Calcd for (C$_{26}$H$_{40}$N$_6$O$_5$+H)$^+$: 517.3123; Found: 517.3144.

Macrocyclization Precursor 18

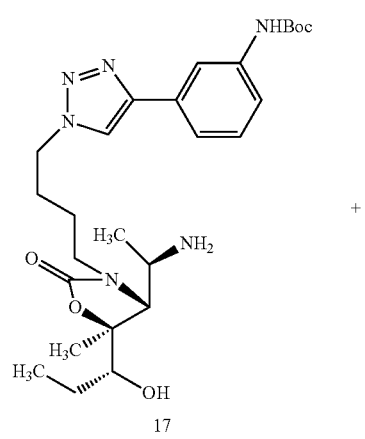

17

+

Western half amine 17 (36 mg, 0.070 mmol) was dissolved in 9:1 methanol/acetic acid (0.4 mL). Sodium cyanoborohydride (8.76 mg, 0.139 mmol) was added, and the solution was cooled to −15° C. Eastern half aldehyde 15 (40.7 mg, 0.070 mmol) was added as a solution in 9:1 methanol/acetic acid (0.2 mL). The reaction was kept stirred at −15° C. for 1 hour, at which point LC-MS indicated full conversion. The reaction mixture was concentrated. The residue was dissolved in dichloromethane (5 mL) and saturated sodium bicarbonate solution (5 mL). The mixture was vigorously stirred, and the aqueous layer was extracted with dichloromethane (2×5 mL). The combined organic layers were dried over sodium sulfate and concentrated. The crude product was purified by flash column chromatography (50% acetone-hexanes+1% triethylamine) to give the product (18) as a white foam (60 mg, 79%).

TLC (50% acetone-hexanes): R$_f$=0.29 (UV, p-anisaldehyde). $^1$H NMR (500 MHz, CDCl$_3$) δ 7.90 (s, 1H), 7.81 (s, 1H), 7.52-7.47 (m, 1H), 7.36 (d, J=8.4 Hz, 1H), 7.34-7.29 (m, 1H), 6.85 (s, 1H), 4.65-4.57 (m, 2H), 4.48-4.35 (m, 2H), 3.92 (d, J=4.1 Hz, 1H), 3.77 (s, 3H), 3.71 (d, J=2.3 Hz, 1H), 3.65-3.50 (m, 3H), 3.44 (dd, J=8.3, 1.8 Hz, 1H), 3.41 (dd, J=11.2, 6.0 Hz, 1H), 3.37-3.28 (m, 1H), 3.17 (dd, J=13.1, 2.7 Hz, 1H), 2.99 (s, 3H), 2.84-2.71 (m, 2H), 2.48-2.36 (m, 2H), 2.30 (s, 6H), 2.09-1.99 (m, 1H), 1.99-1.87 (m, 1H), 1.84 (s, 3H), 1.70 (s, 3H), 1.77-1.54 (m, 7H), 1.66 (s, 3H), 1.53 (s, 9H), 1.51-1.40 (m, 1H), 1.39-1.33 (m, 1H), 1.32 (s, 3H), 1.21 (s, 3H), 1.08-1.00 (m, 9H), 0.87 (d, J=6.7 Hz, 3H). $^{13}$C NMR (126 MHz, CDCl$_3$) δ 167.46, 162.98, 158.23, 155.05, 152.76, 147.40, 138.86, 131.20, 129.44, 120.21, 120.18, 118.04, 115.42, 104.56, 100.07, 99.26, 83.50, 80.47, 79.15, 77.53, 76.86, 75.13, 62.70, 61.01, 54.84, 54.45, 54.38, 54.06, 49.72, 46.16, 42.46, 40.60, 37.37, 34.18, 29.22, 28.51, 28.30, 26.87, 26.15, 25.77, 24.15, 23.65, 23.50, 21.13, 19.58, 16.48, 15.50, 13.40, 11.05, 9.82. FTIR (neat), cm$^{-1}$: 3439 (br), 2938 (m), 2098 (s), 1749 (s), 1720 (s), 1641 (s), 1442 (s), 1278 (s), 1238 (s), 1159 (s), 1049 (s), 993 (s), 693 (s). HRMS (ESI): Calcd for $(C_{53}H_{84}N_{10}O_{14}+H)^+$: 1085.6241; Found: 1085.6241.

Cyclization of a 6-Azido-D-Desosamine Analog

Macrolide 19

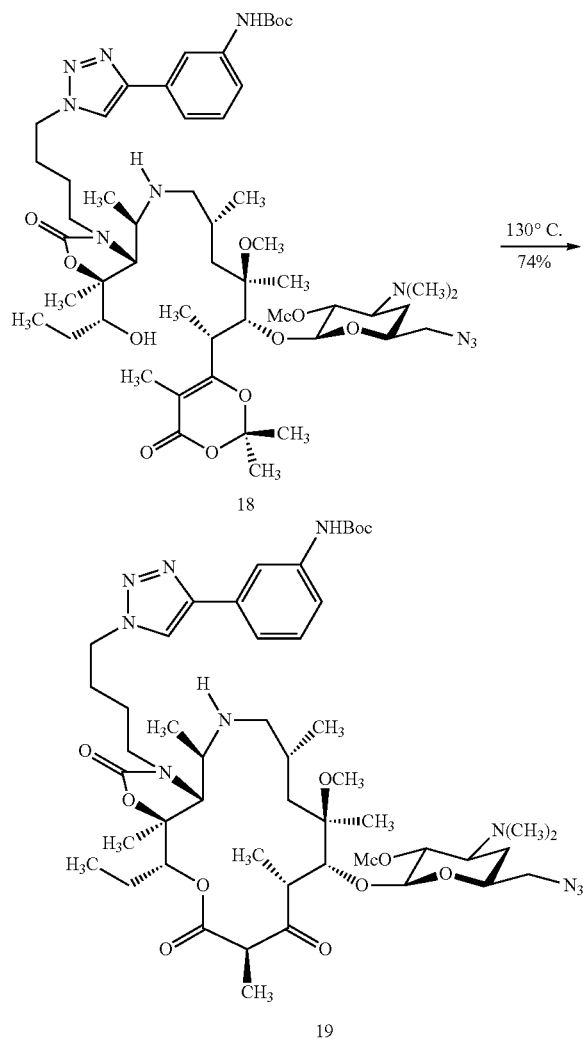

Macrocyclization precursor 18 (60 mg, 0.055 mmol) was dissolved in chlorobenzene (55 mL) in a 100-mL flask. The flask was fitted with a dry reflux condensor. The solution was degassed by bubbling argon through for 10 minutes. The reaction was heated to reflux (130° C., 150° C. oil bath). After 16 hours, the reaction mixture was cooled and concentrated. The residue was purified by flash column chromatography (25% acetone-hexanes+1% triethylamine) to give the product (19) as a white foam.

TLC (50% acetone-hexanes): $R_f$=0.37 (UV, p-anisaldehyde). $^1$H NMR (4:1 diastereomeric mixture at C2, major isomer reported, 500 MHz, CDCl$_3$) δ 7.82 (s, 1H), 7.67 (s, 1H), 7.51-7.45 (m, 2H), 7.38-7.29 (m, 1H), 6.82 (s, 1H), 4.95 (dd, J=10.9, 1.9 Hz, 1H), 4.60-4.51 (m, 2H), 4.51-4.35 (m, 3H), 3.84 (q, J=6.9 Hz, 1H), 3.76 (s, 3H), 3.75-3.68 (m, 1H), 3.68-3.61 (m, 1H), 3.40-3.34 (m, 2H), 3.26 (dd, J=13.1, 3.3 Hz, 1H), 3.05 (ddd, J=14.8, 10.0, 5.0 Hz, 1H), 2.88 (s, 3H), 2.80-2.71 (m, 3H), 2.27 (s, 6H), 2.09-1.91 (m, 4H), 1.77-1.43 (m, 8H), 1.51 (s, 9H), 1.41 (s, 3H), 1.37 (d, J=6.9 Hz, 3H), 1.21 (s, 3H), 1.19 (d, J=7.8 Hz, 3H), 1.08-1.01 (m, 1H), 0.95 (d, J=6.0 Hz, 3H), 0.92 (d, J=6.7 Hz, 3H), 0.86 (t, J=7.4 Hz, 3H). $^{13}$C NMR (4:1 diastereomeric mixture at C2, major isomer reported, 126 MHz, CDCl$_3$) δ 205.74, 171.93, 156.93, 154.97, 152.73, 147.40, 138.89, 131.40, 129.45, 120.33, 119.76, 118.06, 115.55, 100.10, 81.04, 78.51, 78.21, 75.05, 73.99, 72.56, 65.73, 62.94, 59.10, 58.23, 54.81, 54.44, 50.04, 49.83, 49.75, 44.52, 42.78, 40.63, 40.59, 28.33, 28.30, 27.60, 27.50, 25.70, 24.21, 21.78, 21.65, 21.47, 18.60, 14.22, 13.99, 13.86, 13.72, 10.40. FTIR (neat), cm$^{-1}$: 3317 (br), 2938 (m), 2100 (s), 1745 (s), 1442 (s), 1265 (s), 1159 (s), 1053 (s), 910 (s), 729 (s). HRMS (ESI): Calcd for $(C_{50}H_{78}N_{10}O_{13}+H)^+$: 1027.5823; Found: 1027.5865.

Post-Cyclization Modification of the 6-Azido-D-Desosamine Sugar to Yield 6-Triazolyl-D-Desosamine Macrolides

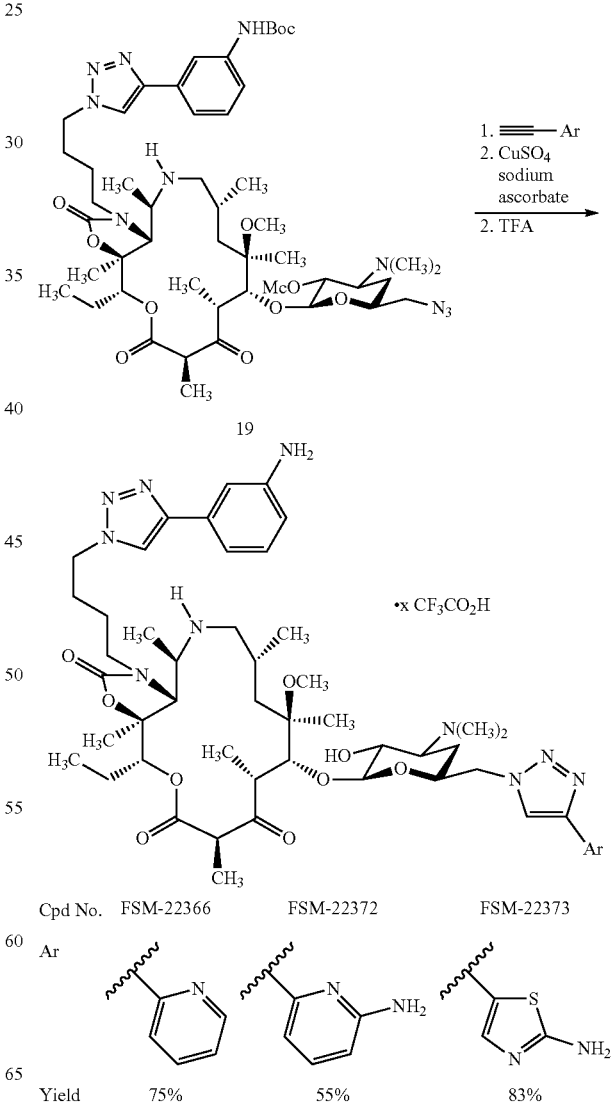

| Cpd No. | FSM-22366 | FSM-22372 | FSM-22373 |
|---|---|---|---|
| Ar | 2-pyridyl | 6-amino-2-pyridyl | 2-amino-5-thiazolyl |
| Yield | 75% | 55% | 83% |

Macrolide 20

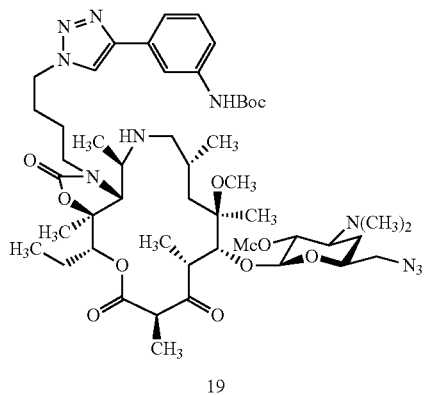
19

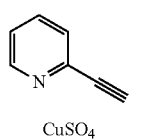
CuSO₄
Na-ascorbate
75%

6'-azido-macrolide 19 (10 mg, 9.73 µmol) was dissolved in tBuOH/methanol/water (2:2:1, 0.5 mL). 2-ethynylpyridine (2.008 mg, 0.019 mmol), sodium ascorbate (0.1 M in water, 19.47 µl, 1.947 µmol), and copper(II) sulfate (0.1 M in water, 4.87 µl, 0.487 µmol) were added sequentially. The reaction was stirred at 23° C. for 16 hours, at which point LC-MS showed full conversion and full deprotection of the methyl carbonate. The reaction mixture was diluted with dichloromethane (2 mL) and saturated aqueous sodium bicarbonate solution (1 mL). The layers were separated and the aqueous layer was extracted with dichloromethane (3×2 mL). The combined organic layers were dried over sodium sulfate and concentrated. The residue was purified by column chromatography (3→5% methanol-dichloromethane+ 0.3→0.5% saturated aqueous ammonium hydroxide solution) to give the product (20) as a colorless film (7.8 mg, 75%).

1H NMR (500 MHz, CDCl₃) δ 8.53 (d, J=4.1 Hz, 1H), 8.30 (s, 1H), 8.12 (d, J=7.9 Hz, 1H), 7.84 (s, 1H), 7.78 (s, 1H), 7.71 (td, J=7.8, 1.8 Hz, 1H), 7.54-7.48 (m, 2H), 7.36 (td, J=7.9, 3.9 Hz, 1H), 7.20-7.12 (m, 1H), 6.91 (s, 1H), 4.93 (dd, J=11.0, 1.9 Hz, 1H), 4.64 (dd, J=14.2, 3.9 Hz, 1H), 4.57 (dd, J=14.1, 7.4 Hz, 1H), 4.41 (t, J=8.0 Hz, 3H), 4.35 (d, J=2.7 Hz, 1H), 4.08 (s, 1H), 3.83 (q, J=6.8 Hz, 1H), 3.79-3.58 (m, 2H), 3.37 (s, 1H), 3.25 (dd, J=10.1, 7.5 Hz, 1H), 3.00 (d, J=7.9 Hz, 1H), 2.80-2.74 (m, 1H), 2.72 (s, 3H), 2.62-2.54 (m, 1H), 2.29 (s, 6H), 2.06-1.90 (m, 4H), 1.90-1.56 (m, 8H), 1.53 (s, 9H), 1.42 (s, 3H), 1.35 (d, J=7.0 Hz, 3H), 1.33 (d, J=8.0 Hz, 3H), 1.20 (s, 3H), 1.16-1.10 (m, 1H), 0.97 (d, J=5.8 Hz, 3H), 0.93 (d, J=6.8 Hz, 3H), 0.87 (t, J=7.4 Hz, 3H). FTIR (neat), cm⁻¹: 3468 (br), 2939 (m), 2096 (m), 1722 (s), 1442 (s), 1265 (s), 1161 (s), 1053 (s), 731 (s). HRMS (ESI): Calcd for $(C_{55}H_{81}N_{11}O_{11}+H)^+$: 1072.6190; Found: 1072.6185.

Macrolide FSM-22366

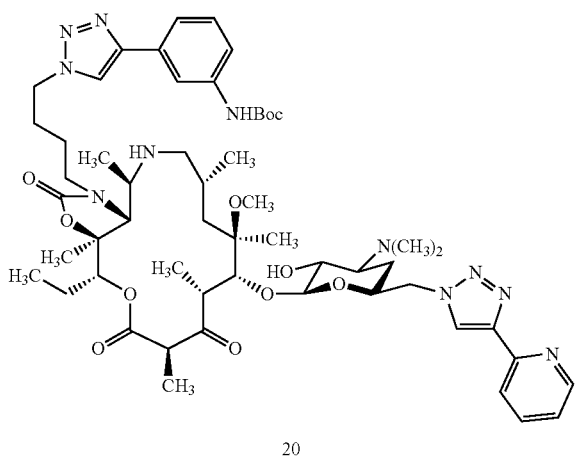
20

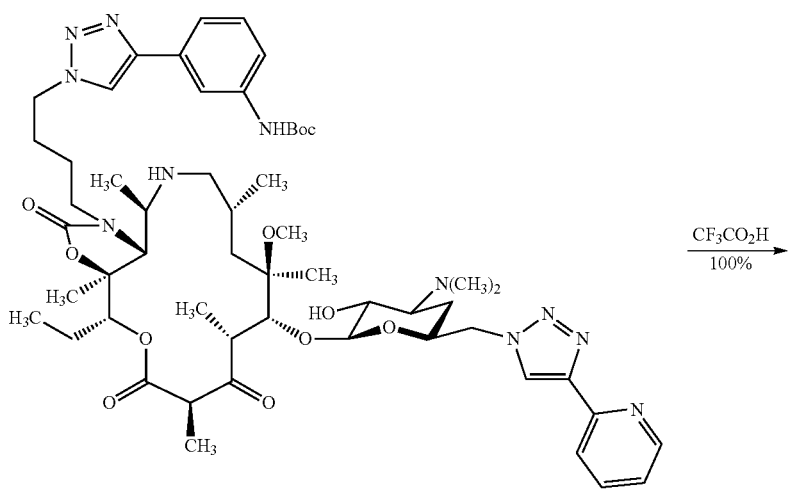
20

CF₃CO₂H
100%

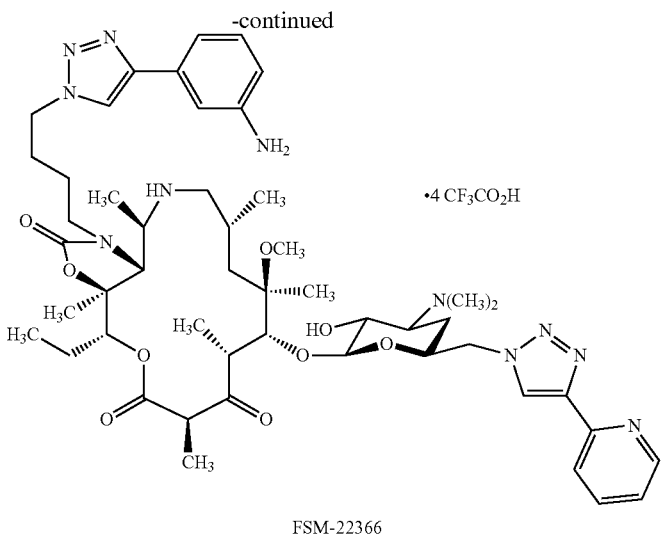

FSM-22366

6'-pyridyltriazolyl-15-macrolide 20 (7.8 mg, 7.27 μmol) was dissolved in 50% TFA/dichloromethane (1.0 mL). The solution was allowed to stand at room temperature for 2 hours, at which point LC-MS indicated full consumption of starting material. The solution was directly concentrated to afford the product (FSM-22366) as its TFA salt.

$^1$H NMR (500 MHz, CD$_3$OD) δ 8.82 (s, 1H), 8.67 (d, J=5.4 Hz, 1H), 8.47 (s, 1H), 8.24 (t, J=6.5 Hz, 1H), 8.14 (t, J=7.8 Hz, 1H), 7.99-7.93 (m, 1H), 7.93-7.86 (m, 1H), 7.62 (t, J=7.9 Hz, 1H), 7.58-7.50 (m, 1H), 7.40-7.35 (m, 1H), 4.89-4.74 (m, 3H), 4.62-4.51 (m, 2H), 4.39 (d, J=6.8 Hz, 1H), 4.30 (t, J=8.7 Hz, 1H), 4.14 (d, J=3.1 Hz, 1H), 4.05 (q, J=6.9 Hz, 1H), 3.84-3.70 (m, 1H), 3.66-3.54 (m, 2H), 3.50 (s, 1H), 3.42-3.35 (m, 1H), 3.11-2.98 (m, 1H), 2.96 (br s, 3H), 2.86 (br s, 3H), 2.85-2.82 (m, 1H), 2.78 (s, 3H), 2.69 (t, J=11.9 Hz, 1H), 2.34 (d, J=12.2 Hz, 1H), 2.08-1.93 (m, 3H), 1.91-1.51 (m, 7H), 1.49 (s, 3H), 1.32-1.29 (m, 4H), 1.25 (d, J=7.3 Hz, 3H), 1.24 (s, 3H), 1.16 (d, J=6.9 Hz, 3H), 1.06 (d, J=7.0 Hz, 3H), 0.87 (t, J=7.4 Hz, 3H). HRMS (ESI): Calcd for (C$_{50}$H$_{73}$N$_{11}$O$_9$+H)$^+$: 972.5665; Found: 972.5666.

Preparation of Macrolides with 6-Oxy-D-Desosamines

Synthesis of 6-benzoyl-D-desosamine donor ((2R,3R,4S,6S)-4-(dimethylamino)-6-(hydroxymethyl)-2-methoxytetrahydro-2H-pyran-3-yl methyl carbonate)

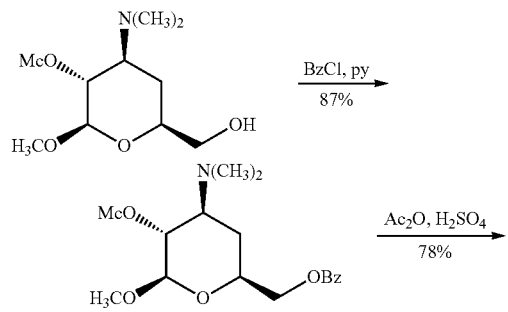

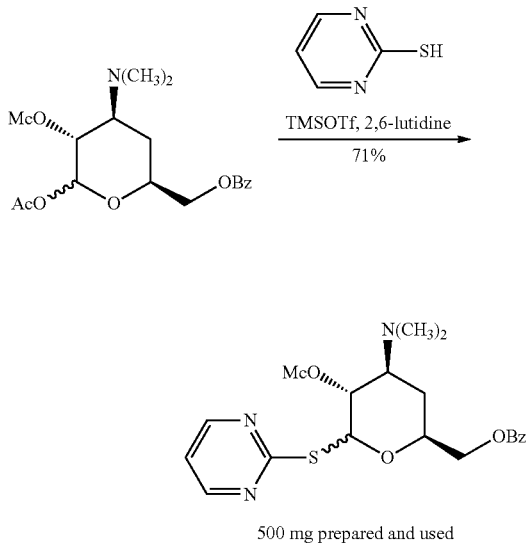

500 mg prepared and used

Preparation of the Eastern Half of a 6-Benzoyl-D-Desosamine Analog

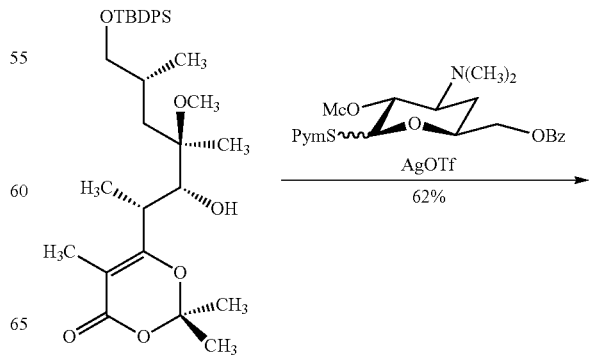

197
-continued
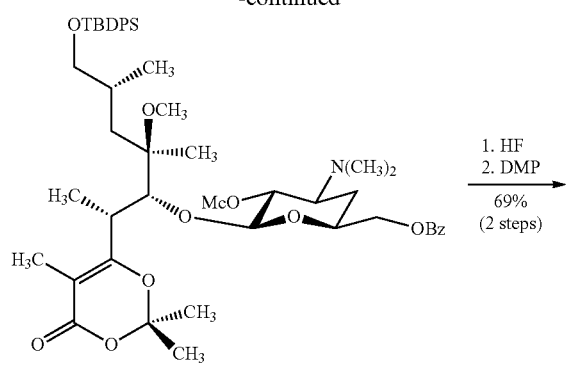
198
-continued
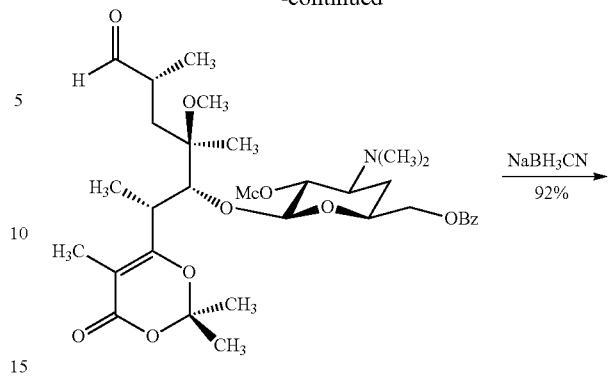
1. HF
2. DMP
69%
(2 steps)
NaBH$_3$CN
92%
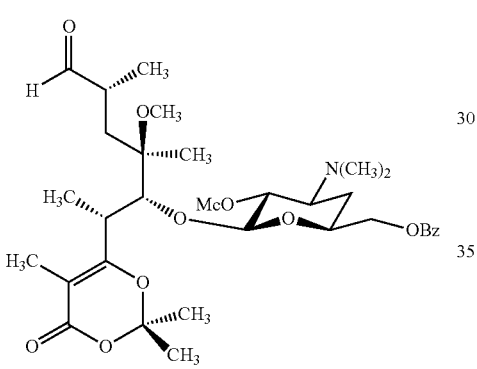
Coupling of the Eastern and Western Halves of a 6-Benzoyl-D-Desosamine Analog
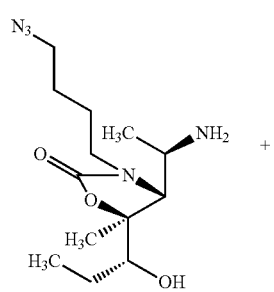
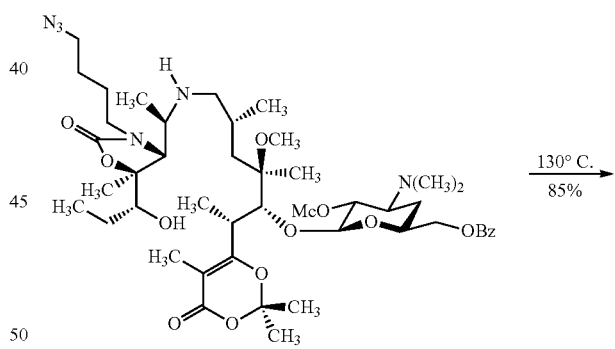
Cyclization of a 6-Benzoyl-D-Desosamine Analog
130° C.
85%
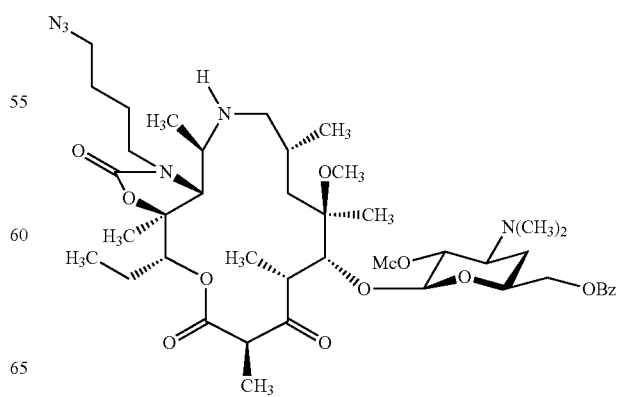

199
Post-Cyclization Modification of a
6-Benzoyl-D-Desosamine Analog
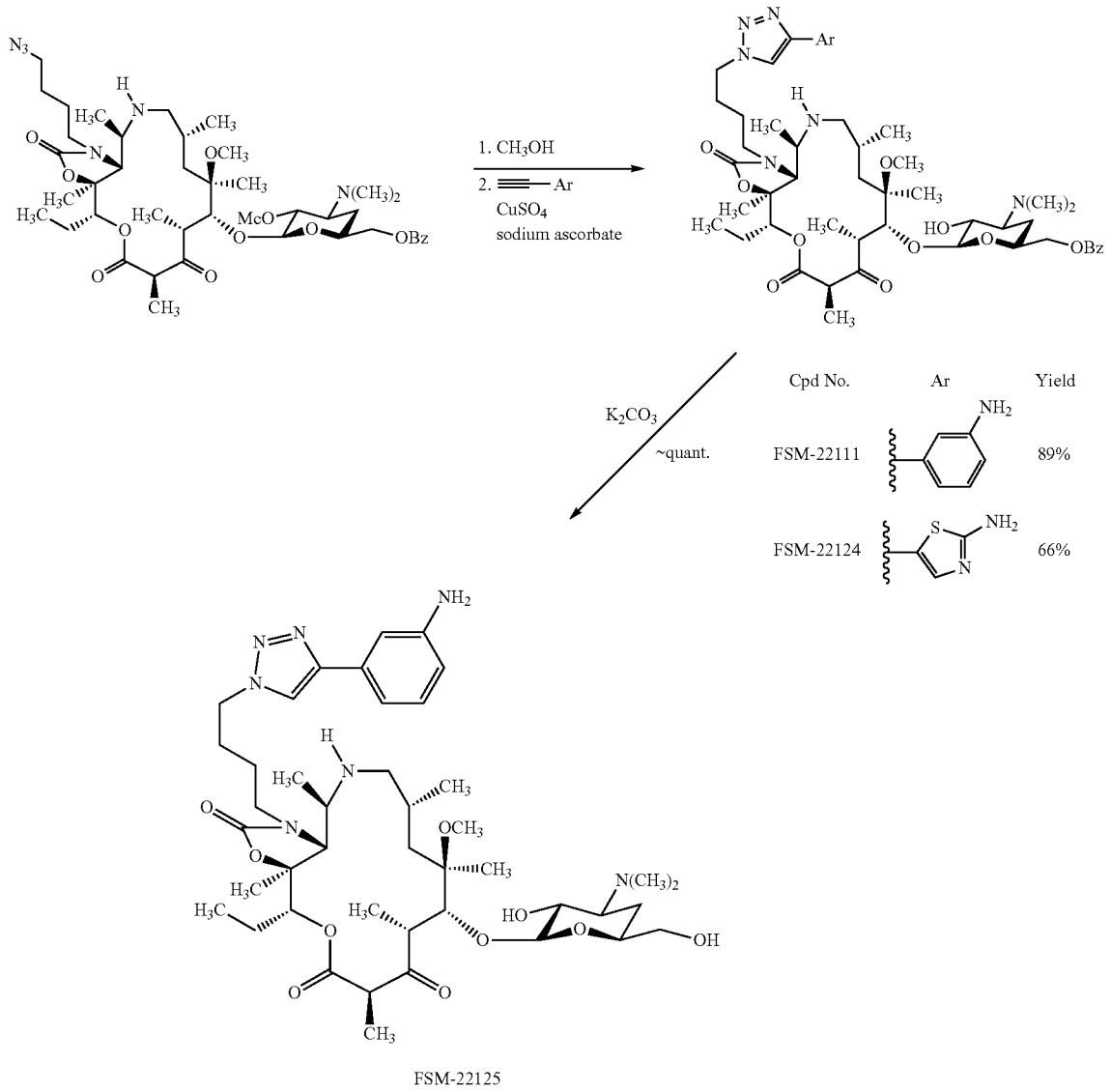
200
Preparation of Macrolides with
6-Amino-D-Desosamines
-continued
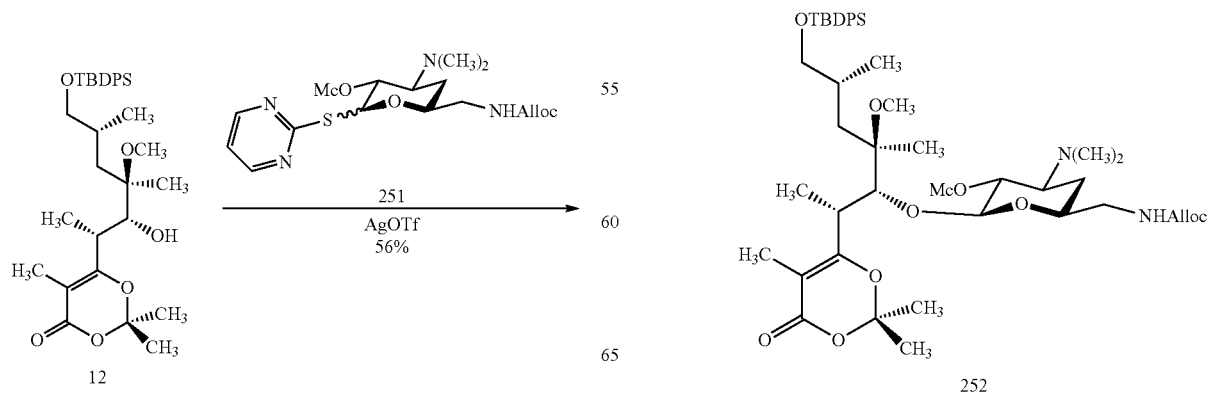

A mixture of alcohol 12 (350 mg, 0.615 mmol, 1 equiv) and thioglycoside 251 (787 mg, 1.85 mmol, 3.00 equiv) were dried by azeotropic distillation (benzene). The residue was dissolved in 1,2-dichloroethane (3.1 mL) and the solution was cooled to 0° C. Silver(I) trifluoromethanesulfonate (790 mg, 3.08 mmol, 5.00 equiv) was added in one portion. The resulting slurry was allowed to warm to 23° C. After 16 h, the reaction mixture was warmed to 40° C. After a total of 48 h, saturated aqueous sodium bicarbonate solution (10 mL) was added. The suspension was filtered through thin pad of Celite (~2 mm). The filtrate was extracted with dichloromethane (3×10 mL). The combined organic layers were dried over sodium sulfate and the dried solution was concentrated. The residue was purified by column chromatography (80→100% ethyl acetate-hexanes) to afford the product as a white foam (302 mg, 56%). TLC (10% methanol-ethyl acetate): $R_f$=0.69 (UV, p-anisaldehyde). 1H NMR (500 MHz, CDCl$_3$) δ 7.74-7.65 (m, 4H), 7.48-7.33 (m, 6H), 5.96-5.85 (m, 1H), 5.30 (d, J=17.0 Hz, 1H), 5.21 (t, J=13.3 Hz, 1H), 4.98-4.87 (m, 1H), 4.64-4.52 (m, 4H), 3.78 (d, J=2.9 Hz, 1H), 3.77 (s, 3H), 3.67 (dd, J=9.7, 4.6 Hz, 1H), 3.51-3.40 (m, 3H), 3.40-3.33 (m, 1H), 3.21 (dd, J=13.6, 7.2 Hz, 1H), 2.94 (s, 3H), 2.83-2.69 (m, 1H), 2.31 (s, 6H), 1.93-1.84 (m, 1H), 1.80 (s, 3H), 1.79-1.75 (m, 1H), 1.66 (s, 3H), 1.65 (s, 3H), 1.55 (dd, J=14.4, 6.8 Hz, 1H), 1.40 (dd, J=24.0, 12.1 Hz, 1H), 1.31-1.23 (m, 1H), 1.15 (s, 3H), 1.07 (s, 9H), 1.06 (d, J=6.9 Hz, 3H), 1.04 (d, J=7.4 Hz, 3H). $^{13}$C NMR (126 MHz, CDCl$_3$) δ 167.61, 162.91, 156.18, 155.11, 135.62, 134.21, 132.56, 129.42, 129.40, 127.50, 117.98, 104.51, 100.32, 99.71, 78.84, 78.30, 75.16, 72.01, 69.08, 65.80, 62.95, 54.74, 49.39, 44.96, 40.64, 36.41, 34.01, 31.15, 26.88, 25.87, 24.19, 20.33, 19.76, 19.35, 12.96, 9.77. FTIR (neat), cm$^{-1}$: 3340 (w), 2936 (m), 1722 (s), 1720 (s), 1267 (s), 1109 (s), 1070 (m), 708 (s). HRMS (ESI): Calcd for $(C_{47}H_{70}N_2O_{12}Si+H)^+$: 883.4771; Found: 883.4794.

Alcohol S26

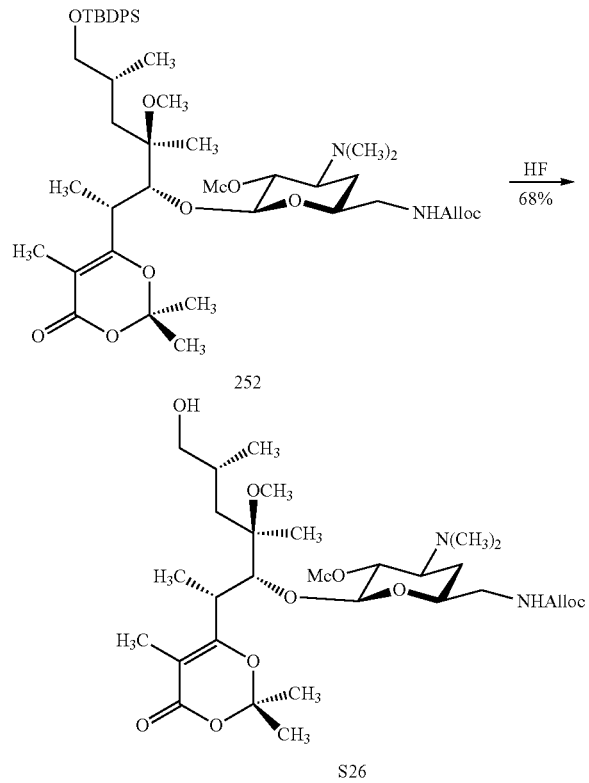

Hydrofluoric acid (48 wt %, 1.23 mL, 34.2 mmol, 100 equiv) was added to a stirred solution of glycoside 252 (302 mg, 0.342 mmol, 1 equiv) in acetonitrile (3.4 mL) at 23° C. After 12 h, the reaction mixture was slowly added to 100 mL saturated aqueous sodium bicarbonate solution. The mixture was extracted with ether (3×20 mL). The combined ether layers were washed with saturated sodium chloride solution and dried over magnesium sulfate. The dried solution was concentrated under reduced pressure. The residue was purified by flash column chromatography (3→4% methanol-dichloromethane+0.3→0.4% 30% aqueous ammonium hydroxide solution) to afford the product as a white foam (150 mg, 68%). TLC (10% methanol-ethyl acetate): $R_f$=0.48 (UV, p-anisaldehyde). $^1$H NMR (500 MHz, CDCl$_3$) δ 5.90 (ddd, J=16.4, 10.8, 5.2 Hz, 1H), 5.30 (d, J=17.3 Hz, 1H), 5.23 (d, J=10.4 Hz, 1H), 4.95 (t, J=5.5 Hz, 1H), 4.69-4.43 (m, 4H), 3.92 (d, J=2.9 Hz, 1H), 3.79 (s, 3H), 3.60 (ddd, J=11.0, 7.2, 3.9 Hz, 1H), 3.50 (dd, J=13.1, 6.5 Hz, 2H), 3.39 (dd, J=10.7, 7.1 Hz, 2H), 3.35-3.20 (m, 2H), 3.14 (s, 3H), 2.83-2.75 (m, 1H), 2.31 (s, 6H), 1.94-1.90 (m, 1H), 1.89 (s, 3H), 1.80 (d, J=12.8 Hz, 1H), 1.69 (s, 3H), 1.67 (s, 3H), 1.59 (dd, J=14.6, 2.8 Hz, 1H), 1.47-1.39 (m, 2H), 1.32 (s, 3H), 1.08 (d, J=7.3 Hz, 3H), 0.95 (d, J=6.9 Hz, 3H). $^{13}$C NMR (126 MHz, CDCl$_3$) δ 167.03, 162.68, 156.15, 155.17, 132.51, 118.01, 104.63, 100.30, 99.88, 79.56, 77.36, 75.14, 72.06, 68.34, 65.80, 62.87, 54.77, 49.59, 44.92, 40.62, 38.56, 33.92, 31.07, 26.04, 25.83, 23.99, 20.04, 19.87, 13.07, 9.87. FTIR (neat), cm$^{-1}$: 3377 (br), 2941 (m), 1716 (s), 1650 (s), 1265 (s), 1051 (s), 993 (s), 914 (s), 731 (s). HRMS (ESI): Calcd for $(C_{31}H_{52}N_2O_{12}+H)^+$: 645.3593; Found: 645.3617.

Aldehyde 253

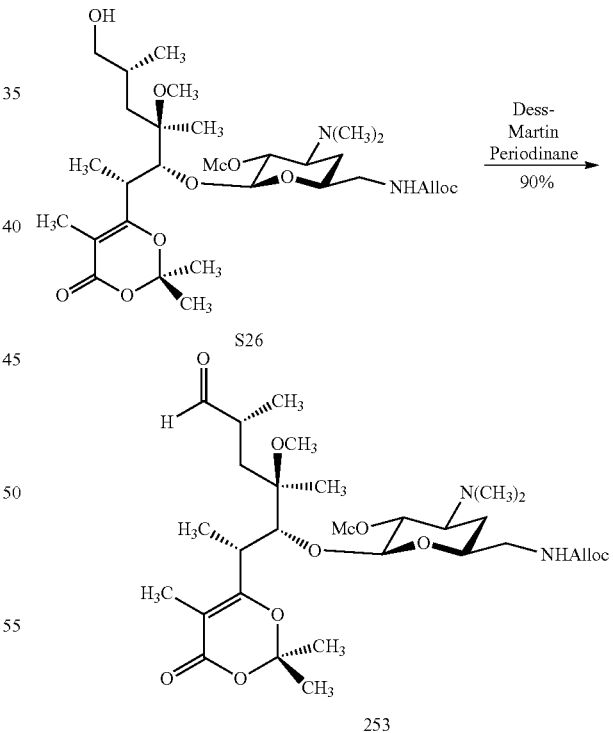

Dess-Martin periodinane (148 mg, 0.349 mmol, 1.50 equiv) was added in one portion to a solution of alcohol S26 (150 mg, 0.233 mmol, 1 equiv) in water-saturated dichloromethane (1.2 mL) at 23° C. After 1 h, to the reaction mixture was added ether (10 mL), saturated aqueous sodium bicarbonate solution (5 mL) and saturated sodium thiosulfate solution (5 mL). The mixture was stirred vigorously for 15 min. The layers were separated and the aqueous layer was extracted with ether (2×10 mL). The combined ether layers were washed with brine and dried over magnesium sulfate. The dried solution was concentrated under reduced pressure to afford the product as a white foam (135 mg, 90%). TLC (10% methanol-ethyl acetate): $R_f$=0.61 (UV, p-anisaldehyde). 1H NMR (500 MHz, CDCl$_3$) δ 9.37 (d, J=4.6 Hz, 1H), 5.98-5.83 (m, 1H), 5.29 (d, J=17.2 Hz, 1H), 5.22 (d, J=10.4 Hz, 1H), 4.97-4.92 (m, 1H), 4.65-4.51 (m, 4H), 3.85 (d, J=3.4 Hz, 1H), 3.79 (s, 3H), 3.55-3.43 (m, 2H), 3.43-3.31 (m, 1H), 3.28-3.17 (m, 1H), 2.98 (s, 3H), 2.84-2.74 (m, 1H), 2.49 (tt, J=15.7, 6.0 Hz, 1H), 2.32 (s, 6H), 1.86 (s, 3H), 1.86-1.78 (m, 2H), 1.68 (s, 3H), 1.66 (s, 3H), 1.58 (dd, J=14.2, 3.1 Hz, 1H), 1.43-1.35 (m, 1H), 1.27 (s, 3H), 1.08 (d, J=7.1 Hz, 6H). $^{13}$C NMR (126 MHz, CDCl$_3$) δ 204.40, 166.99, 162.73, 156.16, 155.17, 132.49, 118.02, 104.61, 100.39, 99.82, 78.22, 78.01, 75.09, 72.04, 65.81, 62.87, 54.79, 49.45, 44.91, 41.89, 40.56, 37.38, 33.93, 30.30, 25.94, 25.82, 24.09, 20.23, 15.60, 13.06, 9.79. FTIR (neat), cm$^{-1}$: 2939 (m), 1751 (s), 1716 (s), 1641 (m), 1265 (s), 1053 (s), 993 (s), 914 (s), 729 (s). HRMS (ESI): Calcd for $(C_{31}H_{50}N_2O_{12}+H)^+$: 643.3437; Found: 643.3466.

Amine 254 adding dry ice). Then a solution of aldehyde 253 (135 mg, 0.21 mmol, 1 equiv) in 9:1 methanol/acetic acid (0.5 mL) was added dropwise over 1 min. The reaction mixture was stirred at −15° C. for 1 h, at which point LC-MS analysis indicated full conversion. The reaction mixture was concentrated under reduced pressure (~30 mmHg, 30° C. water bath). The residue was partitioned between dichloromethane (10 mL) and saturated aqueous sodium bicarbonate solution (5 mL). The aqueous layer was extracted with dichloromethane (2×10 mL). The combined organic layers were dried over sodium sulfate and the dried solution was concentrated under reduced pressure. The residue was purified by flash column chromatography (2→4% methanol-dichloromethane+0.2→0.4% 30% aqueous ammonium hydroxide solution) to afford the product as a white foam (135 mg, 69%). TLC (10% methanol-ethyl acetate): $R_f$=0.50 (UV, p-anisaldehyde). $^1$H NMR (500 MHz, CDCl$_3$) δ 5.97-5.79 (m, 1H), 5.30 (d, J=17.1 Hz, 1H), 5.22 (d, J=10.3 Hz, 1H), 4.97 (t, J=5.7 Hz, 1H), 4.65-4.52 (m, 4H), 3.84 (d, J=4.8 Hz, 1H), 3.79 (s, 3H), 3.72 (d, J=2.8 Hz, 1H), 3.61-3.41 (m, 4H), 3.39 (dd, J=10.3, 1.8 Hz, 1H), 3.33 (t, J=6.5 Hz, 2H), 3.31-3.19 (m, 2H), 3.08 (s, 3H), 2.84-2.72 (m, 2H), 2.53 (d, J=5.4 Hz, 2H), 2.30 (s, 6H), 1.87 (s, 3H), 1.84-1.70 (m, 4H), 1.69 (s, 3H), 1.66 (s, 3H), 1.65-1.56 (m, 3H), 1.45-1.29 (m, 4H), 1.34 (s, 3H), 1.27 (s, 3H), 1.14 (d, J=6.4 Hz, 3H), 1.09 (d, J=7.2 Hz, 3H), 1.05 (t, J=7.4 Hz, 3H), 1.00 (d, J=6.7 Hz, 3H). $^{13}$C NMR (126 MHz, CDCl$_3$) δ 167.56, 163.16, 157.96, 156.18, 155.13, 132.55, 117.94, 104.67, 100.82, 99.09, 83.33, 79.19, 78.36, 78.13, 75.18, 72.00, 65.79, 62.98, 62.10, 54.82, 54.54, 54.42, 51.03, 49.76, 44.94, 43.43, 40.63, 37.90, 34.59, 28.86, 26.32, 26.10, 25.75, 24.11, 23.60, 21.17, 20.08, 16.73, 15.66, 13.50, 11.03, 9.92. FTIR (neat), cm$^{-1}$: 3363 (br), 2939 (m), 2098 (s), 1716 (s), 1265 (s), 1240 (s), 1049 (s), 912 (s), 729 (s). HRMS (ESI): Calcd for $(C_{44}H_{75}N_7O_{14}+H)^+$: 926.5445; Found: 926.5469.

Macrolactone 255

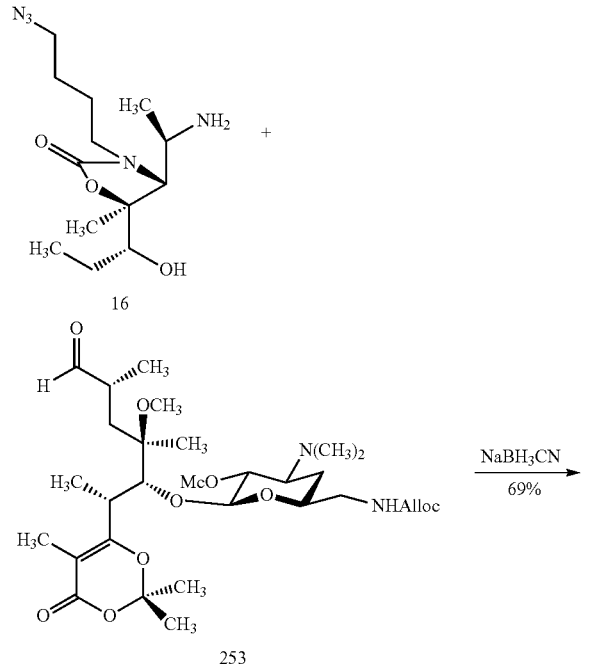

253

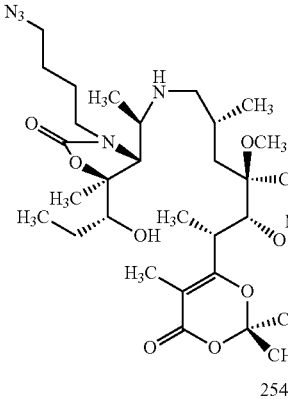

254

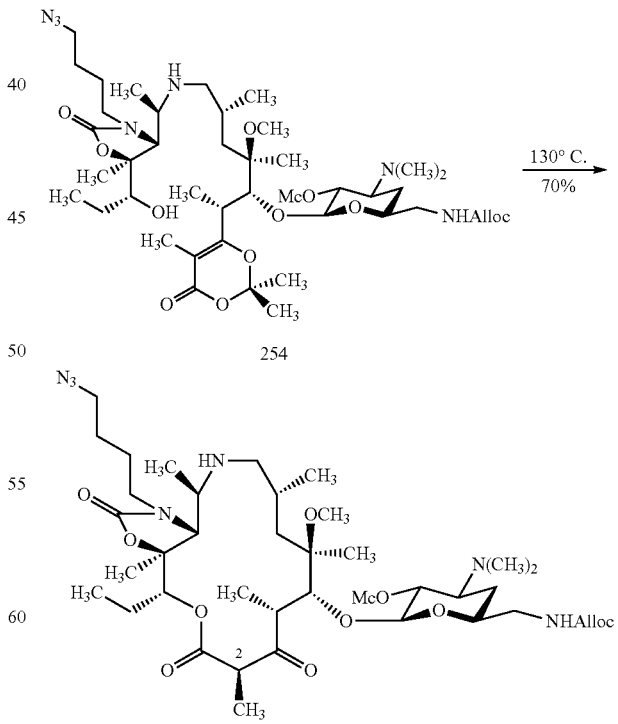

255
6:1 mixture of epimers at C2

Sodium cyanoborohydride (26 mg, 0.42 mmol, 2.0 equiv) was added to a solution of amine 16 (69 mg, 0.23 mmol, 1.1 equiv) in 9:1 methanol:acetic acid (2.0 mL) at −15° C. (acetone bath, temperature was maintained by periodically Macrocyclization precursor 254 (135 mg, 0.146 mmol) was dissolved in chlorobenzene (146 mL) in a 250-mL flask. The flask was fitted with a dry reflux condenser. Dry argon was bubbled through the solution via a 19-gauge needle for 10 min. The flask was then immersed in a 150° C. oil bath to allow a gentle reflux of the reaction solution. After 16 h, the heating bath was removed and the solution was allowed to cool to 23° C. The cooled solution was concentrated under reduced pressure (rotary evaporation, ~10 mmHg, 40° C. water bath) and the residue was purified by flash column chromatography (2→4% methanol-dichloromethane+ 0.2→0.4% 30% aqueous ammonium hydroxide solution) to afford the product as a white foam (88 mg, 70%). TLC (10% methanol-ethyl acetate): $R_f$=0.56 (p-anisaldehyde). $^1$H NMR (6:1 diastereomeric mixture at C2, major isomer is reported, 500 MHz, CDCl$_3$) δ 6.01-5.85 (m, 1H), 5.32 (d, J=17.2 Hz, 1H), 5.23 (d, J=10.2 Hz, 1H), 5.01 (t, J=4.7 Hz, 1H), 4.96 (dd, J=10.9, 2.0 Hz, 1H), 4.65-4.44 (m, 5H), 3.83 (q, J=7.2 Hz, 1H), 3.78 (s, 3H), 3.71-3.56 (m, 3H), 3.55-3.45 (m, 1H), 3.41 (s, 1H), 3.39-3.25 (m, 4H), 3.11-3.04 (m, 1H), 3.01 (s, 3H), 2.84-2.71 (m, 3H), 2.28 (s, 6H), 2.08-1.52 (m, 10H), 1.48-1.43 (m, 1H), 1.42 (s, 3H), 1.38 (d, J=6.9 Hz, 3H), 1.26 (s, 3H), 1.20 (d, J=7.8 Hz, 3H), 0.97 (app t, J=6.1 Hz, 6H), 0.89 (t, J=7.4 Hz, 3H). $^{13}$C NMR (6:1 diastereomeric mixture at C2, major isomer is reported, 126 MHz, CDCl$_3$) δ 205.53, 171.65, 156.84, 156.34, 155.03, 132.75, 117.71, 100.38, 80.96, 78.47, 78.18, 75.15, 74.68, 71.82, 65.71, 65.45, 63.03, 59.09, 58.17, 54.79, 50.92, 49.87, 49.79, 44.90, 44.68, 40.59, 27.60, 26.21, 25.47, 24.17, 21.80, 21.66, 18.96, 14.24, 14.03, 13.93, 13.70, 10.33. FTIR (neat), cm$^{-1}$: 2943 (m), 2096 (s), 1743 (s), 1716 (s), 1442 (s), 1263 (s), 1057 (s), 908 (s), 729 (s). HRMS (ESI): Calcd for $(C_{41}H_{69}N_7O_{13}+H)^+$: 868.5026; Found: 868.5042.

Macrolactone S27

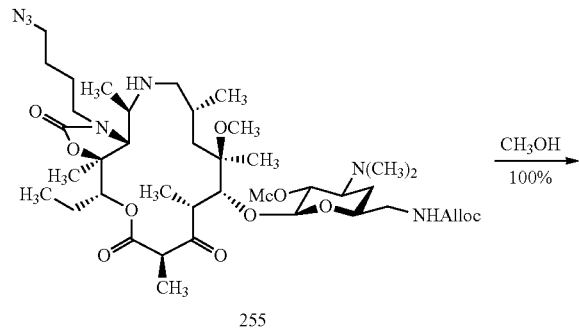

255

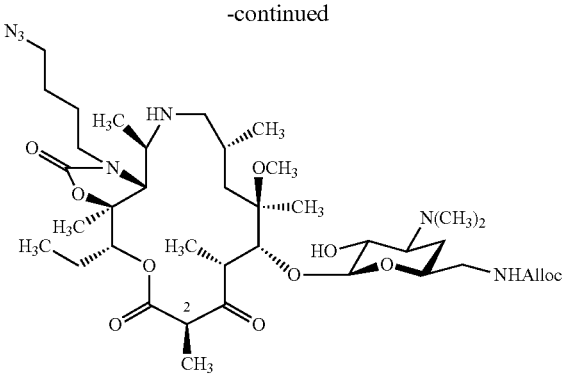

S27
6:1 mixture of epimers at C2

A solution of macrolactone 255 (70 mg, 0.081 mmol) in methanol (1 mL) was allowed to stand at 23° C. for 24 h. The solution was then concentrated under reduced pressure to afford the product as a white foam (65 mg, ~100%). TLC (10% methanol-dichloromethane+1% 30% aqueous ammonium hydroxide solution): $R_f$=0.45 (p-anisaldehyde). $^1$H NMR (6:1 diastereomeric mixture at C2, major isomer is reported, 500 MHz, CDCl$_3$) δ 6.02-5.83 (m, 1H), 5.32 (d, J=17.2 Hz, 1H), 5.23 (d, J=10.1 Hz, 1H), 5.05-4.99 (m, 1H), 4.95 (dd, J=10.8, 2.0 Hz, 1H), 4.73-4.47 (m, 3H), 4.41 (d, J=7.4 Hz, 1H), 3.86 (q, J=6.9 Hz, 1H), 3.70-3.57 (m, 3H), 3.55-3.44 (m, 1H), 3.41 (s, 1H), 3.38-3.13 (m, 5H), 3.11-3.04 (m, 1H), 3.02 (s, 3H), 2.82-2.71 (m, 2H), 2.57-2.46 (m, 1H), 2.27 (s, 6H), 2.03-1.82 (m, 1H), 1.82-1.53 (m, 9H), 1.43 (s, 3H), 1.40 (d, J=6.9 Hz, 3H), 1.37 (d, J=7.8 Hz, 3H), 1.28 (s, 3H), 1.24-1.17 (m, 1H), 0.98 (d, J=6.1 Hz, 3H), 0.96 (d, J=6.9 Hz, 3H), 0.89 (t, J=7.4 Hz, 3H). $^{13}$C NMR (6:1 diastereomeric mixture at C2, major isomer is reported, 126 MHz, CDCl$_3$) δ 205.74, 171.51, 156.86, 156.34, 132.78, 117.69, 103.02, 80.99, 78.41, 78.26, 75.56, 72.22, 70.11, 65.68, 65.55, 65.30, 59.13, 57.96, 50.92, 49.98, 49.84, 45.50, 45.11, 43.03, 40.91, 40.18, 27.75, 26.20, 24.13, 23.53, 21.76, 21.66, 19.06, 14.39, 14.32, 14.26, 14.09, 10.36. FTIR (neat), cm$^{-1}$: 3317 (w), 2941 (m), 2096 (s), 1737 (s), 1716 (s), 1427 (s), 1240 (s), 1070 (s), 1045 (s), 910 (s), 729 (s). HRMS (ESI): Calcd for $(C_{39}H_{67}N_7O_{11}+H)^+$: 810.4971; Found: 810.4983.

Triazole 256

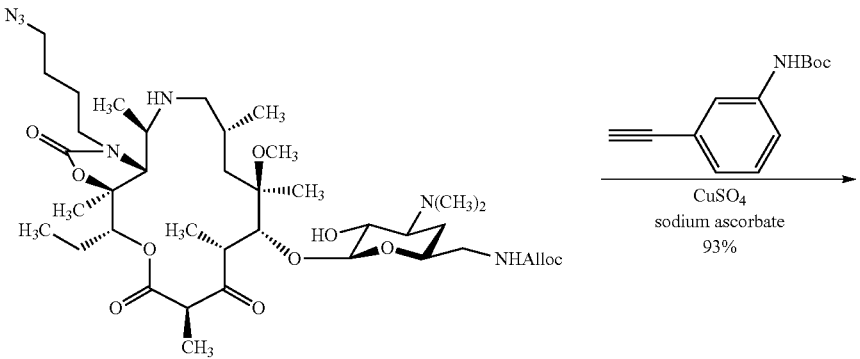

S27

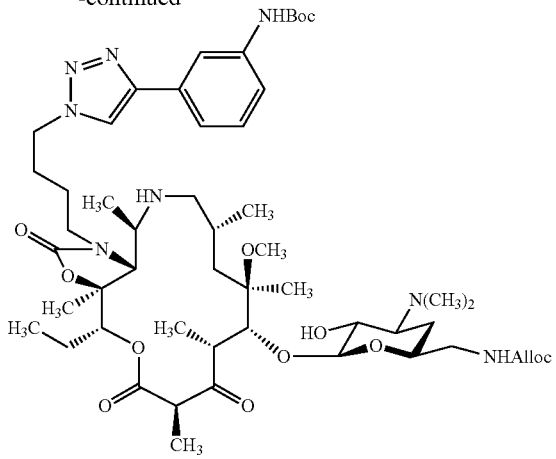

256
6:1 mixture of epimers at C2

To a solution of macrolactone S27 (65 mg, 0.080 mmol, 1 equiv) in 1:1 tert-butanol:water (1.0 mL) were added sequentially tert-butyl (3-ethynylphenyl)carbamate (52 mg, 0.24 mmol, 3.0 equiv), an aqueous solution of sodium ascorbate (0.10 M, 0.16 mL, 0.016 mmol, 0.20 equiv) and an aqueous solution of copper(II) sulfate (0.10 M, 40 μL, 4.0 μmol, 0.050 equiv). The mixture was stirred at 23° C. for 16 h, then was partitioned between saturated aqueous sodium bicarbonate solution (1 mL) and dichloromethane (1 mL). The aqueous layer was extracted with dichloromethane (3×2 mL). The combined organic layers were dried over sodium sulfate and the dried solution was concentrated under reduced pressure. The residue was purified by flash column chromatography (3→5% methanol-dichloromethane+0.3→0.5% 30% aqueous ammonium hydroxide solution) to afford the product (256) as a white foam (77 mg, 93%). $^1$H NMR (6:1 diastereomeric mixture at C2, major isomer is reported, 500 MHz, CDCl$_3$) δ 7.86 (s, 1H), 7.73 (s, 1H), 7.56-7.41 (m, 2H), 7.36 (t, J=7.9 Hz, 1H), 6.82 (s, 1H), 5.99-5.85 (m, 1H), 5.30 (d, J=12.9 Hz, 1H), 5.21 (d, J=10.3 Hz, 1H), 5.02 (t, J=4.7 Hz, 1H), 4.96 (d, J=10.7 Hz, 1H), 4.59 (s, 2H), 4.54-4.33 (m, 4H), 3.89 (q, J=6.6 Hz, 1H), 3.79-3.55 (m, 3H), 3.45 (s, 1H), 3.40 (s, 1H), 3.31 (d, J=12.6 Hz, 1H), 3.24-3.10 (m, 2H), 3.10-2.99 (m, 1H), 2.93 (s, 3H), 2.83-2.69 (m, 2H), 2.56-2.46 (m, 1H), 2.28 (s, 6H), 2.16-1.85 (m, 2H), 1.85-1.60 (m, 8H), 1.58-1.48 (m, 9H), 1.44 (s, 3H), 1.41 (d, J=6.9 Hz, 3H), 1.37 (d, J=7.8 Hz, 3H), 1.24 (s, 3H), 1.22-1.16 (m, 1H), 0.99 (d, J=6.0 Hz, 3H), 0.94 (d, J=6.8 Hz, 3H), 0.89 (t, J=7.3 Hz, 3H). $^{13}$C NMR (6:1 diastereomeric mixture at C2, major isomer is reported, 126 MHz, CDCl$_3$) δ 205.72, 171.68, 156.94, 156.35, 152.75, 147.41, 138.92, 132.77, 131.41, 129.43, 120.29, 119.74, 118.03, 117.66, 115.59, 103.04, 81.06, 78.44, 78.25, 75.52, 72.22, 70.05, 65.64, 65.52, 59.01, 57.87, 50.03, 49.83, 49.70, 45.54, 45.02, 42.73, 40.81, 40.14, 28.32, 27.68, 27.53, 24.11, 23.49, 21.71, 21.63, 19.00, 14.45, 14.30, 14.23, 14.05, 10.42. FTIR (neat), cm$^{-1}$: 3313 (w), 2945 (m), 1732 (s), 1529 (s), 1454 (s), 1240 (s), 1180 (s), 1070 (s), 1051 (s), 732 (s). HRMS (ESI): Calcd for (C$_{52}$H$_{82}$N$_8$O$_{13}$+H)$^+$: 1027.6074; Found: 1027.6092.

Amine 257

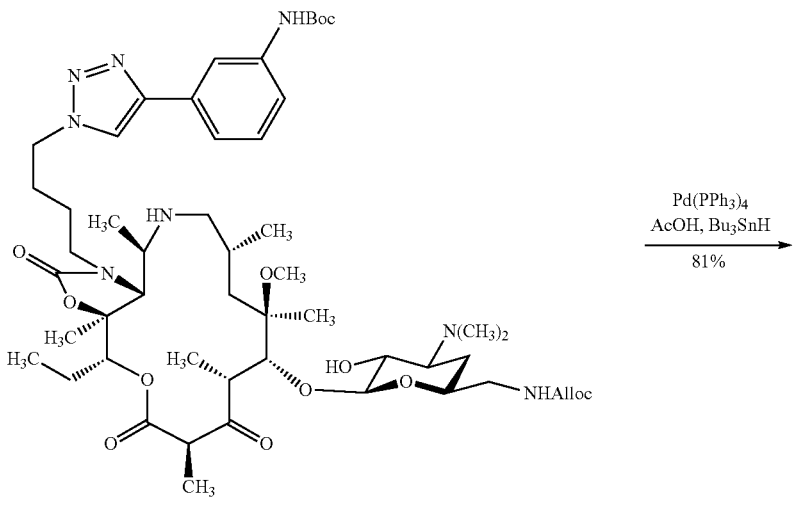

256

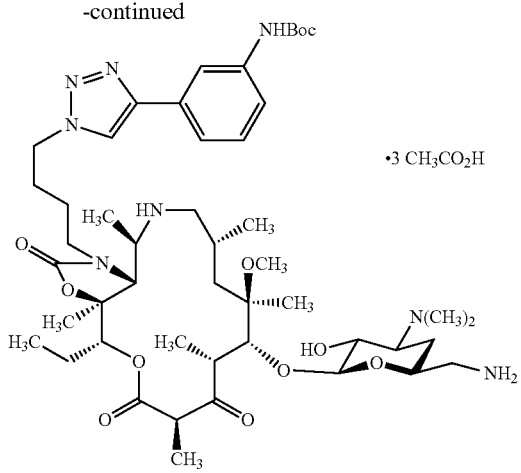

257
4:1 mixture of epimers at C2

Tetrakis(triphenylphosphine)palladium(0) (1.7 mg, 1.5 μmol, 0.020 equiv) and tri-n-butyltinhydride (40 μL, 0.15 mmol, 2.0 equiv) were added sequentially to a solution of macrocycle 256 (77 mg, 0.075 mmol, 1 equiv) and acetic acid (21 μL, 0.38 mmol, 5.0 equiv) in THF (0.75 mL) at 23° C. The reaction mixture was stirred for 1 h at 23° C. and then partitioned between ethyl ether (5 mL) and water (5 mL). The aqueous layer was extracted with ether (2×5 mL). The ether layers were discarded, and the aqueous layer was concentrated under reduced pressure (0.1 mmHg) to afford to the product in its triacetate salt form as a white solid (68 mg, 81%). $^1$H NMR (4:1 diastereomeric mixture at C2, major isomer is reported, 500 MHz, CD$_3$OD) δ 8.29 (s, 1H), 7.83 (d, J=11.9 Hz, 1H), 7.50-7.29 (m, 3H), 4.96 (dd, J=10.7, 2.2 Hz, 1H), 4.60-4.45 (m, 5H), 4.42 (d, J=7.4 Hz, 1H), 4.07 (q, J=6.8 Hz, 1H), 3.88-3.80 (m, 1H), 3.64 (t, J=6.9 Hz, 2H), 3.52-3.42 (m, 1H), 3.28-3.16 (m, 2H), 3.15-3.05 (m, 2H), 2.97 (s, 3H), 2.94-2.83 (m, 1H), 2.81-2.72 (m, 1H), 2.68 (s, 6H), 2.10-1.98 (m, 2H), 1.91-1.80 (m, 2H), 1.76-1.57 (m, 6H), 1.55 (s, 9H), 1.48 (s, 3H), 1.37 (d, J=8.4 Hz, 3H), 1.32 (d, J=6.4 Hz, 3H), 1.29 (s, 3H), 1.28-1.24 (m, 1H), 0.99 (d, J=6.1 Hz, 3H), 0.95 (d, J=7.1 Hz, 3H), 0.90 (t, J=7.3 Hz, 3H). $^{13}$C NMR (4:1 diastereomeric mixture at C2, major isomer is reported, 126 MHz, CD$_3$OD) δ 207.80, 178.28, 173.37, 158.94, 155.20, 148.78, 141.26, 132.28, 130.38, 122.36, 120.96, 119.57, 116.91, 103.35, 83.35, 83.18, 80.94, 79.75, 79.38, 76.04, 71.06, 70.72, 66.88, 65.98, 59.91, 59.14, 50.99, 50.95, 46.51, 44.29, 44.15, 42.08, 40.33, 31.90, 28.87, 28.74, 28.54, 25.39, 22.83, 22.16, 19.60, 14.68, 14.66, 14.35, 14.07, 11.02, 10.93. FTIR (neat), cm$^{-1}$: 2960 (m), 1732 (s), 1570 (s), 1456 (s), 1390 (s), 1240 (s), 1166 (s), 1070 (s). HRMS (ESI): Calcd for (C$_{48}$H$_{78}$N$_8$O$_{11}$+H)$^+$: 943.5863; Found: 942.5870.

FSM-21795

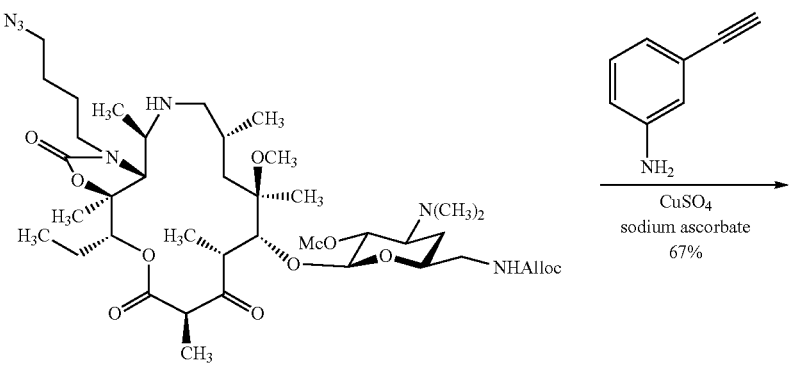

257

-continued

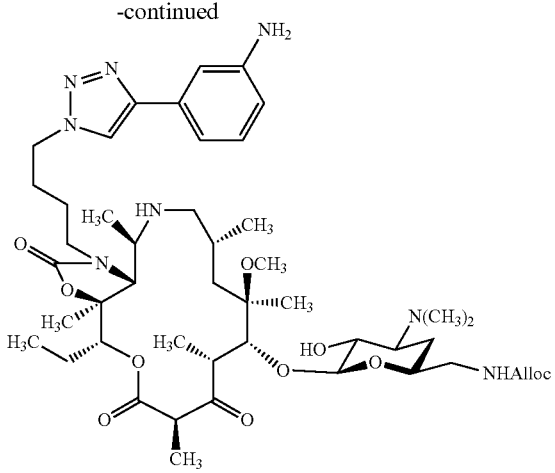

259 (FSM-21795)
10:1 mixture of epimers at C2

To a solution of macrocycle 257 (13 mg, 0.016 mmol, 1 equiv) in 1:1 tert-butanol:water (0.20 mL) were added sequentially 3-ethynylaniline (5.6 mg, 0.048 mmol, 3.0 equiv), an aqueous solution of sodium ascorbate (0.10 M, 32 μL, 3.2 μmol, 0.20 equiv) and an aqueous solution of copper(II) sulfate (0.10 M, 8 μL, 0.8 μmol, 0.05 equiv). The mixture was stirred at 23° C. for 16 h, then was partitioned between saturated aqueous sodium bicarbonate solution (1 mL) and dichloromethane (1 mL). The aqueous layer was extracted with dichloromethane (3×2 mL). The combined organic layers were dried over sodium sulfate and the dried solution was concentrated under reduced pressure. The residue was purified by flash column chromatography (3→5% methanol-dichloromethane+0.3→0.5% 30% aqueous ammonium hydroxide solution) to afford the product as a white foam (10 mg, 67%). $^1$H NMR (10:1 diastereomeric mixture at C2, major isomer is reported, 500 MHz, CDCl$_3$) δ 7.81 (s, 1H), 7.26-7.12 (m, 3H), 6.71-6.62 (m, 1H), 6.00-5.85 (m, 1H), 5.30 (d, J=16.2 Hz, 1H), 5.21 (d, J=10.3 Hz, 1H), 5.05 (t, J=5.6 Hz, 1H), 4.97 (dd, J=10.8, 1.8 Hz, 1H), 4.58 (br s, 2H), 4.56-4.35 (m, 4H), 3.89 (q, J=6.8 Hz, 1H), 3.82 (br s, 2H), 3.79-3.60 (m, 4H), 3.51-3.43 (m, 1H), 3.42 (s, 1H), 3.40-3.26 (m, 1H), 3.21 (dd, J=10.1, 7.5 Hz, 1H), 3.10-3.03 (m, 1H), 2.95 (s, 3H), 2.81-2.73 (m, 2H), 2.57-2.47 (m, 1H), 2.28 (s, 6H), 2.07-1.93 (m, 3H), 1.80-1.48 (m, 7H), 1.44 (s, 3H), 1.41 (d, J=6.9 Hz, 3H), 1.38 (d, J=7.8 Hz, 3H), 1.25 (s, 3H), 1.19 (d, J=12.9 Hz, 1H), 0.99 (d, J=6.1 Hz, 3H), 0.94 (d, J=6.9 Hz, 3H), 0.89 (t, J=7.4 Hz, 3H). HRMS (ESI): Calcd for (C$_{47}$H$_{74}$N$_8$O$_{11}$+H)$^+$: 927.5550; Found: 927.5557.

FSM-21700

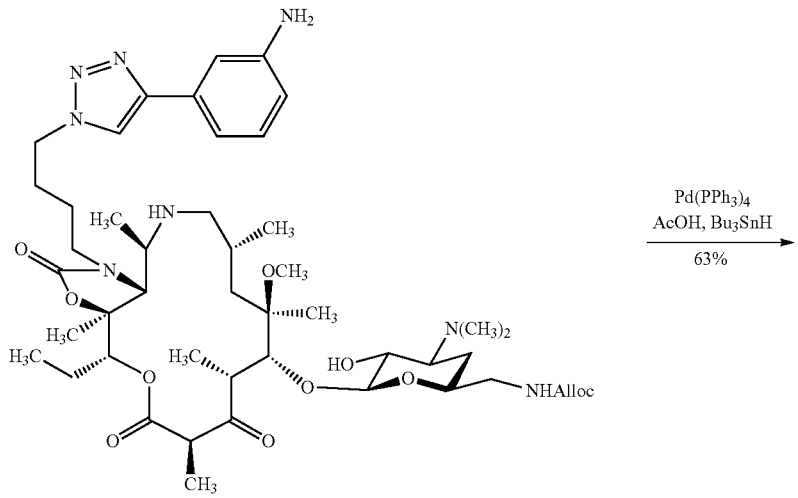

259

-continued

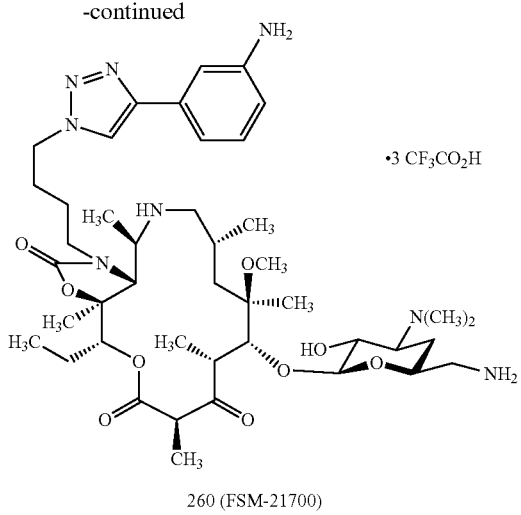

260 (FSM-21700)

Acetic acid (1.2 µL, 0.022 mmol, 5.0 equiv) and tri-n-butyltin hydride (2.3 µL, 8.6 µmol, 2.0 equiv) were added sequentially to a solution of 259 (4.0 mg, 4.3 µmol, 1 equiv) in THF (0.1 mL). Tetrakis(triphenylphosphine)palladium(0) (5.0 mg, 4.3 µmol, 1.0 equiv) was added in one portion. After 30 min, water (2 mL) was added to the reaction solution. The resulting suspension was extracted with ether (3×2 mL). The ether layers were discarded, and the aqueous layer was concentrated under reduced pressure (rotary evaporation, 10 mmHg, 40° C. water bath). To the residue was added 50% trifluoroacetic acid-dichloromethane (0.2 mL). The solution was then concentrated under reduced pressure to afford the product as a white solid (3.2 mg, 63%).

$^1$H NMR (500 MHz, CD$_3$OD) δ 8.43 (s, 1H), 7.84 (d, J=6.8 Hz, 2H), 7.60 (t, J=8.2 Hz, 1H), 7.34 (d, J=8.5 Hz, 1H), 4.94 (d, J=10.7 Hz, 1H), 4.62 (d, J=3.3 Hz, 1H), 4.59-4.47 (m, 3H), 4.18 (q, J=6.9 Hz, 1H), 4.06-3.98 (m, 1H), 3.85-3.75 (m, 1H), 3.70-3.65 (m, 1H), 3.63 (s, 1H), 3.57 (d, J=6.6 Hz, 2H), 3.46-3.41 (m, 1H), 3.27-3.20 (m, 1H), 3.19 (s, 3H), 3.16-3.09 (m, 1H), 3.09-3.00 (m, 1H), 2.91 (s, 3H), 2.84 (s, 3H), 2.77 (t, J=11.8 Hz, 1H), 2.22-1.58 (m, 10H), 1.55 (s, 3H), 1.44 (s, 3H), 1.38 (d, J=7.6 Hz, 3H), 1.37-1.29 (m, 7H), 1.10 (d, J=7.1 Hz, 3H), 0.95 (t, J=7.5 Hz, 3H). HRMS (ESI): Calcd for (C$_{43}$H$_{70}$N$_8$O$_9$+H)$^+$: 843.5339; Found: 843.5352.

Dichloroacetamide S27

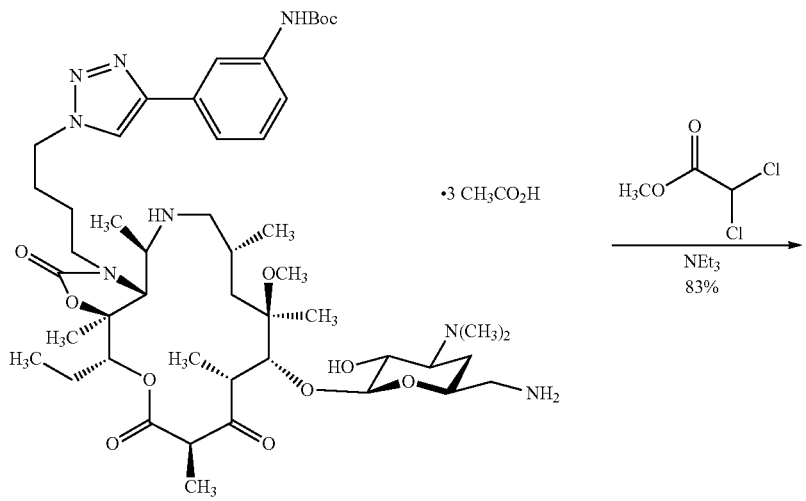

257

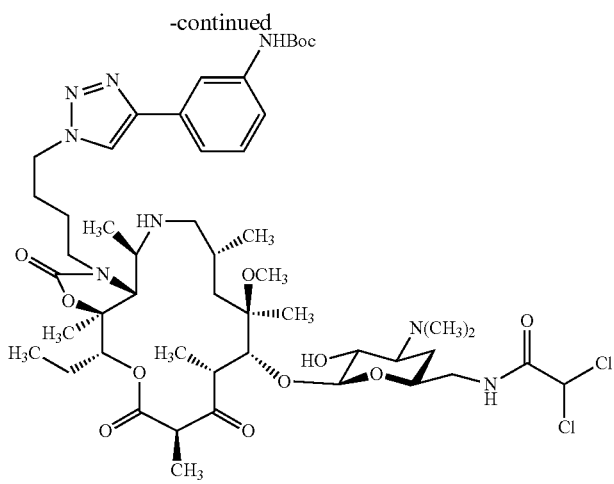

S27

Methyl 2,2-dichloroacetate (2.5 mg, 0.018 mmol, 5 equiv) and triethylamine (2.5 µL, 0.018 mmol, 5 equiv) were added sequentially to a solution of amine 257 (4.0 mg, 3.6 µmol, 1 equiv) in methanol (0.2 mL) at 23° C. The solution was warmed to 50° C. and held at that temperature for 19 h. After cooling to 23° C., the mixture was concentrated under reduced pressure, and the residue was purified by column chromatography (3→5% methanol-dichloromethane+ 0.3→0.5% 30% aqueous ammonium hydroxide solution) to afford the product as a white solid (3.1 mg, 83%). $^1$H NMR (12:1 diastereomeric mixture at C2, major isomer is reported, 500 MHz, CDCl$_3$) δ 7.85 (s, 1H), 7.73 (s, 1H), 7.53 (d, J=7.6 Hz, 1H), 7.51-7.45 (m, 1H), 7.37 (t, J=7.9 Hz, 1H), 6.98 (t, J=5.3 Hz, 1H), 6.75 (s, 1H), 5.97 (s, 1H), 4.97 (d, J=9.1 Hz, 1H), 4.56 (d, J=3.1 Hz, 1H), 4.53-4.36 (m, 3H), 3.90 (q, J=7.3 Hz, 1H), 3.80-3.59 (m, 4H), 3.41 (s, 1H), 3.38-3.28 (m, 1H), 3.24 (dd, J=10.1, 7.5 Hz, 1H), 3.12-3.02 (m, 1H), 2.94 (s, 3H), 2.82-2.72 (m, 2H), 2.59-2.47 (m, 1H), 2.28 (s, 6H), 2.12-1.91 (m, 3H), 1.83-1.58 (m, 8H), 1.54 (s, 9H), 1.44 (s, 3H), 1.41 (d, J=6.9 Hz, 3H), 1.38 (d, J=7.8 Hz, 3H), 1.28 (s, 3H), 1.23-1.17 (m, 1H), 0.99 (d, J=6.0 Hz, 3H), 0.95 (d, J=6.8 Hz, 3H), 0.89 (t, J=7.4 Hz, 3H). HRMS (ESI): Calcd for (C$_{50}$H$_{78}$Cl$_2$N$_8$O$_{12}$+H)$^+$: 1053.5189; Found: 1053.5198.

FSM-21842

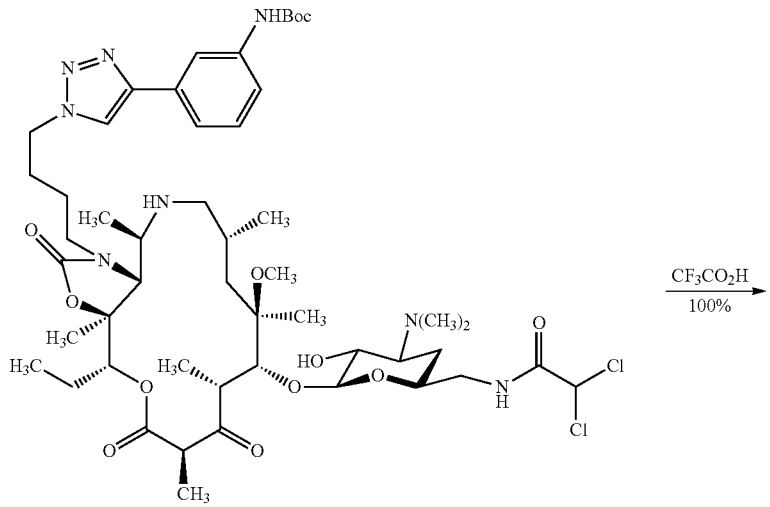

S27

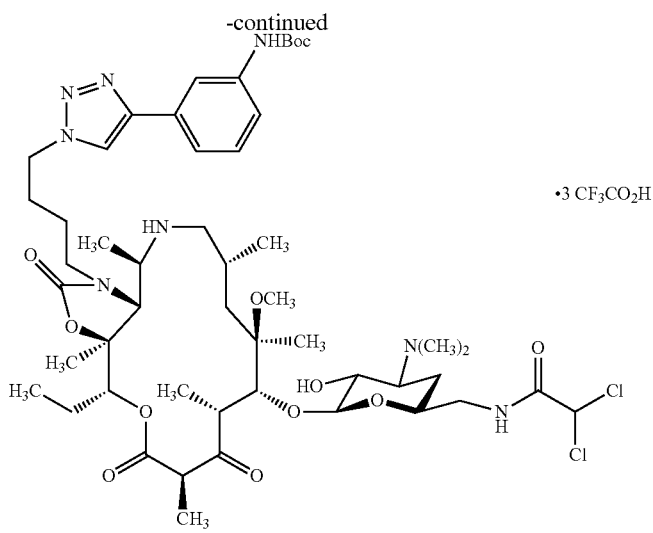

261 (FSM-21842)

Dichloroacetamide S27 (3.1 mg, 2.9 μmol) was dissolved in 50% trifluoroacetic acid-dichloromethane at 23° C. After 2 h, the solution was concentrated under reduced pressure to afford the product as a pale yellow solid (3.8 mg, 100%). 1H NMR (500 MHz, CD$_3$OD) δ 8.41 (s, 1H), 7.84-7.70 (m, 2H), 7.56 (t, J=7.9 Hz, 1H), 7.28 (d, J=8.0 Hz, 1H), 6.35 (s, 1H), 4.94 (d, J=8.5 Hz, 1H), 4.60-4.49 (m, 4H), 4.15 (q, J=6.8 Hz, 1H), 3.93-3.77 (m, 2H), 3.68 (d, J=6.6 Hz, 1H), 3.63 (s, 1H), 3.59 (dd, J=13.9, 7.5 Hz, 1H), 3.55-3.44 (m, 4H), 3.15 (s, 3H), 3.13-3.05 (m, 1H), 3.01 (dd, J=7.7, 3.4 Hz, 1H), 2.91 (s, 3H), 2.82 (s, 3H), 2.76 (t, J=11.8 Hz, 1H), 2.14-1.97 (m, 3H), 1.97-1.59 (m, 7H), 1.54 (s, 3H), 1.50-1.43 (m, 1H), 1.42 (s, 3H), 1.37-1.27 (m, 9H), 1.10 (d, J=7.1 Hz, 3H), 0.92 (t, J=7.3 Hz, 3H). HRMS (ESI): Calcd for (C$_{45}$H$_{70}$Cl$_2$N$_8$O$_{10}$+H)$^+$: 953.4665; Found: 953.4674.

Guanidine S28

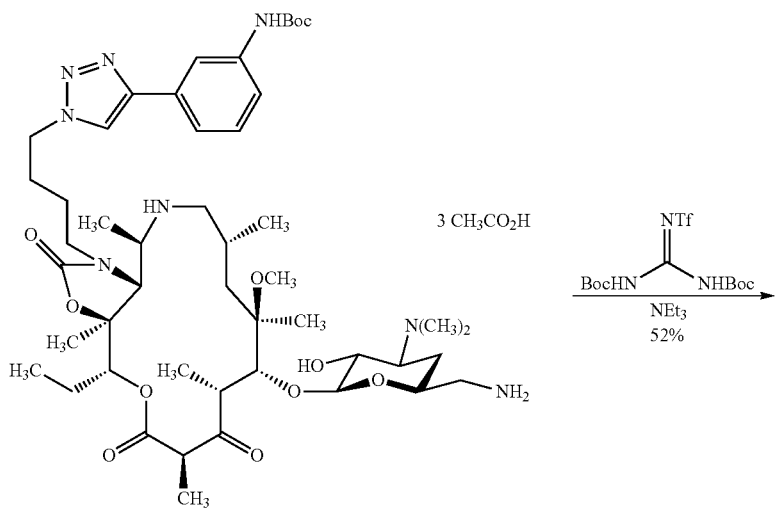

257

-continued

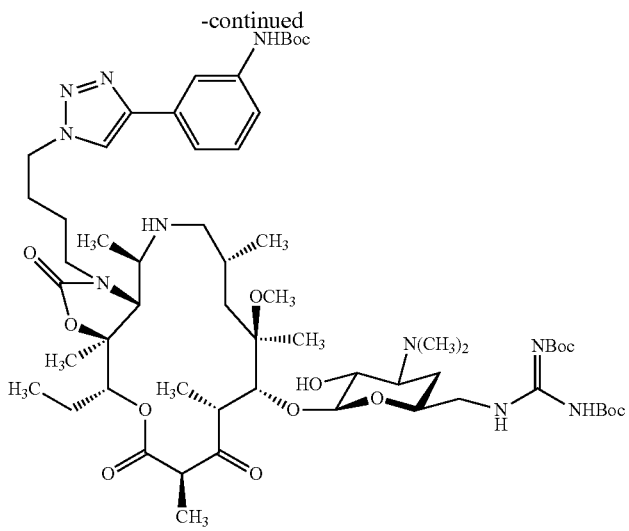

S28

Triethylamine (2.5 μL, 0.018 mmol, 5 equiv) and N,N'-bis(tert-butoxycarbonyl)-N''-trifluorosulfonylguanidine (4.2 mg, 0.011 mmol, 3 equiv) were added sequentially to a solution of amine 257 (4 mg, 3.6 μmol, 1 equiv) in dichloromethane (0.2 mL) at 23° C. The resulting solution was stirred at 23° C. for 5 h, and was concentrated under reduced pressure. The residue was purified by column chromatography (3→5% methanol-dichloromethane+0.3→0.5% 30% aqueous ammonium hydroxide solution) to afford the product as a white solid (2.2 mg, 52%). 1H NMR (500 MHz, CDCl$_3$) δ 8.79-8.66 (m, 1H), 7.86 (s, 1H), 7.78 (s, 1H), 7.73 (br s, 1H), 7.60-7.39 (m, 2H), 7.35 (t, J=7.9 Hz, 1H), 6.70 (s, 1H), 4.97 (d, J=9.3 Hz, 1H), 4.60 (d, J=3.2 Hz, 1H), 4.51-4.39 (m, 3H), 4.39-4.20 (m, 1H), 4.08-3.93 (m, 1H), 3.88 (q, J=6.9 Hz, 1H), 3.80-3.61 (m, 2H), 3.44 (s, 1H), 3.32-3.14 (m, 2H), 3.14-3.08 (m, 1H), 3.05 (s, 3H), 2.83-2.72 (m, 2H), 2.58-2.48 (m, 1H), 2.29 (s, 6H), 2.08-1.91 (m, 4H), 1.82-1.56 (m, 7H), 1.54 (s, 9H), 1.53 (s, 9H), 1.51 (s, 9H), 1.48-1.24 (m, 13H), 0.99 (d, J=6.0 Hz, 3H), 0.95 (d, J=6.7 Hz, 3H), 0.89 (t, J=6.6 Hz, 3H). HRMS (ESI): Calcd for $(C_{59}H_{96}N_{10}O_{15}+H)^+$: 1185.7129; Found: 1185.7145. FSM-21843

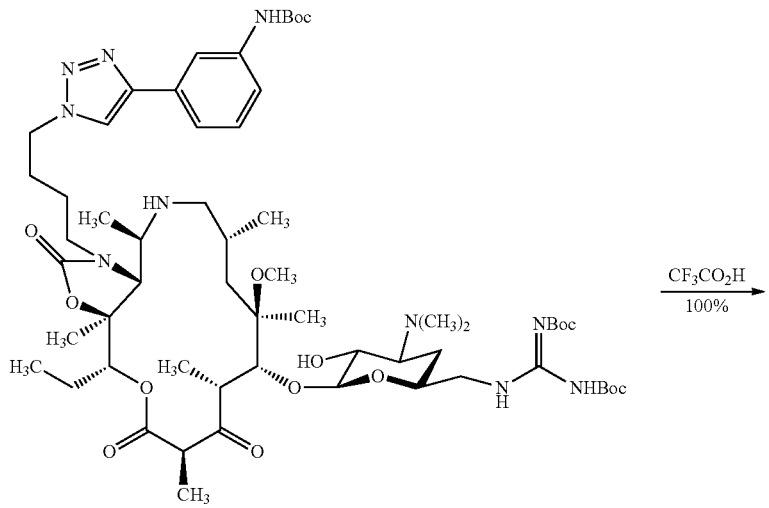

S28

-continued
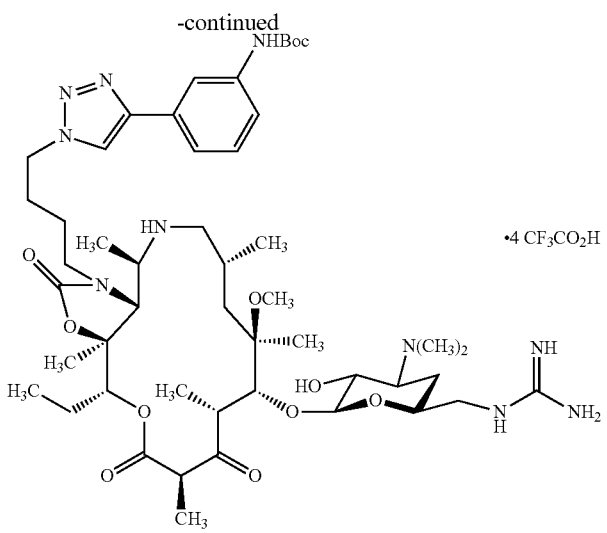
262 (FSM-21843)
Guanidine S28 (2.2 mg, 1.9 μmol) was dissolved in 50% trifluoroacetic acid-dichloromethane at 23° C. After 2 h, the solution was concentrated under reduced pressure to afford the product as a pale yellow solid (2.5 mg, 100%). $^1$H NMR (500 MHz, CD$_3$OD) δ 8.42 (s, 1H), 7.77-7.61 (m, 3H), 7.29-7.16 (m, 1H), 4.62-4.43 (m, 4H), 4.43-4.22 (m, 2H), 4.16 (q, J=6.9 Hz, 1H), 3.93-3.85 (m, 1H), 3.85-3.72 (m, 1H), 3.70-3.62 (m, 1H), 3.61 (s, 1H), 3.59-3.49 (m, 4H), 3.13 (s, 3H), 3.12-3.06 (m, 1H), 3.06-2.97 (m, 1H), 2.92 (s, 3H), 2.83 (s, 3H), 2.74 (t, J=11.8 Hz, 1H), 2.19-1.95 (m, 3H), 1.95-1.55 (m, 7H), 1.54 (s, 3H), 1.49-1.43 (m, 1H), 1.41 (s, 3H), 1.38-1.25 (m, 9H), 1.09 (d, J=6.9 Hz, 3H), 0.90 (t, J=6.7 Hz, 3H). HRMS (ESI): Calcd for (C$_{44}$H$_{72}$N$_{10}$O$_9$+ H)$^+$: 885.5557; Found: 885.5562.
FSM-21861
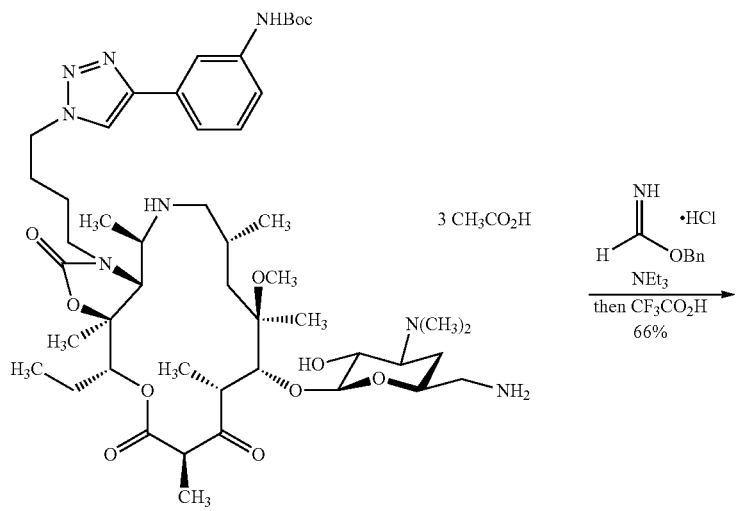
257

-continued

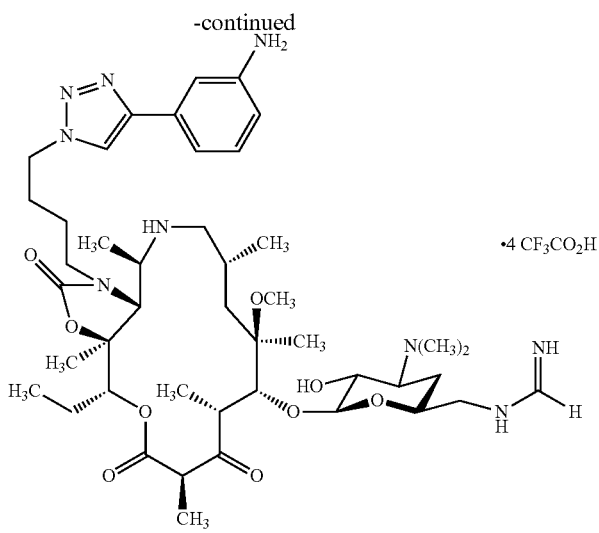

263 (FSM-21861)

Benzyl formimidate hydrochloride (2.3 mg, 0.013 mmol, 3.0 equiv) was added to a solution of amine 257 (5.0 mg, 4.5 μmol, 1 equiv) and triethylamine (6.2 μL, 0.045 mmol, 10 equiv) in dichloromethane (0.2 mL) at −50° C. The solution was allowed to warm to −20° C. over 30 min. After 1 h, trifluoroacetic acid (0.20 mL, 2.6 mmol, 580 equiv) was added at −20° C. The solution was allowed to warm to 23° C. and stirred for 2 h. The reaction mixture was concentrated under reduced pressure, and the residue was purified by reverse phase HPLC (10→40% acetonitrile-water, with 0.1% trifluoroacetic acid, detection wavelength=254 nm, $t_R$=23.0 min) to afford the product as a white solid (3.9 mg, 66%). 1H NMR (500 MHz, CD$_3$OD) δ 8.44 (s, 1H), 8.02 (s, 1H), 7.85 (d, J=6.7 Hz, 2H), 7.60 (t, J=7.9 Hz, 1H), 7.34 (d, J=7.7 Hz, 1H), 4.65-4.42 (m, 4H), 4.21-4.12 (m, 1H), 3.99 (s, 1H), 3.92-3.47 (m, 6H), 3.47-3.38 (m, 1H), 3.21-3.15 (m, 1H), 3.13 (s, 3H), 3.07-3.00 (m, 1H), 2.92 (s, 3H), 2.84 (s, 3H), 2.77 (t, J=11.7 Hz, 1H), 2.22-1.98 (m, 3H), 1.92-1.57 (m, 7H), 1.54 (s, 3H), 1.44-1.25 (m, 13H), 1.09 (d, J=6.7 Hz, 3H), 0.94-0.85 (m, 3H). Note: C13-proton is covered by water peak at 4.87 ppm. HRMS (ESI): Calcd for (C$_{44}$H$_{71}$N$_9$O$_9$+H)$^+$: 870.5448; Found: 870.5447.

Sulfonamide S29

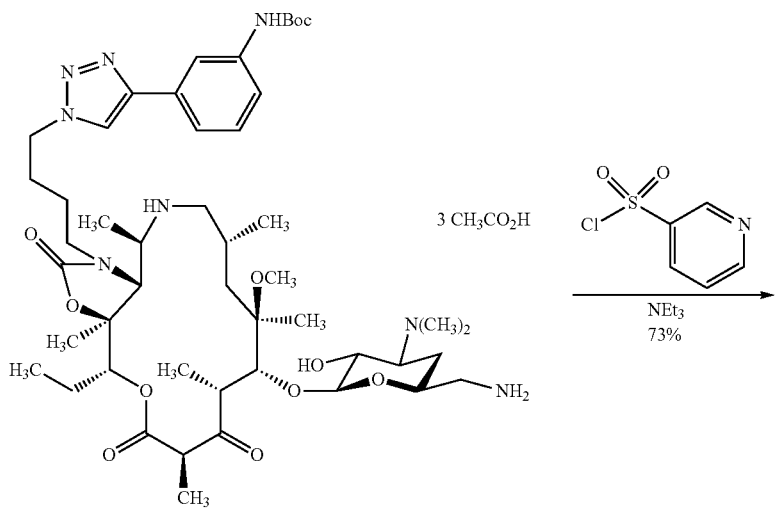

257

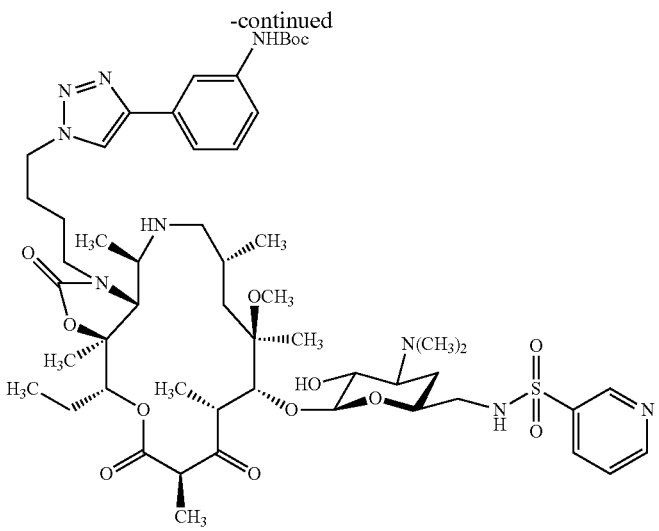

S29

Pyridine-3-sulfonyl chloride hydrochloride (2.9 mg, 0.013 mmol, 3.0 equiv) was added as solid to a solution of amine 257 (5.0 mg, 4.5 µmol, 1 equiv) and triethylamine (6.2 µL, 0.045 mmol, 10 equiv) in dichloromethane (0.2 mL) at −50° C. The resulting solution was allowed to warm to −20° C. over 30 min and stirred at that temperature for 1 h. The reaction mixture was partitioned between dichloromethane (1 mL) and saturated aqueous sodium bicarbonate solution (1 mL). The aqueous layer was extracted with dichloromethane (2×1 mL). The combined organic layers were dried over sodium sulfate and the dried solution was concentrated under reduced pressure. The residue was purified by column chromatography (3→5% methanol-dichloromethane+0.3→0.5% 30% aqueous ammonium hydroxide solution) to afford the product as a white solid (3.5 mg, 73%). 1H NMR (500 MHz, CDCl$_3$) δ 9.12 (s, 1H), 8.86 (d, J=4.8 Hz, 1H), 8.18 (d, J=8.0 Hz, 1H), 7.86 (s, 1H), 7.68 (s, 1H), 7.57-7.45 (m, 3H), 7.34 (t, J=7.9 Hz, 1H), 6.94 (s, 1H), 5.11 (br s, 1H), 4.95 (d, J=9.3 Hz, 1H), 4.56-4.37 (m, 3H), 4.34 (d, J=7.4 Hz, 1H), 3.88 (q, J=6.9 Hz, 1H), 3.83-3.49 (m, 3H), 3.38 (s, 1H), 3.25-3.07 (m, 3H), 3.07-2.96 (m, 1H), 2.85 (s, 3H), 2.81-2.68 (m, 2H), 2.54-2.41 (m, 1H), 2.27 (s, 6H), 2.12-1.90 (m, 3H), 1.77-1.57 (m, 8H), 1.54 (s, 9H), 1.43 (s, 3H), 1.41-1.30 (m, 6H), 1.27 (s, 3H), 1.26-1.22 (m, 1H), 0.99 (d, J=6.1 Hz, 3H), 0.94 (d, J=6.8 Hz, 3H), 0.89 (t, J=7.3 Hz, 3H). HRMS (ESI): Calcd for (C$_{53}$H$_{81}$N$_9$O$_{13}$S+ H)$^+$: 1084.5747; Found: 1084.5740.

FSM-21876

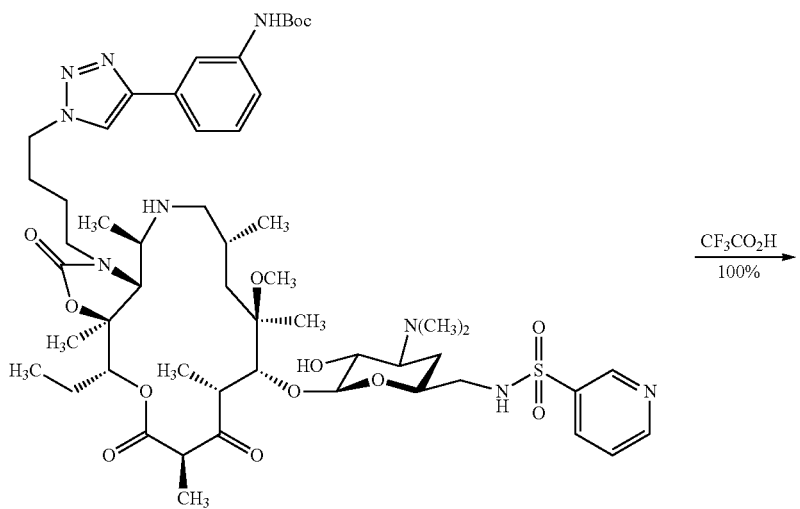

S29

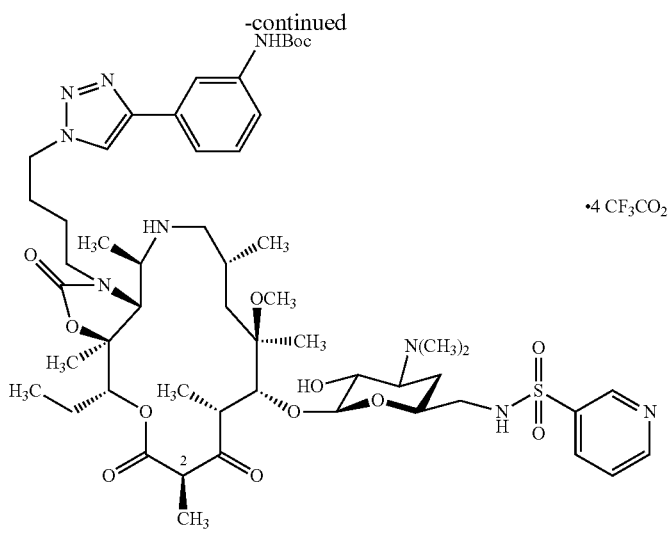

264 (FSM-21876)
5:1 mixture of epimers at C2

Sulfonamide S29 (3.5 mg, 3.2 μmol) was dissolved in 50% trifluoroacetic acid-dichloromethane at 23° C. After 2 h, the solution was concentrated under reduced pressure to afford the product as a pale yellow solid (4.6 mg, 100%). $^1$H NMR (5:1 diastereomeric mixture at C2, major isomer is reported, 500 MHz, CD$_3$OD) δ 9.04 (s, 1H), 8.81 (d, J=4.4 Hz, 1H), 8.39 (s, 1H), 8.31 (d, J=8.1 Hz, 1H), 7.77 (s, 1H), 7.73 (d, J=7.9 Hz, 1H), 7.66 (dd, J=8.0, 4.9 Hz, 1H), 7.53 (t, J=7.9 Hz, 1H), 7.25 (d, J=9.9 Hz, 1H), 4.93 (d, J=8.6 Hz, 1H), 4.63-4.49 (m, 4H), 4.20-4.12 (m, 1H), 3.87-3.77 (m, 2H), 3.70-3.64 (m, 1H), 3.63 (s, 1H), 3.56-3.40 (m, 3H), 3.29-3.17 (m, 2H), 3.15 (s, 2H), 3.10-2.94 (m, 2H), 2.90 (s, 3H), 2.81 (s, 3H), 2.75 (t, J=11.8 Hz, 1H), 2.16-1.96 (m, 3H), 1.96-1.58 (m, 7H), 1.54 (s, 3H), 1.43 (s, 3H), 1.42-1.38 (m, 1H), 1.38-1.26 (m, 10H), 1.11 (d, J=7.2 Hz, 3H), 0.92 (t, J=7.4 Hz, 3H). HRMS (ESI): Calcd for (C$_{48}$H$_{73}$N$_9$O$_{11}$S+ H)$^+$: 984.5223; Found: 984.5216.

Amide S30

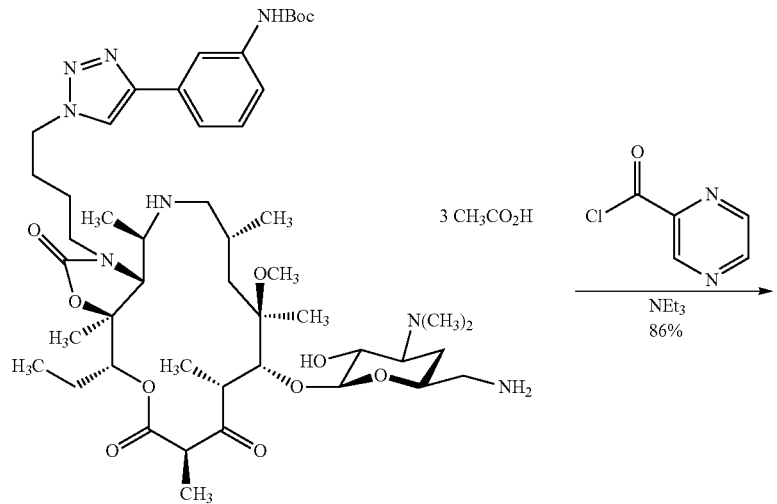

257

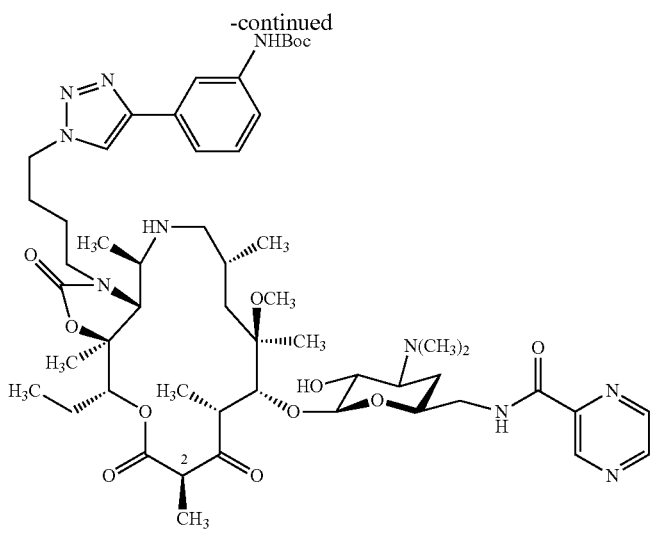

S30
11:1 mixture of epimers at C2

Pyrazine-2-carbonyl chloride (3.2 mg, 0.022 mmol, 5.0 equiv) was added to a solution of amine 257 (5.0 mg, 4.4 μmol, 1 equiv) and triethylamine (6.2 μL, 0.045 mmol, 10 equiv) in dichloromethane (0.2 mL) at −50° C. The resulting solution was allowed to warm to −20° C. over 30 min and stirred at that temperature for 1 h. Methanol (0.5 mL) was then added and the solution was allowed to warm to 23° C. After 1 h, the solution was concentrated under reduced pressure, and the residue was purified by column chromatography (5% methanol-dichloromethane+0.5% 30% aqueous ammonium hydroxide solution) to afford the product as a white solid (4.0 mg, 86%). 1H NMR (11:1 diastereomeric mixture at C2, major isomer is reported, 500 MHz, CDCl$_3$) δ 9.42 (s, 1H), 8.79 (d, J=2.3 Hz, 1H), 8.45 (s, 1H), 8.23 (dd, J=7.5, 3.6 Hz, 1H), 7.88 (s, 1H), 7.73 (s, 1H), 7.59-7.40 (m, 2H), 7.34 (t, J=7.9 Hz, 1H), 6.82 (s, 1H), 4.96 (d, J=9.2 Hz, 1H), 4.64-4.39 (m, 3H), 4.39-4.24 (m, 1H), 4.04-3.94 (m, 1H), 3.87 (q, J=6.9 Hz, 1H), 3.82-3.60 (m, 3H), 3.41 (s, 1H), 3.38-3.20 (m, 2H), 3.10-3.02 (m, 1H), 2.99 (s, 3H), 2.84-2.69 (m, 2H), 2.63-2.51 (m, 1H), 2.31 (s, 6H), 2.15-1.93 (m, 3H), 1.87-1.59 (m, 8H), 1.54 (s, 9H), 1.44 (s, 3H), 1.42-1.13 (m, 10H), 0.99 (d, J=6.0 Hz, 3H), 0.95 (d, J=6.9 Hz, 3H), 0.89 (t, J=7.3 Hz, 3H). HRMS (ESI): Calcd for (C$_{52}$H$_{80}$N$_{10}$O$_{12}$+H)$^+$: 1049.6030; Found: 1049.6038.

FSM-21881

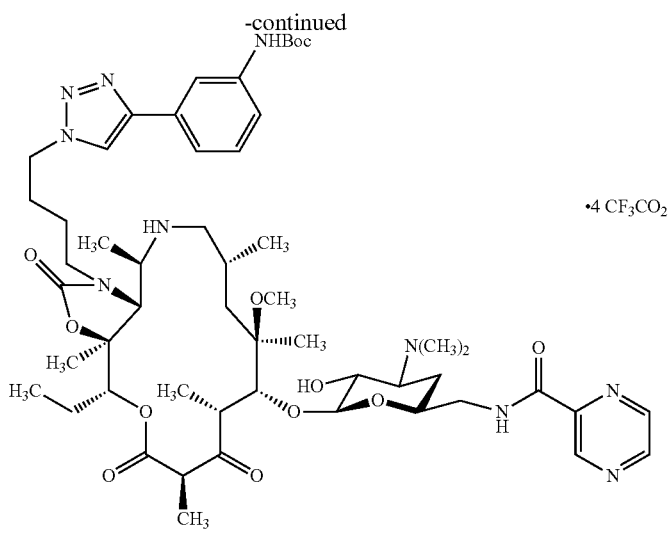

265 (FSM-21881)
10:1 mixture of epimers at C2

Amide S30 (4.0 mg, 3.8 μmol) was dissolved in 50% trifluoroacetic acid-dichloromethane at 23° C. After 2 h, the solution was concentrated under reduced pressure to afford the product as a pale yellow solid (4.7 mg, 88%). 1H NMR (10:1 diastereomeric mixture at C2, major isomer is reported, 500 MHz, CD$_3$OD) δ 9.28 (s, 1H), 8.81 (d, J=2.3 Hz, 1H), 8.69 (s, 1H), 8.47 (s, 1H), 7.86 (s, 1H), 7.83 (d, J=7.9 Hz, 1H), 7.59 (t, J=7.9 Hz, 1H), 7.33 (d, J=7.9 Hz, 1H), 4.66-4.52 (m, 3H), 4.46 (d, J=6.9 Hz, 1H), 4.09 (q, J=6.9 Hz, 1H), 4.02-3.91 (m, 1H), 3.86-3.60 (m, 4H), 3.58 (s, 1H), 3.57-3.37 (m, 3H), 3.26-3.03 (m, 2H), 2.99 (s, 3H), 2.93 (s, 3H), 2.84 (s, 3H), 2.74 (t, J=11.8 Hz, 1H), 2.23-1.97 (m, 3H), 1.97-1.55 (m, 7H), 1.53 (d, J=9.3 Hz, 3H), 1.41 (s, 3H), 1.39-1.28 (m, 7H), 1.20 (d, J=6.8 Hz, 3H), 1.09 (d, J=7.1 Hz, 3H), 0.90 (t, J=7.4 Hz, 3H). Note: C13-proton is covered by water peak at 4.87 ppm. HRMS (ESI): Calcd for (C$_{48}$H$_{72}$N$_{10}$O$_{10}$+H)$^+$: 949.5506; Found: 949.5499.

Amide S31

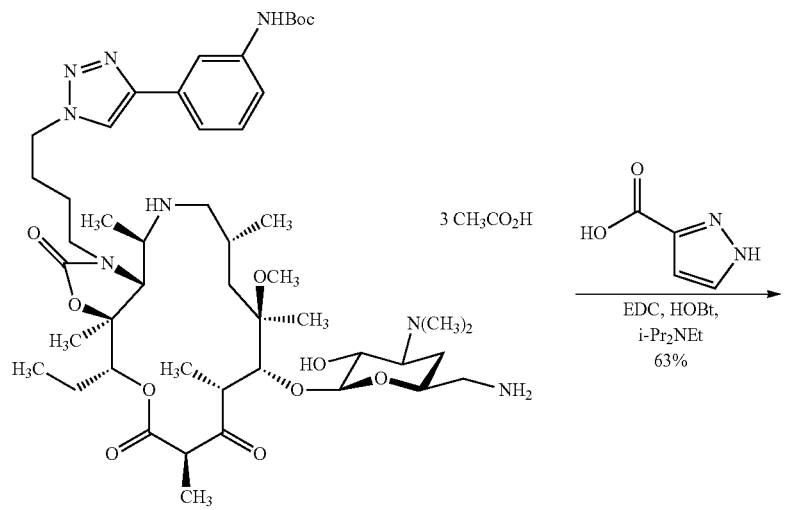

257

-continued

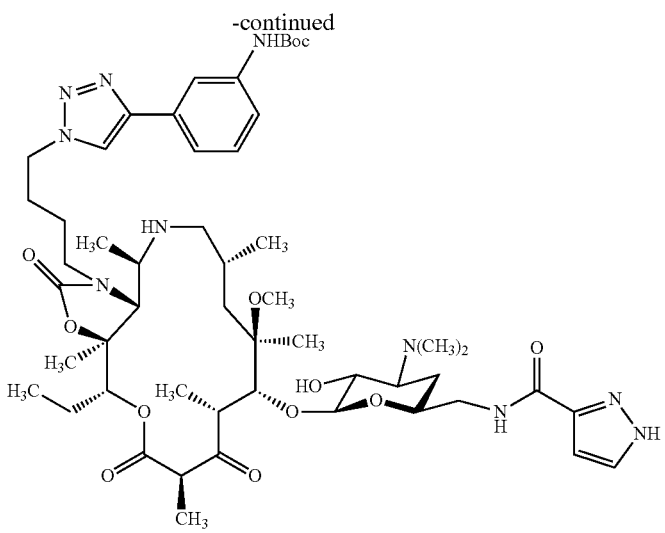

S31
10:1 mixture of epimers at C2

1H-pyrazole-3-carboxylic acid (1.0 mg, 8.9 μmol, 2.0 equiv), N-hydroxybenzotriazole (1.4 mg, 8.9 μmol, 2.0 equiv) and N-(3-dimethylaminopropyl)-N'-ethylcarbodiimide hydrochloride (1.7 mg, 8.9 μmol, 2 equiv) were added sequentially to a solution of N,N-diisopropylethylamine (7.8 μL, 0.045 mmol, 10 equiv) in DMF (0.1 mL) at 23° C. After 2 min, amine 257 (5.0 mg, 4.5 μmol, 1 equiv) was added as solid. The reaction was stirred at 23° C. for 16 h. The solution was concentrated under reduced pressure (0.1 mmHg, 35° C. water bath). The residue was purified by column chromatography (3→5% methanol-dichloromethane+0.3→0.5% 30% aqueous ammonium hydroxide solution) to afford the product as a white solid (2.9 mg, 63%). 1H NMR (10:1 diastereomeric mixture at C2, major isomer is reported, 500 MHz, CDCl$_3$) δ 7.79 (s, 1H), 7.75 (s, 1H), 7.59 (d, J=2.4 Hz, 1H), 7.57-7.50 (m, 2H), 7.37-7.30 (m, 2H), 6.90 (s, 1H), 6.85 (d, J=2.4 Hz, 1H), 4.80 (dd, J=10.8, 2.0 Hz, 1H), 4.67-4.36 (m, 4H), 4.07-3.99 (m, 1H), 3.81-3.56 (m, 4H), 3.34-3.24 (m, 2H), 3.20-3.12 (m, 1H), 3.03-2.93 (m, 1H), 2.85 (s, 3H), 2.80-2.64 (m, 2H), 2.62-2.45 (m, 1H), 2.30 (s, 6H), 2.11-1.86 (m, 3H), 1.86-1.55 (m, 8H), 1.52 (s, 9H), 1.39 (s, 3H), 1.32-1.19 (m, 7H), 1.13 (d, J=7.0 Hz, 3H), 0.97 (d, J=6.1 Hz, 3H), 0.91 (d, J=7.0 Hz, 3H), 0.83 (t, J=7.4 Hz, 3H). HRMS (ESI): Calcd for (C$_{52}$H$_{80}$N$_{10}$O$_{12}$+H)$^+$: 1037.6030; Found: 1037.6044.

FSM-21888

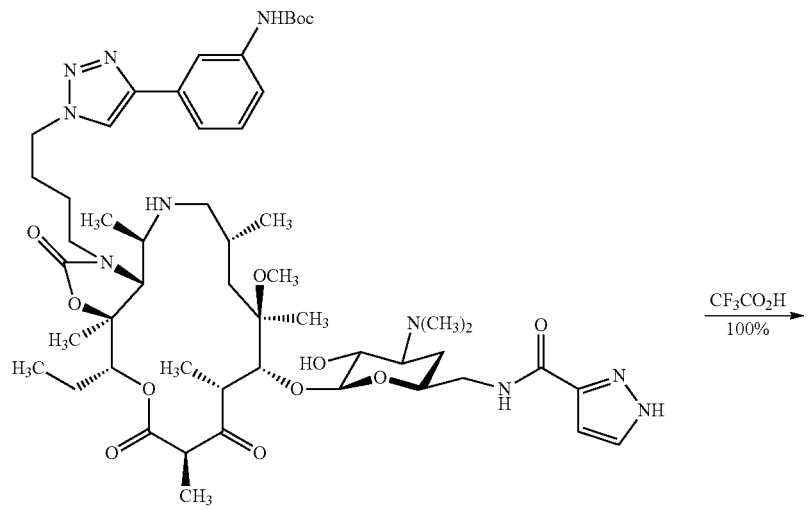

S31

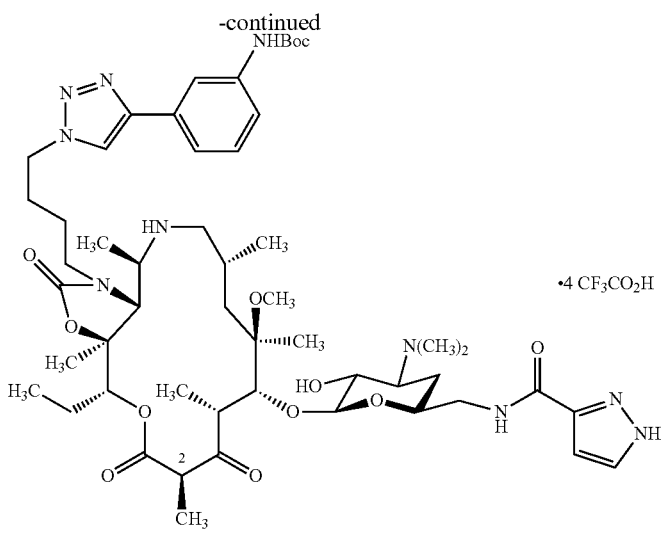

266 (FSM-21888)
7:1 mixture of epimers at C2

Amide S31 (2.9 mg, 2.8 μmol) was dissolved in 50% trifluoroacetic acid-dichloromethane at 23° C. After 2 h, the solution was concentrated under reduced pressure to afford the product as a pale yellow solid (3.9 mg, 100%). 1H NMR (7:1 diastereomeric mixture at C2, major isomer is reported, 500 MHz, CD$_3$OD) δ 8.40 (s, 1H), 7.77-7.70 (m, 1H), 7.66 (d, J=7.8 Hz, 1H), 7.53-7.47 (m, 1H), 7.20 (d, J=8.2 Hz, 1H), 6.80 (d, J=2.1 Hz, 1H), 4.67-4.43 (m, 4H), 4.11 (q, J=6.9 Hz, 1H), 3.99-3.92 (m, 1H), 3.84-3.69 (m, 2H), 3.69-3.44 (m, 6H), 3.41 (dd, J=12.0, 3.2 Hz, 1H), 3.11-3.00 (m, 1H), 3.00-2.93 (m, 1H), 2.92 (s, 3H), 2.89 (s, 3H), 2.83 (s, 3H), 2.73 (t, J=11.8 Hz, 1H), 2.21-1.94 (m, 3H), 1.94-1.56 (m, 7H), 1.52 (s, 3H), 1.36 (s, 3H), 1.35-1.23 (m, 10H), 1.08 (d, J=7.1 Hz, 3H), 0.91 (t, J=7.4 Hz, 3H). HRMS (ESI): Calcd for (C$_{47}$H$_{72}$N$_{10}$O$_{10}$+H)$^+$: 937.5506; Found: 937.5500.

Benzamide S32

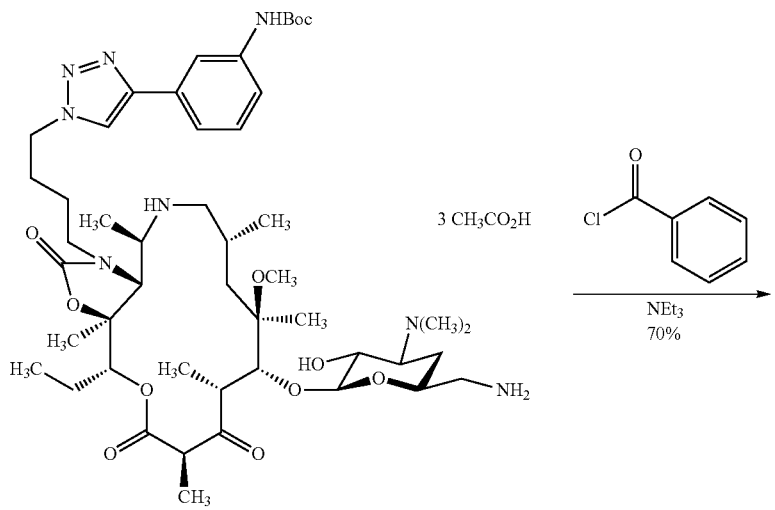

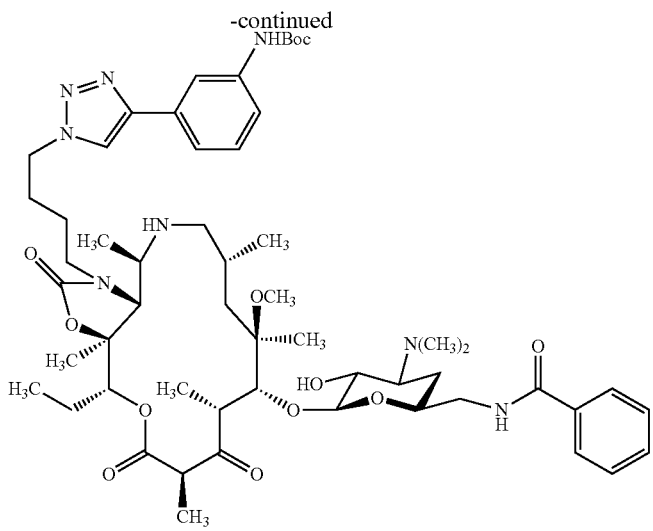

S32

Benzoyl chloride (1.6 μL, 0.013 mmol, 3.0 equiv) was added to a solution of amine 257 (5.0 mg, 4.5 μmol) and triethylamine (6.2 μL, 0.045 mmol, 10 equiv) in dichloromethane (0.2 mL) at −50° C. The resulting solution was allowed to warm to −20° C. over 30 min and stirred at that temperature for 1 h. The reaction mixture was partitioned between dichloromethane (1 mL) and saturated aqueous sodium bicarbonate solution (1 mL). The aqueous layer was extracted with dichloromethane (2×1 mL). The combined organic layers were dried over sodium sulfate and the dried solution was concentrated under reduced pressure. The residue, containing the desired product and 2'-OH acetylated product, was dissolved in methanol (1 mL). After 24 h, the solution was concentrated under reduced pressure. The residue was purified by column chromatography (3→5% methanol-dichloromethane+0.3→0.5% 30% aqueous ammonium hydroxide solution) to afford the product as a white solid (3.4 mg, 70%). $^1$H NMR (500 MHz, CDCl$_3$) δ 7.89 (s, 1H), 7.81 (d, J=7.7, 2H), 7.76 (s, 1H), 7.58-7.31 (m, 6H), 6.78 (s, 1H), 6.63 (t, J=5.3 Hz, 1H), 4.96 (dd, J=10.9, 2.0 Hz, 1H), 4.60 (d, J=3.6 Hz, 1H), 4.54-4.36 (m, 3H), 3.89 (q, J=6.8 Hz, 1H), 3.90-3.82 (m, 1H), 3.82-3.61 (m, 3H), 3.55-3.46 (m, 1H), 3.41 (s, 1H), 3.25 (dd, J=10.1, 7.4 Hz, 1H), 3.07 (dd, J=7.8, 3.1 Hz, 1H), 2.81 (s, 3H), 2.79-2.70 (m, 2H), 2.62-2.50 (m, 1H), 2.30 (s, 6H), 2.11-1.88 (m, 3H), 1.88-1.55 (m, 8H), 1.57 (s, 9H), 1.43 (s, 3H), 1.40-1.32 (m, 6H), 1.24-1.17 (m, 4H), 0.99 (d, J=6.1 Hz, 3H), 0.96 (d, J=6.9 Hz, 3H), 0.89 (t, J=7.2 Hz, 3H). HRMS (ESI): Calcd for (C$_{55}$H$_{82}$N$_8$O$_{12}$+H)$^+$: 1047.6125; Found: 1047.6123. FSM-21880

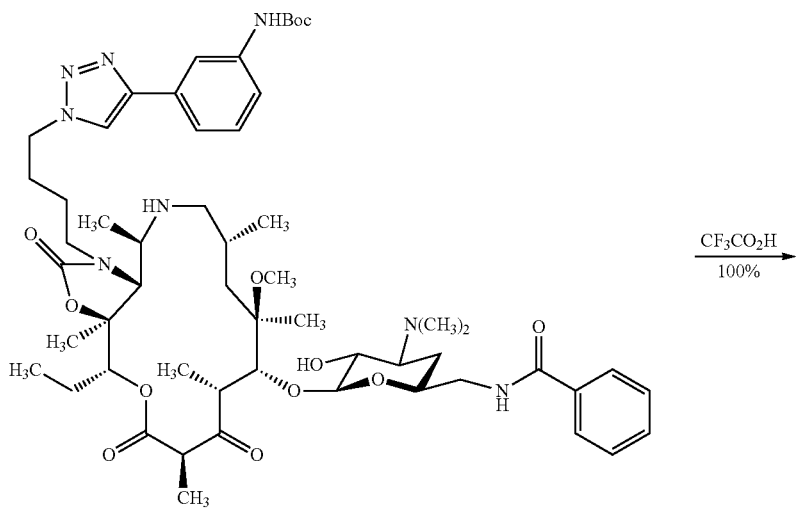

S32

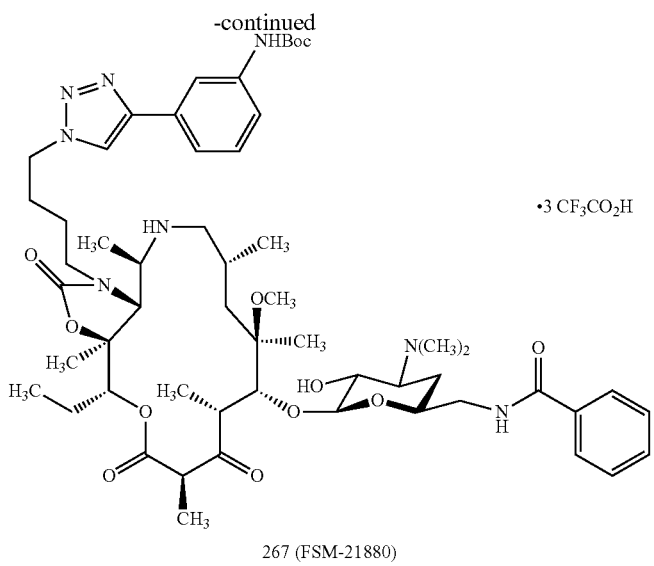

267 (FSM-21880)

Amide S32 (3.3 mg, 3.15 μmol) was dissolved in 50% trifluoroacetic acid-dichloromethane at 23° C. After 2 h, the solution was concentrated under reduced pressure to afford the product as a pale yellow solid (3.7 mg, 91%). $^1$H NMR (500 MHz, CD$_3$OD) δ 8.44 (s, 1H), 7.93-7.79 (m, 4H), 7.64-7.38 (m, 4H), 7.34 (d, J=8.0 Hz, 1H), 4.92 (d, J=10.9 Hz, 1H), 4.57-4.51 (m, 3H), 4.48 (d, J=6.9 Hz, 1H), 4.16 (q, J=6.7 Hz, 1H), 4.00-3.92 (m, 1H), 3.90-3.71 (m, 2H), 3.68-3.47 (m, 5H), 3.41 (d, J=9.2 Hz, 1H), 3.07-2.98 (m, 1H), 2.98-2.88 (m, 4H), 2.84 (s, 3H), 2.74 (s, 3H), 2.71 (t, J=11.8 Hz, 1H), 2.17 (d, J=10.7 Hz, 1H), 2.09-1.94 (m, 2H), 1.94-1.55 (m, 7H), 1.53 (s, 3H), 1.40-1.25 (m, 13H), 1.08 (d, J=7.1 Hz, 3H), 0.93 (t, J=7.2 Hz, 3H). HRMS (ESI): Calcd for (C$_{50}$H$_{74}$N$_8$O$_{10}$+H)$^+$: 947.5601; Found: 947.5595.

Amide S33

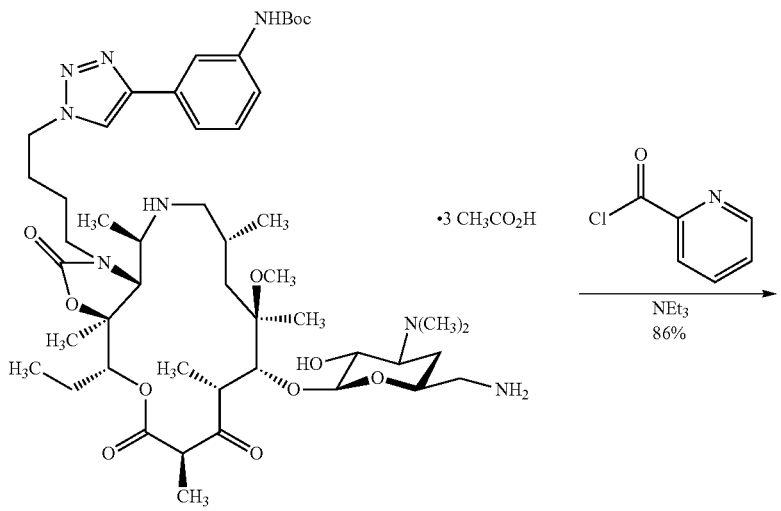

257

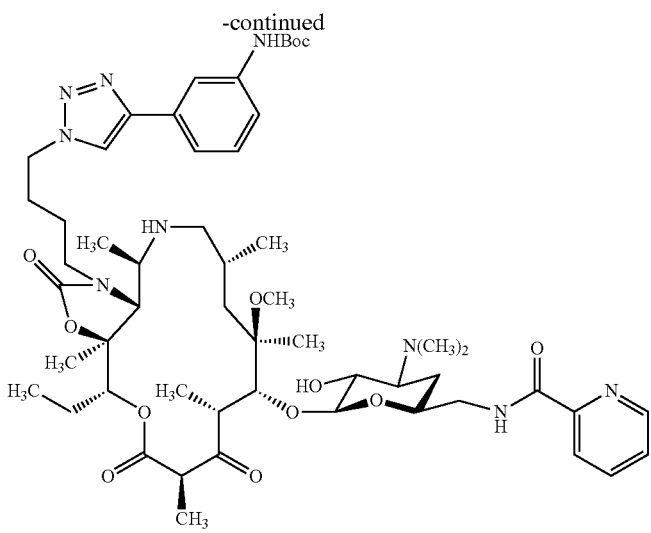

S33

Picolinoyl chloride (3.2 mg, 0.022 mmol, 5.0 equiv) was added to a solution of amine 257 (5.0 mg, 4.4 μmol, 1 equiv) and triethylamine (6.2 μL, 0.045 mmol, 10 equiv) in dichloromethane (0.2 mL) at −50° C. The resulting solution was allowed to warm to −20° C. over 30 min and stirred at that temperature for 1 h. Methanol (0.5 mL) was then added and the solution was allowed to warm to 23° C. After 1 h, the solution was concentrated under reduced pressure, and the residue was purified by column chromatography (5% methanol-dichloromethane+0.5% 30% aqueous ammonium hydroxide solution) to afford the product as a white solid (4.0 mg, 86%). 1H NMR (7:1 diastereomeric mixture at C2, major isomer is reported, 500 MHz, CDCl$_3$) δ 8.49-8.43 (m, 1H), 8.42 (d, J=4.6 Hz, 1H), 8.19 (d, J=7.8 Hz, 1H), 7.89 (s, 1H), 7.81 (td, J=7.7, 1.6 Hz, 1H), 7.74 (s, 1H), 7.58-7.31 (m, 4H), 6.80 (s, 1H), 4.96 (dd, J=10.9, 2.0 Hz, 1H), 4.58-4.41 (m, 4H), 3.96-3.82 (m, 2H), 3.82-3.61 (m, 3H), 3.45-3.31 (m, 2H), 3.27 (dd, J=10.1, 7.5 Hz, 1H), 3.10-3.01 (m, 1H), 2.94 (s, 3H), 2.82-2.70 (m, 2H), 2.58-2.50 (m, 1H), 2.30 (s, 6H), 2.11-1.88 (m, 3H), 1.88-1.55 (m, 8H), 1.54 (s, 9H), 1.44 (s, 3H), 1.40-1.32 (m, 9H), 1.24-1.17 (m, 1H), 0.99 (d, J=6.1 Hz, 3H), 0.96 (d, J=6.9 Hz, 3H), 0.89 (t, J=7.2 Hz, 3H). HRMS (ESI): Calcd for $(C_{54}H_{81}N_9O_{12}+H)^+$: 1048.6077; Found: 1048.6085.

FSM-21887

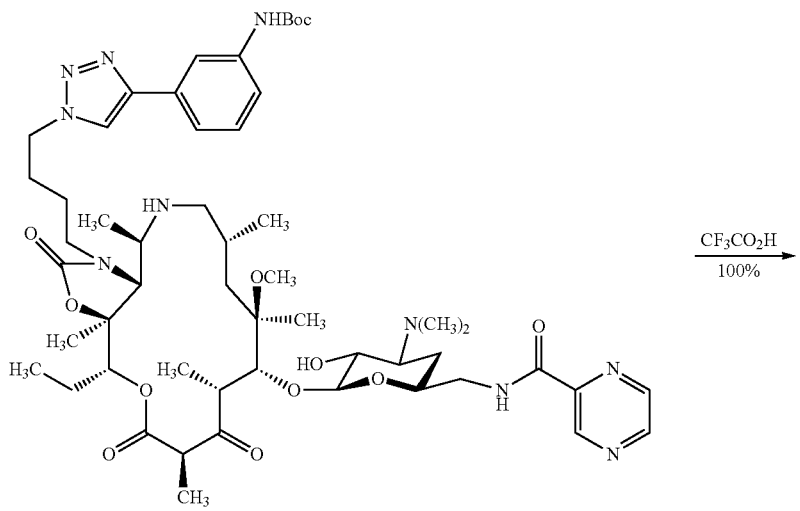

S33

CF$_3$CO$_2$H
100%

-continued

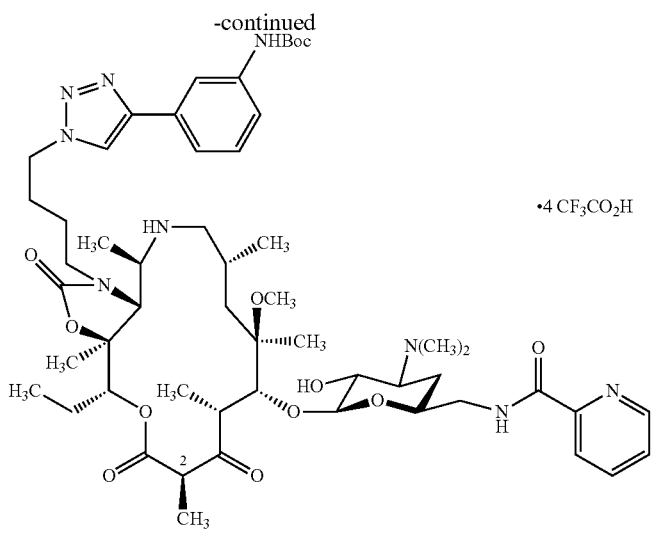

258 (FSM-21887)
7:1 mixture of epimers at C2

Amide S33 (4.0 mg, 3.8 μmol) was dissolved in 50% trifluoroacetic acid-dichloromethane at 23° C. After 2 h, the solution was concentrated under reduced pressure to afford the product as a pale yellow solid (5.4 mg, 100%). 1H NMR (7:1 diastereomeric mixture at C2, major isomer is reported, 500 MHz, CD$_3$OD) δ 8.61 (d, J=4.8 Hz, 1H), 8.42 (s, 1H), 8.13 (d, J=7.8 Hz, 1H), 7.94 (td, J=7.7, 1.6 Hz, 1H), 7.77 (s, 1H), 7.72 (d, J=7.9 Hz, 1H), 7.57-7.50 (m, 2H), 7.24 (d, J=7.9 Hz, 1H), 4.94-4.90 (m, 1H), 4.61-4.49 (m, 4H), 4.12 (q, J=6.9 Hz, 1H), 4.02-3.90 (m, 1H), 3.86-3.48 (m, 7H), 3.42 (dd, J=12.1, 3.3 Hz, 1H), 3.14-3.03 (m, 1H), 3.03-2.96 (m, 1H), 2.95 (s, 3H), 2.92 (s, 3H), 2.83 (s, 3H), 2.74 (t, J=11.7 Hz, 1H), 2.22-1.97 (m, 3H), 1.97-1.54 (m, 7H), 1.53 (s, 3H), 1.40 (s, 3H), 1.38-1.28 (m, 7H), 1.27 (d, J=6.9 Hz, 3H), 1.09 (d, J=7.1 Hz, 3H), 0.91 (t, J=7.4 Hz, 3H). HRMS (ESI): Calcd for (C$_{49}$H$_{73}$N$_9$O$_{10}$+H)$^+$: 948.5553; Found: 948.5537.

Amide S34

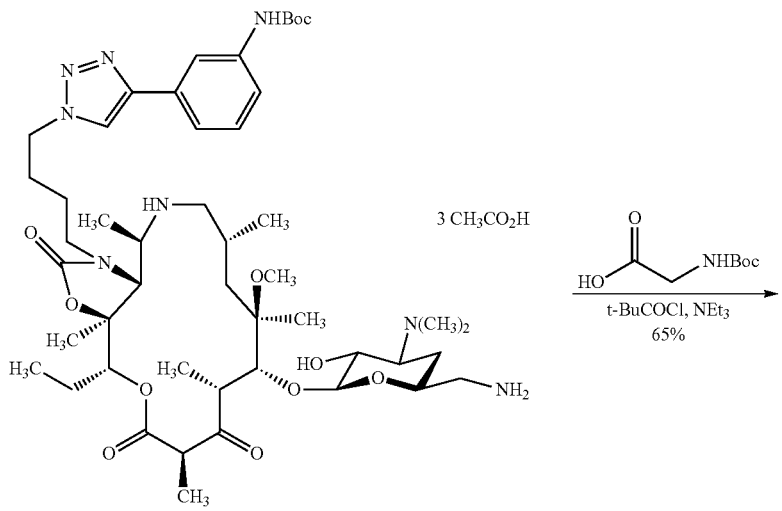

257

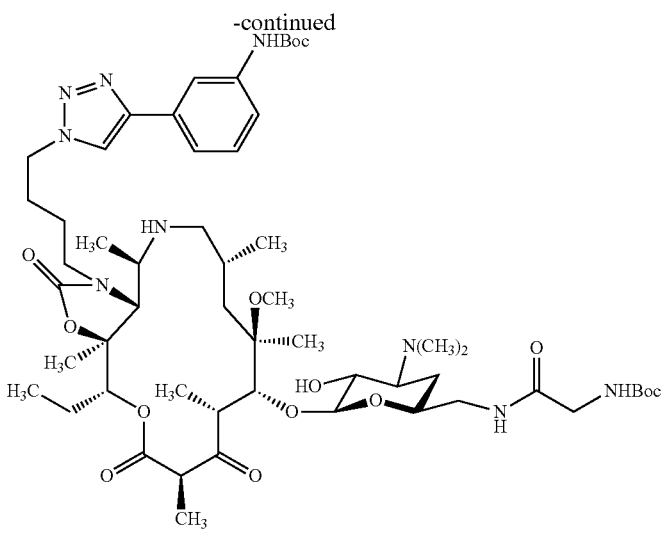

S34

Pivaloyl chloride (11.0 μL, 0.090 mmol, 20 equiv) was added dropwise via syringe to a solution of N-(tert-butoxycarbonyl)glycine (15.6 mg, 0.090 mmol, 20 equiv) and triethylamine (12.4 μL, 0.090 mmol, 20 equiv) in dichloromethane (200 μL) at 0° C. During the addition a fine white solid precipitated. The suspension was stirred at 0° C. for 30 min. 20 L of the supernatant was retrieved by syringe, and added to a solution (in another flask) of amine 257 (5.0 mg, 4.5 μmol, 1 equiv) and triethylamine (6.20 μl, 0.045 mmol) in dichloromethane (0.2 mL) at 0° C. After 1 h, methanol (1.0 mL) was added, and the mixture was allowed to warm to 23° C. After 1 h, the mixture was concentrated under reduced pressure. The residue was purified by column chromatography (5% methanol-dichloromethane+0.5% 30% aqueous ammonium hydroxide solution) to afford the product as a white solid (3.2 mg, 65%). $^1$H NMR (11:1 diastereomeric mixture at C2, major isomer is reported; 500 MHz, CDCl$_3$) δ 7.84 (s, 1H), 7.71 (s, 1H), 7.50 (dd, J=21.3, 7.4 Hz, 2H), 7.41-7.32 (m, 1H), 6.95 (s, 1H), 6.48 (s, 1H), 5.46 (t, J=5.4 Hz, 1H), 4.94 (dd, J=10.7, 1.8 Hz, 1H), 4.55 (d, J=3.1 Hz, 1H), 4.53-4.37 (m, 2H), 4.34 (d, J=7.4 Hz, 1H), 3.88 (q, J=6.9 Hz, 1H), 3.86-3.54 (m, 6H), 3.42-3.38 (m, 1H), 3.38 (s, 1H), 3.21 (dd, J=10.1, 7.4 Hz, 1H), 3.03 (qd, J=7.5, 3.7 Hz, 1H), 2.90 (s, 3H), 2.80-2.72 (m, 2H), 2.55-2.45 (m, 1H), 2.28 (s, 6H), 2.08-1.91 (m, 3H), 1.83-1.57 (m, 8H), 1.54 (s, 9H), 1.47-1.39 (m, 15H), 1.36 (d, J=7.8 Hz, 3H), 1.24 (s, 3H), 1.22-1.16 (m, 1H), 0.99 (d, J=6.0 Hz, 3H), 0.94 (d, J=6.8 Hz, 3H), 0.89 (t, J=7.2 Hz, 3H). HRMS (ESI): Calcd for $(C_{55}H_{89}N_9O_{14}+H)^+$: 1100.6602; Found: 1100.6597.

FSM-21878

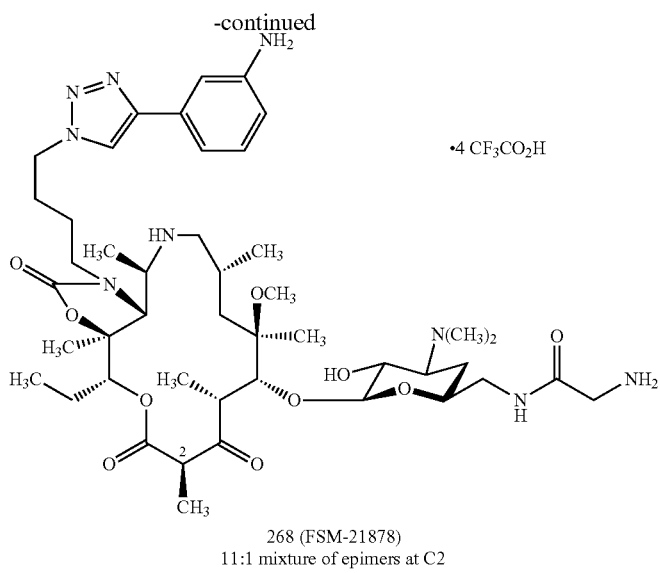

268 (FSM-21878)
11:1 mixture of epimers at C2

Amide S34 (3.2 mg, 2.9 μmol) was dissolved in 50% trifluoroacetic acid-dichloromethane at 23° C. After 2 h, the solution was concentrated under reduced pressure to afford the product as a pale yellow solid (3.9 mg, 100%). 1H NMR (11:1 diastereomeric mixture at C2, major isomer is reported, 500 MHz, CD$_3$OD) δ 9.28 (s, 1H), 8.81 (d, J=2.3 Hz, 1H), 8.69 (s, 1H), 8.47 (s, 1H), 7.86 (s, 1H), 7.83 (d, J=7.9 Hz, 1H), 7.59 (t, J=7.9 Hz, 1H), 7.33 (d, J=7.9 Hz, 1H), 4.66-4.52 (m, 3H), 4.46 (d, J=6.9 Hz, 1H), 4.09 (q, J=6.9 Hz, 1H), 4.02-3.91 (m, 1H), 3.86-3.60 (m, 4H), 3.58 (s, 1H), 3.57-3.37 (m, 3H), 3.26-3.03 (m, 2H), 2.99 (s, 3H), 2.93 (s, 3H), 2.84 (s, 3H), 2.74 (t, J=11.8 Hz, 1H), 2.23-1.97 (m, 3H), 1.97-1.55 (m, 7H), 1.53 (d, J=9.3 Hz, 3H), 1.41 (s, 3H), 1.39-1.28 (m, 7H), 1.20 (d, J=6.8 Hz, 3H), 1.09 (d, J=7.1 Hz, 3H), 0.90 (t, J=7.4 Hz, 3H). Note: C13-proton is covered by water peak at 4.87 ppm. HRMS (ESI): Calcd for (C$_{45}$H$_{73}$N$_9$O$_{10}$+H)$^+$: 900.5553; Found: 900.5550.

Amide S35

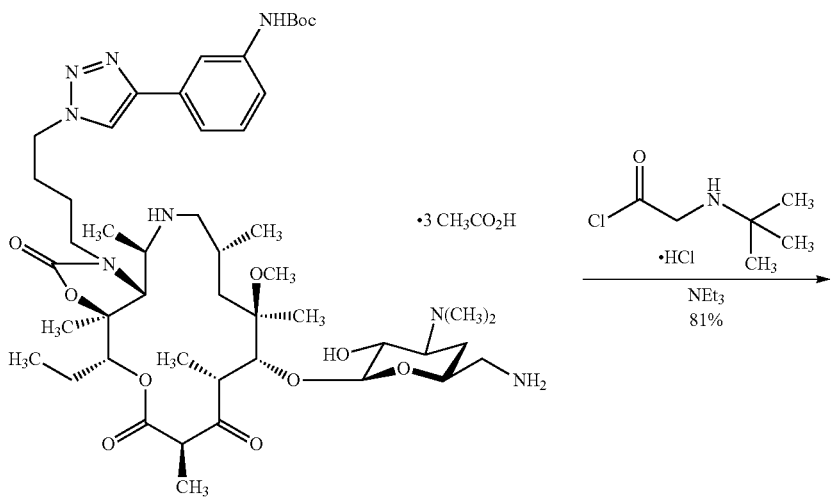

257

-continued

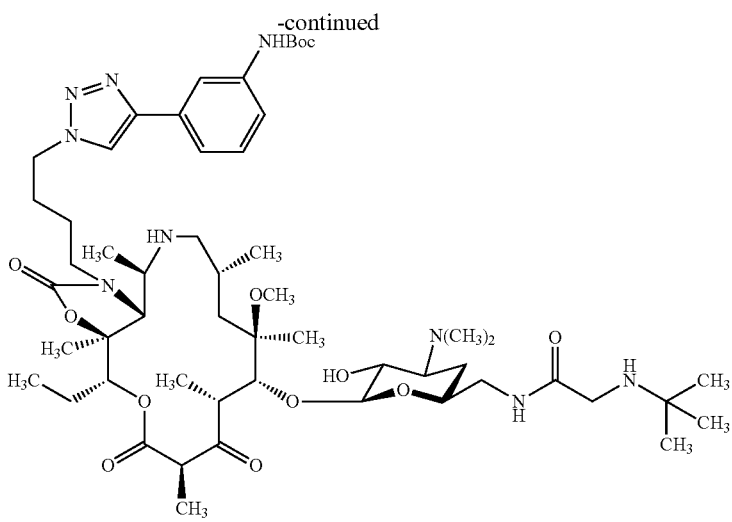

S35

2-(tert-butylamino)acetyl chloride hydrochloride (2.5 mg, 0.013 mmol, 3.0 equiv) was added to a solution of amine 257 (5.0 mg, 4.5 µmol, 1 equiv) and triethylamine (6.2 µL, 0.045 mmol, 10 equiv) in dichloromethane (0.2 mL) at −50° C. The solution was allowed to warm to −20° C. over 30 min and stirred at that temperature for 1 h. Additional 2-(tert-butylamino)acetyl chloride hydrochloride (2.5 mg, 0.013 mmol, 3.0 equiv) was added, and stirring was continued at −20° C. After 1 h, the reaction mixture was allowed to warm to 23° C. and concentrated under reduced pressure. The residue was purified by column chromatography (3→5% methanol-dichloromethane+0.3→0.5% 30% aqueous ammonium hydroxide solution) to afford the product as a white solid (3.8 mg, 81%). 1H NMR (500 MHz, CDCl$_3$) δ 7.86 (s, 1H), 7.83 (t, J=6.0 Hz, 1H), 7.73 (s, 1H), 7.54-7.46 (m, 2H), 7.37 (t, J=7.9 Hz, 1H), 6.85 (s, 1H), 4.96 (d, J=8.9 Hz, 1H), 4.54 (d, J=3.6 Hz, 1H), 4.52-4.36 (m, 3H), 3.89 (q, J=6.8 Hz, 1H), 3.81-3.50 (m, 4H), 3.47-3.33 (m, 2H), 3.26 (d, J=9.1 Hz, 2H), 3.24-3.13 (m, 2H), 3.10-3.01 (m, 1H), 2.93 (s, 3H), 2.86-2.68 (m, 2H), 2.57-2.45 (m, 1H), 2.26 (s, 6H), 2.12-1.91 (m, 3H), 1.88-1.58 (m, 8H), 1.54 (s, 9H), 1.44 (s, 3H), 1.41 (d, J=6.9 Hz, 3H), 1.37 (d, J=7.8 Hz, 3H), 1.30 (s, 3H), 1.20 (d, J=14.8 Hz, 1H), 1.06 (s, 9H), 0.99 (d, J=6.1 Hz, 3H), 0.94 (d, J=6.9 Hz, 3H), 0.90 (t, J=7.3 Hz, 3H). HRMS (ESI): Calcd for (C$_{54}$H$_{89}$N$_9$O$_{12}$+H)$^+$: 1056.6703; Found: 1056.6692.

FSM-21879

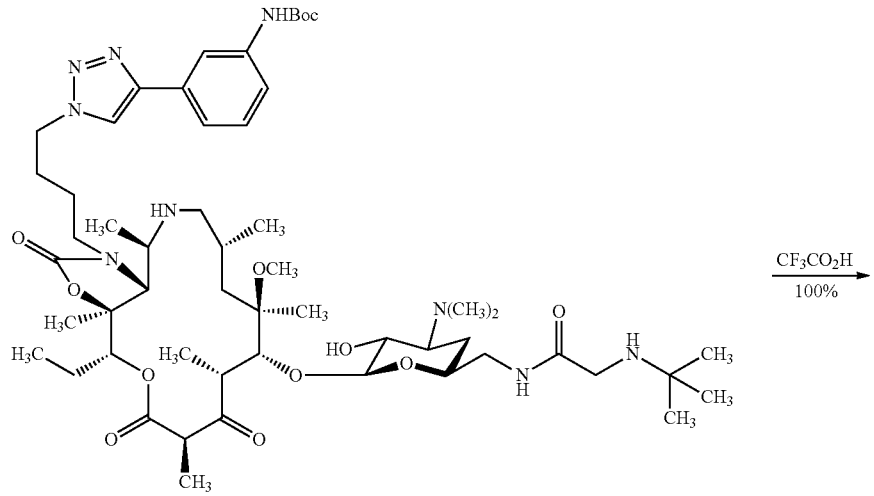

S35

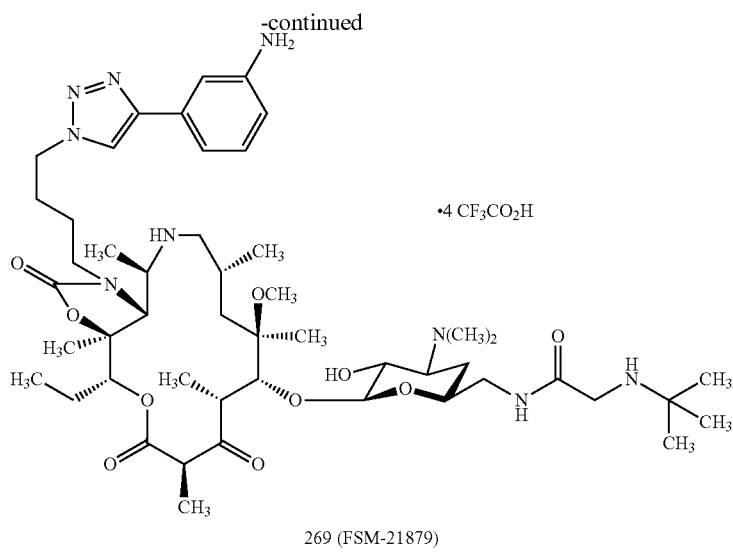

269 (FSM-21879)

Amide S35 (3.8 mg, 3.6 μmol) was dissolved in 50% trifluoroacetic acid-dichloromethane at 23° C. After 2 h, the solution was concentrated under reduced pressure to afford the product as a pale yellow solid (4.5 mg, 89%). $^1$H NMR (500 MHz, CD$_3$OD) δ 8.38 (s, 1H), 7.63 (d, J=8.7 Hz, 2H), 7.49 (t, J=7.8 Hz, 1H), 7.18 (d, J=8.1 Hz, 1H), 4.61-4.46 (m, 4H), 4.17 (q, J=6.8 Hz, 1H), 3.86 (s, 2H), 3.85-3.73 (m, 2H), 3.71-3.37 (m, 8H), 3.10 (s, 3H), 3.05-2.98 (m, 1H), 2.91 (s, 3H), 2.83 (s, 3H), 2.74 (t, J=11.7 Hz, 1H), 2.17-1.94 (m, 3H), 1.94-1.57 (m, 7H), 1.54 (s, 3H), 1.46-1.43 (m, 1H), 1.42 (s, 3H), 1.39-1.29 (m, 18H), 1.09 (d, J=7.1 Hz, 3H), 0.90 (t, J=7.4 Hz, 3H). Note: C13-proton is covered by water peak at 4.87 ppm. HRMS (ESI): Calcd for (C$_{49}$H$_{81}$N$_9$O$_{10}$+H)$^+$: 956.6179; Found: 956.6180.

Amine S36

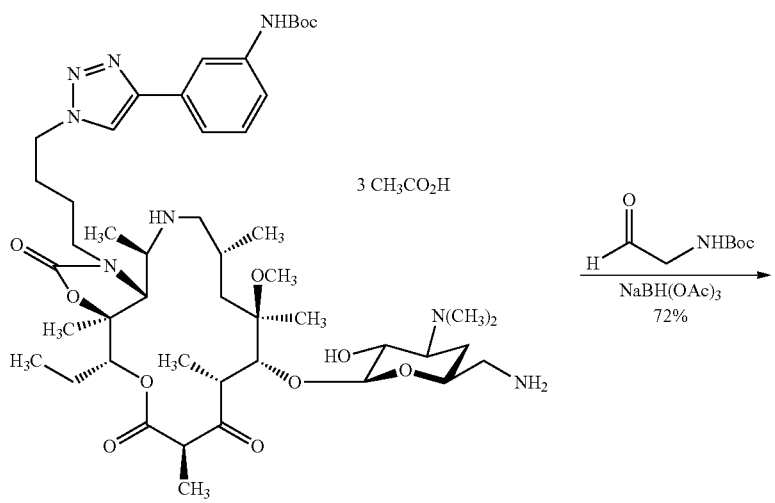

257

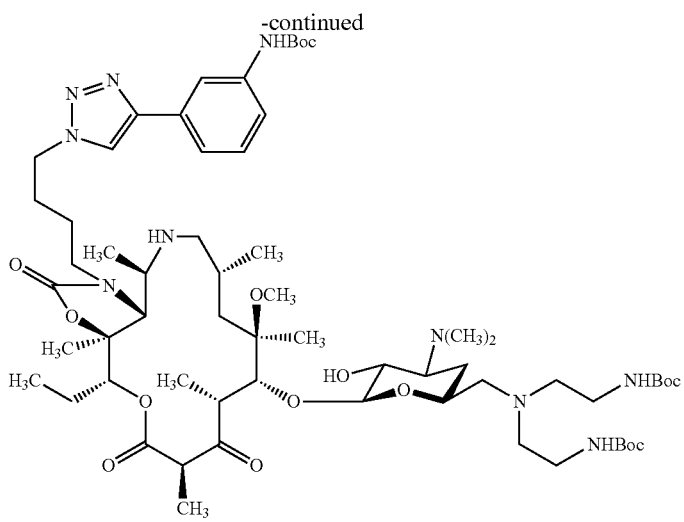

S36

Sodium triacetoxyborohydride (5.6 mg, 0.027 mmol, 5.0 equiv) was added to a solution of amine 257 (5.0 mg, 4.50 μmol, 1 equiv) and tert-butyl (2-oxoethyl)carbamate (4.2 mg, 0.027 mmol, 5.0 equiv) in dichloromethane (0.2 mL) at 23° C. After 1 h, 30% aqueous ammonium hydroxide solution (0.01 mL) was added, and the mixture was concentrated under reduced pressure. The residue was purified by column chromatography (5% methanol-dichloromethane+0.5% 30% aqueous ammonium hydroxide solution) to afford the product as a white solid (4.7 mg, 72%). $^1$H NMR (500 MHz, CDCl$_3$) δ 7.86 (s, 1H), 7.73 (s, 1H), 7.50 (t, J=8.2 Hz, 2H), 7.36 (t, J=7.9 Hz, 1H), 6.86 (s, 1H), 5.29 (br s, 2H), 4.97 (d, J=10.9 Hz, 1H), 4.62-4.37 (m, 3H), 4.29 (d, J=7.4 Hz, 1H), 4.10 (d, J=4.3 Hz, 1H), 3.92 (q, J=6.8 Hz, 1H), 3.84-3.52 (m, 4H), 3.41 (s, 1H), 3.32-2.99 (m, 6H), 2.91 (s, 3H), 2.81-2.72 (m, 2H), 2.72-2.57 (m, 4H), 2.56-2.42 (m, 1H), 2.31 (s, 6H), 2.09-1.92 (m, 3H), 1.86-1.56 (m, 8H), 1.54 (s, 9H), 1.49-1.32 (m, 28H), 1.27 (s, 3H), 0.99 (d, J=6.0 Hz, 3H), 0.94 (d, J=6.8 Hz, 3H), 0.90 (t, J=7.3 Hz, 3H). HRMS (ESI): Calcd for (C$_{62}$H$_{104}$N$_{10}$O$_{15}$+H)$^+$: 1229.7755; Found: 1229.7747.

FSM-21877

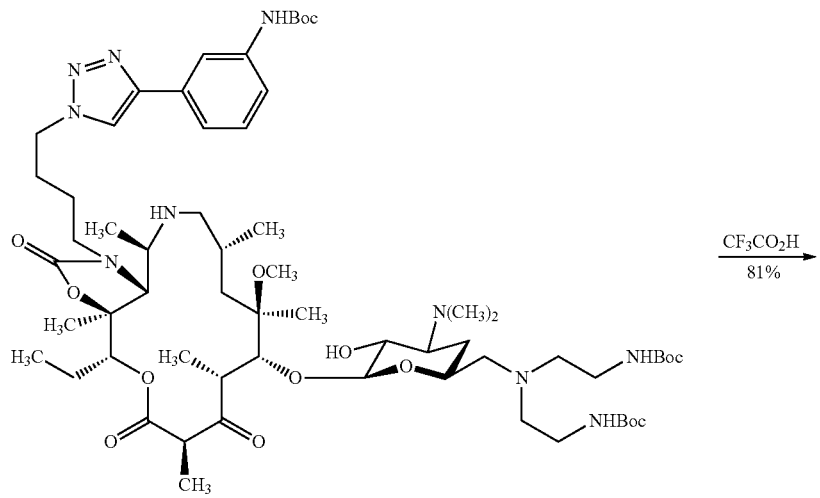

S36

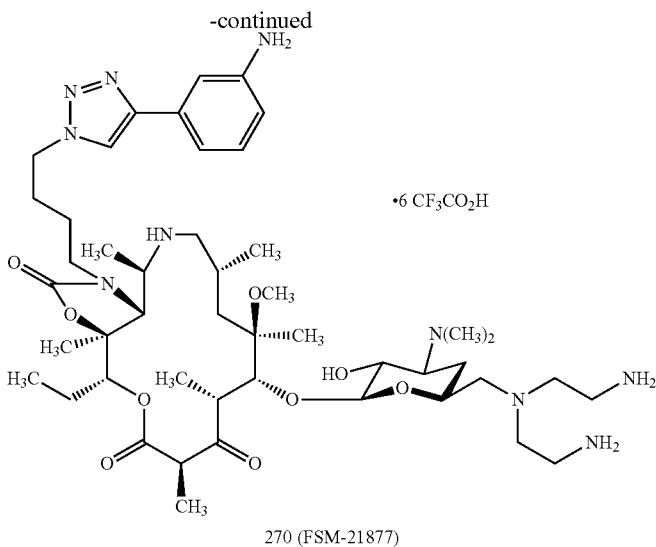

270 (FSM-21877)

Amine S36 (4.7 mg, 3.8 μmol) was dissolved in 50% trifluoroacetic acid-dichloromethane at 23° C. After 2 h, the solution was concentrated under reduced pressure to afford the product as a pale yellow solid (5.0 mg, 81%). H NMR (500 MHz, CD$_3$OD) δ 8.42 (s, 1H), 7.83 (d, J=7.5 Hz, 2H), 7.59 (t, J=8.1 Hz, 1H), 7.32 (d, J=7.6 Hz, 1H), 4.64-4.40 (m, 4H), 4.21 (q, J=6.7 Hz, 1H), 4.09-3.99 (m, 1H), 3.84-3.73 (m, 1H), 3.73-3.63 (m, 1H), 3.61 (s, 1H), 3.55-3.39 (m, 3H), 3.22-3.00 (m, 10H), 3.12 (s, 3H), 2.96 (d, J=5.2 Hz, 2H), 2.91 (s, 3H), 2.83 (s, 3H), 2.74 (t, J=11.9 Hz, 1H), 2.16-1.98 (m, 3H), 1.98-1.58 (m, 7H), 1.54 (s, 3H), 1.41-1.26 (m, 13H), 1.10 (d, J=7.0 Hz, 3H), 0.90 (t, J=7.3 Hz, 3H). Note: C13-proton is covered by water peak at 4.87 ppm. HRMS (ESI): Calcd for $(C_{47}H_{80}N_{10}O_9+H)^+$: 929.6183; Found: 929.6179.

Amine S37

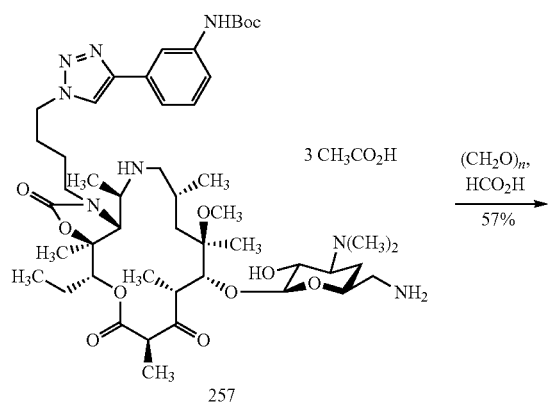

257

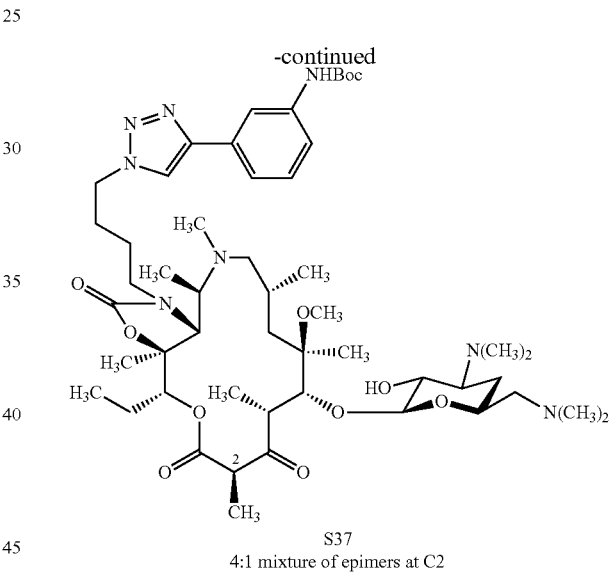

S37
4:1 mixture of epimers at C2

Formic acid (1.2 μL, 3.2 μmol, 6.0 equiv) was added to a suspension of amine 257 (6.0 mg, 5.3 μmol, 1 equiv) and paraformaldehyde (1.6 mg, 5.3 μmol, 10 equiv) in chloroform (ethanol-free, 0.2 mL). The mixture was warmed to 70° C. and held at that temperature for 1 h. After cooling to 23° C., the mixture was concentrated under reduced pressure. The residue was purified by column chromatography (5% methanol-dichloromethane+0.5% 30% aqueous ammonium hydroxide solution) to afford the product as a white solid (3.0 mg, 57%). $^1$H NMR (4:1 diastereomeric mixture at C2, major isomer is reported, 500 MHz, CDCl$_3$) δ 7.87 (s, 1H), 7.80 (s, 1H), 7.50 (d, J=7.5 Hz, 1H), 7.41-7.31 (m, 2H), 6.52 (s, 1H), 4.74 (dd, J=9.8, 2.1 Hz, 1H), 4.54-4.37 (m, 3H), 4.34-4.28 (m, 1H), 4.11-4.02 (m, 1H), 3.79 (d, J=10.4 Hz, 1H), 3.74-3.62 (m, 1H), 3.62-3.41 (m, 1H), 3.23-3.15 (m, 1H), 3.11-2.93 (m, 3H), 2.85 (s, 3H), 2.67 (d, J=13.8 Hz, 1H), 2.54-2.37 (m, 3H), 2.28 (s, 12H), 2.06-1.95 (m, 2H), 1.94 (s, 3H), 1.81 (app d, J=10.7 Hz, 1H), 1.76-1.58 (m, 8H), 1.57 (s, 3H), 1.53 (s, 9H), 1.35-1.30 (m, 1H), 1.28 (s, 3H), 1.20 (d, J=6.7 Hz, 3H), 1.16 (d, J=6.8 Hz, 3H), 1.01-0.98 (m, 6H), 0.93 (t, J=7.1 Hz, 3H). HRMS (ESI): Calcd for $(C_{51}H_{84}N_8O_{11}+H)^+$: 985.6332; Found: 985.6328.

FSM-22003

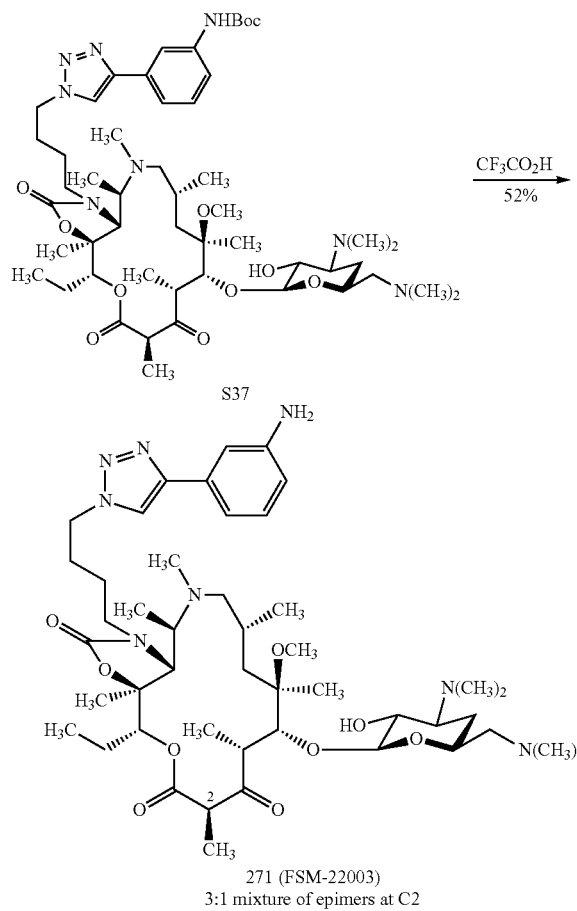

271 (FSM-22003)
3:1 mixture of epimers at C2

Amine S37 (3.0 mg, 3.04 μmol) was dissolved in 50% trifluoroacetic acid-dichloromethane at 23° C. After 2 h, the solution was concentrated under reduced pressure. The residue was partitioned between dichloromethane (1 mL) and saturated aqueous sodium bicarbonate solution (1 mL). The aqueous layer was extracted with dichloromethane (2×1 mL). The combined organic layers were dried over sodium sulfate and the dried solution was concentrated under reduced pressure. The residue was purified by column chromatography (5% methanol-dichloromethane+0.5% 30% aqueous ammonium hydroxide solution) to afford the product as a slightly yellow solid (1.4 mg, 52%). $^1$H NMR (3:1 diastereomeric mixture at C2, major isomer is reported, 500 MHz, CDCl$_3$) δ 7.84 (s, 1H), 7.23-7.13 (m, 3H), 6.67 (d, J=6.9 Hz, 1H), 4.76 (dd, J=9.7, 2.2 Hz, 1H), 4.54-4.19 (m, 4H), 4.17-3.93 (m, 1H), 3.87-3.42 (m, 4H), 3.21 (dd, J=10.1, 7.2 Hz, 1H), 3.14-2.94 (m, 3H), 2.87 (s, 3H), 2.69 (d, J=14.3 Hz, 1H), 2.57-2.39 (m, 3H), 2.31 (s, 12H), 2.05-1.99 (m, 2H), 1.95 (s, 3H), 1.87-1.79 (m, 1H), 1.74-1.60 (m, 8H), 1.59 (s, 3H), 1.30 (s, 3H), 1.22 (d, J=6.7 Hz, 3H), 1.18 (d, J=6.8 Hz, 3H), 1.02 (d, J=6.6 Hz, 3H), 0.94 (d, J=6.2 Hz, 3H), 0.90 (t, J=6.9 Hz, 3H). HRMS (ESI): Calcd for $(C_{46}H_{76}N_8O_9+H)^+$: 885.5808; Found: 885.5811.

Preparation of Macrolides with Sugars Modified at C3 Position of the Sugar

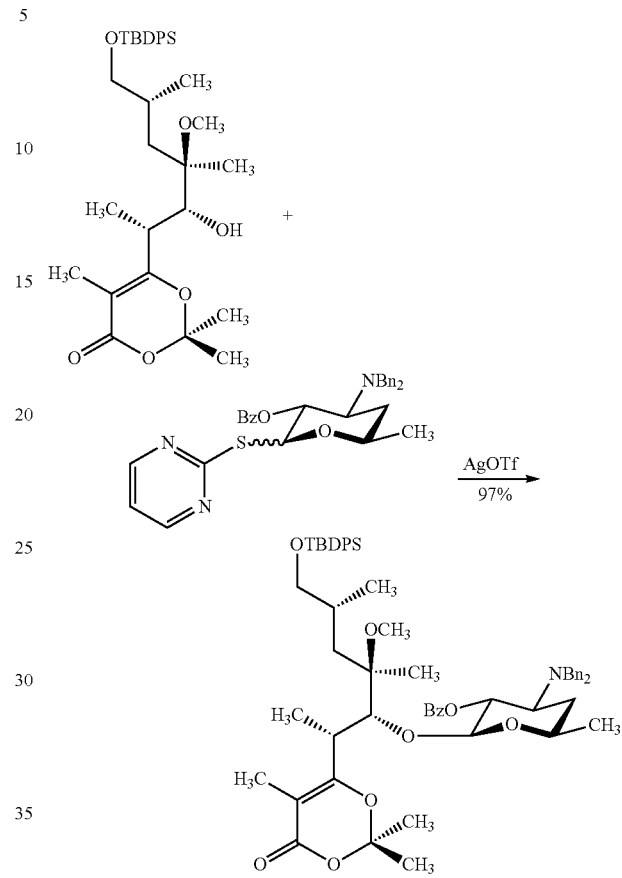

In a 50-mL round-bottom flask, 3 angstrom molecular sieves (1.1 g) were dried by heating with a gentle flame under vacuum (0.1 mmHg). After the flask had cooled to 23° C., 6-((2R,3R,4R,6R)-7-((tert-butyldiphenylsilyl)oxy)-3-hydroxy-4-methoxy-4,6-dimethylheptan-2-yl)-2,2,5-trimethyl-4H-1,3-dioxin-4-one (560 mg, 0.984 mmol) and (2S, 3R,4S,6R)-4-(dibenzylamino)-6-methyl-2-(pyrimidin-2-ylthio)tetrahydro-2H-pyran-3-yl benzoate (998 mg, 1.899 mmol) in Dichloromethane (9.84 mL) was added. The suspension was cooled to −20° C. Silver trifluoromethanesulfonate (759 mg, 2.95 mmol) was added. The reaction mixture was allowed to warm to 23° C. over 30 min, then stirred at 23° C. for 24 h. Saturated sodium bicarbonate solution (10 mL) was added. The mixture was filtered through a thin pad of Celite, eluting with dichloromethane (10 mL). The biphasic filtrate was partitioned, and the aqueous layer was extracted with dichloromethane (2×10 mL). The combined organic layers were dried over magnesium sulfate, filtrated, and concentrated. The crude product was purified by column chromatography (15-30% ether-hexanes) to afford the product as a white foam (937 mg, 97%).

(2S,3R,4S,6R)-2-(((2R,3R,4R,6R)-7-((tert-butyldiphenylsilyl)oxy)-4-methoxy-4,6-dimethyl-2-(2,2,5-trimethyl-4-oxo-4H-1,3-dioxin-6-yl)heptan-3-yl)oxy)-4-(dibenzylamino)-6-methyltetrahydro-2H-pyran-3-yl benzoate (939 mg, 0.956 mmol) was dissolved in MeCN (9.6 mL) in a plastic vial and 48% hydrofluoric acid (3.4 mL, 96 mmol)

was added. The reaction was stirred at 23° C. After 1.5 h, the reaction mixture was added carefully to saturated aqueous sodium bicarbonate solution (50 mL), and extracted with ethyl acetate (3×40 mL). The combined organic layers were dried over magnesium sulfate, filtrated, and concentrated. The crude product was purified with column chromatography (30-50% ethyl acetate-hexanes) to afford the primary alcohol (684 mg, 96%). $R_f$: 0.38 (50% ethyl acetate-hexanes).

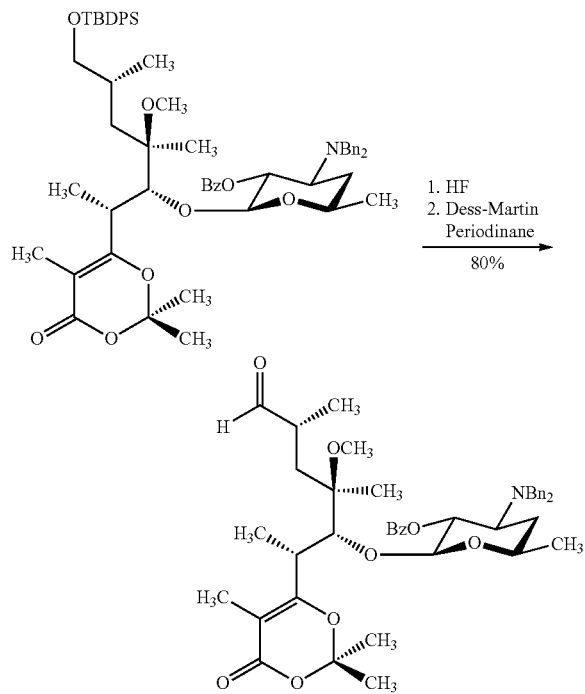

The primary alcohol obtained from the previous reaction (684 mg, 0.919 mmol) was dissolved in dichloromethane (9.2 mL), and water (1 µL) was added. Dess-Martin periodinane (585 mg, 1.379 mmol) was added in one portion and the mixture was stirred at 23° C. After 2 h, the reaction mixture was diluted with ether (20 mL). Saturated aqueous sodium bicarbonate solution (10 mL), saturated aqueous sodium thiosulfate (10 mL) were added. The mixture was stirred vigorously for 30 min and the layers were separated. The aqueous layer was extracted with ether (3×20 mL). The combined organic layers were washed with brine, dried over magnesium sulfate and concentrated. The crude product was purified by column chromatography (30→50% ether-hexanes) to give the title compound as white foam (570 mg, 84%). $R_f$: 0.32 (50% ethyl acetate-hexanes).

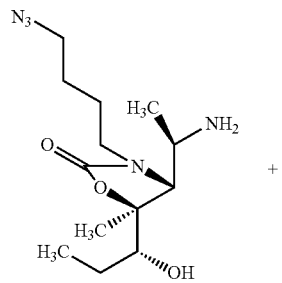

+

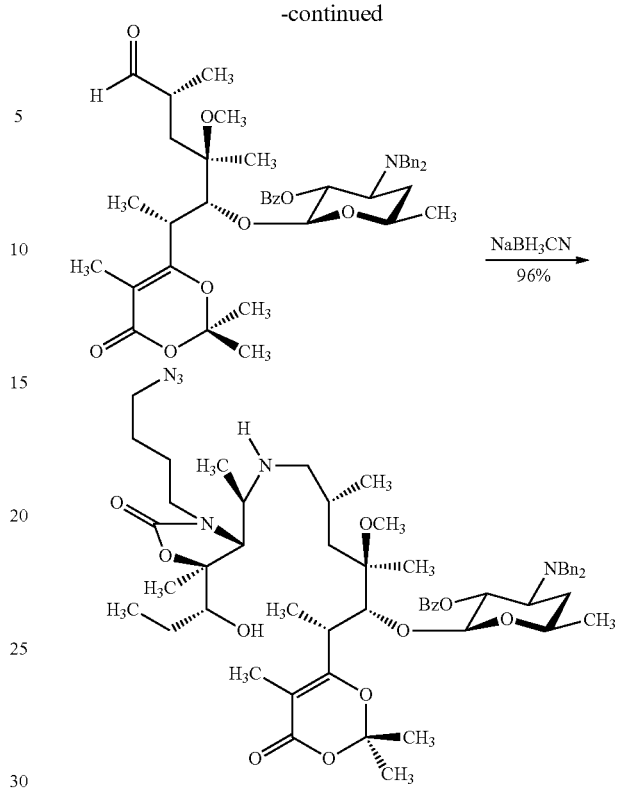

To a solution of (4R,5S)-4-((R)-1-aminoethyl)-3-(4-azidobutyl)-5-((R)-1-hydroxypropyl)-5-methyloxazolidin-2-one (245 mg, 0.817 mmol) and sodium cyanoborohydride (93 mg, 1.485 mmol) in 9:1 CH3OH:AcOH (5.0 mL) was added a solution of (2S,3R,4S,6R)-4-(dibenzylamino)-2-(((2R,3R,4R,6R)-4-methoxy-4,6-dimethyl-7-oxo-2-(2,2,5-trimethyl-4-oxo-4H-1,3-dioxin-6-yl)heptan-3-yl)oxy)-6-methyltetrahydro-2H-pyran-3-yl benzoate (551 mg, 0.743 mmol) in 9:1 CH3OH:AcOH (2.4 mL) at −20° C. The mixture was allowed to warm to −10° C. over 30 min. After 1 h, the reaction mixture was directly concentrated. The residue was diluted with dichloromethane (20 mL) and saturated aqueous sodium bicarbonate solution (10 mL). The aqueous layer was extracted with dichloromethane (3×10 mL). The combined organic layers were washed with brine, dried over magnesium sulfate and concentrated. The crude product was purified with column chromatography (30→50% ethyl acetate-hexanes) to afford the product as a white foam (729 mg, 96%). $R_f$: 0.29 (50% ethyl acetate-hexanes).

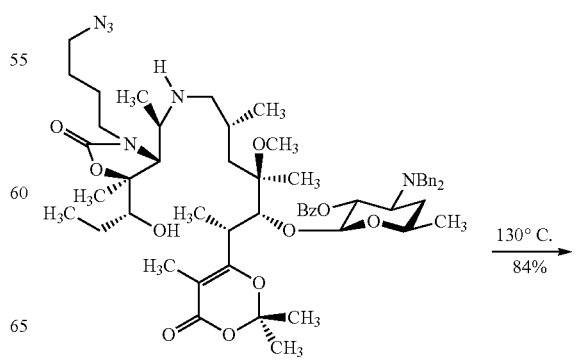

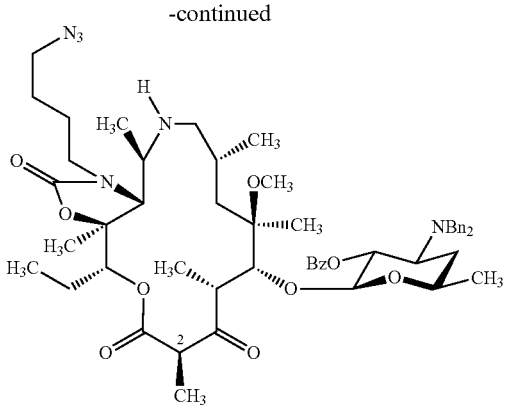

(2S,3R,4S,6R)-2-(((2R,3R,4R,6R)-7-(((R)-1-((4R,5S)-3-(4-azidobutyl)-5-((R)-1-hydroxypropyl)-5-methyl-2-oxooxazolidin-4-yl)ethyl)amino)-4-methoxy-4,6-dimethyl-2-(2,2,5-trimethyl-4-oxo-4H-1,3-dioxin-6-yl)heptan-3-yl)oxy)-4-(dibenzylamino)-6-methyltetrahydro-2H-pyran-3-yl benzoate (729 mg, 0.711 mmol) was azeotroped from benzene (2 times) and dissolved in chlorobenzene (711 mL). The flask was fitted with a reflux condenser. A stream of argon was bubbled through the solution for 30 min. The solution was then heated to reflux (130° C., bath temp 150° C.). After 16 h, the flask and its contents were cooled to 23° C., then the solution was concentrated. The residue was purified by column chromatography (20→40% ethyl acetate-hexanes) to afford the product as a white foam (580 mg, 84%).

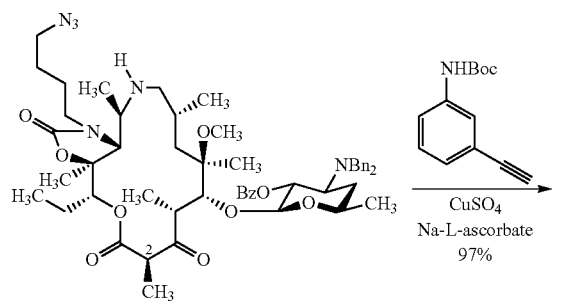

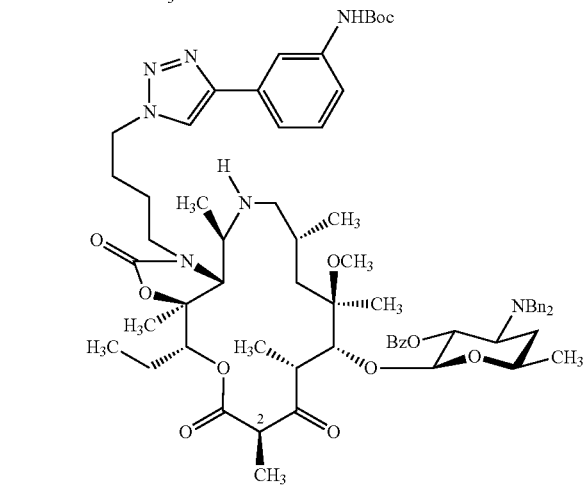

tert-Butyl (3-ethynylphenyl)carbamate (381 mg, 1.752 mmol) was added to a solution of the macrocyclic azide (565 mg, 0.584 mmol) in 1:1 t-BuOH:water (11.7 mL). Sodium ascorbate (23.14 mg, 0.117 mmol) and copper(II) sulfate (4.66 mg, 0.029 mmol) were added sequentially. The mixture was stirred at 23° C. for 16 h, then was diluted with saturated aqueous sodium bicarbonate (20 mL). The resulting biphasic mixture was extracted with dichloromethane (3×20 mL). The combined organic layers were dried over magnesium sulfate and concentrated. The residue was purified by column chromatography (50-70% ethyl acetate-hexane) to afford the product as a white foam (674 mg, 97%). $R_f$ (ethyl acetate/Hexane=1/1): 0.10.

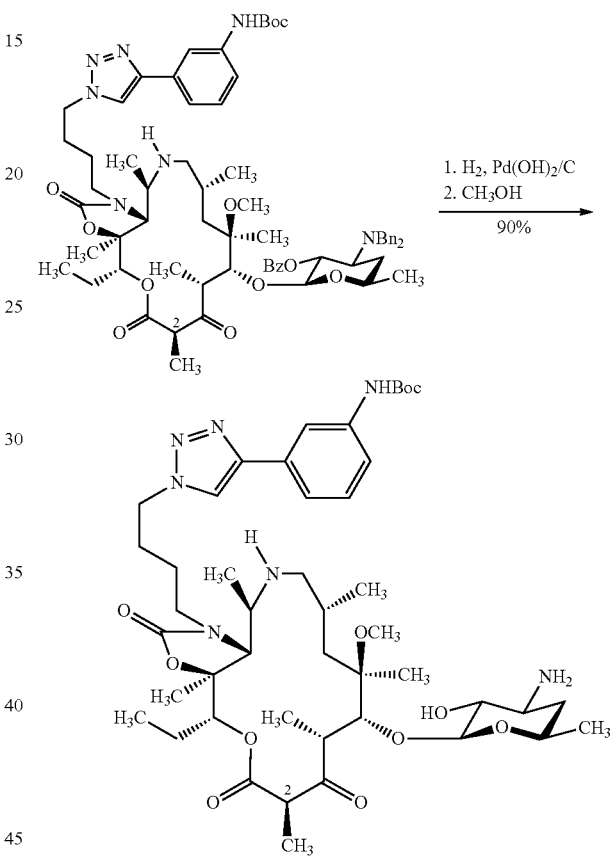

Dibenzylamine macrocycle (674 mg, 0.569 mmol) was dissolved in methanol (114 mL) in a 250-mL flask. The flask was evacuated (0.1 mmHg) and flushed with argon (2 times). Palladium hydroxide on carbon (40.0 mg, 0.285 mmol) was added. The flask was evacuated (0.1 mmHg) and flushed with hydrogen. The slurry was stirred under hydrogen atmosphere (triple-layered balloon) at 60° C. After 48 h, the mixture was allowed to cool to 23° C. and filtered through a pad of Celite. The filtrate was concentrated. The crude product contained a mixture of depicted product and 2'-benzoylated product. The residue was dissolved in methanol (100 mL), and the solution was heated at 60° C. After 24 h, the solution was concentrated, and the residue was purified by column chromatography (5-15% methanol-dichloromethane+0.5% 30% aqueous ammonium hydroxide solution) to afford the product as a white foam (453 mg, 90%). $R_f$ (10% methanol-dichloromethane+0.5% 30% aqueous ammonium hydroxide solution): 0.44.

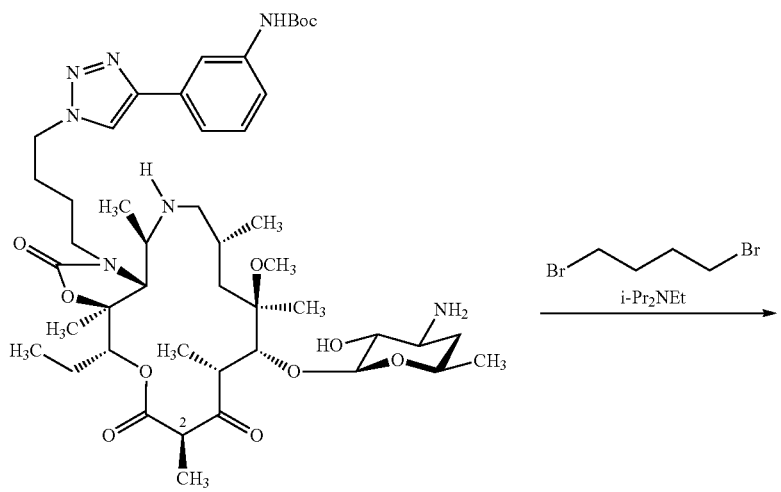

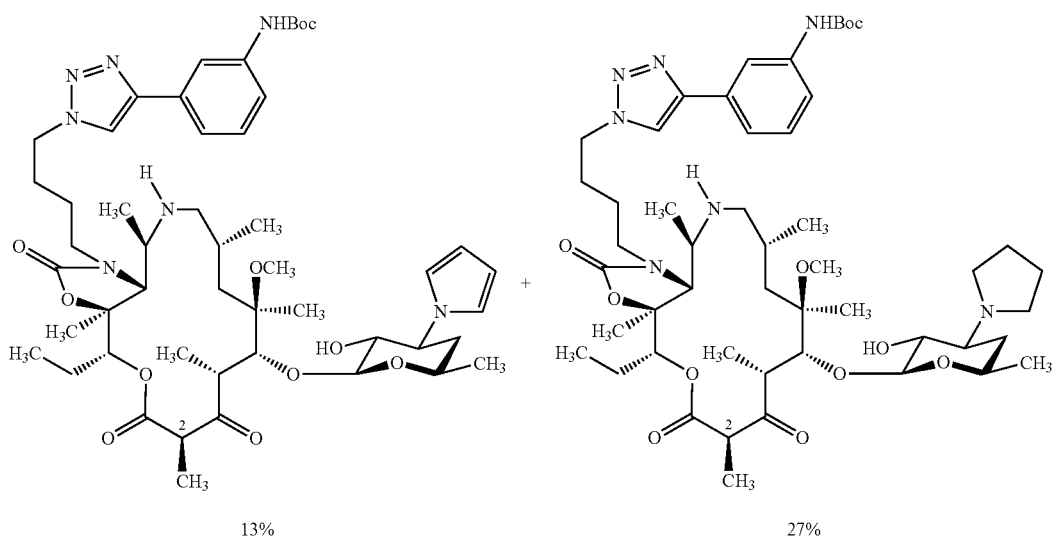

13%   27%

To a solution of tert-butyl (3-(1-(4-((3aR,4R,7R,9R,10R,11R,13R,16R,16aS)-10-(((2S,3R,4S,6R)-4-amino-3-hydroxy-6-methyltetrahydro-2H-pyran-2-yl)oxy)-16-ethyl-9-methoxy-4,7,9,11,13,16a-hexamethyl-2,12,14-trioxotetradecahydrooxazolo[5,4-c][1]oxa[6]azacyclopentadecin-3 (2H)-yl)butyl)-1H-1,2,3-triazol-4-yl)phenyl)carbamate (27.0 mg, 0.016 mmol) in MeCN (162 μl) were added Hunig's base (8.5 μL, 0.049 mmol) and 1,4-dibromobutane (2.1 μL, 0.018 mmol). The solution was warmed to 50° C. After 4 h, additional portions of Hunig's base (56.0 uL, 0.16 mmol) and 1,4-dibromobutane (10.7 uL, 0.054 mmol) were added. The mixture was warmed to 70° C. After another 24 h, the reaction solution was cooled to 23° C. and concentrated. The crude product was purified by preparative TLC (5% methanol-dichloromethane+0.5% 30% aqueous ammonium hydroxide solution) to afford the depicted pyrrole product (higher $R_f$, 2.0 mg, 13%) and the pyrrolidine product (lower $R_f$, 4.1 mg, 27%).

FSM-120361

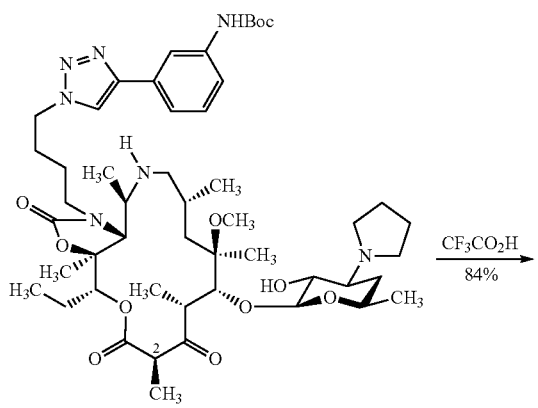

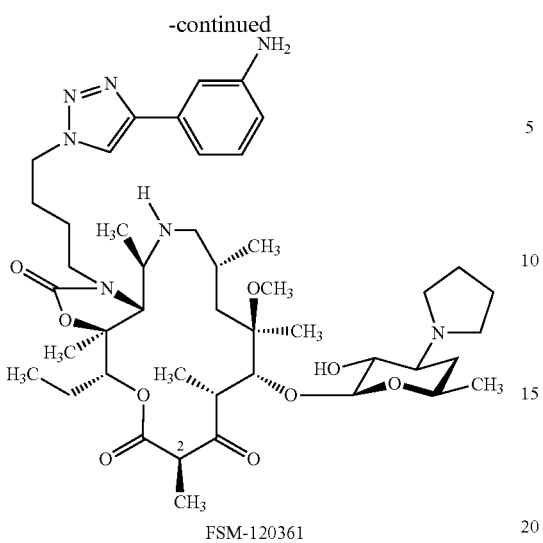

FSM-120361

Trifluoroacetic acid (0.1 mL) was added to a solution of tert-butyl (3-(1-(4-(((3aR,4R,7R,9R,10R,11R,13R,16R,16aS)-16-ethyl-10-(((2S,3R,4S,6R)-3-hydroxy-6-methyl-4-(pyrrolidin-1-yl)tetrahydro-2H-pyran-2-yl)oxy)-9-methoxy-4,7,9,11,13,16a-hexamethyl-2,12,14-trioxotetradecahydrooxazolo[5,4-c][1]oxa[6]azacyclopentadecin-3 (2H)-yl)butyl)-1H-1,2,3-triazol-4-yl)phenyl)carbamate (4.1 mg, 4.30 μmol) in dichloromethane (0.1 mL) at 23° C. The mixture was allowed to stand at 23° C. for 1 h, then was concentrated to afford FSM-120361 as a yellow solid (4.3 mg, 84%).

TABLE E1

Exemplary macrolides

| Compound and ID | $^1$H NMR Data | MS Data |
|---|---|---|
| FSM-21700 · 4 CF$_3$CO$_2$H | $^1$H NMR (500 MHz, CD$_3$OD) δ 8.43 (s, 1H), 7.84 (d, J = 6.8 Hz, 2H), 7.60 (t, J = 8.2 Hz, 1H), 7.34 (d, J = 8.4 Hz, 1H), 4.94 (dd, J = 10.6, 1.9 Hz, 1H), 4.62 (d, J = 3.2 Hz, 1H), 4.61-4.45 (m, 3H), 4.18 (q, J = 6.9 Hz, 1H), 4.01 (dd, J = 10.3, 8.6 Hz, 1H), 3.80 (dt, J = 15.2, 7.8 Hz, 1H), 3.67 (q, J = 6.1 Hz, 1H), 3.63 (s, 1H), 3.60-3.52 (m, 2H), 3.44 (dd, J = 11.9, 3.1 Hz, 1H), 3.23 (dd, J = 13.4, 8.1 Hz, 1H), 3.19 (s, 3H), 3.17-3.00 (m, 2H), 2.91 (s, 3H), 2.84 (s, 3H), 2.77 (t, J = 11.8 Hz, 1H), 2.25-1.97 (m, 3H), 1.97-1.59 (m, 8H), 1.55 (s, 3H), 1.44 (s, 3H), 1.38 (d, J = 7.6 Hz, 3H), 1.35 (d, J = 6.5 Hz, 3H), 1.33 (d, J = 4.7 Hz, 3H), 1.29-1.25 (m, 1H), 1.10 (d, J = 7.1 Hz, 3H), 0.91 (t, J = 7.7 Hz, 3H). | HRMS (ESI): Calcd for (C$_{43}$H$_{70}$N$_8$O$_9$ + H)$^+$: 843.5339; Found: 843.5353. |
| FSM-21795 | $^1$H NMR (500 MHz, CDCl$_3$) δ 7.81 (s, 1H), 7.25-7.06 (m, 3H), 6.73-6.62 (m, 1H), 5.98-5.86 (m, 1H), 5.33-5.25 (m, 1H), 5.25-5.14 (m, 1H), 5.05 (t, J = 5.6 Hz, 1H), 4.97 (dd, J = 10.8, 1.8 Hz, 1H), 4.59 (d, J = 10.1 Hz, 2H), 4.52 (t, J = 4.1 Hz, 1H), 4.50-4.42 (m, 2H), 4.40 (d, J = 7.4 Hz, 1H), 3.89 (q, J = 6.8 Hz, 1H), 3.78-3.58 (m, 3H), 3.46 (dd, J = 8.9, 4.7 Hz, 1H), 3.42 (s, 1H), 3.37-3.28 (m, 1H), 3.21 (dd, J = 10.1, 7.5 Hz, 1H), 3.11-2.98 (m, 1H), 2.95 (s, 3H), 2.77 (dt, J = 9.8, 4.3 Hz, 2H), 2.60-2.45 (m, 1H), 2.28 (s, 6H), 2.13-1.83 (m, 4H), 1.83-1.51 (m, 7H), 1.44 (s, 3H), 1.41 (d, J = 6.9 Hz, 3H), 1.38 (d, J = 7.8 Hz, 3H), 1.25 (s, 3H), 1.19 (d, J = 12.9 Hz, 1H), 0.99 (d, J = 6.1 Hz, 3H), 0.94 (d, J = 6.9 Hz, 3H), 0.89 (t, J = 7.4 Hz, 3H). | HRMS (ESI): Calcd for (C$_{47}$H$_{74}$N$_8$O$_{11}$ + H)$^+$: 927.5550; Found: 927.5557. |

TABLE E1-continued

Exemplary macrolides

| Compound and ID | $^1$H NMR Data | MS Data |
|---|---|---|
| 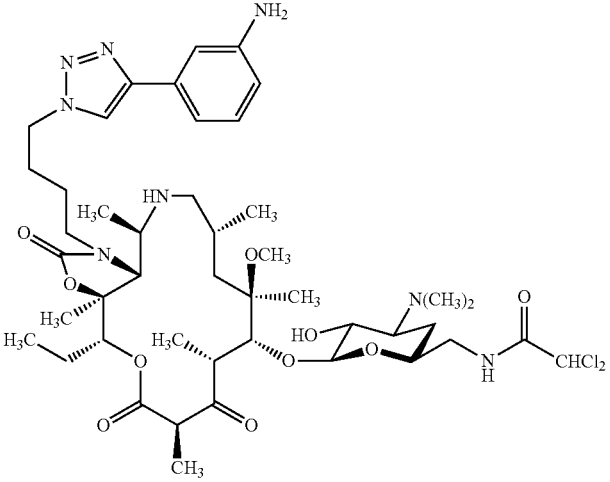<br>FSM-21842 | $^1$H NMR (500 MHz, CD$_3$OD) δ 8.41 (s, 1H), 7.80 (s, 1H), 7.77 (d, J = 8.0 Hz, 1H), 7.56 (t, J = 7.9 Hz, 1H), 7.28 (d, J = 8.0 Hz, 1H), 4.94 (d, J = 8.5 Hz, 1H), 4.60-4.44 (m, 3H), 4.15 (q, J = 6.8 Hz, 1H), 3.92-3.76 (m, 2H), 3.68 (d, J = 6.6 Hz, 1H), 3.63 (s, 1H), 3.60-3.38 (m, 5H), 3.15 (s, 3H), 3.12-2.95 (m, 2H), 2.91 (s, 3H), 2.82 (s, 3H), 2.14-1.96 (m, 4H), 1.96-1.58 (m, 7H), 1.54 (s, 3H), 1.51-1.44 (m, 1H), 1.42 (s, 3H), 1.38-1.27 (m, 12H), 1.10 (d, J = 7.1 Hz, 3H), 0.92 (t, J = 7.3 Hz, 3H). | HRMS (ESI): Calcd for (C$_{45}$H$_{70}$N$_8$O$_{10}$ + H)$^+$: 953.4665; Found: 953.4674. |
| 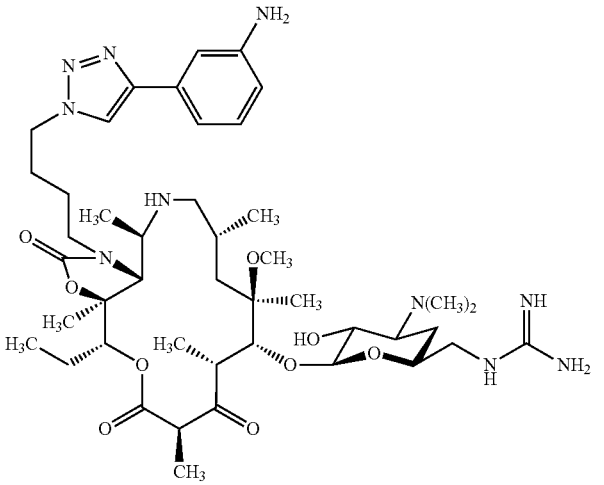<br>FSM-21843 | $^1$H NMR (500 MHz, CD$_3$OD) δ 8.42 (s, 1H), 7.80-7.59 (m, 2H), 7.53 (d, J = 9.0 Hz, 1H), 7.29-7.17 (m, 1H), 4.53 (ddd, J = 18.7, 13.2, 5.0 Hz, 3H), 4.39-4.23 (m, 2H) 4.16 (q, J = 6.9 Hz, 1H), 3.93-3.72 (m, 2H), 3.66 (d, J = 7.0 Hz, 1H), 3.61 (s, 1H), 3.58-3.39 (m, 4H), 3.13 (s, 3H), 3.02 (d, J = 7.5 Hz, 1H), 2.92 (s, 3H), 2.83 (s, 3H), 2.74 (t, J = 11.8 Hz 1H), 2.21-1.91 (m, 4H), 1.91-1.56 (m, 7H), 1.54 (s, 3H), 1.51-1.43 (m, 1H), 1.41 (s, 3H), 1.39-1.17 (m, 9H), 1.09 (d, J = 6.9 Hz, 3H), 0.90 (t, J = 6.7 Hz, 3H). Note: the C13—H proton is covered by the water peak in CD$_3$OD. | HRMS (ESI): Calcd for (C$_{44}$H$_{72}$N$_{10}$O$_9$ + H)$^+$: 885.5557; Found: 885.5562. |
| 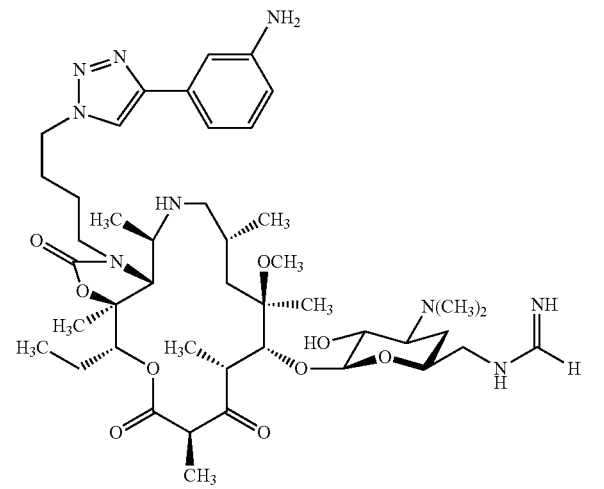<br>FSM-21861 | This compound exists as a 1:1 mixture of C2-epimers. Peaks are reported as seen. $^1$H NMR (500 MHz, CD$_3$OD) δ 8.44 (s, 1H), 8.02 (d, J = 22.2 Hz, 1H), 7.85 (d, J = 6.7 Hz, 2H), 7.60 (t, J = 7.9 Hz, 1H), 7.34 (d, J = 7.7 Hz, 1H), 4.63-4.41 (m, 3H), 4.17 (d, J = 5.1 Hz, 1H), 3.99 (s, 1H), 3.92-3.72 (m, 2H), 3.72-3.48 (m, 5H), 3.47-3.38 (m, 1H), 3.22 (dd, J = 20.9, 13.5 Hz, 1H), 3.13 (d, J = 3.1 Hz, 3H), 2.90 (d, J = 21.9 Hz, 3H), 2.84 (s, 3H), 2.77 (t, J = 11.7 Hz, 1H), 2.12 (dd, J = 55.4, 27.5 Hz, 3H), 1.92-1.58 (m, 8H), 1.54 (s, 3H), 1.47-1.43 (m, 1H), 1.44-1.32 (m, 9H), 1.30 (s, 3H), 1.09 (d, J = 6.7 Hz, 3H), 0.95-0.85 (m, 3H). Note: the C13—H proton is covered by the water peak in CD$_3$OD. | HRMS (ESI): Calcd for (C$_{44}$H$_{71}$N$_9$O$_9$ + H)$^+$: 870.5448; Found: 870.5447. |

TABLE E1-continued

Exemplary macrolides

| Compound and ID | ¹H NMR Data | MS Data |
|---|---|---|
| 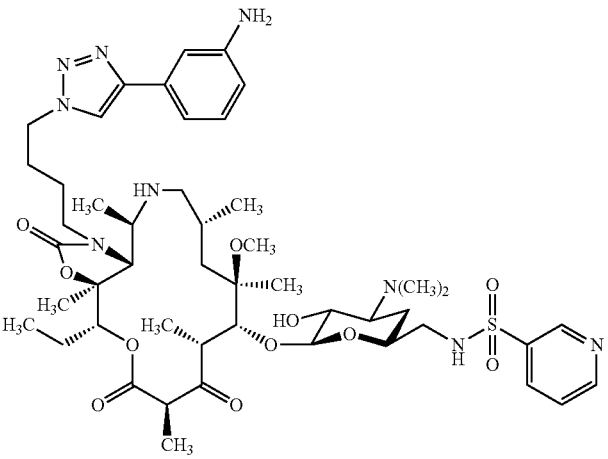<br>FSM-21876 | This compound exists as a 4:1 mixture of C2-epimers. The major epimer is reported. ¹H NMR (500 MHz, CD$_3$OD) δ 9.04 (s, 1H), 8.81 (d, J = 4.4 Hz, 1H), 8.39 (s, 1H), 8.31 (d, J = 8.1 Hz, 1H), 7.77 (s, 1H), 7.73 (d, J = 7.9 Hz, 1H), 7.66 (dd, J = 8.0, 4.9 Hz, 1H), 7.53 (t, J = 7.7 Hz, 1H), 7.25 (d, J = 9.9 Hz, 1H), 4.93 (d, J = 8.6 Hz, 1H), 4.64-4.48 (m, 4H), 4.21-4.11 (m, 1H), 3.88-3.78 (m, 1H), 3.69-3.64 (m, 1H), 3.63 (s, 1H), 3.52 (s, 1H), 3.47 (dd, J = 22.6, 10.6 Hz, 2H), 3.28-3.17 (m, 3H), 3.15 (s, 3H), 3.09-2.96 (m, 2H), 2.90 (s, 3H), 2.81 (s, 3H), 2.75 (t, J = 11.8 Hz, 1H), 2.15-1.94 (m, 3H), 1.94-1.58 (m, 8H), 1.54 (s, 3H), 1.42 (d, J = 9.7 Hz, 3H), 1.41-1.37 (m, 1H), 1.37-1.26 (m, 9H), 1.11 (d, J = 7.2 Hz, 3H), 0.92 (t, J = 7.4 Hz, 3H). | HRMS (ESI): Calcd for (C$_{48}$H$_{73}$N$_9$O$_{11}$S + H)$^+$: 984.5223; Found: 984.5216. |
| 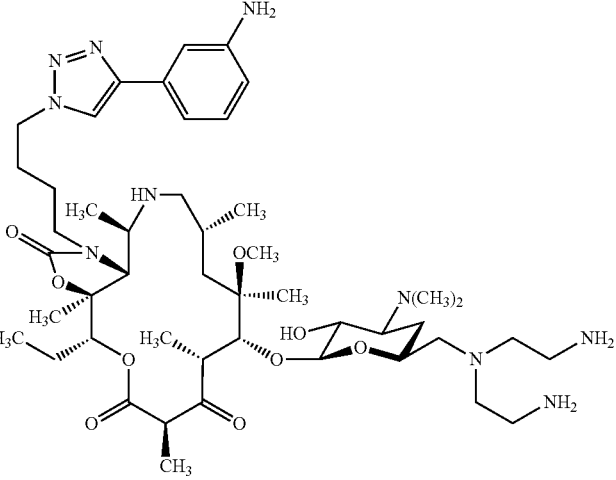<br>FSM-21877 | ¹H NMR (500 MHz, CD$_3$OD) δ 8.42 (s, 1H), 7.83 (d, J = 6.8 Hz, 2H), 7.59 (t, J = 8.1 Hz, 1H), 7.33 (d, J = 8.1 Hz, 1H), 4.64-4.42 (m, 5H), 4.21 (q, J = 6.8 Hz, 1H), 4.08-3.98 (m, 2H), 3.79 (d, J = 6.9 Hz, 1H), 3.67 (d, J = 6.7 Hz, 1H), 3.61 (s, 1H), 3.55-3.37 (m, 4H), 3.22-3.13 (m, 6H), 3.11 (s, 3H), 2.96 (d, J = 5.2 Hz, 2H), 2.91 (s, 3H), 2.82 (s, 3H), 2.74 (t, J = 12.0 Hz, 1H), 2.03 (dd, J = 23.3, 15.7 Hz, 3H), 1.79 (ddd, J = 94.7, 38.7, 13.2 Hz, 8H), 1.54 (s, 3H), 1.46-1.40 (m, 1H), 1.43-1.26 (m, 12H), 1.10 (d, J = 7.0 Hz, 3H), 0.90 (t, J = 7.4 Hz, 3H). Note: the C13—H proton is covered by the water peak in CD$_3$OD. | HRMS (ESI): Calcd for (C$_{47}$H$_{80}$N$_{10}$O$_9$ + H)$^+$: 929.6183; Found: 929.6179. |
| 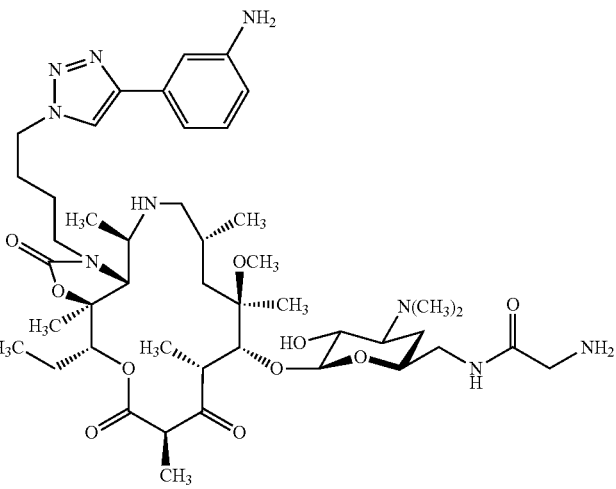<br>FSM-21878 | ¹H NMR (500 MHz, CD$_3$OD) δ 8.41 (s, 1H), 7.77-7.72 (m, 1H), 7.54 (t, J = 8.1 Hz, 1H), 7.26 (d, J = 7.3 Hz, 1H), 4.62-4.44 (m, 4H), 4.16 (q, J = 6.9 Hz, 1H), 3.86-3.75 (m, 4H), 3.65 (q, J = 6.6 Hz, 1H), 3.62-3.38 (m, 6H), 3.09 (s, 3H), 3.06-2.97 (m, 2H), 2.91 (s, 3H), 2.82 (s, 3H), 2.74 (t, J = 11.8 Hz, 1H), 2.20-1.95 (m, 3H), 1.95-1.56 (m, 8H), 1.53 (s, 3H), 1.44-1.42 (m, 1H), 1.41 (s, 3H), 1.38-1.25 (m, 9H), 1.09 (d, J = 7.1 Hz, 3H), 0.90 (t, J = 7.3 Hz, 3H). Note: the C13—H proton is covered by the water peak in CD$_3$OD. | HRMS (ESI): Calcd for (C$_{45}$H$_{73}$N$_9$O$_{10}$ + H)$^+$: 900.5553; Found: 900.5555. |

TABLE E1-continued

Exemplary macrolides

| Compound and ID | $^1$H NMR Data | MS Data |
|---|---|---|
| 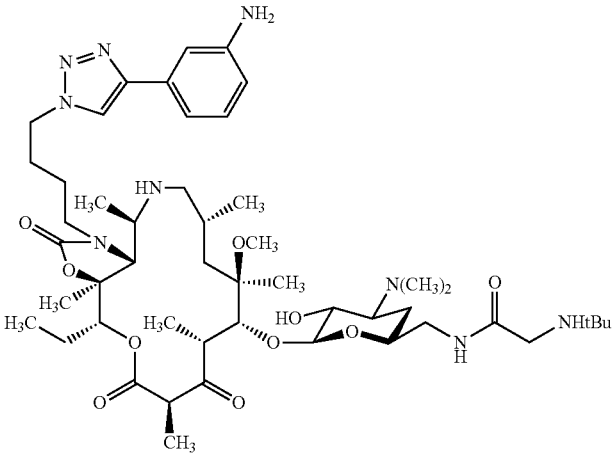<br>FSM-21879 | $^1$H NMR (500 MHz, CD$_3$OD) δ 8.40 (s, 1H), 7.74-7.67 (m, 2H), 7.53 (t, J = 8.1 Hz, 1H), 7.24 (d, J = 8.7 Hz, 1H), 4.62-4.46 (m, 4H), 4.17 (q, J = 6.8 Hz, 1H), 3.86 (s, 2H), 3.85-3.73 (m, 2H), 3.65 (q, J = 6.2 Hz, 1H), 3.63-3.35 (m, 6H), 3.20-3.13 (m, 1H), 3.11 (s, 3H), 3.07-3.00 (m, 1H), 2.91 (s, 3H), 2.82 (s, 3H), 2.74 (t, J = 11.6 Hz, 1H), 2.22-1.94 (m, 4H), 1.94-1.57 (m, 8H), 1.54 (s, 3H), 1.44-1.29 (m, 21H), 1.09 (d, J = 7.1 Hz, 3H), 0.90 (t, J = 7.3 Hz, 3H). Note: the C13—H proton is covered by the water peak in CD$_3$OD. | HRMS (ESI): Calcd for (C$_{49}$H$_{81}$N$_9$O$_{10}$ + H)$^+$: 956.6179; Found: 956.6180. |
| 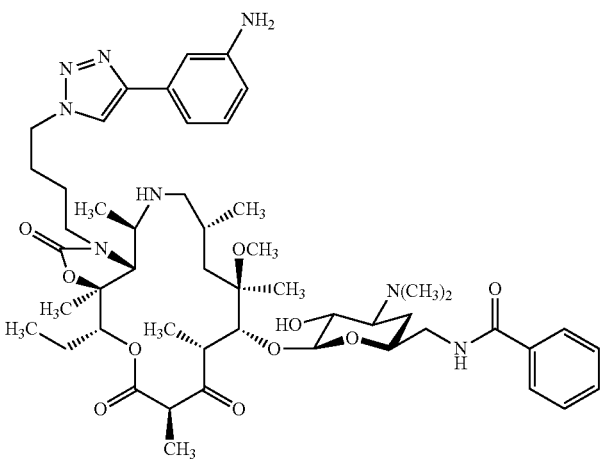<br>FSM-21880 | $^1$H NMR (500 MHz, CD$_3$OD) δ 8.44 (s, 1H), 7.92-7.80 (m, 4H), 7.63-7.55 (m, 1H), 7.46 (dt, J = 28.6, 7.4 Hz, 3H), 7.34 (d, J = 8.0 Hz, 1H), 4.92 (dd, J = 10.7, 2.0 Hz, 1H), 4.60-4.45 (m, 4H), 4.16 (q, J = 6.7 Hz, 1H), 3.97 (s, 1H), 3.82 (ddd, J = 21.9, 14.1, 7.9 Hz, 2H), 3.68-3.61 (m, 1H), 3.61-3.37 (m, 5H), 3.08-2.98 (m, 1H), 2.95-2.77 (m, 1H), 2.93 (s, 3H), 2.84 (s, 3H), 2.74 (s, 3H), 2.22-1.54 (m, 12H), 1.53 (s, 3H), 1.38-1.27 (m, 12H), 1.08 (d, J = 7.1 Hz, 3H), 0.93 (t, J = 7.2 Hz, 3H). | HRMS (ESI): Calcd for (C$_{50}$H$_{74}$N$_8$O$_{11}$ + H)$^+$: 947.5601; Found: 947.5595. |
| 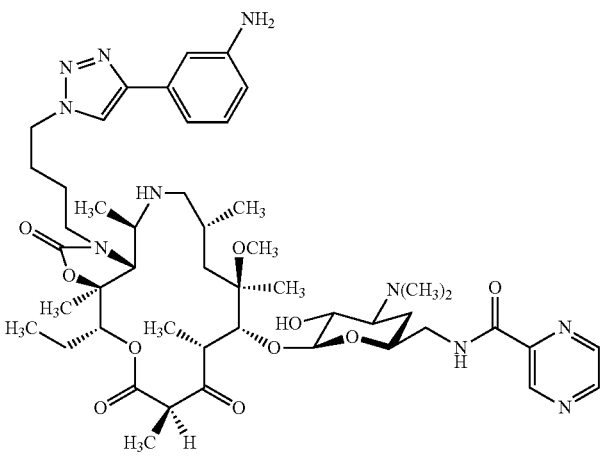<br>FSM-21881 | $^1$H NMR (500 MHz, CD$_3$OD) δ 9.28 (s, 1H), 8.81 (d, J = 2.3 Hz, 1H), 8.69 (s, 1H), 8.47 (s, 1H), 7.91-7.80 (m, 2H), 7.59 (t, J = 7.9 Hz, 1H), 7.33 (d, J = 7.9 Hz, 1H), 4.60-4.45 (m, 4H), 4.46 (d, J = 6.9 Hz, 1H), 4.09 (q, J = 6.9 Hz, 1H), 3.97 (s, 1H), 3.90-3.60 (m, 4H), 3.58 (s, 1H), 3.57-3.35 (m, 3H), 3.15-3.03 (m, 1H), 2.99 (s, 3H), 2.94-2.90 (m, 1H), 2.93 (s, 3H), 2.84 (s, 3H), 2.74 (t, J = 11.8 Hz, 1H), 2.23-1.96 (m, 3H), 1.94-1.55 (m, 8H), 1.53 (d, J = 9.3 Hz, 3H), 1.41 (s, 3H), 1.40-1.25 (m, 6H), 1.20 (d, J = 6.8 Hz, 3H), 1.09 (d, J = 7.1 Hz, 3H), 0.90 (t, J = 7.4 Hz, 3H). Note: C13—H proton is covered by the water peak in CD$_3$OD. | HRMS (ESI): Calcd for (C$_{48}$H$_{72}$N$_{10}$O$_{10}$ + H)$^+$: 949.5506; Found: 949.5499. |

TABLE E1-continued

Exemplary macrolides

| Compound and ID | $^1$H NMR Data | MS Data |
|---|---|---|
| 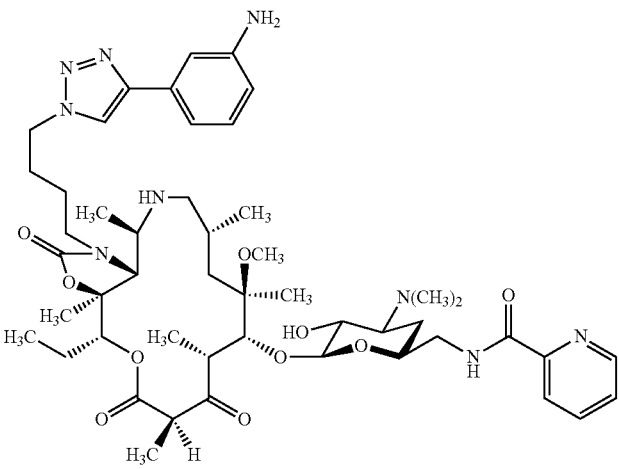<br>FSM-21887 | $^1$H NMR (500 MHz, CD$_3$OD) δ 8.61 (d, J = 4.8 Hz, 1H), 8.42 (s, 1H), 8.13 (d, J = 7.8 Hz, 1H), 7.94 (td, J = 7.7, 1.6 Hz, 1H), 7.7 (s, 1H), 7.72 (d, J = 7.9 Hz, 1H), 7.59-7.49 (m, 2H), 7.24 (d, J = 7.9 Hz, 1H), 4.92 (dd, J = 10.7, 2.2 Hz, 1H), 4.61-4.48 (m, 4H), 4.12 (q, J = 6.9 Hz, 1H), 3.97 (s, 1H), 3.83-3.61 (m, 4H), 3.60 (s, 1H), 3.58-3.35 (m, 3H), 3.15-3.01 (m, 1H), 3.01-2.96 (m, 1H), 2.95 (s, 3H), 2.92 (s, 3H), 2.83 (s, 3H), 2.74 (t, J = 11.7 Hz, 1H), 2.26-1.94 (m, 3H), 1.94-1.57 (m, 8H), 1.53 (s, 3H), 1.40 (s, 3H), 1.37-1.35 (m, 1H), 1.35-1.24 (m, 9H), 1.09 (d, J = 7.1 Hz, 3H), 0.91 (t, J = 7.4 Hz, 3H). | HRMS (ESI): Calcd for (C$_{49}$H$_{73}$N$_9$O$_{10}$ + H)$^+$: 948.5553; Found: 948.5537. |
| 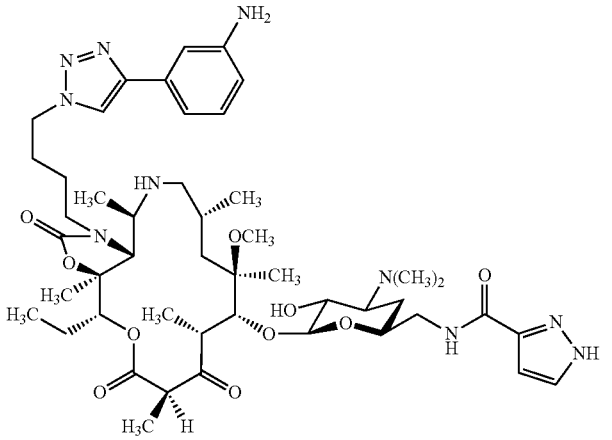<br>FSM-21888 | $^1$H NMR (500 MHz, CD$_3$OD) δ 8.40 (s, 1H), 7.76-7.70 (m, 2H), 7.66 (d, J = 7.8 Hz, 1H), 7.50 (t, J = 7.9 Hz, 1H), 7.20 (d, J = 8.2 Hz 1H), 6.80 (d, J = 2.1 Hz, 1H), 4.65-4.47 (m, 4H), 4.11 (q, J = 6.9 Hz, 1H), 3.94 (s, 1H), 3.86-3.59 (m, 3H), 3.57 (s, 1H), 3.57-3.38 (m, 3H), 3.09-2.94 (m, 2H), 2.92 (s, 3H), 2.89 (s, 3H), 2.83 (s, 3H), 2.73 (t, J = 11.8 Hz, 1H), 2.19-1.55 (m, 11H), 1.52 (s, 3H), 1.41 (d, J = 8.5 Hz, 1H), 1.36 (s, 3H), 1.34-1.22 (m, 9H), 1.08 (d, J = 7.1 Hz, 3H), 0.91 (t, J = 7.4 Hz, 3H).<br>Note: the C13—H proton is covered by the water peak in CD$_3$OD. | HRMS (ESI): Calcd for (C$_{47}$H$_{72}$N$_{10}$O$_{10}$ + H)$^+$: 937.5506; Found: 937.5500. |
| 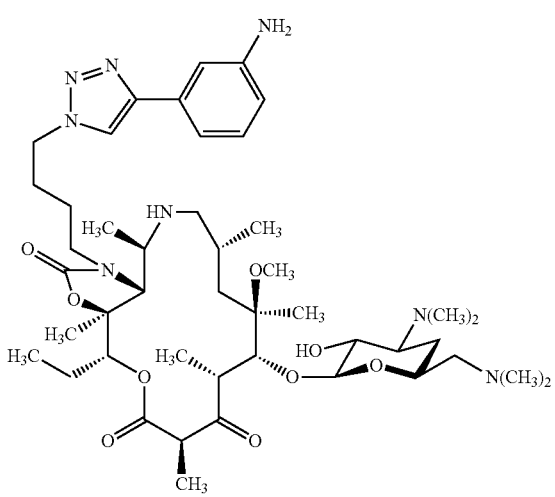<br>FSM-22003 | This compound exists as a 3:1 mixture of C2-epimers. Major epimer is reported. $^1$H NMR (500 MHz, CDCl$_3$) δ 7.84 (s, 1H), 7.23-7.13 (m, 3H), 6.67 (d, J = 6.9 Hz, 1H), 4.76 (dd, J = 9.7, 2.2 Hz, 1H), 4.54-4.41 (m, 3H), 4.33 (t, J = 6.8 Hz, 1H), 4.05 (dd, J = 14.2, 8.1 Hz, 1H), 3.81 (d, J = 10.4 Hz, 1H), 3.77-3.65 (m, 2H), 3.59 (s, 1H), 3.55 (s, 1H), 3.25-3.18 (m, 1H), 3.15-2.96 (m, 2H), 2.87 (s, 3H), 2.58-2.39 (m, 3H), 2.31 (s, 12H), 2.02 (t, J = 10.3 Hz, 3H), 1.95 (s, 3H), 1.89-1.72 (m, 4H), 1.70-1.60 (m, 4H), 1.59 (s, 3H), 1.37-1.32 (m, 1H), 1.30 (s, 3H), 1.22 (d, J = 6.7 Hz, 3H), 1.18 (d, J = 6.8 Hz, 3H), 1.03-0.93 (m, 6H), 0.90 (t, J = 6.9 Hz, 3H). | HRMS (ESI): Calcd for (C$_{46}$H$_{76}$N$_8$O$_9$ + H)$^+$: 885.5808; Found: 885.5811. |

TABLE E1-continued

Exemplary macrolides

| Compound and ID | ¹H NMR Data | MS Data |
|---|---|---|
| 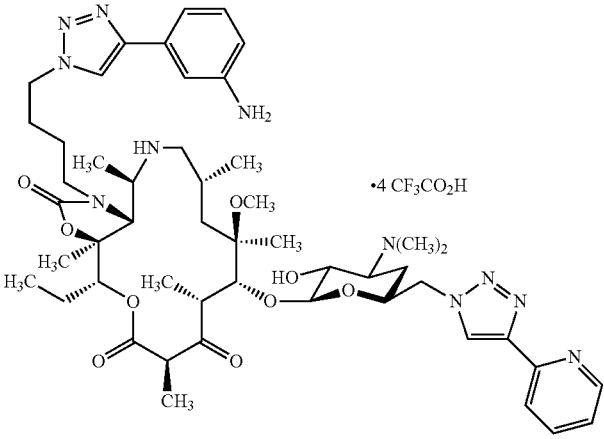<br>FSM-22366 | ¹H NMR (500 MHz, CD₃OD) δ 8.82 (s, 1H), 8.67 (d, J = 5.4 Hz, 1H), 8.47 (s, 1H), 8.24 (t, J = 6.5 Hz, 1H), 8.14 (t, J = 7.8 Hz, 1H), 7.99-7.93 (m, 1H), 7.93-7.86 (m, 1H), 7.62 (t, J = 7.9 Hz, 1H), 7.58-7.50 (m, 1H), 7.40-7.35 (m, 1H), 4.89-4.74 (m, 3H), 4.62-4.51 (m, 2H), 4.39 (d, J = 6.8 Hz, 1H), 4.30 (t, J = 8.7 Hz, 1H), 4.14 (d, J = 3.1 Hz, 1H), 4.05 (q, J = 6.9 Hz, 1H), 3.84-3.70 (m, 1H), 3.66-3.54 (m, 2H), 3.50 (s, 1H), 3.42-3.35 (m, 1H), 3.11-2.98 (m, 1H), 2.96 (br s, 3H), 2.86 (br, s, 3H), 2.85-2.82 (m, 1H), 2.78 (s, 3H), 2.69 (t, J = 11.9 Hz, 1H), 2.34 (d, J = 12.2 Hz, 1H), 2.08-1.93 (m, 3H), 1.91-1.51 (m, 7H), 1.49 (s, 3H), 1.32-1.29 (m, 4H), 1.25 (d, J = 7.3 Hz, 3H), 1.24 (s, 3H), 1.16 (d, J = 6.9 Hz, 3H), 1.06 (d, J = 7.0 Hz, 3H), 0.87 (t, J = 7.4 Hz, 3H). | HRMS (ESI): Calcd for $(C_{50}H_{73}N_{11}O_9 + H)^+$: 972.5665; Found: 972.5666. |
| 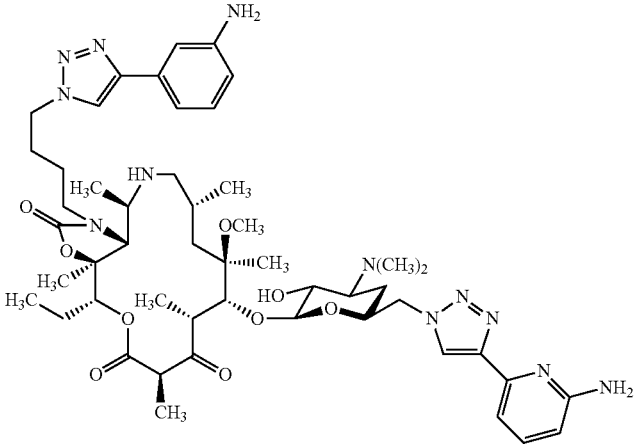<br>FSM-22372 | This compound exists as a 5:1 mixture of C2-epimers. Major epimer is reported. ¹H NMR (500 MHz, CD₃OD) δ 8.98 (s, 1H), 8.42 (s, 1H), 7.97-7.90 (m, 1H), 7.78-7.64 (m, 2H), 7.51 (t, J = 7.9 Hz, 1H), 7.35 (d, J = 7.3 Hz, 1H), 7.22 (d, J = 8.2 Hz, 1H), 6.93 (d, J = 8.9 Hz, 1H), 4.87-4.69 (m, 3H), 4.63-4.41 (m, 2H), 4.37 (s, 1H), 4.29 (s, 1H), 4.15 (d, J = 3.1 Hz, 1H), 4.10 (q, J = 6.8 Hz, 1H), 3.82-3.70 (m, 1H), 3.70-3.52 (m, 2H), 3.50 (s, 1H), 3.48-3.37 (m, 1H), 3.14-3.07 (m, 1H), 2.96 (s, 3H), 2.86 (s, 3H), 2.84 (s, 3H), 2.69 (t, J = 11.6 Hz, 1H), 2.32 (dd, J =22.6, 9.9 Hz, 1H), 2.13-1.93 (m, 3H), 1.93-1.55 (m, 7H), 1.51 (s, 3H), 1.39-1.33 (m, 1H), 1.33-1.21 (m, 12H), 1.06 (d, J = 7.1 Hz, 3H), 0.88 (t, J = 7.3 Hz, 3H). Note: the C13—H proton is covered by the water peak in CD₃OD. | HRMS (ESI): Calcd for $(C_{50}H_{74}N_{12}O_9 + H)^+$: 987.5774 Found: 987.5772. |
| 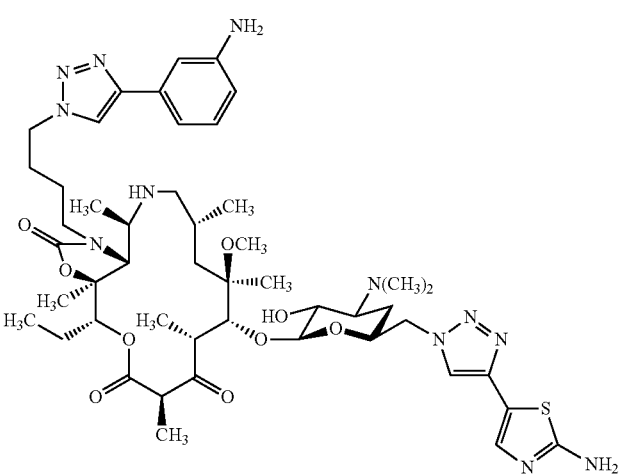<br>FSM-22373 | ¹H NMR (500 MHz, CD₃OD) δ 8.55 (s, 1H), 8.47 (s, 1H), 7.86 (dd, J = 13.0, 4.9 Hz, 2H), 7.66-7.49 (m, 2H), 7.33 (dd, J = 7.6, 1.7 Hz, 1H), 4.87 (dd, J = 10.8, 2.2 Hz, 1H), 4.81-4.70 (m, 2H), 4.63-4.52 (m, 2H), 4.38 (d, J = 6.8 Hz, 1H), 4.26 (d, J = 6.8 Hz, 1H), 4.12 (dd, J = 12.2, 5.1 Hz, 2H), 3.86-3.70 (m, 1H), 3.64 (q, J = 6.5 Hz, 1H), 3.60-3.46 (m, 2H), 3.46-3.37 (m, 1H), 3.14-3.02 (m, 1H), 2.95 (s, 3H), 2.92 (s, 3H), 2.90-2.88 (m, 1H), 2.86 (s, 3H), 2.70 (t, J = 11.8 Hz, 1H), 2.32 (d, J = 12.4 Hz, 1H), 2.14-1.94 (m, 2H), 1.94-1.61 (m, 8H), 1.51 (s, 3H), 1.45-1.36 (m, 1H), 1.32 (d, J = 6.6 Hz, 3H), 1.31-1.24 (m, 6H), 1.23 (d, J = 5.0 Hz, 3H), 1.06 (d, J = 7.1 Hz, 3H), 0.88 (t, J = 7.4 Hz, 3H). | HRMS (ESI): Calcd for $(C_{48}H_{72}N_{12}O_9S + H)^+$: 993.5339; Found: 993.5345. |

TABLE E1-continued

Exemplary macrolides

| Compound and ID | ¹H NMR Data | MS Data |
|---|---|---|
| 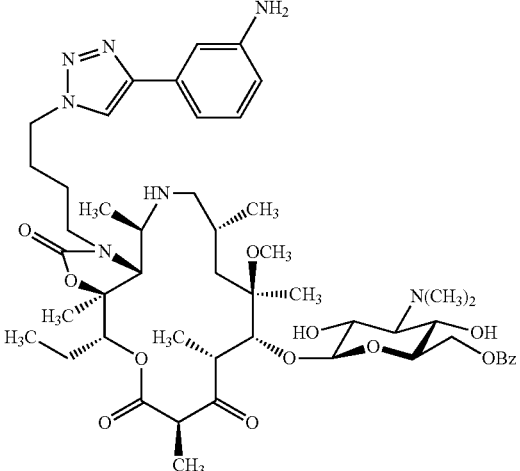<br>FSM-21797 | This compounds exists as a 2:1 mixture of C2-epimers. Protons are reported as seen. ¹H NMR (500 MHz, CDCl3) δ 8.06 (d, J = 7.3 Hz, 2H), 8.03 (d, J = 7.2 Hz, 2H), 7.88 (s, 1H), 7.83 (d, J = 9.2 Hz, 1H), 7.61-7.52 (m, 2H), 7.44 (dt, J = 22.5, 8.0 Hz, 4H), 7.26-7.12 (m, 6H), 6.68-6.61 (m, 2H), 4.94-4.77 (m, 2H), 4.72-4.52 (m, 2H), 4.52-4.35 (m, 6H), 4.27-4.14 (m, 2H), 4.14-3.51 (m, 12H), 3.23 (s, 2H), 3.09 (t, J = 39.7 Hz, 2H), 2.78 (dd, J = 21.3, 15.0 Hz, 2H), 2.74-2.53 (m, 4H), 2.52 (s, 6H), 2.51 (s, 6H), 2.08-1.82 (m, 8H), 1.82-1.50 (m, 8H), 1.50-1.41 (m, 6H), 1.38 (s, 6H), 1.32-1.29 (m, 2H), 1.29-1.23 (m, 6H), 1.21 (s, 1H), 1.20 (s, 1H), 1.02 (d, J = 3.2 Hz, 3H), 1.01 (d, J = 3.4 Hz, 3H), 0.96 (d, J = 3.2 Hz, 3H), 0.94 (d, J = 6.5 Hz, 3H), 0.86 (t, J = 5.6 Hz, 6H). | HRMS (ESI): Calcd for ($C_{50}H_{73}N_7O_{12}$ + H)⁺: 964.5390; Found: 964.5407. |
| 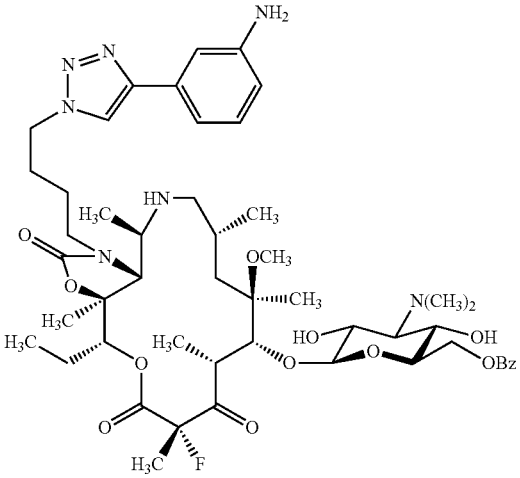<br>FSM-21798 | ¹H NMR (500 MHz, CDCl₃) δ 8.08 (d, J = 7.3 Hz, 2H), 7.82 (d, J = 4.0 Hz, 1H), 7.58 (t, J = 7.4 Hz, 1H), 7.47 (t, J = 7.8 Hz, 2H), 7.25-7.09 (m, 3H), 6.65 (dd, J = 7.4, 2.2 Hz, 1H), 4.92 (d, J = 9.0 Hz, 1H), 4.86 (d, J = 6.8 Hz, 1H), 4.69 (dd, J = 12.0, 7.4 Hz, 1H), 4.46 (t, J = 7.2 Hz, 2H), 4.39 (dd, J = 11.9, 4.1 Hz, 1H), 4.28-4.22 (m, 1H), 4.14 (d, J = 8.1 Hz, 1H), 4.06 (s, 1H), 3.90 (dd, J = 10.0, 6.7 Hz, 1H), 3.82-3.73 (m, 2H), 3.64 (d, J = 6.7 Hz, 2H), 3.20 (s, 3H), 3.04 (s, 1H), 2.93-2.85 (m, 2H), 2.68-2.59 (m, 2H), 2.55 (s, 6H), 2.12-1.77 (m, 5H), 1.71 (d, J = 21.5 Hz, 3H), 1.68-1.53 (m, 5H), 1.48 (s, 3H), 1.43 (d, J = 14.9 Hz, 1H), 1.37 (d, J = 7.0 Hz, 3H), 1.33 (s, 3H), 1.30-1.21 (m, 1H), 0.95 (d, J = 6.9 Hz, 6H), 0.90 (t, J = 7.3 Hz, 3H). | HRMS (ESI): Calcd for ($C_{50}H_{72}FN_7O_{12}$ + H)⁺: 982.5296; Found: 982.5294. |
| 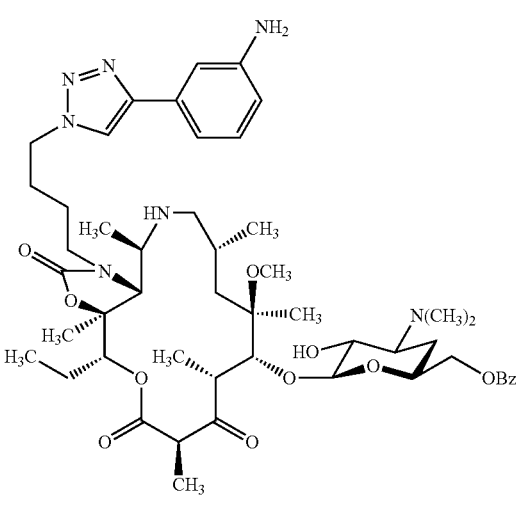<br>FSM-22111 | ¹H NMR (500 MHz, CDCl₃) δ 8.10-8.06 (m, 2H), 7.80 (s, 1H), 7.54-7.48 (m, 1H), 7.40 (t, J = 7.8 Hz, 2H), 7.25-7.13 (m, 3H), 6.69-6.63 (m, 1H), 4.95 (dd, J = 10.9, 1.9 Hz, 1H), 4.55-4.37 (m, 5H), 4.34 (dd, J = 11.4, 3.7 Hz, 1H), 3.94 (dd, J = 7.5, 5.7 Hz, 1H), 3.88 (dd, J = 13.7, 6.8 Hz, 1H), 3.75-3.60 (m, 2H), 3.39 (s, 1H), 3.29 (dd, J = 10.1, 7.5 Hz, 1H), 3.08-3.01 (m, 1H), 2.79-2.73 (m, 2H), 2.72 (s, 3H), 2.58 (td, J = 12.1, 3.9 Hz, 1H), 2.31 (s, 6H), 2.07-1.92 (m, 3H), 1.85-1.48 (m, 8H), 1.43 (s, 3H), 1.41 (d, J = 6.9 Hz, 3H), 1.36 (d, J = 7.8 Hz, 3H), 1.30-1.22 (m, 1H), 1.17 (s, 3H), 0.97 (d, J = 6.1 Hz, 3H), 0.91 (d, J = 6.9 Hz, 3H), 0.88 (t, J = 7.4 Hz, 3H). | HRMS (ESI): Calcd for ($C_{50}H_{73}N_7O_{11}$ + H)⁺: 948.5441; Found: 948.5457. |

TABLE E1-continued

Exemplary macrolides

| Compound and ID | $^1$H NMR Data | MS Data |
|---|---|---|
| 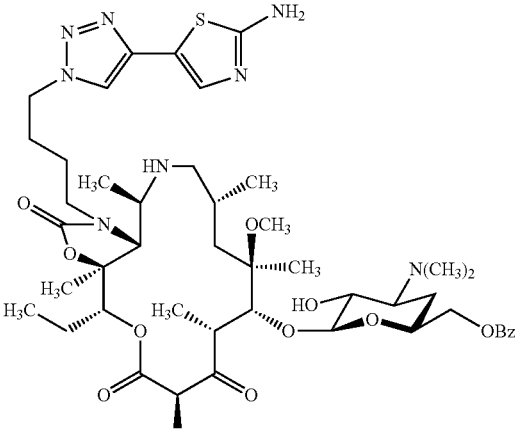{width=0} FSM-22124 | This compound exists as a 5:1 mixture of C2-epimers. Major epimer is reported. $^1$H NMR (500 MHz, CD$_3$OD) δ 8.35 (s, 1H), 8.14-8.10 (m, 2H), 7.64-7.45 (m, 4H), 4.66 (dd, J = 11.6, 7.9 Hz, 1H), 4.60-4.42 (m, 5H), 4.17 (q, J = 6.7 Hz, 1H), 3.80-3.69 (m, 1H), 3.68-3.59 (m, 1H), 3.59-3.48 (m, 4H), 3.38 (dd, J = 11.9, 3.2 Hz, 1H), 3.08-2.96 (m, 2H), 2.94 (s, 3H), 2.85 (s, 3H), 2.71 (s, 3H), 2.20 (d, J = 12.0 Hz, 1H), 2.07-1.56 (m, 10H), 1.53 (s, 3H), 1.44-1.40 (m, 1H), 1.38 (d, J = 6.9 Hz, 3H), 1.33 (d, J = 7.7 Hz, 3H), 1.31 (d, J = 6.7 Hz, 3H), 1.27 (s, 3H), 1.05 (d, J = 7.1 Hz, 3H), 0.94 (t, J = 7.4 Hz, 3H). Note: the C13—H proton is covered by the water peak in CD$_3$OD. | HRMS (ESI): Calcd for (C$_{47}$H$_{70}$N$_8$O$_{11}$S + H)$^+$: 955.4958; Found: 955.4962. |
| 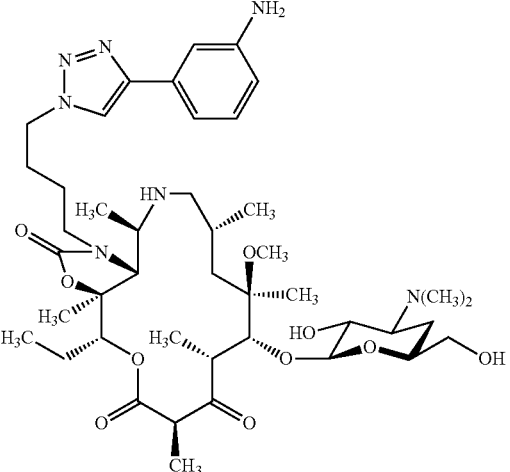 FSM-22125 | This compound exists as a 11:1 mixture of C2-epimers. Major epimer is reported. $^1$H NMR (500 MHz, CDCl$_3$) δ 7.81 (s, 1H), 7.25-7.11 (m, 3H), 6.73-6.60 (m, 1H), 4.97 (dd, J = 10.8, 1.5 Hz, 1H), 4.57-4.36 (m, 4H), 3.89 (q, J = 6.8 Hz, 1H), 3.82-3.58 (m, 4H), 3.41 (s, 1H), 3.23 (dt, J = 16.0, 8.0 Hz, 1H), 3.08-3.01 (m, 1H), 2.92 (s, 3H), 2.84-2.71 (m, 2H), 2.62-2.48 (m, 1H), 2.30 (s, 6H), 2.02 (ddd, J = 19.9, 13.8, 7.5 Hz, 3H), 1.83-1.49 (m, 8H), 1.44 (s, 3H), 1.41 (d, J = 6.9 Hz, 3H), 1.38 (d, J = 7.7 Hz, 4H), 1.30-1.26 (m, 1H), 1.25 (s, 3H), 0.99 (d, J = 6.1 Hz, 3H), 0.94 (d, J = 6.9 Hz, 3H), 0.90 (t, J = 7.3 Hz, 3H). | HRMS (ESI): Calcd for (C$_{43}$H$_{69}$N$_7$O$_{10}$ + H)$^+$: 844.5179; Found: 844.5188. |
| 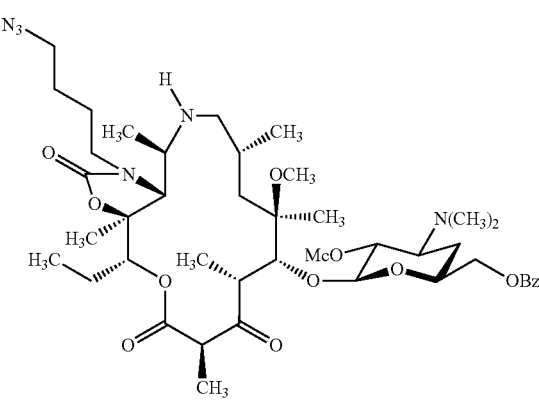 | | |

TABLE E1-continued

Exemplary macrolides

| Compound and ID | ¹H NMR Data | MS Data |
|---|---|---|
| 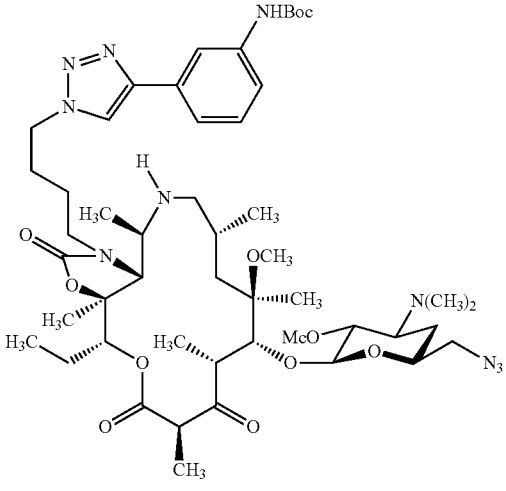 19 | ¹H NMR (4:1 diastereomeric mixture at C2, major isomer reported, 500 MHz, CDCl₃) δ 7.82 (s, 1H), 7.67 (s, 1H), 7.51-7.45 (m, 2H), 7.38-7.29 (m, 1H), 6.82 (s, 1H), 4.95 (dd, J = 10.9, 1.9 Hz, 1H), 4.60-4.51 (m, 2H), 4.51-4.35 (m, 3H), 3.84 (q, J = 6.9 Hz, 1H), 3.76 (s, 3H), 3.75-3.68 (m, 1H), 3.68-3.61 (m, 1H), 3.40-3.34 (m, 2H), 3.26 (dd, J = 13.1, 3.3 Hz, 1H), 3.05 (ddd, J = 14.8, 10.0, 5.0 Hz, 1H), 2.88 (s, 3H), 2.80-2.71 (m, 3H), 2.27 (s, 6H), 2.09-1.91 (m, 4H), 1.77-1.43 (m, 8H), 1.51 (s, 9H), 1.41 (s, 3H), 1.37 (d, J = 6.9 Hz, 3H), 1.21 (s, 3H), 1.19 (d, J = 7.8 Hz, 3H), 1.08-1.01 (m, 1H), 0.95 (d, J = 6.0 Hz, 3H), 0.92 (d, J = 6.7 Hz, 3H), 0.86 (t, J = 7.4 Hz, 3H). | HRMS (ESI): Calcd for ($C_{50}H_{78}N_{10}O_{13}$ + H)⁺: 1027.5823; Found: 1027.5865. |
| 20 | ¹H NMR (500 MHz, CDCl₃) δ 8.53 (d, J = 4.1 Hz, 1H), 8.30 (s, 1H), 8.12 (d, J = 7.9 Hz, 1H), 7.84 (s, 1H), 7.78 (s, 1H), 7.71 (td, J = 7.8, 1.8 Hz, 1H), 7.54-7.48 (m, 2H), 7.36 (td, J = 7.9, 3.9 Hz, 1H), 7.20-7.12 (m, 1H), 6.91 (s, 1H), 4.93 (dd, J = 11.0, 1.9 Hz, 1H), 4.64 (dd, J = 14.2, 3.9 Hz, 1H), 4.57 (dd, J = 14.1, 7.4 Hz, 1H), 4.41 (t, J = 8.0 Hz, 3H), 4.35 (d, J = 2.7 Hz, 1H), 4.08 (s, 1H), 3.83 (q, J = 6.8 Hz, 1H), 3.79-3.58 (m, 2H), 3.37 (s, 1H), 3.25 (dd, J = 10.1, 7.5 Hz, 1H), 3.00 (d, J = 7.9 Hz, 1H), 2.80-2.74 (m, 1H), 2.72 (s, 3H), 2.62-2.54 (m, 1H), 2.29 (s, 6H), 2.06-1.90 (m, 4H), 1.90-1.56 (m, 8H), 1.53 (s, 9H), 1.42 (s, 3H), 1.35 (d, J = 7.0 Hz, 3H), 1.33 (d, J = 8.0 Hz, 3H), 1.20 (s, 3H), 1.16-1.10 (m, 1H), 0.97 (d, J = 5.8 Hz, 3H), 0.93 (d, J = 6.8 Hz, 3H), 0.87 (t, J = 7.4 Hz, 3H). | HRMS (ESI): Calcd for ($C_{55}H_{81}N_{11}O_{11}$ + H)⁺: 1072.6190; Found: 1072.6185. |
|  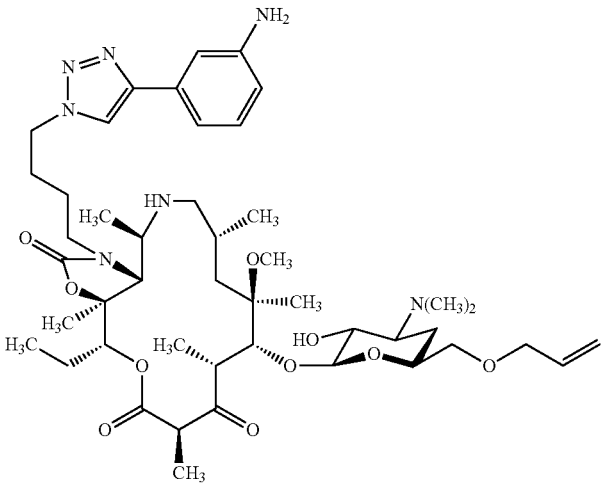 FSM-120383 | | |

TABLE E1-continued
Exemplary macrolides
| Compound and ID | ¹H NMR Data | MS Data |
|---|---|---|
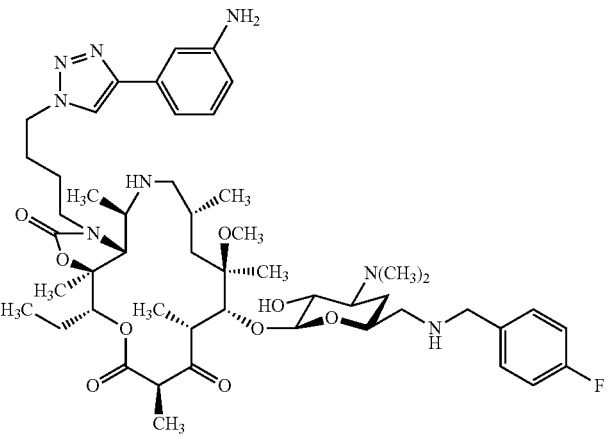
FSM-120391
TABLE E1-N
Exemplary macrolides with C3 modified sugars
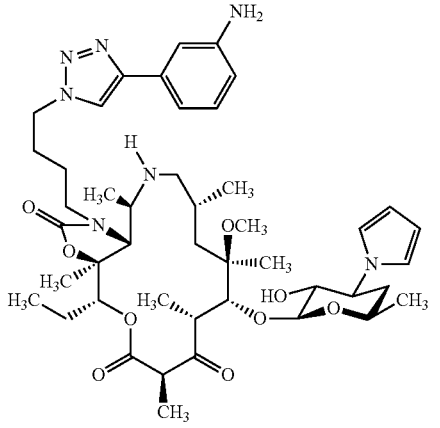
FSM-120362
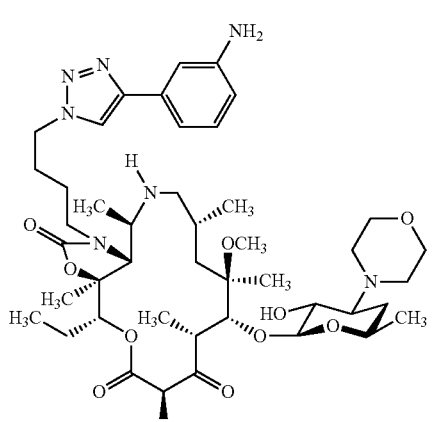
FSM-120367
TABLE E1-N-continued
Exemplary macrolides with C3 modified sugars
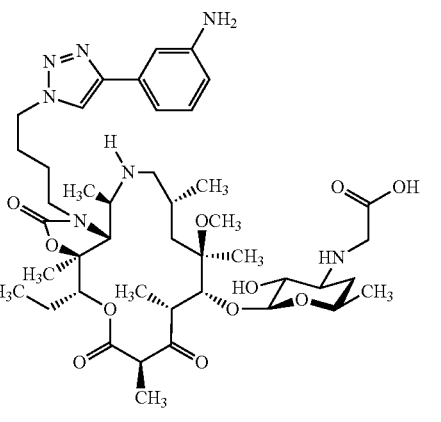
FSM-120368
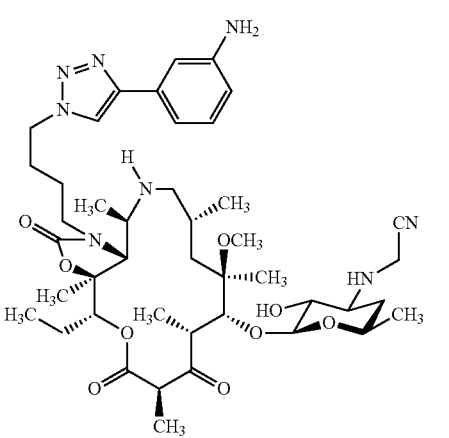
FSM-120369

TABLE E1-N-continued
Exemplary macrolides with C3 modified sugars
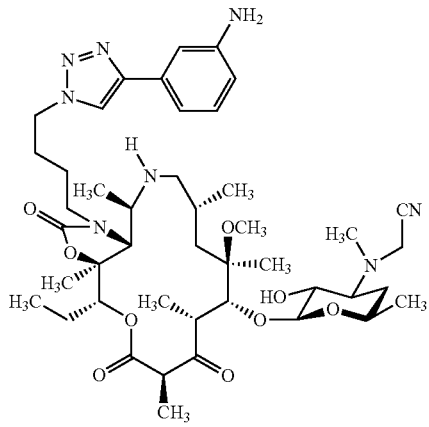
FSM-120371
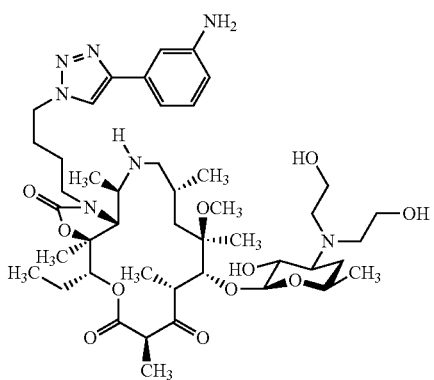
FSM-120379
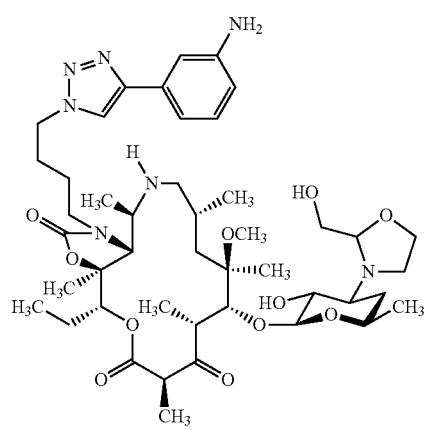
FSM-120380
TABLE E1-N-continued
Exemplary macrolides with C3 modified sugars
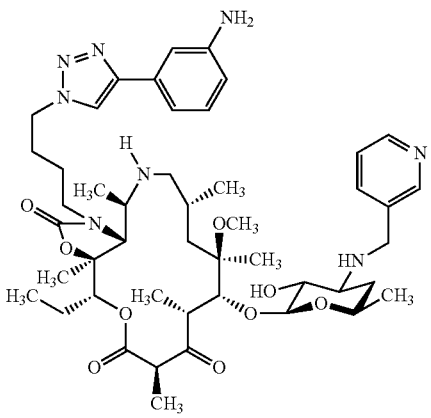
FSM-120384
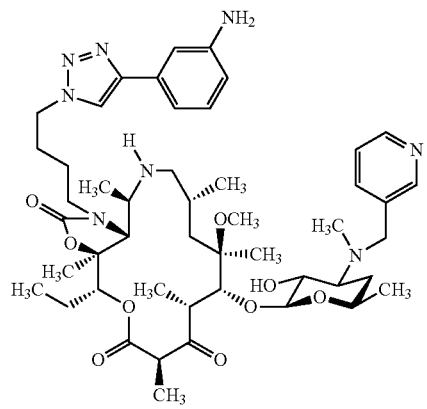
FSM-120385
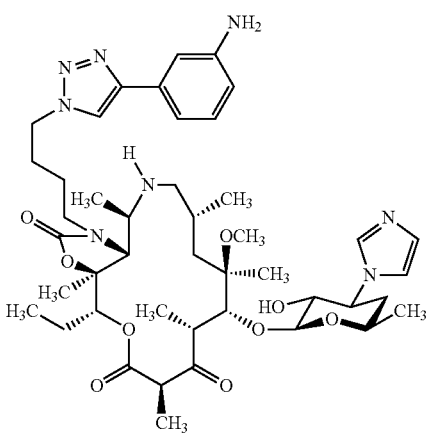
FSM-120394

TABLE E1-N-continued
Exemplary macrolides with C3 modified sugars
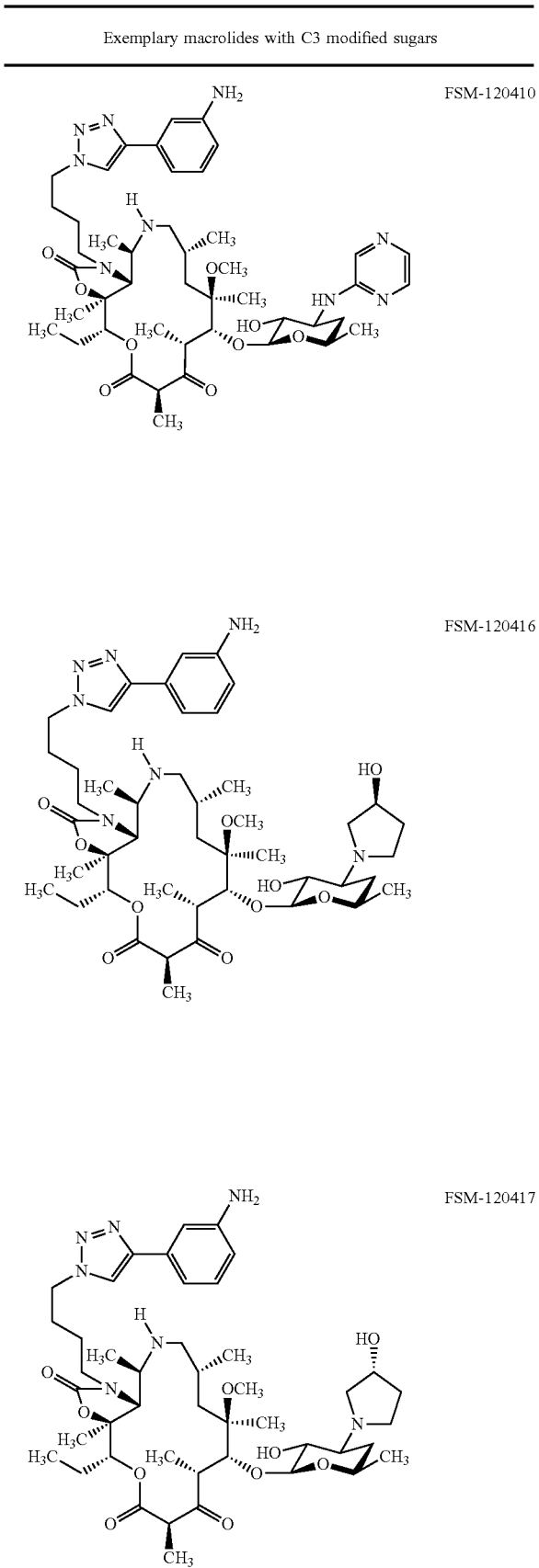
FSM-120410
FSM-120416
FSM-120417
TABLE E1-N-continued
Exemplary macrolides with C3 modified sugars
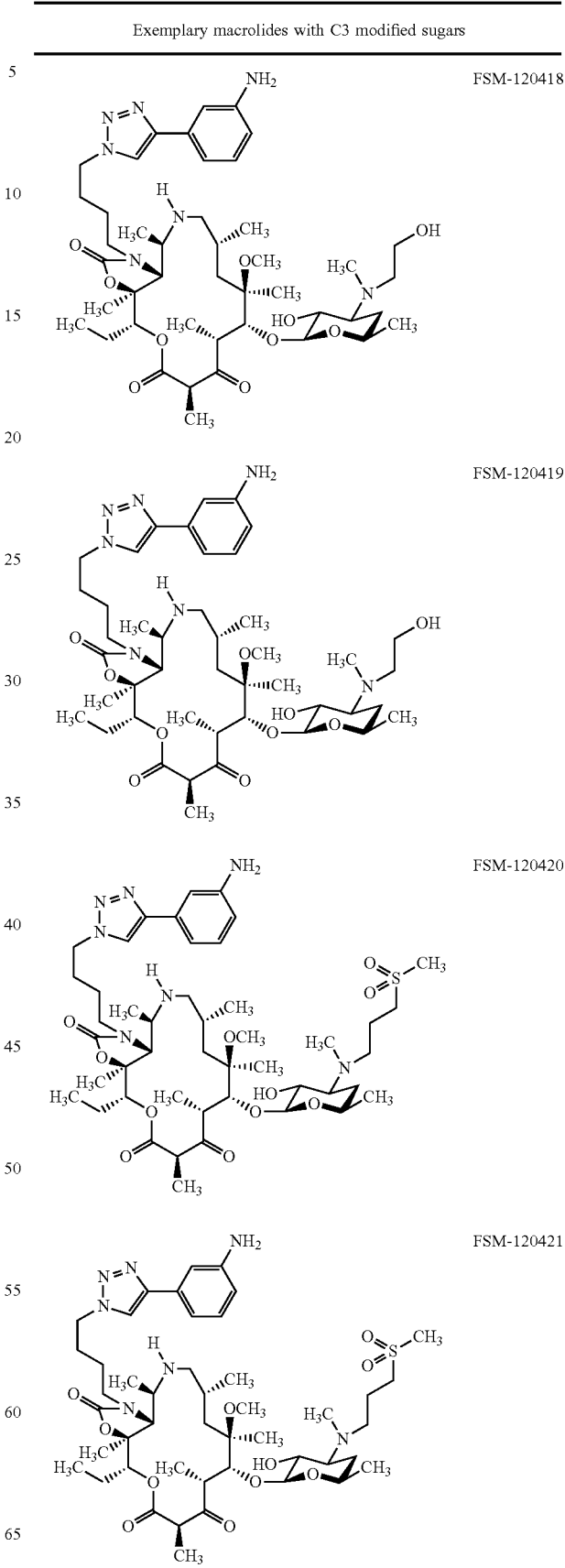
FSM-120418
FSM-120419
FSM-120420
FSM-120421

TABLE E1-N-continued

Exemplary macrolides with C3 modified sugars

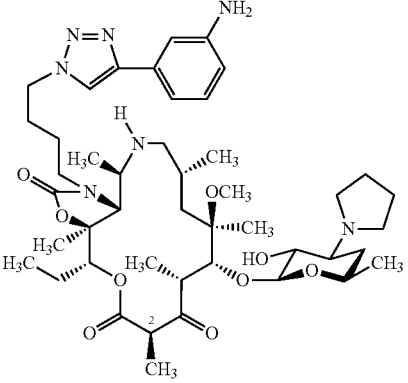

FSM-120361

Biological Assays

Minimum inhibitory concentrations (MICs) for macrolides described herein have been determined for unique strains of *S. aureus, S. pneumoniae, S. pyogenes, E. faecilis, E. coli, A. baumannii, K. pneumoniae, P. aeruginosa*, and *H. influenzae*, including several multidrug-resistant strains, with a special focus on macrolide resistant mechanisms. Azithromycin and solithromycin were included as control compounds. CLSI standard procedures for broth dilution MIC determination were used. Data for exemplary compounds described herein is shown in Tables M1-M7 and in Tables N1-N4.

TABLE M1

MIC (µg/mL) of macrolides against *S. aureus* strains.

| Entry | Macrolides | *S. aureus* ATCC29213 | *S. aureus* MRSA: USA300 | *S. aureus* MRSA: USA100 | *S. aureus* erm A genotype | *S. aureus* USA600, GISA |
|---|---|---|---|---|---|---|
|  | Azithromycin | 1 | 32 | >32 | >32 | >32 |
|  | Solithromycin | 0.125 | 1 | >32 | >32 | >32 |
| 1 | FSM-21700 | 8 | >32 | >32 | 32 | >32 |
| 2 | FSM-21795 | 16 | >32 | >32 | >32 | >32 |
| 3 | FSM-21797 | >32 | >32 | >32 | >32 | >32 |
| 4 | FSM-21798 | >32 | >32 | >32 | >32 | >32 |
| 5 | FSM-21842 | 4 | >32 | >32 | >32 | >32 |
| 6 | FSM-21843 | >32 | >32 | >32 | >32 | >32 |
| 7 | FSM-21861 | >32 | >32 | >32 | >32 | >32 |
| 8 | FSM-21876 | 16 | >32 | >32 | >32 | >32 |
| 9 | FSM-21877 | >32 | >32 | >32 | >32 | >32 |
| 10 | FSM-21878 | 32 | >32 | >32 | >32 | >32 |
| 11 | FSM-21879 | 32 | >32 | >32 | >32 | >32 |
| 12 | FSM-21880 | 32 | >32 | >32 | >32 | >32 |
| 13 | FSM-21881 | 8 | >32 | >32 | >32 | >32 |
| 14 | FSM-21887 | 8 | >32 | >32 | >32 | >32 |
| 15 | FSM-21888 | 32 | >32 | >32 | >32 | >32 |
| 16 | FSM-22003 | 8 | >32 | >32 | >32 | >32 |
| 17 | FSM-22111 | 2 | >32 | >32 | >32 | >32 |
| 18 | FSM-22124 | 4 | >32 | >32 | >32 | >32 |
| 19 | FSM-22125 | 4 | >32 | >32 | >32 | >32 |
| 20 | FSM-22366 | 32 | >32 | >32 | >32 | >32 |
| 21 | FSM-22372 | >32 | >32 | >32 | >32 | >32 |
| 22 | FSM-22373 | >32 | >32 | >32 | >32 | >32 |

TABLE M2

MIC (µg/mL) of macrolides against *S. pneumoniae* strains.

| Entry | Macrolides | *S. pneumoniae* ATCC49619 | *S. pneumoniae* mef A genotype | *S. pneumoniae* mef A genotype | *S. pneumoniae* erm B + tet(M, O) genotype | *S. pneumoniae* erm B + mef A genotype |
|---|---|---|---|---|---|---|
|  | Azithromycin | <0.03125 | 0.25 | 4 | <0.03125 | >32 |
|  | Solithromycin | <0.03125 | <0.03125 | 0.125 | <0.03125 | 0.25 |
| 1 | FSM-21700 | ≤0.03125 | 0.5 | 2 | 0.0625 | 16 |
| 2 | FSM-21795 | 0.25 | 4 | 16 | 0.0625 | >32 |
| 3 | FSM-21797 | 32 | >32 | >32 | 16 | >32 |
| 4 | FSM-21798 | >32 | >32 | >32 | >32 | >32 |
| 5 | FSM-21842 | ≤0.03125 | 0.125 | 1 | ≤0.03125 | 8 |
| 6 | FSM-21843 | 0.5 | 4 | 8 | 0.25 | 32 |
| 7 | FSM-21861 | 0.5 | 4 | 8 | 0.25 | 32 |
| 8 | FSM-21876 | 0.125 | 4 | 16 | 0.0313 | 8 |
| 9 | FSM-21877 | 1 | 8 | 16 | 0.5 | 32 |
| 10 | FSM-21878 | <0.0313 | 0.5 | 8 | <0.0313 | 4 |

TABLE M2-continued

MIC (μg/mL) of macrolides against *S. pneumoniae* strains.

| Entry | Macrolides | *S. pneumoniae* ATCC49619 | *S. pneumoniae* mef A genotype | *S. pneumoniae* mef A genotype | *S. pneumoniae* erm B + tet(M, O) genotype | *S. pneumoniae* erm B + mef A genotype |
|---|---|---|---|---|---|---|
| 11 | FSM-21879 | <0.0313 | 0.25 | 4 | <0.0313 | 1 |
| 12 | FSM-21880 | <0.0313 | 0.0625 | 2 | <0.0313 | 1 |
| 13 | FSM-21881 | ≤0.03125 | 0.5 | 2 | ≤0.03125 | 4 |
| 14 | FSM-21887 | ≤0.03125 | 0.0625 | 0.5 | ≤0.03125 | 1 |
| 15 | FSM-21888 | <0.0313 | 0.25 | 2 | <0.0313 | 2 |
| 16 | FSM-22003 | ≤0.03125 | 0.0625 | 0.5 | ≤0.03125 | 32 |
| 17 | FSM-22111 | ≤0.03125 | ≤0.03125 | 0.125 | ≤0.03125 | 2 |
| 18 | FSM-22124 | ≤0.03125 | ≤0.03125 | 0.5 | ≤0.03125 | 0.5 |
| 19 | FSM-22125 | ≤0.03125 | 0.5 | 4 | ≤0.03125 | >32 |
| 20 | FSM-22366 | <0.03125 | 0.5 | 4 | <0.03125 | >32 |
| 21 | FSM-22372 | <0.03125 | 4 | 8 | <0.03125 | >32 |
| 22 | FSM-22373 | <0.03125 | 4 | 8 | <0.03125 | 32 |

TABLE M3

MIC (μg/mL) of macrolides against *S. pyogenes* and *E. faecalis* strains.

| Entry | Macrolides | *S. pyogenes* ATCC 19615 | *S. pyogenes* macrolide-resistant | *E. faecalis* ATCC29212 | *E. faecalis* Vancomycin-resistant |
|---|---|---|---|---|---|
|  | Azithromycin | <0.03125 | 2 | 4 | >32 |
|  | Solithromycin | <0.03125 | 0.0625 | <0.03125 | 32 |
| 1 | FSM-21700 | 0.0625 | 2 | 8 | >32 |
| 2 | FSM-21795 | 0.0625 | 2 | 1 | >32 |
| 3 | FSM-21797 | 8 | 32 | 32 | >32 |
| 4 | FSM-21798 | 8 | 32 | 32 | >32 |
| 5 | FSM-21842 | ≤0.03125 | 0.5 | 1 | >32 |
| 6 | FSM-21843 | 2 | 8 | >32 | >32 |
| 7 | FSM-21861 | 0.5 | 8 | 4 | >32 |
| 8 | FSM-21876 | 0.0625 | 2 | 2 | >32 |
| 9 | FSM-21877 | 0.5 | 16 | 8 | >32 |
| 10 | FSM-21878 | <0.0313 | 4 | 16 | >32 |
| 11 | FSM-21879 | <0.0313 | 2 | 16 | >32 |
| 12 | FSM-21880 | <0.0313 | 1 | 4 | >32 |
| 13 | FSM-21881 | ≤0.03125 | 2 | 2 | >32 |
| 14 | FSM-21887 | ≤0.03125 | 1 | 0.5 | >32 |
| 15 | FSM-21888 | <0.0313 | 1 | 4 | >32 |
| 16 | FSM-22003 | ≤0.03125 | 2 | 4 | >32 |
| 17 | FSM-22111 | ≤0.03125 | 1 | 0.25 | >32 |
| 18 | FSM-22124 | ≤0.03125 | 2 | 0.25 | >32 |
| 19 | FSM-22125 | ≤0.03125 | 4 | 0.5 | >32 |
| 20 | FSM-22366 | <0.03125 | 1 | 2 | >32 |
| 21 | FSM-22372 | <0.03125 | 8 | 16 | >32 |
| 22 | FSM-22373 | 8 | >32 | 32 | >32 |

TABLE M4

MIC (μg/mL) of macrolides against *E. coli* strains.

| Entry | Macrolides | *E. coli* ATCC25922 | *E. coli* NDM-1 | *E. coli* TEM-1 | *E. coli* CTX-M-14 |
|---|---|---|---|---|---|
|  | Azithromycin | 4 | >32 | 1 | >32 |
|  | Solithromycin | 32 | >32 | 32 | >32 |
| 1 | FSM-21700 | 32 | 16 | 8 | >32 |
| 2 | FSM-21795 | 16 | >32 | nt | nt |
| 3 | FSM-21797 | >32 | >32 | nt | nt |
| 4 | FSM-21798 | >32 | >32 | nt | nt |
| 5 | FSM-21842 | 16 | 32 | 16 | >32 |
| 6 | FSM-21843 | >32 | >32 | nt | nt |
| 7 | FSM-21861 | >32 | >32 | nt | nt |
| 8 | FSM-21876 | 32 | >32 | nt | nt |
| 9 | FSM-21877 | >32 | 32 | nt | nt |
| 10 | FSM-21878 | >32 | >32 | nt | nt |
| 11 | FSM-21879 | 32 | 32 | nt | nt |
| 12 | FSM-21880 | 16 | 32 | nt | nt |
| 13 | FSM-21881 | 16 | >32 | 32 | >32 |
| 14 | FSM-21887 | 16 | 32 | 16 | >32 |
| 15 | FSM-21888 | 32 | >32 | nt | nt |
| 16 | FSM-22003 | >32 | >32 | 32 | >32 |
| 17 | FSM-22111 | 16 | 32 | 16 | >32 |
| 18 | FSM-22124 | 16 | >32 | 16 | >32 |
| 19 | FSM-22125 | 32 | >32 | 16 | >32 |
| 20 | FSM-22366 | >32 | >32 | 16 | >32 |
| 21 | FSM-22372 | >32 | >32 | >32 | >32 |
| 22 | FSM-22373 | >32 | >32 | >32 | >32 |

TABLE M5

MIC (μg/mL) of macrolides against *A. baumannii* strains.

| Entry | Macrolides | *A. baumannii* ATCC19606 | *A. baumannii* imipenem-resistant | *A. baumannii* chromosomal class C | *A. baumannii* IMP-4 |
|---|---|---|---|---|---|
|  | Azithromycin | 16 | 8 | 32 | >32 |
|  | Solithromycin | 8 | 4 | 8 | >32 |
| 1 | FSM-21700 | >32 | >32 | >32 | >32 |
| 2 | FSM-21795 | 32 | 32 | nt | nt |
| 3 | FSM-21797 | >32 | >32 | nt | nt |
| 4 | FSM-21798 | >32 | >32 | nt | nt |
| 5 | FSM-21842 | 32 | >32 | >32 | >32 |
| 6 | FSM-21843 | >32 | >32 | nt | nt |
| 7 | FSM-21861 | >32 | >32 | nt | nt |
| 8 | FSM-21876 | >32 | 32 | nt | nt |
| 9 | FSM-21877 | >32 | >32 | nt | nt |
| 10 | FSM-21878 | >32 | >32 | nt | nt |
| 11 | FSM-21879 | >32 | >32 | nt | nt |
| 12 | FSM-21880 | >32 | 32 | nt | nt |
| 13 | FSM-21881 | >32 | >32 | >32 | >32 |
| 14 | FSM-21887 | 32 | 32 | 32 | >32 |
| 15 | FSM-21888 | >32 | >32 | nt | nt |
| 16 | FSM-22003 | >32 | >32 | >32 | >32 |
| 17 | FSM-22111 | 16 | 16 | 16 | >32 |
| 18 | FSM-22124 | 16 | 16 | 16 | >32 |
| 19 | FSM-22125 | >32 | >32 | 32 | >32 |
| 20 | FSM-22366 | >32 | 32 | >32 | >32 |
| 21 | FSM-22372 | >32 | >32 | >32 | >32 |
| 22 | FSM-22373 | >32 | >32 | >32 | >32 |

TABLE M6

MIC (μg/mL) of macrolides against *K. pneumoniae* strains.

| Entry | Macrolides | *K. pneumoniae* ATCC10031 | *K. pneumoniae* KPC-2 | *K. pneumoniae* TEM-10 | *K. pneumoniae* SHV-12 |
|---|---|---|---|---|---|
|  | Azithromycin | 4 | >32 | 8 | 16 |
|  | Solithromycin | 8 | >32 | >32 | >32 |
| 1 | FSM-21700 | 4 | >32 | 32 | >32 |
| 2 | FSM-21795 | 8 | >32 | nt | nt |
| 3 | FSM-21797 | >32 | >32 | nt | nt |
| 4 | FSM-21798 | >32 | >32 | nt | nt |
| 5 | FSM-21842 | 4 | >32 | 32 | >32 |
| 6 | FSM-21843 | 32 | >32 | nt | nt |
| 7 | FSM-21861 | 16 | >32 | nt | nt |
| 8 | FSM-21876 | 16 | 32 | nt | nt |
| 9 | FSM-21877 | 16 | 32 | nt | nt |
| 10 | FSM-21878 | 16 | >32 | nt | nt |
| 11 | FSM-21879 | 8 | >32 | nt | nt |
| 12 | FSM-21880 | 8 | >32 | nt | nt |
| 13 | FSM-21881 | 8 | >32 | 32 | >32 |
| 14 | FSM-21887 | 8 | >32 | 16 | >32 |
| 15 | FSM-21888 | 8 | >32 | nt | nt |
| 16 | FSM-22003 | 8 | >32 | >32 | >32 |
| 17 | FSM-22111 | 8 | 32 | 8 | >32 |
| 18 | FSM-22124 | 4 | 32 | 8 | >32 |
| 19 | FSM-22125 | 32 | >32 | 32 | >32 |
| 20 | FSM-22366 | 16 | >32 | 32 | >32 |
| 21 | FSM-22372 | >32 | >32 | >32 | >32 |
| 22 | FSM-22373 | >32 | >32 | 32 | >32 |

TABLE M7

MIC (μg/mL) of macrolides against *P. aeruginosa* and *H. influenzae* strains.

| Entry | Macrolides | *P. aeruginosa* ATCC27853 | *P. aeruginosa* HPA101-1477 | *H. influenzae* ATCC49247 | *H. influenzae* erythro >4, azithro 1 |
|---|---|---|---|---|---|
|  | Azithromycin | >32 | >32 | 0.5 | 0.125 |
|  | Solithromycin | >32 | >32 | 4 | 2 |
| 1 | FSM-21700 | >32 | >32 | 32 | 16 |
| 2 | FSM-21795 | 32 | nt | 4 | 8 |

TABLE M7-continued

MIC (μg/mL) of macrolides against *P. aeruginosa* and *H. influenzae* strains.

| Entry | Macrolides | P. aeruginosa ATCC27853 | P. aeruginosa HPA101-1477 | H. influenzae ATCC49247 | H. influenzae erythro >4, azithro 1 |
|---|---|---|---|---|---|
| 3 | FSM-21797 | >32 | nt | >32 | >32 |
| 4 | FSM-21798 | >32 | nt | >32 | >32 |
| 5 | FSM-21842 | >32 | >32 | 4 | 4 |
| 6 | FSM-21843 | >32 | nt | 32 | 32 |
| 7 | FSM-21861 | >32 | nt | 32 | 32 |
| 8 | FSM-21876 | >32 | nt | 4 | 16 |
| 9 | FSM-21877 | >32 | nt | 32 | 32 |
| 10 | FSM-21878 | >32 | nt | >32 | 32 |
| 11 | FSM-21879 | >32 | nt | 16 | 8 |
| 12 | FSM-21880 | >32 | nt | 4 | 4 |
| 13 | FSM-21881 | >32 | >32 | 8 | 2 |
| 14 | FSM-21887 | >32 | >32 | 2 | 2 |
| 15 | FSM-21888 | >32 | nt | 8 | 8 |
| 16 | FSM-22003 | >32 | >32 | 8 | 4 |
| 17 | FSM-22111 | >32 | >32 | 2 | 1 |
| 18 | FSM-22124 | >32 | >32 | 2 | 1 |
| 19 | FSM-22125 | >32 | >32 | 4 | 2 |
| 20 | FSM-22366 | >32 | >32 | 4 | 4 |
| 21 | FSM-22372 | >32 | >32 | 16 | 16 |
| 22 | FSM-22373 | >32 | >32 | >32 | 16 |

TABLE N1

MIC (μg/mL) of Macrolides

| Species | Genotype | Strata No. | FSM-120361 | FSM-120362 | FSM-120367 | FSM-120368 | FSM-120369 |
|---|---|---|---|---|---|---|---|
| S. aureus | ATCC29213 | MP-12 | 32 | >64 | >64 | >64 | 32 |
| S. aureus (MRSA) | USA300 | MP-549 | 32 | >64 | >64 | >64 | 32 |
| S. aureus (MRSA) | USA100 | MP-618 UNT-096 | >64 | >64 | >64 | >64 | >64 |
| S. aureus (MRSA) | ermA phenotype | MP-620 UNT-146 | >64 | >32 | >64 | >64 | >64 |
| S. aureus (MRSA) | GISA USA600 | MP-619 UNT-120 | >64 | >32 | >64 | >64 | >64 |
| S. pneumoniae | ATCC49619 | MP-21 | 0.25 | 8 | 32 | 16 | 0.5 |
| S. pneumoniae | mefA | MP-626 UNT-038 | 0.125 | 4 | 16 | 16 | 0.25 |
| S. pneumoniae | mefA | MP-627 UNT-039 | 0.125 | 8 | 16 | 8 | 0.25 |
| S. pyogenes | ATCC19615 | MP-19 | 0.06 | 2 | 8 | 8 | 0.5 |
| S. pyogenes | mac resistant | MP-625 UNT-014 | 0.5 | 16 | 64 | 32 | 2 |
| E. faecalis | ATCC29212 | MP-24 | 4 | 64 | 64 | >64 | 4 |
| E. faecalis | van resistant | UNT-039 | >64 | >32 | >64 | >64 | >64 |
| A. baumannii | ATCC19606 | MP-15 | 32 | >64 | >64 | >64 | >64 |
| K. pneumoniae | ATCC10031 | MP-14 | 4 | >64 | >64 | >64 | 16 |
| P. aeruginosa | ATCC27853 | MP-3 | >64 | >32 | >64 | >64 | >64 |
| E. coli | ATCC25922 | MP-4 | 32 | >32 | >64 | >64 | >64 |
| E. coli | ATCC25922:tolC | MP-9 | 4 | >64 | >64 | >64 | >64 |
| P. aeruginosa | PAO1 | MP-7 | >64 | >32 | >64 | >64 | >64 |
| P. aeruginosa | PAO1:mex | MP-8 | 16 | >64 | >64 | >64 | >64 |
| S. aureus | ATCCBAA-977 | MP-17 | 32 | >64 | >64 | >64 | 32 |
| S. aureus (MRSA) | ST-228 cErm | MP-513 | >64 | >64 | >64 | >64 | >64 |
| E. coli | clinical | MP541 | 32 | >32 | >64 | >64 | >64 |
| E. coli | clinical - cErm | MP532 | >64 | >32 | >64 | >64 | >64 |
| K. pneumoniae | clinical | MP548 | 64 | >32 | >64 | >64 | >64 |
| K. pneumoniae | clinical | MP546 | >64 | >32 | >64 | >64 | >64 |

TABLE N1-continued

MIC (μg/mL) of Macrolides

| Species | Genotype | Strata No. | FSM-120361 | FSM-120362 | FSM-120367 | FSM-120368 | FSM-120369 |
|---|---|---|---|---|---|---|---|
| A. baumannii | clinical | MP577 | 64 | >32 | >64 | >64 | >64 |
| A. baumannii | clinical | MP576 | >64 | >32 | >64 | >64 | >64 |

TABLE N2

MIC (μg/mL) of Macrolides

| Species | Genotype | Strain No. | FSM-120371 | FSM-120379 | FSM-120380 | FSM-120384 | FSM-120385 |
|---|---|---|---|---|---|---|---|
| S. aureus | ATCC29213 | MP-12 | 32 | >64 | >64 | >64 | 4 |
| S. aureus (MRSA) | USA300 | MP-549 | 64 | >64 | >64 | >64 | 16 |
| S. aureus (MRSA) | USA100 | MP-618 UNT-096 | >64 | >64 | >64 | >64 | >64 |
| S. aureus (MRSA) | ermA phenotype | MP-620 UNT-146 | >64 | >64 | >64 | >64 | >64 |
| S. aureus (MRSA) | GISA USA600 | MP-619 UNT-120 | >64 | >64 | >64 | >64 | >64 |
| S. pneumoniae | ATCC49619 | MP-21 | 0.25 | 2 | 8 | 2 | 0.06 |
| S. pneumoniae | mefA | MP-626 UNT-038 | 0.25 | 1 | 4 | 0.5 | 0.125 |
| S. pneumoniae | mefA | MP-627 UNT-039 | 0.5 | 1 | 4 | 1 | 0.25 |
| S. pyogenes | ATCC19615 | MP-19 | 0.125 | 4 | 8 | 1 | <0.03 |
| S. pyogenes | mac resistant | MP-625 UNT-014 | 1 | 16 | 32 | 4 | 1 |
| E. faecalis | ATCC29212 | MP-24 | 4 | 32 | 64 | 32 | 1 |
| E. faecalis | van resistant | UNT-039 | 64 | >64 | >64 | >64 | >64 |
| A. baumannii | ATCC19606 | MP-15 | 32 | >64 | >64 | 64 | 16 |
| K. pneumoniae | ATCC10031 | MP-14 | 8 | 32 | >64 | 16 | 8 |
| P. aeruginosa | ATCC27853 | MP-3 | >64 | >64 | >64 | >64 | >64 |
| E. coli | ATCC25922 | MP-4 | 64 | >64 | >64 | >64 | 64 |
| E. coli | ATCC25922:tolC | MP-9 | 16 | 32 | 32 | 8 | 4 |
| P. aeruginosa | PAO1 | MP-7 | >64 | >64 | >64 | >64 | >64 |
| P. aeruginosa | PAO1:mex | MP-8 | 32 | >64 | >64 | >64 | 32 |
| S. aureus | ATCCBAA-977 | MP-17 | 32 | >64 | >64 | >64 | 4 |
| S. aureus (MRSA) | ST-228 cErm | MP-513 | >64 | >64 | >64 | >64 | >64 |
| E. coli | clinical | MP541 | 64 | >64 | >64 | >64 | 64 |
| E. coli | clinical - cErm | MP532 | >64 | >64 | >64 | >64 | >64 |
| K. pneumoniae | clinical | MP548 | >64 | >64 | >64 | >64 | >64 |
| K. pneumoniae | clinical | MP546 | >64 | >64 | >64 | >64 | >64 |
| A. baumannii | clinical | MP577 | >64 | >64 | >64 | >64 | 64 |
| A. baumannii | clinical | MP576 | >64 | >64 | >64 | >64 | >64 |

TABLE N3

MIC (μg/mL) of Macrolides

| Species | Genotype | Strain No. | FSM-120394 | FSM-120383 | FSM-120391 |
|---|---|---|---|---|---|
| S. aureus | ATCC29213 | MP-12 | >64 | >64 | 4 |
| S. aureus (MRSA) | USA300 | MP-549 | >64 | >64 | 4 |
| S. aureus (MRSA) | USA100 | MP-618 UNT-096 | >64 | >64 | >64 |
| S. aureus (MRSA) | ermA phenotype | MP-620 UNT-146 | >64 | >64 | >64 |
| S. aureus (MRSA) | GISA USA600 | MP-619 UNT-120 | >64 | >64 | >64 |
| S. pneumoniae | ATCC49619 | MP-21 | 0.5 | 0.5 | <0.03 |
| S. pneumoniae | mefA | MP-626 UNT-038 | 0.5 | 0.5 | 0.06 |
| S. pneumoniae | mefA | MP-627 UNT-039 | 0.25 | 0.5 | 0.125 |
| S. pyogenes | ATCC19615 | MP-19 | 0.5 | 0.25 | <0.03 |
| S. pyogenes | mac resistant | MP-625 UNT-014 | 4 | 1 | 0.5 |
| E. faecalis | ATCC29212 | MP-24 | 4 | 8 | 1 |
| E. faecalis | van resistant | UNT-039 | >64 | >64 | >64 |
| A. baumannii | ATCC19606 | MP-15 | 64 | 32 | 64 |
| K. pneumoniae | ATCC10031 | MP-14 | 16 | 8 | 4 |
| P. aeruginosa | ATCC27853 | MP-3 | >64 | 32 | 64 |
| E. coli | ATCC25922 | MP-4 | >64 | 32 | 4 |
| E. coli | ATCC25922:tolC | MP-9 | 16 | 4 | 0.25 |
| P. aeruginosa | PAO1 | MP-7 | >64 | 64 | >64 |
| P. aeruginosa | PAO1:mex | MP-8 | >64 | 8 | 16 |
| S. aureus | ATCCBAA-977 | MP-17 | >64 | 64 | 4 |
| S. aureus (MRSA) | ST-228 cErm | MP-513 | >64 | >64 | >64 |
| E. coli | clinical | MP541 | >64 | 32 | 8 |
| E. coli | clinical-cErm | MP532 | >64 | >64 | >64 |

TABLE N3-continued

MIC (µg/mL) of Macrolides

| Species | Genotype | Strain No. | FSM-120394 | FSM-120383 | FSM-120391 |
|---|---|---|---|---|---|
| K. pneumoniae | clinical | MP548 | >64 | >64 | 32 |
| K. pneumoniae | clinical | MP546 | >64 | >64 | 64 |
| A. baumannii | clinical | MP577 | >64 | 64 | 16 |
| A. baumannii | clinical | MP576 | >64 | >64 | >64 |

TABLE N4

MIC (µg/mL) of Macrolides

| Species | Description | Strain No. | FSM-120410 | FSM-120416 | FSM-120417 | FSM-120418 | FSM-120419 | FSM-120420 | FSM-120421 |
|---|---|---|---|---|---|---|---|---|---|
| S. aureus | ATCC29213 | MP-12 | >64 | >64 | 32 | 16 | 32 | 32 | >64 |
| S. aureus | BAA 977 iErm | MP-17 | >64 | >64 | 64 | 16 | 32 | 32 | >64 |
| S. aureus | Clinical-cErm | MP-513 | >64 | >64 | >64 | >64 | >64 | >64 | >64 |
| S. aureus | USA300 - msr(a) | MP-549 | >64 | >64 | 64 | 16 | 32 | 64 | >64 |
| E. coli | ATCC25922 | MP-4 | >64 | >64 | 16 | 8 | >64 | 64 | >64 |
| E. coli | tolC | MP-9 | >64 | 8 | 2 | 1 | 4 | 2 | 64 |
| E. coli | Clinical | MP-541 | >64 | >64 | 16 | 8 | >64 | 32 | >64 |
| E. coli | clinical-cErmB | MP-532 | >64 | >64 | >64 | >64 | >64 | >64 | >64 |
| K. pneumoniae | ATCC 10031 | MP-14 | >64 | 32 | 4 | 8 | 16 | 16 | 64 |
| K. pneumoniae | Clinical | MP-548 | >64 | >64 | 64 | 64 | >64 | >64 | >64 |
| K. pneumoniae | Clinical - MDR | MP-546 | >64 | >64 | >64 | >64 | >64 | >64 | >64 |
| P. aeruginosa | ATCC27853 | MP-3 | >64 | >64 | >64 | >64 | >64 | >64 | >64 |
| P. aeruginosa | mex-oprM-deletion | MP-8 | >64 | >64 | 32 | 32 | >64 | 64 | >64 |
| P. aeruginosa | PAO1 | MP-7 | >64 | >64 | >64 | >64 | >64 | >64 | >64 |
| A. baumannii | ATCC 19606 | MP-15 | >64 | >64 | 32 | 16 | >64 | 32 | >64 |
| A. baumannii | Clinical - AZT low | MP-577 | >64 | >64 | 32 | 32 | >64 | 64 | >64 |
| A. baumannii | Clinical - MDR | MP-576 | >64 | >64 | >64 | >64 | >64 | >64 | >64 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I-c):

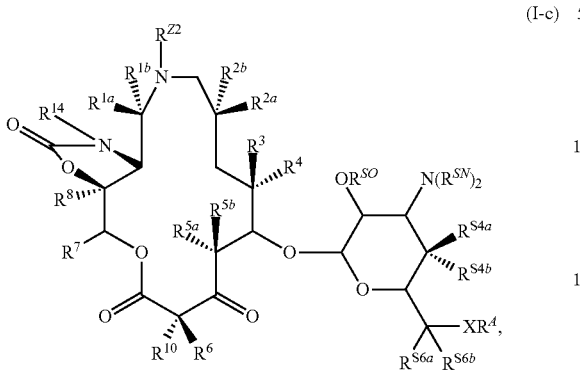

or pharmaceutically acceptable salt thereof, wherein:

X is —$NR^B$— or —O—;

$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, acyl, or a nitrogen protecting group;

$R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)-$L^{S2}$-$R^S$, —C(=$NR^{SN2}$)-$L^{S2}$-$R^S$, —S(=O)-$L^{S2}$-$R^S$, —S(=O)$_2$-$L^{S2}$-$R^S$, a nitrogen protecting group when attached to a nitrogen atom, or an oxygen protecting group when attached to an oxygen atom, and $R^{SN2}$ is independently hydrogen, optionally substituted $C_1$-$C_6$ alkyl, or a nitrogen protecting group;

$R^B$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

or $R^A$ and $R^B$ are taken together to form =$N_2$ or an optionally substituted heterocyclyl or heteroaryl ring;

$L^{S2}$ is a bond, —$NR^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;

each $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ groups attached to the same nitrogen atom are joined to form an optionally substituted heterocyclyl or heteroaryl ring;

each of $R^{S4a}$ and $R^{S4b}$ is independently hydrogen, halogen, optionally substituted $C_1$-$C_6$ alkyl, or —$OR^{SO}$;

each of $R^{S6a}$ and $R^{S6b}$ is independently hydrogen, halogen, or optionally substituted $C_1$-$C_6$ alkyl;

each $R^{SN}$ is independently hydrogen, optionally substituted $C_1$-$C_6$ alkyl, or a nitrogen protecting group, or two $R^{SN}$ groups attached to the same nitrogen atom are joined to form an optionally substituted heterocyclyl or heteroaryl ring;

each $R^{SO}$ is independently hydrogen, optionally substituted $C_1$-$C_6$ alkyl, a carbohydrate, or an oxygen protecting group;

each of $R^{1a}$ and $R^{1b}$ is independently hydrogen, halogen, acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each of $R^{2a}$ and $R^{2b}$ is independently hydrogen, halogen, optionally substituted alkyl, or optionally substituted alkenyl;

each of $R^3$ and $R^4$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or —$OR^{3a}$;

each $R^{3a}$ is independently hydrogen, optionally substituted alkyl, optionally substituted alkenyl, optionally substituted alkynyl, an oxygen protecting group, or of formula:

each $L^{C3}$ is independently a bond, or is a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

each $A^3$ is independently optionally substituted carbocyclyl, optionally substituted heterocyclyl, optionally substituted aryl, or optionally substituted heteroaryl;

each of $R^{5a}$ and $R^{5b}$ is independently hydrogen, halogen, optionally substituted alkyl, optionally substituted carbocyclyl, or optionally substituted heterocyclyl;

$R^6$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

$R^{10}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

$R^7$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

R[8] is hydrogen, halogen, or optionally substituted $C_1$-$C_6$ alkyl;

R[14] is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or of formula:

$$\text{\Large{\}}-L^{C1}-A^1 \quad (L^{C1}\text{-ii})$$

or $$\text{\Large{\}}-L^{C1}-A-L^{C2}-R^{23}; \quad (L^{C1}\text{-iii})$$

$L^{C1}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

$A^1$ is a leaving group (LG), —SH, —OH, —NH$_2$, —NH—NH$_2$, —N$_2$, —N$_3$, —O—NH$_2$, —CCH, —OC(=O)R$^{Z8}$, —C(=O)OR$^{Z8}$, or of formula:

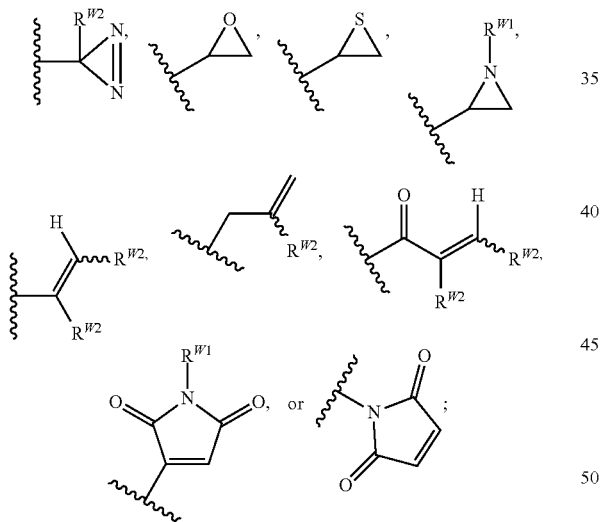

A is —NH—, —NH—NH—, —NH—O—, —O—NH—, —S—, —SS—, —O—, or of formula:

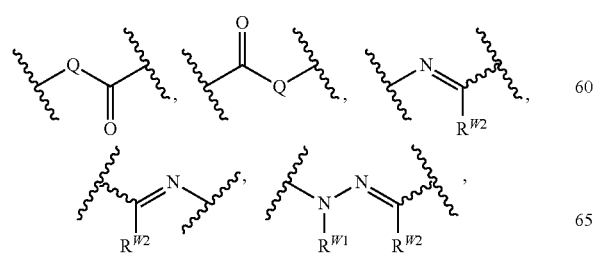

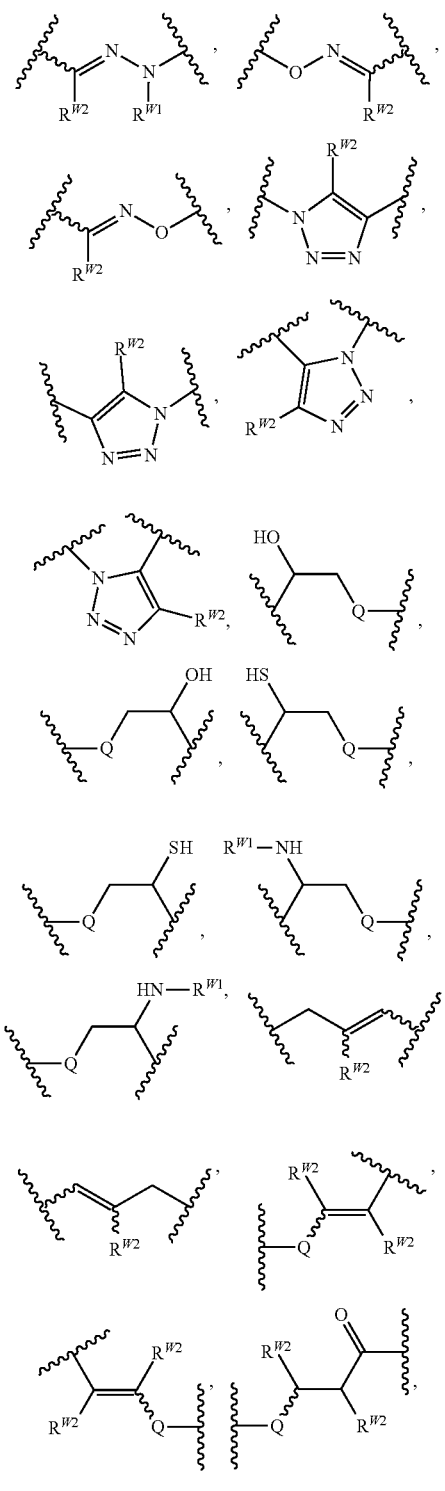

-continued

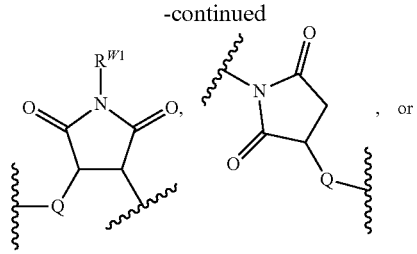

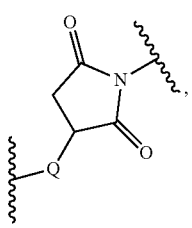

Q is —NH—, —NH—NH—, —O—NH—, —NH—O—, —S—, or —O—;

$L^{C2}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

$R^{W1}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each $R^{W2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two $R^{W2}$ groups are joined to form an optionally substituted cyclic moiety;

$R^{23}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups attached to the same nitrogen atom are joined to form an optionally substituted heterocyclyl or optionally substituted heteroaryl ring.

2. The compound of claim 1, wherein the compound is of formula:

(L$^{C3}$-ii)

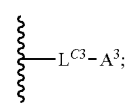

or pharmaceutically acceptable salt thereof, wherein $R^{14a}$ is hydrogen, optionally substituted alkyl, or a nitrogen protecting group.

3. The compound of claim 1, wherein the compound is of formula:

(II-c)

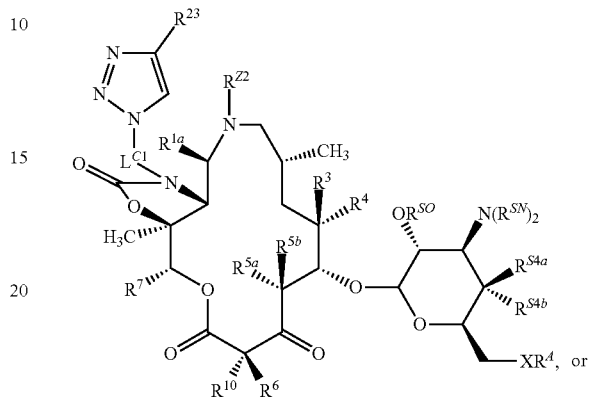

(II-e)

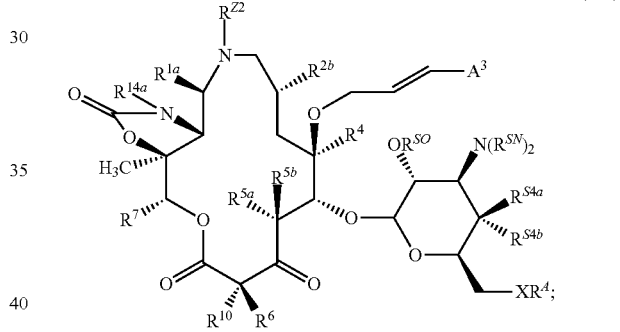

or pharmaceutically acceptable salt thereof, wherein $R^{14a}$ is hydrogen, optionally substituted alkyl, or a nitrogen protecting group.

4. The compound of claim 1, wherein the compound is of formula:

(III-c)

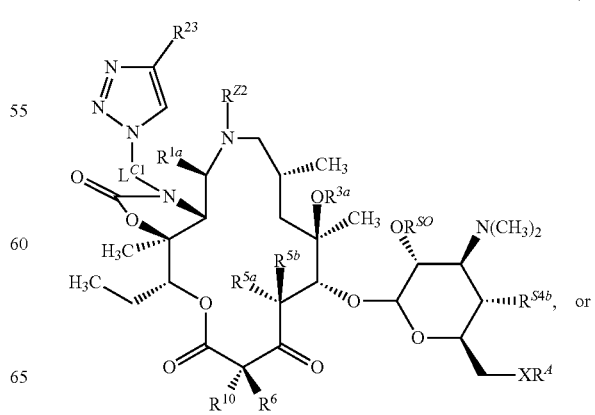

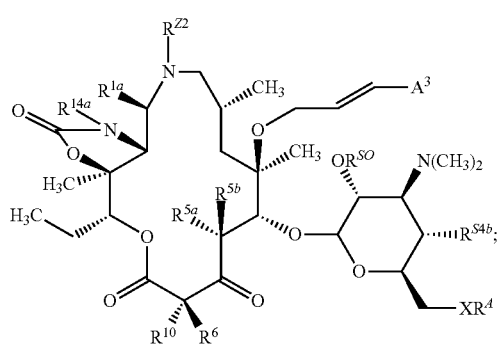

(III-e)

or pharmaceutically acceptable salt thereof, wherein $R^{14a}$ is hydrogen, optionally substituted alkyl, or a nitrogen protecting group.

5. The compound of claim 1, or pharmaceutically acceptable salt thereof, wherein X is —O—.

6. The compound of claim 1, or pharmaceutically acceptable salt thereof, wherein each of $R^{S6a}$ and $R^{S6b}$ is independently hydrogen or methyl.

7. The compound of claim 1, or pharmaceutically acceptable salt thereof, wherein the substituent —N($R^{SN}$)$_2$ is:

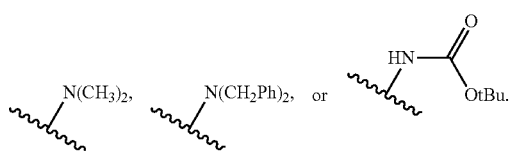

8. The compound of claim 1, or pharmaceutically acceptable salt thereof, wherein $R^{S4a}$ is hydrogen; and $R^{S4b}$ is —$OR^{SO}$.

9. The compound of claim 1, or pharmaceutically acceptable salt thereof, wherein $R^{S4a}$ is hydrogen.

10. The compound of claim 1, or pharmaceutically acceptable salt thereof, wherein $R^{S4b}$ is hydrogen.

11. The compound of claim 1, or pharmaceutically acceptable salt thereof, wherein X is —$NR^B$—.

12. The compound of claim 1, wherein the compound is of formula:

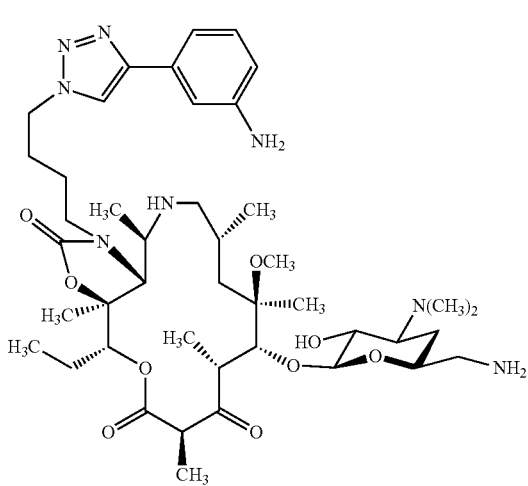

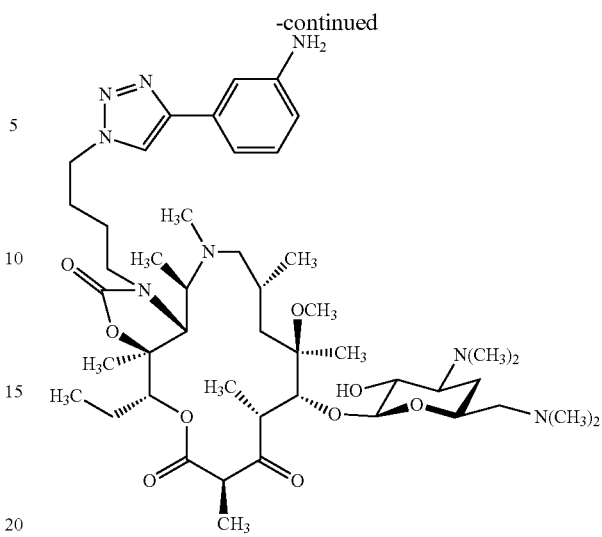

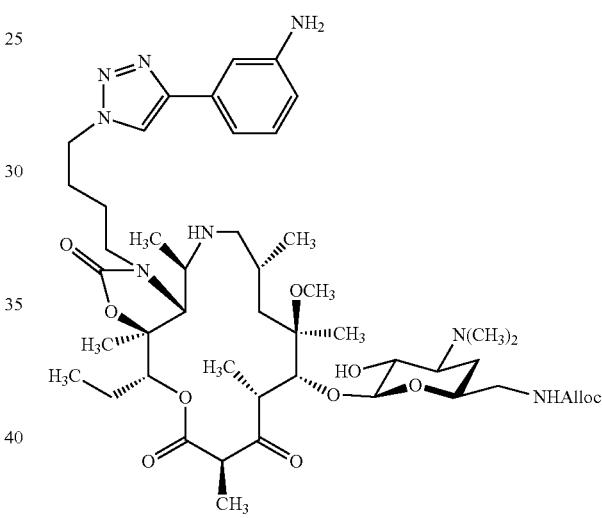

309
-continued
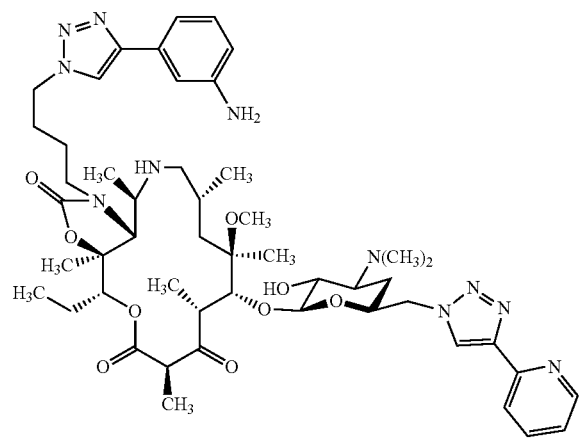
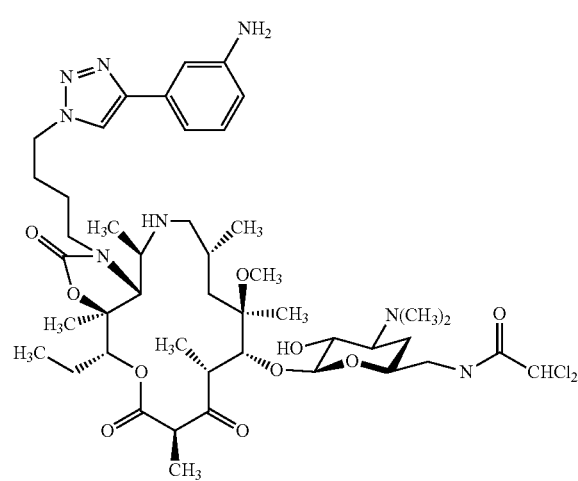
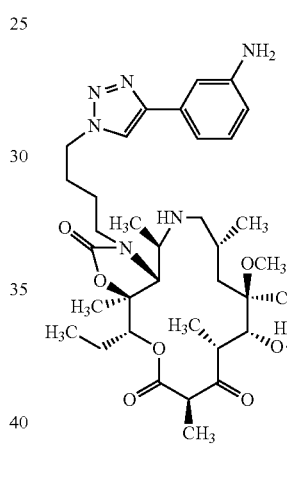
310
-continued
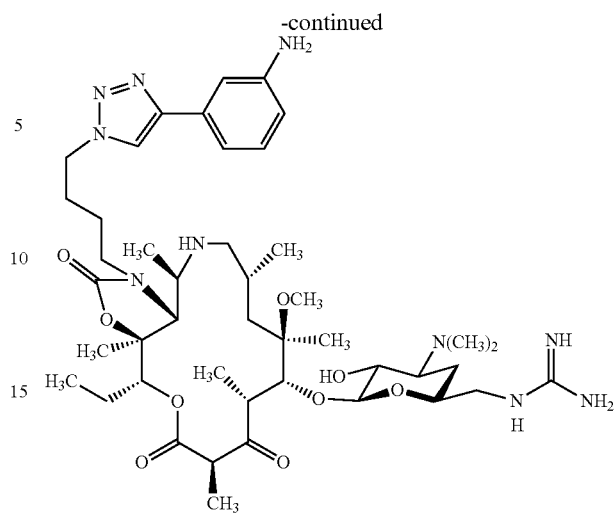
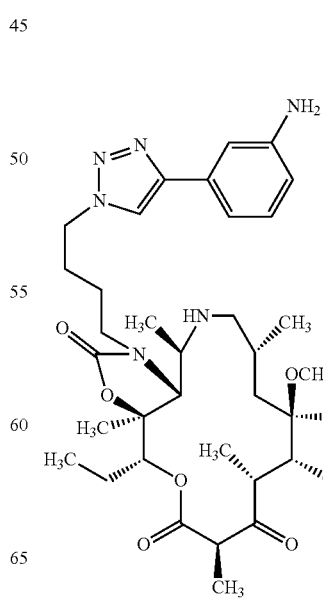

311
-continued
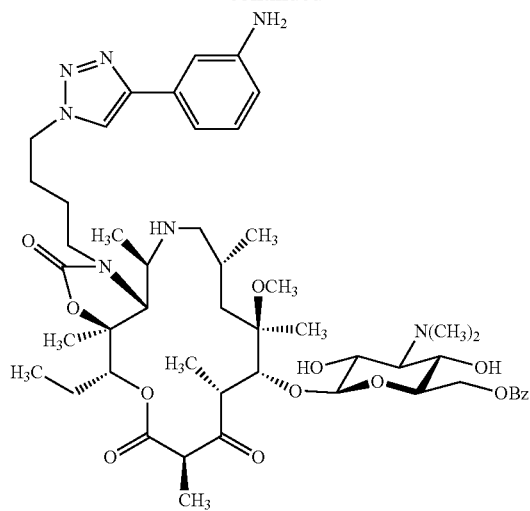
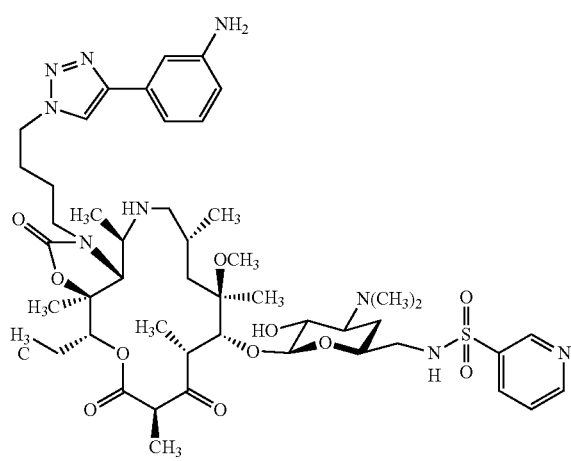
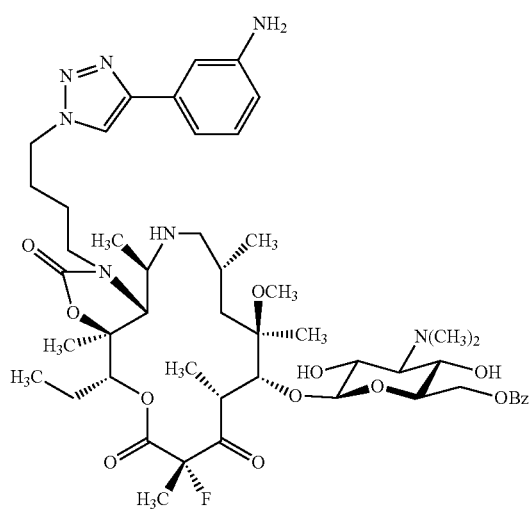
312
-continued
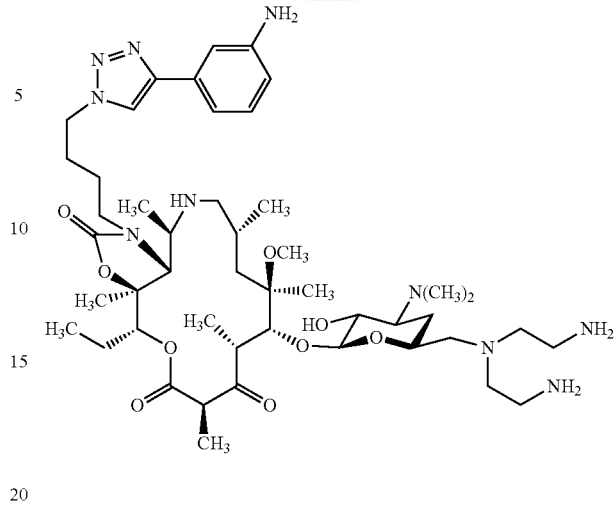
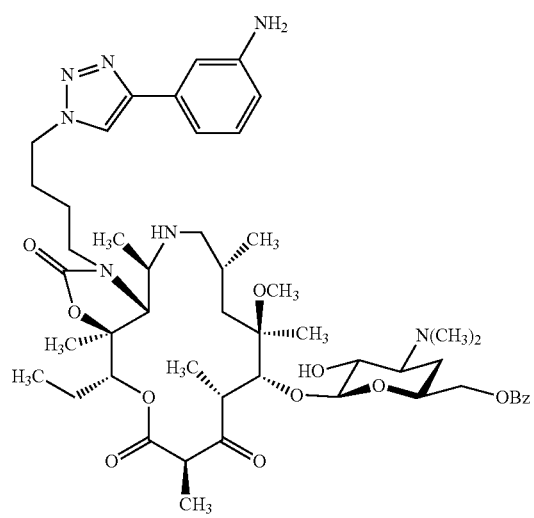
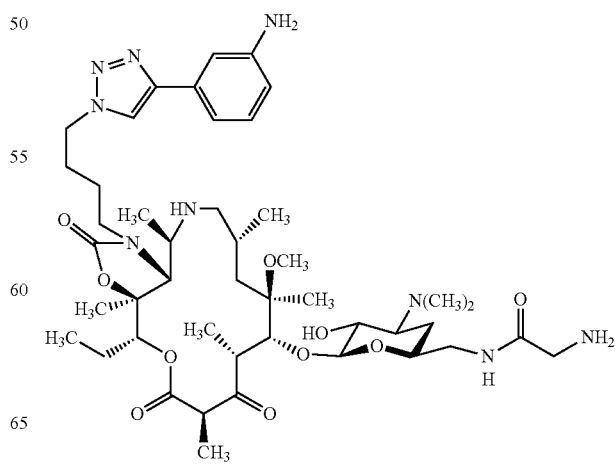

313
-continued
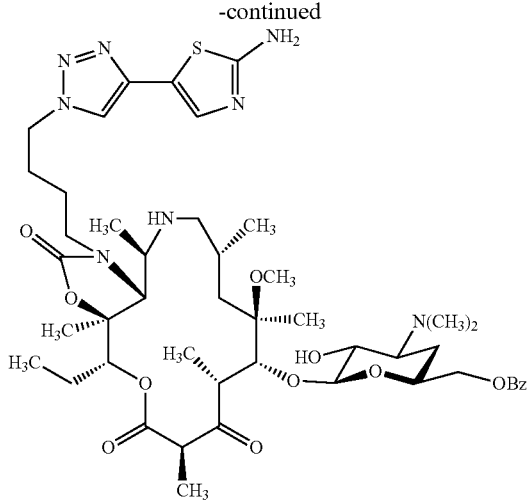
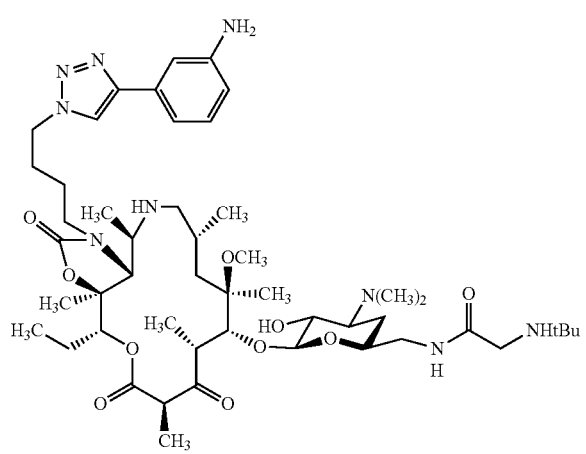
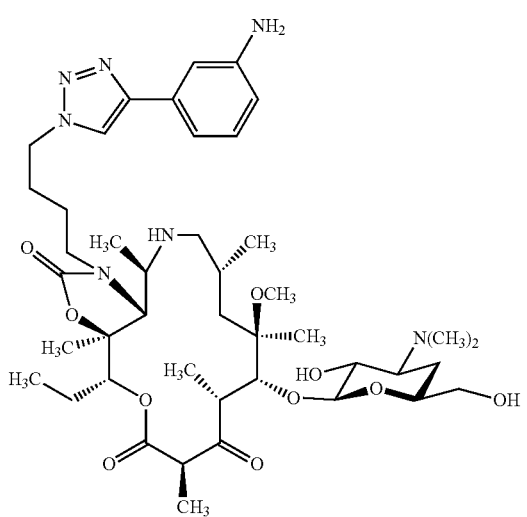
314
-continued
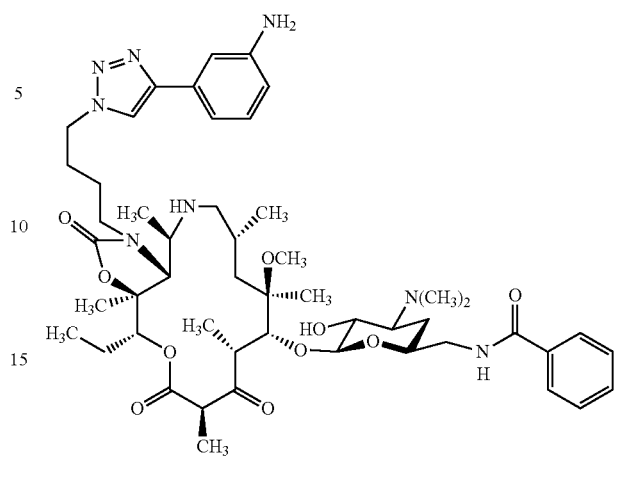
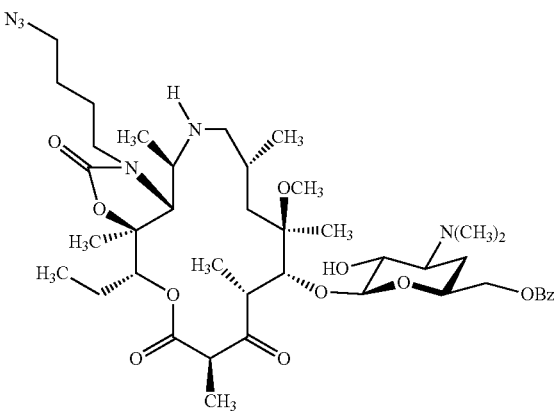
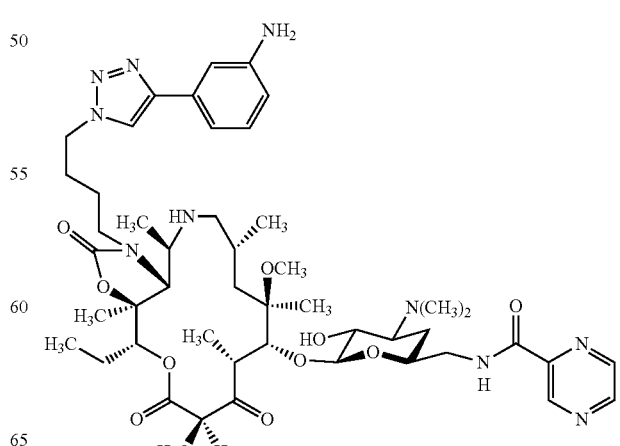

315
-continued
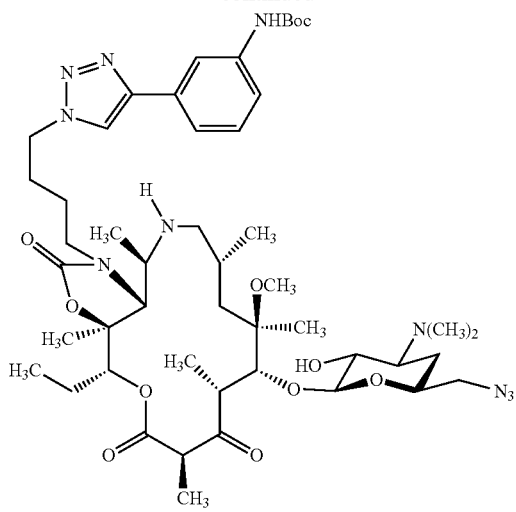
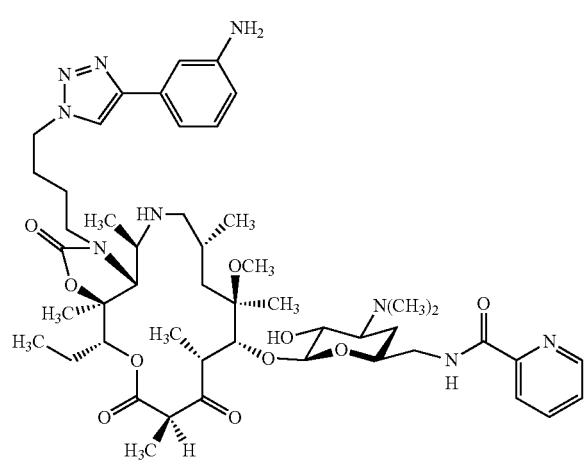
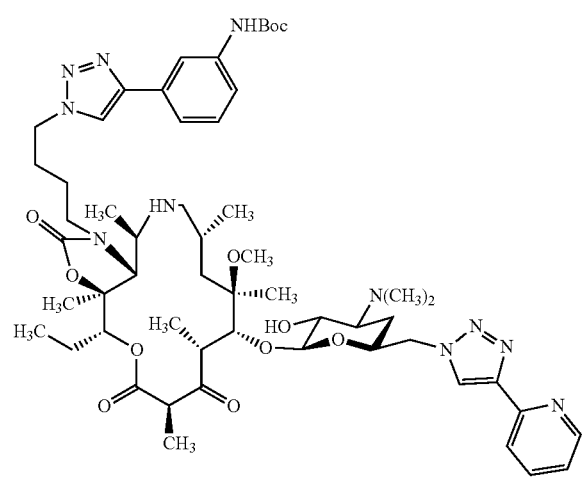
316
-continued
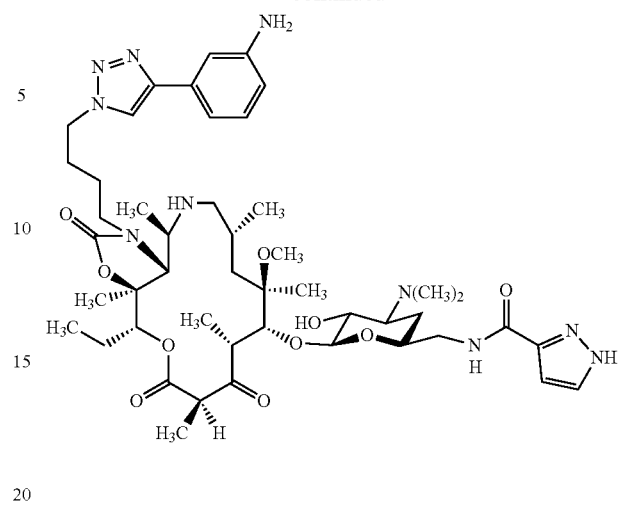
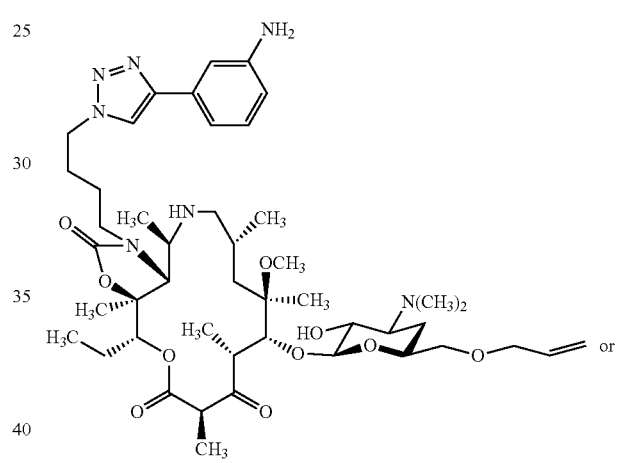
or
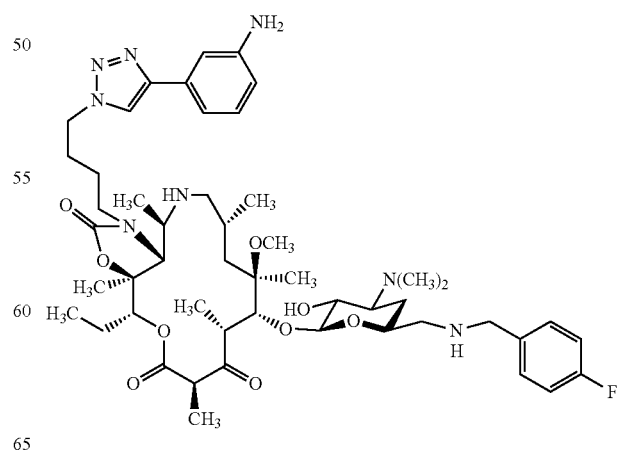
or a pharmaceutically acceptable salt thereof.

13. A compound of Formula (I-c-N):

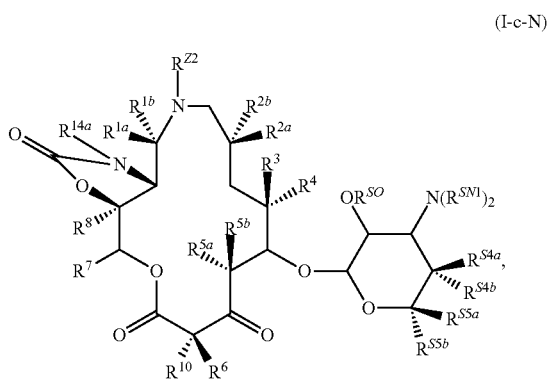

or pharmaceutically acceptable salt thereof, wherein:
$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, acyl, or a nitrogen protecting group;
each instance of $R^{S5a}$ and $R^{S5b}$ is independently hydrogen, halogen, optionally substituted $C_1$-$C_6$ alkyl, —$OR^{SO5}$, or of the formula:

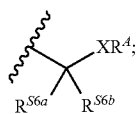

X is —$NR^B$— or —O—;
$R^A$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —C(=O)-$L^{S2}$-$R^S$, —C(=$NR^{SN2}$)-$L^{S2}$-$R^S$, —S(=O)-$L^{S2}$-$R^S$, —S(=O)$_2$-$L^{S2}$-$R^S$, a nitrogen protecting group when attached to a nitrogen atom, or an oxygen protecting group when attached to an oxygen atom, and $R^{SN2}$ is independently hydrogen, optionally substituted $C_1$-$C_6$ alkyl, or a nitrogen protecting group;
$R^B$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;
or $R^A$ and $R^B$ are taken together to form =$N_2$ or an optionally substituted heterocyclyl or heteroaryl ring;
$L^{S2}$ is a bond, —$NR^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;
each $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ groups attached to the same nitrogen atom are joined to form an optionally substituted heterocyclyl or heteroaryl ring;
each of $R^{S4a}$ and $R^{S4b}$ is independently hydrogen, halogen, optionally substituted $C_1$-$C_6$ alkyl, or —$OR^{SO4}$;
each instance of $R^{S6a}$ and $R^{S6b}$ is independently hydrogen, halogen, or optionally substituted $C_1$-$C_6$alkyl;
each $R^{SN1}$ is independently hydrogen, optionally substituted $C_1$-$C_6$ alkyl, optionally substituted carbocyclyl, optionally substituted aryl, optionally substituted heterocyclyl, optionally substituted heteroaryl, optionally substituted acyl, or a nitrogen protecting group, or optionally two $R^{SN1}$ groups are joined to form an optionally substituted heterocyclyl or heteroaryl ring;
each of $R^{SO}$, $R^{SO4}$, and $R^{SO5}$ is independently hydrogen, optionally substituted $C_1$-$C_6$ alkyl, a carbohydrate, or an oxygen protecting group;
each of $R^{1a}$ and $R^{1b}$ is independently hydrogen, halogen, acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;
each of $R^{2a}$ and $R^{2b}$ is independently hydrogen, halogen, optionally substituted alkyl, or optionally substituted alkenyl;
each of $R^3$ and $R^4$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or —$OR^{3a}$;
each $R^{3a}$ is independently hydrogen, optionally substituted alkyl, optionally substituted alkenyl, optionally substituted alkynyl, an oxygen protecting group, or of formula:

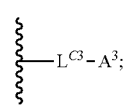

each $L^{C3}$ is independently a bond, or is a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;
each $A^3$ is independently optionally substituted carbocyclyl, optionally substituted heterocyclyl, optionally substituted aryl, or optionally substituted heteroaryl;
each of $R^{5a}$ and $R^{5b}$ is independently hydrogen, halogen, optionally substituted alkyl, optionally substituted carbocyclyl, or optionally substituted heterocyclyl;
$R^6$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

$R^{10}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

$R^{7}$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^{8}$ is hydrogen, halogen, or optionally substituted $C_1$-$C_6$ alkyl;

$R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or of formula:

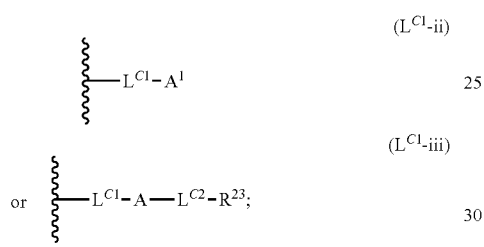

$L^{C1}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

$A^{1}$ is a leaving group (LG), —SH, —OH, —NH$_2$, —NH—NH$_2$, —N$_2$, —N$_3$, —O—NH$_2$, —CCH, —OC(=O)R$^{Z8}$, —C(=O)OR$^{Z8}$, or of formula:

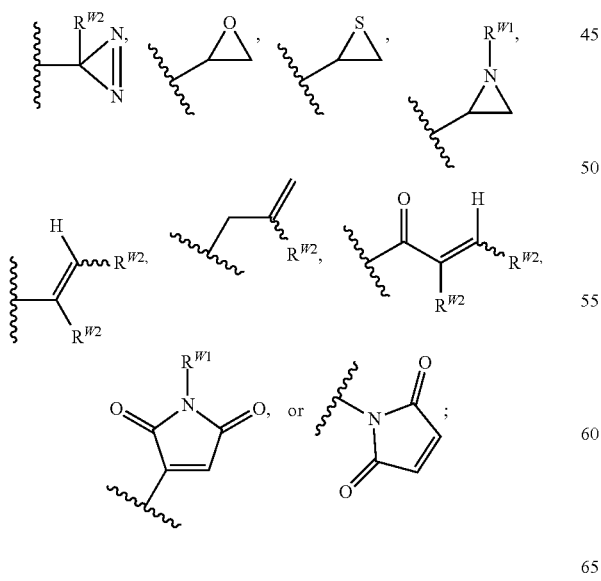

A is —NH—, —NH—NH—, —NH—O—, —O—NH—, —S—, —SS—, —O—, or of formula:

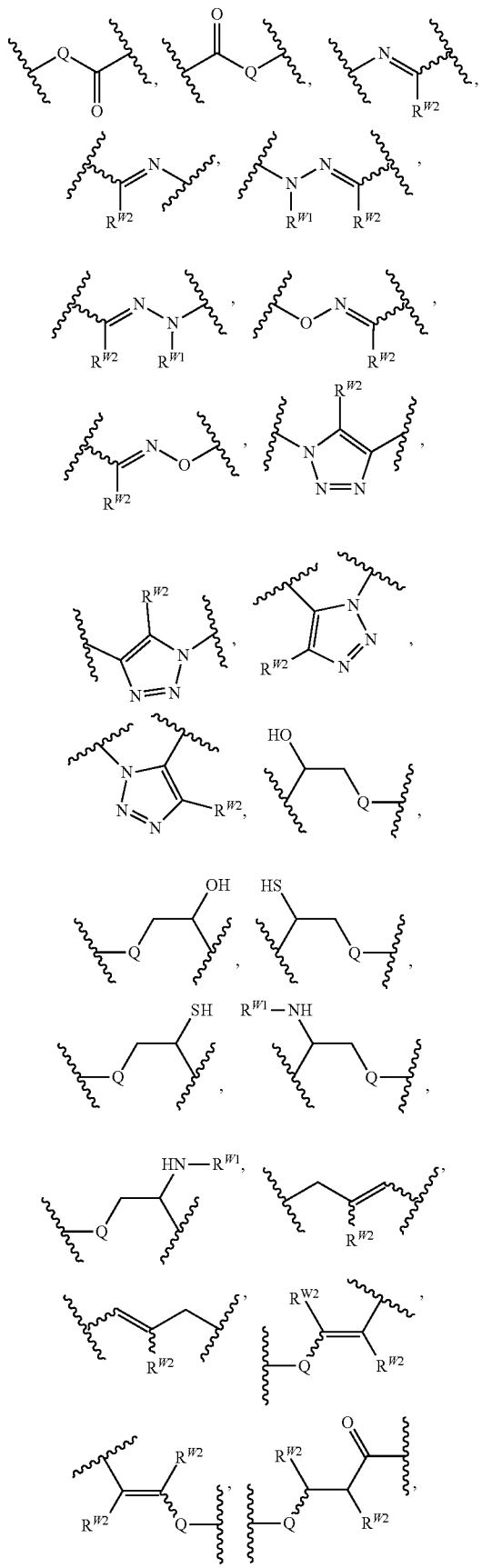

-continued

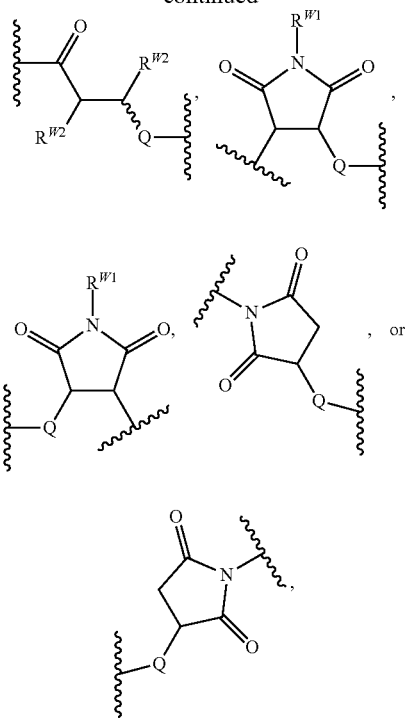

Q is —NH—, —NH—NH—, —O—NH—, —NH—O—, —S—, or —O—;

$L^{C2}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

$R^{W1}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each $R^{W2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two $R^{W2}$ groups are joined to form an optionally substituted cyclic moiety;

$R^{23}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups attached to the same nitrogen atom are joined to form an optionally substituted heterocyclyl or optionally substituted heteroaryl ring; provided that at least one instance of $R^{SN1}$ is not methyl.

14. The compound of claim 13, wherein the compound is of formula:

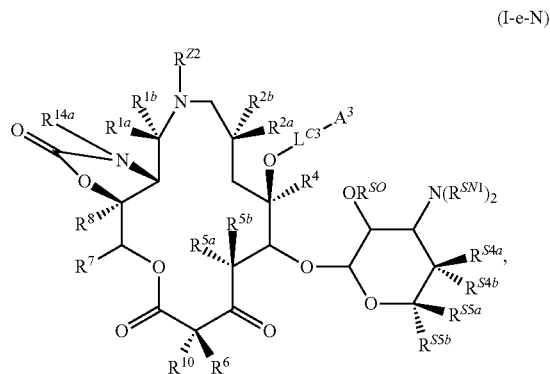

(I-e-N)

or pharmaceutically acceptable salt thereof.

15. The compound of claim 13, wherein the compound is of formula:

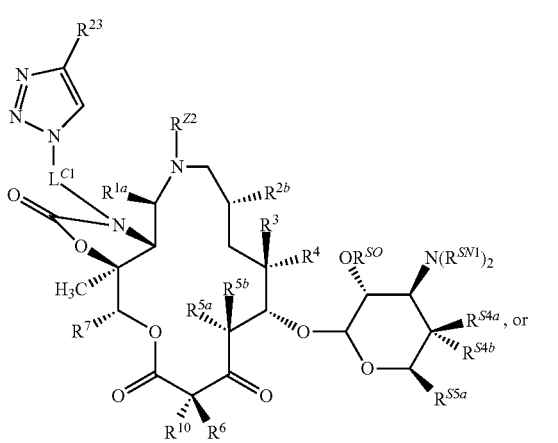

(II-c-N)

or (II-e-N)

or pharmaceutically acceptable salt thereof;

wherein $R^{14a}$ is hydrogen, optionally substituted alkyl, or a nitrogen protecting group.

16. The compound of claim 13, wherein the compound is of formula:

(III-c-N)
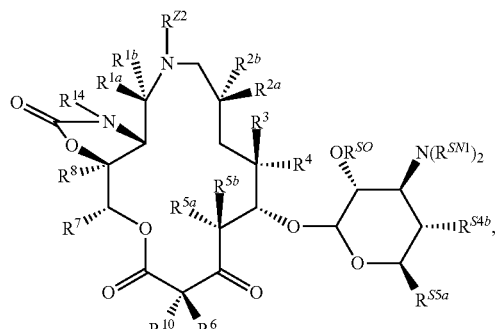
(III-d-N)
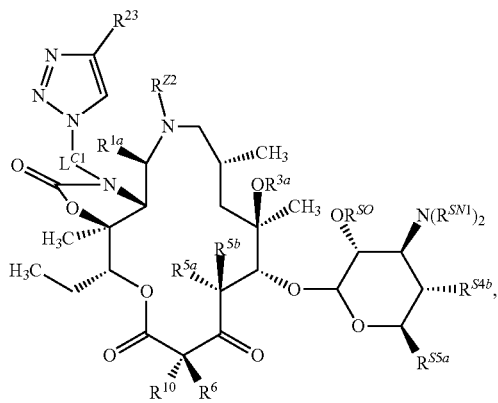
(III-d-N-2)
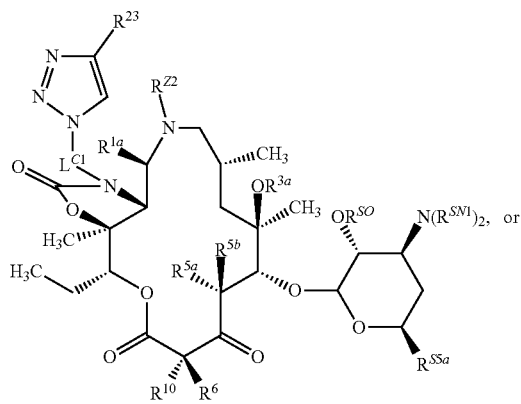
(III-e-N)
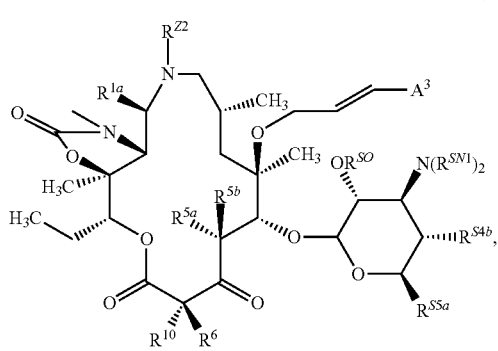
or pharmaceutically acceptable salt thereof;
wherein R$^{14a}$ is hydrogen, optionally substituted alkyl, or a nitrogen protecting group.
17. The compound of claim 13, wherein the compound is of formula:
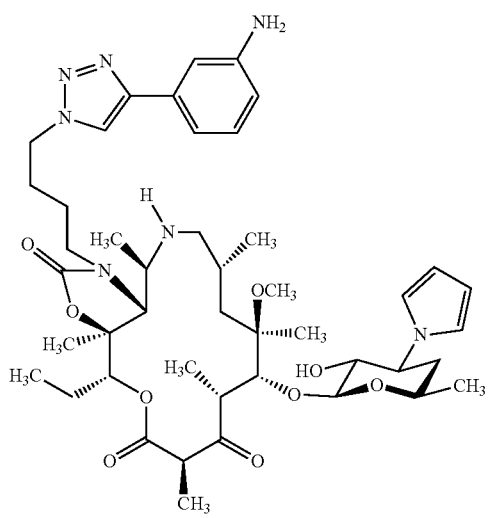
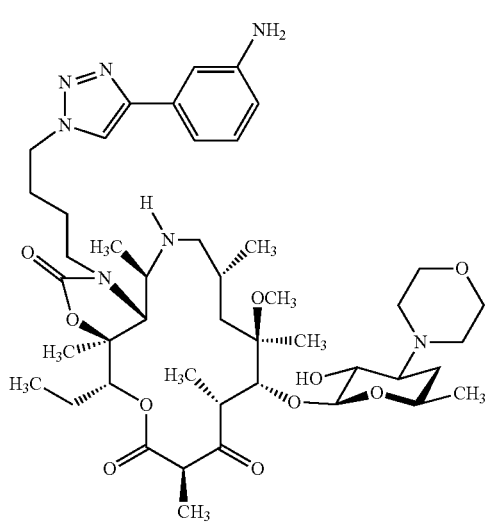
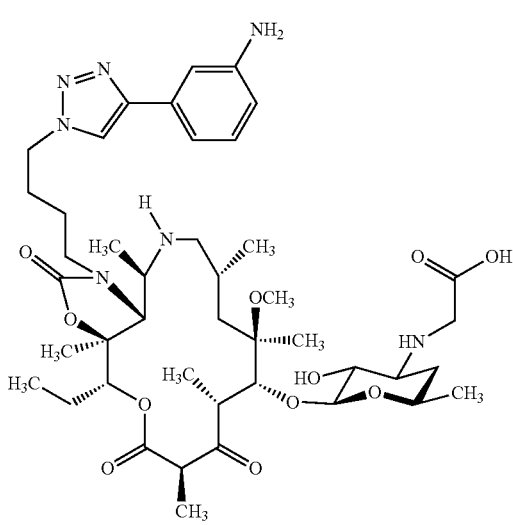

325
-continued
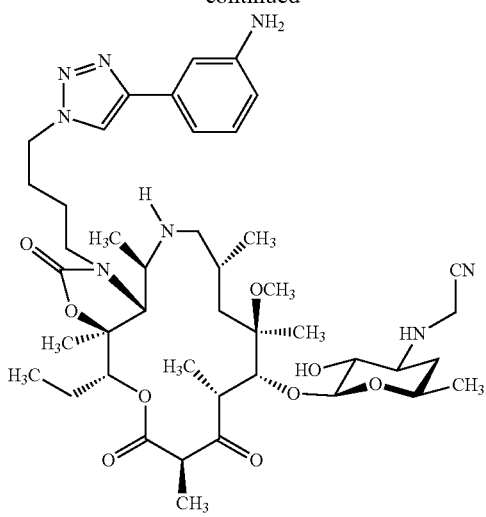
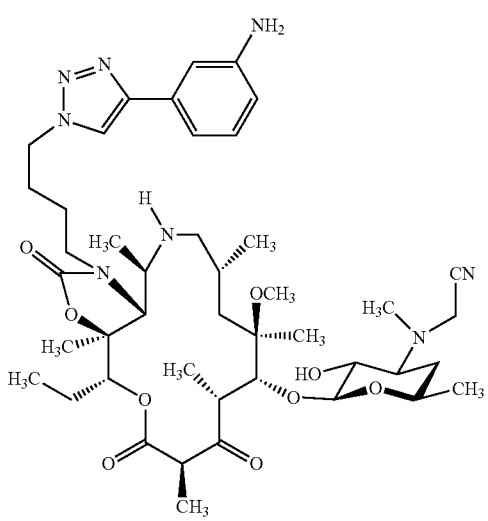
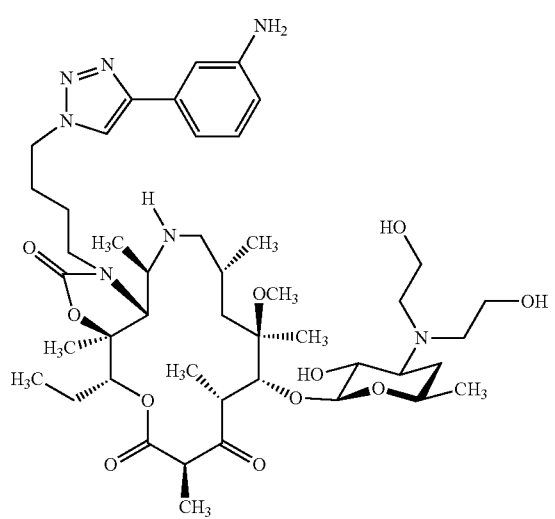
326
-continued
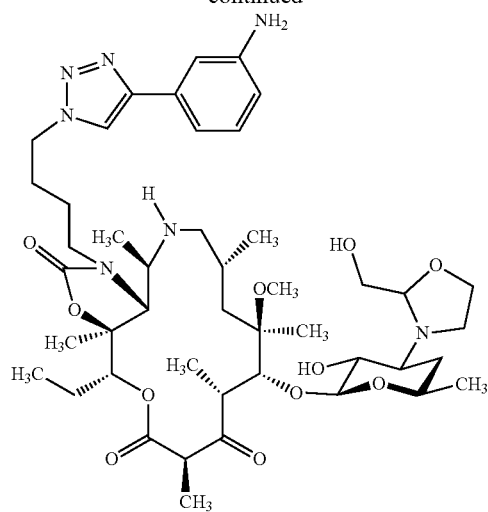
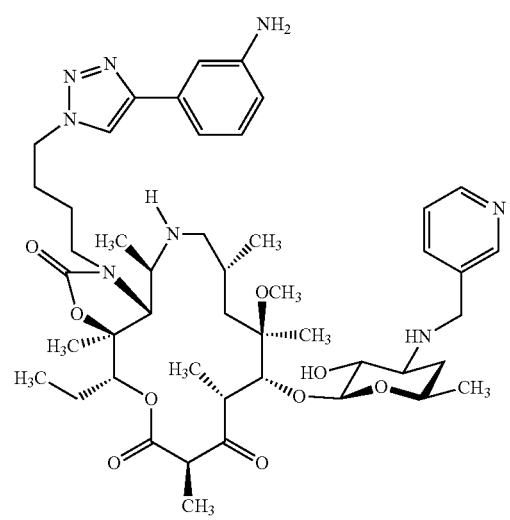
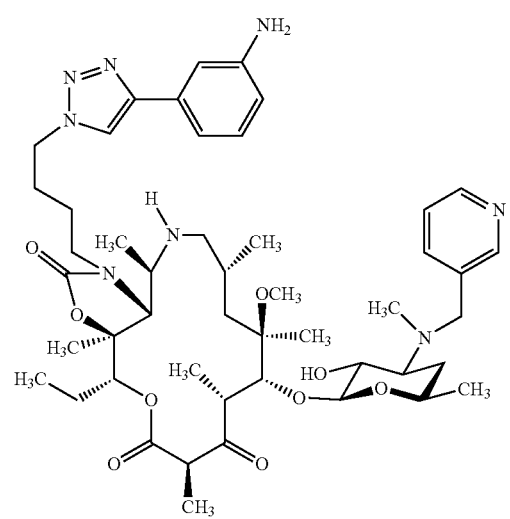

327
-continued
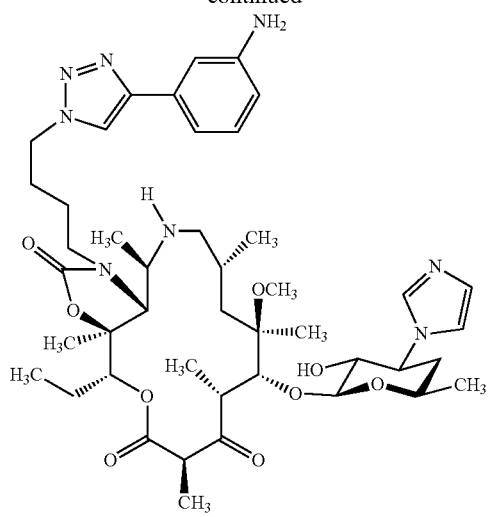
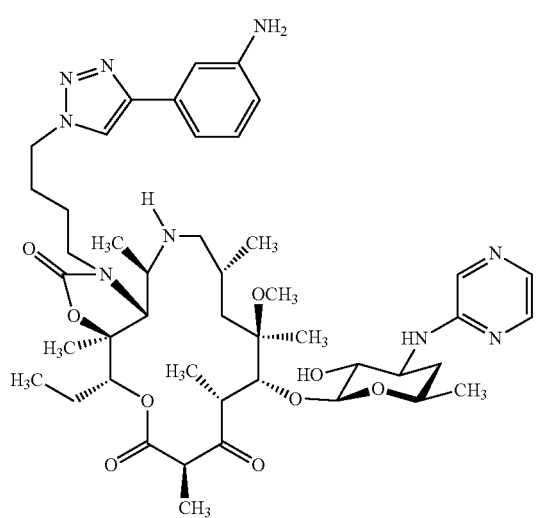
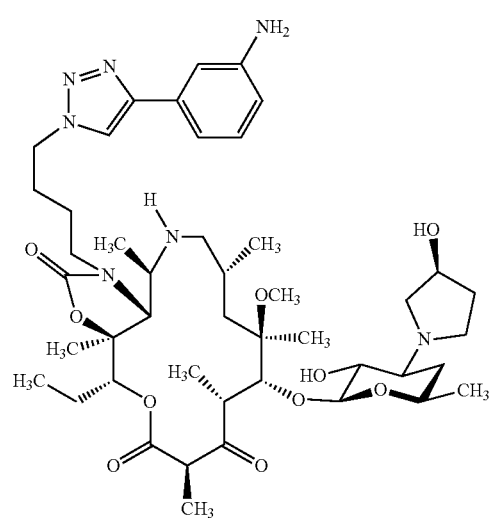
328
-continued
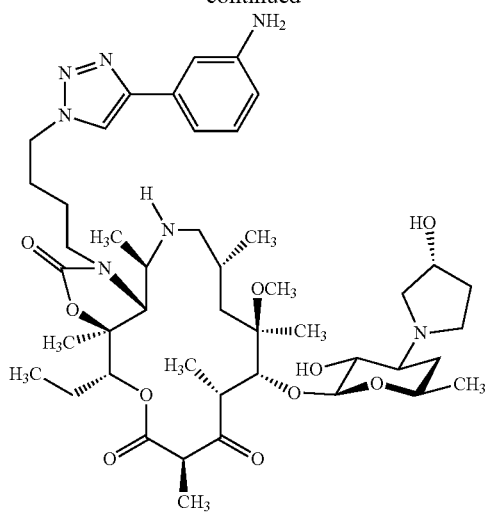
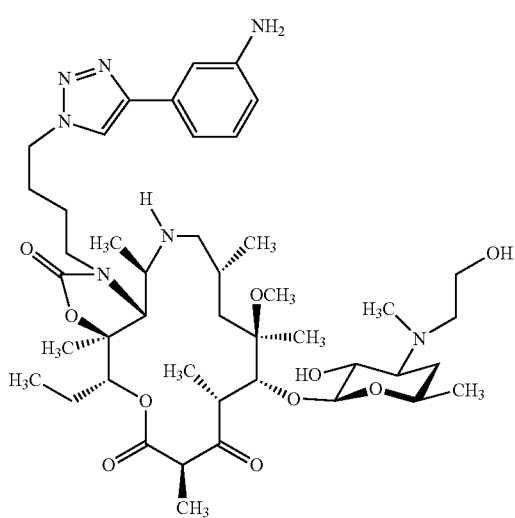
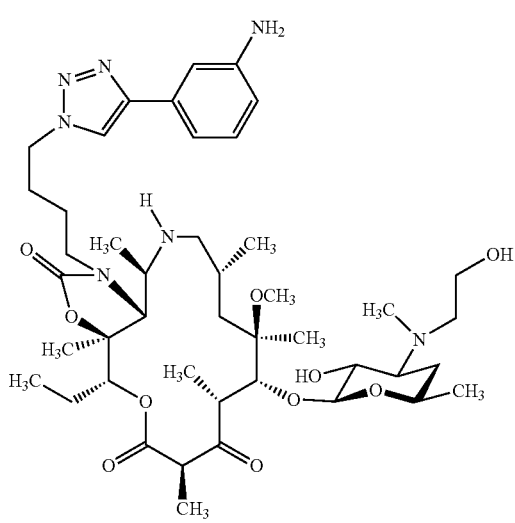

-continued

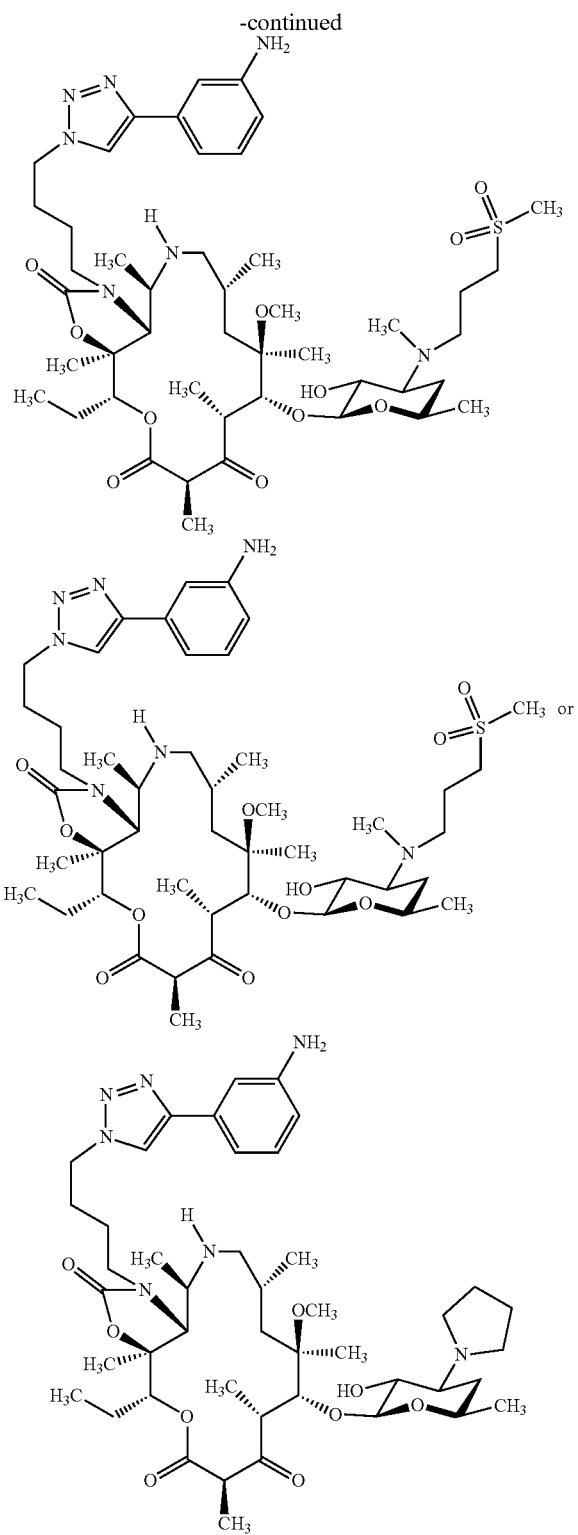

or a pharmaceutically acceptable salt thereof.

18. A method of treating an infectious disease comprising administering an effective amount of a compound of claim 1, or pharmaceutically acceptable salt thereof, to a subject in need thereof.

19. A method of treating an inflammatory condition comprising administering an effective amount of a compound of claim 1, or pharmaceutically acceptable salt thereof, to a subject in need thereof.

20. A method of preparing a compound of Formula (I):

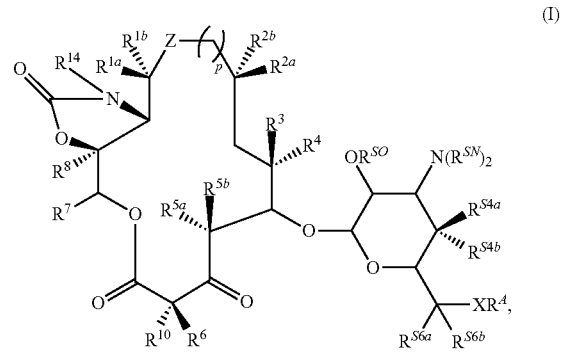

(I)

or salt thereof, the method comprising cyclizing a compound of Formula (N):

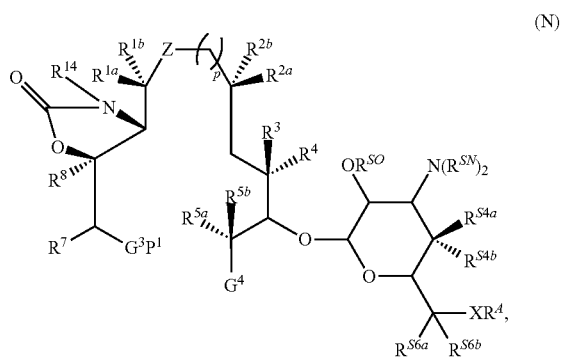

(N)

or salt thereof, to yield a compound of Formula (I), wherein:

Z is $-NR^{Z2}-$;

X is $-NR^{B}-$ or $-O-$;

$R^{Z2}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, acyl, or a nitrogen protecting group;

p is 1;

$R^{A}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, $-C(=O)-L^{S2}-R^{S}$, $-C(=NR^{SN2})-L^{S2}-R^{S}$, $-S(=O)-L^{S2}-R^{S}$, $-S(=O)_2-L^{S2}-R^{S}$, a nitrogen protecting group when attached to a nitrogen atom, or an oxygen protecting group when attached to an oxygen atom, and $R^{SN2}$ is independently hydrogen, optionally substituted $C_1$-$C_6$ alkyl, or a nitrogen protecting group;

$R^{B}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

or $R^{A}$ and $R^{B}$ are taken together to form $=N_2$ or an optionally substituted heterocyclyl or heteroaryl ring;

$L^{S2}$ is a bond, —$NR^S$—, —O—, or —S—, or a linking group selected from the group consisting of optionally substituted alkylene, optionally substituted alkenylene, optionally substituted alkynylene, optionally substituted heteroalkylene, optionally substituted heteroalkenylene, and optionally substituted heteroalkynylene, and combinations thereof;

each $R^S$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a nitrogen protecting group when attached to a nitrogen atom, or a sulfur protecting group when attached to a sulfur atom, or two $R^S$ groups attached to the same nitrogen atom are joined to form an optionally substituted heterocyclyl or heteroaryl ring;

each of $R^{S4a}$ and $R^{S4b}$ is independently hydrogen, halogen, optionally substituted $C_1$-$C_6$ alkyl, or —$OR^{SO}$;

each of $R^{S6a}$ and $R^{S6b}$ is independently hydrogen, halogen, or optionally substituted $C_1$-$C_6$ alkyl;

each $R^{SN}$ is independently hydrogen, optionally substituted $C_1$-$C_6$ alkyl, or a nitrogen protecting group, or two $R^{SN}$ groups attached to the same nitrogen atom are joined to form an optionally substituted heterocyclyl or heteroaryl ring;

each $R^{SO}$ is independently hydrogen, optionally substituted $C_1$-$C_6$ alkyl, a carbohydrate, or an oxygen protecting group;

each of $R^{1a}$ and $R^{1b}$ is independently hydrogen, halogen, acyl, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each of $R^{2a}$ and $R^{2b}$ is independently hydrogen, halogen, optionally substituted alkyl, or optionally substituted alkenyl;

each of $R^3$ and $R^4$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or —$OR^{3a}$;

each $R^{3a}$ is independently hydrogen, optionally substituted alkyl, optionally substituted alkenyl, optionally substituted alkynyl, an oxygen protecting group, or of formula:

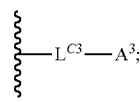
($L^{C3}$-ii)

each $L^{C3}$ is independently a bond, or is a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

each $A^3$ is independently optionally substituted carbocyclyl, optionally substituted heterocyclyl, optionally substituted aryl, or optionally substituted heteroaryl;

each of $R^{5a}$ and $R^{5b}$ is independently hydrogen, halogen, optionally substituted alkyl, optionally substituted carbocyclyl, or optionally substituted heterocyclyl;

$R^6$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

$R^{10}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted aralkyl, optionally substituted heteroaryl, or optionally substituted heteroaralkyl;

$R^7$ is hydrogen, halogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

$R^8$ is hydrogen, halogen, or optionally substituted $C_1$-$C_6$ alkyl;

$R^{14}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or of formula:

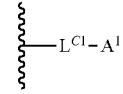
($L^{C1}$-ii)

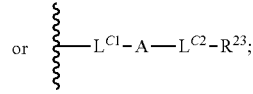
($L^{C1}$-iii)

$L^{C1}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

$A^1$ is a leaving group (LG), —SH, —OH, —$NH_2$, —NH—$NH_2$, —$N_2$, —$N_3$, —O—$NH_2$, —CCH, —OC(=O)$R^{Z8}$, —C(=O)O$R^{Z8}$, or of formula:

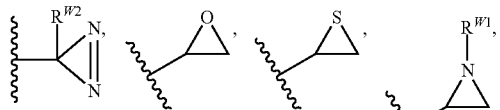

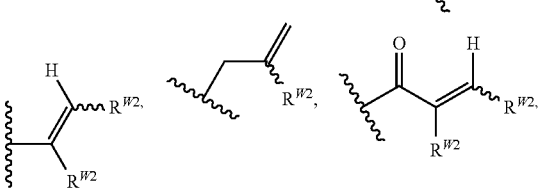

-continued

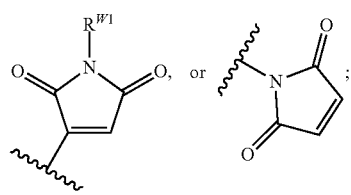

A is —NH—, —NH—NH—, —NH—O—, —O—NH—, —S—, —SS—, —O—, or of formula:

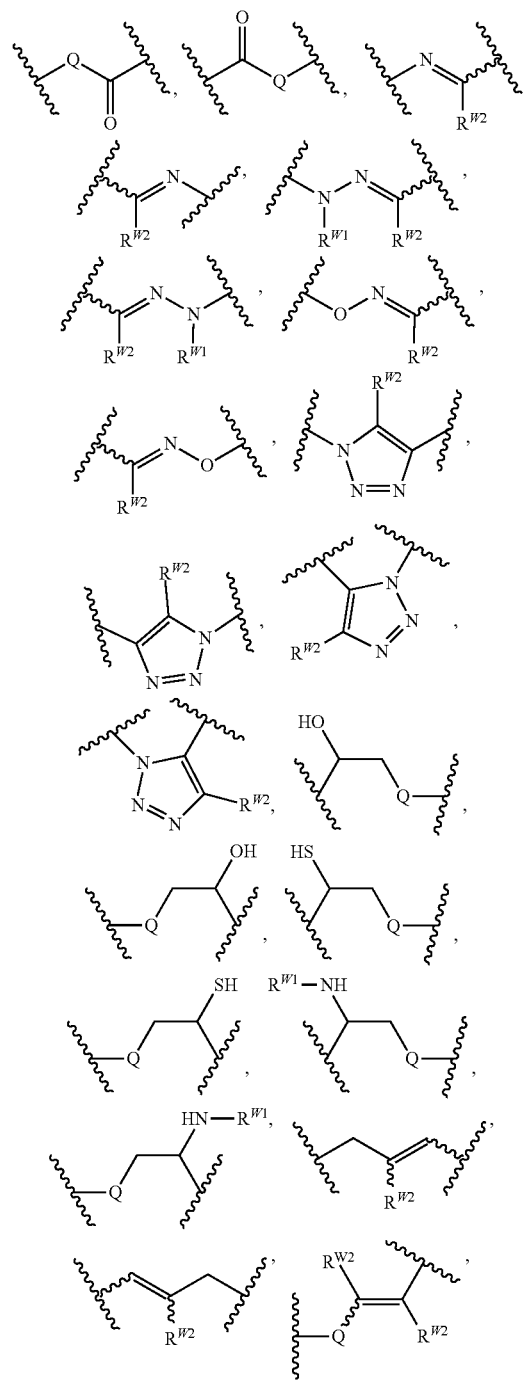

-continued

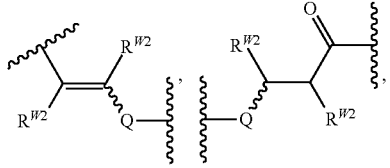

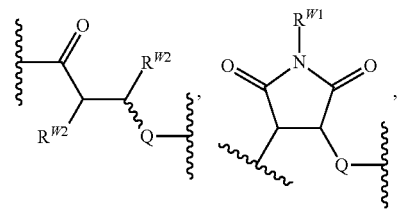

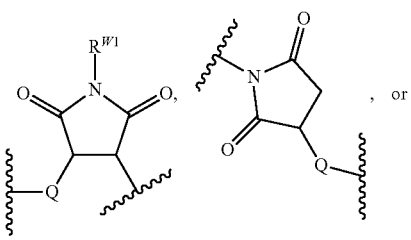

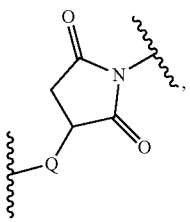

Q is —NH—, —NH—NH—, —O—NH—, —NH—O—, —S—, or —O—;

$L^{C2}$ is a bond, or a linking group selected from the group consisting of optionally substituted alkylene, optionally substituted alkenylene, optionally substituted alkynylene; optionally substituted heteroalkylene, optionally substituted heteroalkenylene, and optionally substituted heteroalkynylene, and combinations thereof;

$R^{W1}$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group;

each $R^{W2}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or two $R^{W2}$ groups are joined to form an optionally substituted cyclic moiety;

$R^{23}$ is hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl;

each $R^{Z8}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{Z8}$ groups attached to the same nitrogen atom are joined to form an optionally substituted heterocyclyl or optionally substituted heteroaryl ring;

$P^1$ is hydrogen, silyl, optionally substituted alkyl, optionally substituted alkenyl, optionally substituted alkynyl, optionally substituted carbocyclyl, optionally substituted heterocyclyl, optionally substituted aryl, optionally substituted heteroaryl, or an oxygen, nitrogen, or thiol protecting group;

$G^3$ is —O—, —S—, or —N($R^{G1}$)—, wherein $R^{G1}$ is hydrogen, optionally substituted alkyl, or a nitrogen protecting group;

$G^4$ is of formula:

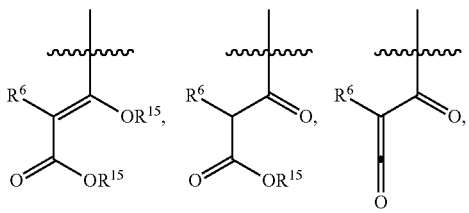

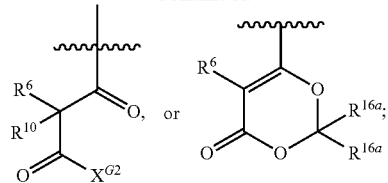

each instance of $X^{G2}$ is —$OR^{15}$, —$SR^{15}$, or —$N(R^{15})_2$;

each instance of $R^{15}$ is independently silyl, optionally substituted alkyl, optionally substituted alkenyl, optionally substituted alkynyl, optionally substituted carbocyclyl, optionally substituted heterocyclyl, optionally substituted aryl, or optionally substituted heteroaryl, or two $R^{15}$ groups are joined to form an optionally substituted heterocyclyl or heteroaryl ring; and each instance of $R^{16a}$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl.

* * * * *

UNITED STATES PATENT AND TRADEMARK OFFICE
CERTIFICATE OF CORRECTION

PATENT NO. : 10,640,528 B2
APPLICATION NO. : 15/558896
DATED : May 5, 2020
INVENTOR(S) : Andrew G. Myers et al.

Page 1 of 4

It is certified that error appears in the above-identified patent and that said Letters Patent is hereby corrected as shown below:

In the Claims

In Claim 2, at Column 305, Lines 60-65, formula: 

Should be replaced with the formula: 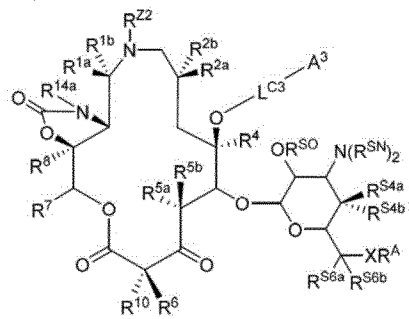

In Claim 3, at Column 306, Lines 6-25, formula: 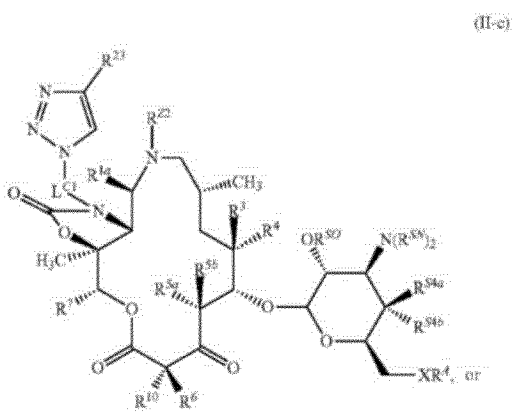

Signed and Sealed this
Seventh Day of July, 2020

Andrei Iancu
*Director of the United States Patent and Trademark Office*

CERTIFICATE OF CORRECTION (continued)
U.S. Pat. No. 10,640,528 B2

Page 2 of 4

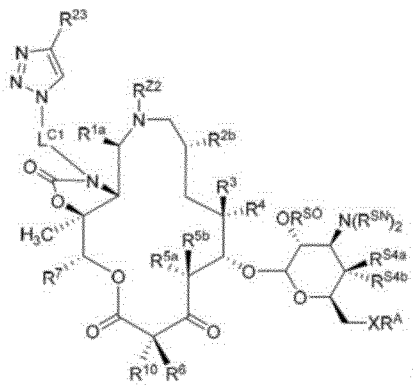

Should be replaced with the formula:

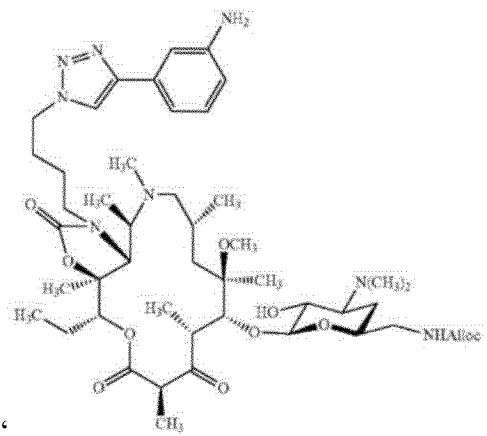

In Claim 12, at Column 308, Lines 50-65, formula: " " should be deleted

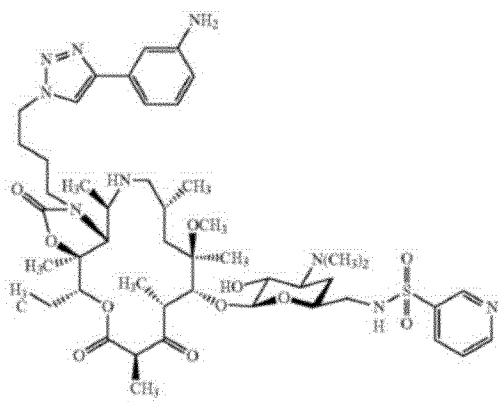

In Claim 12, at Column 311, Lines 25-40, formula:

CERTIFICATE OF CORRECTION (continued)
U.S. Pat. No. 10,640,528 B2

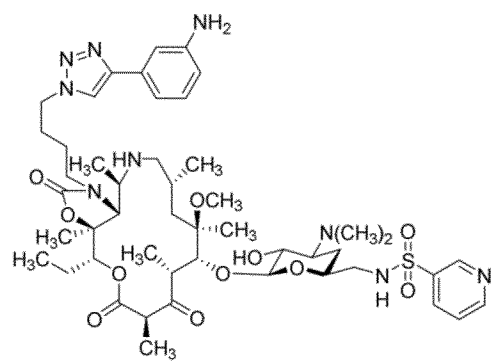

Should be replaced with the formula:

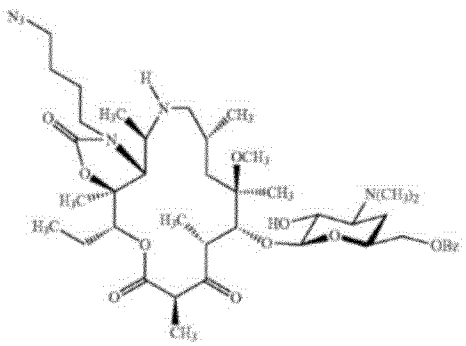

In Claim 12, at Column 314, Lines 25-40, formula:

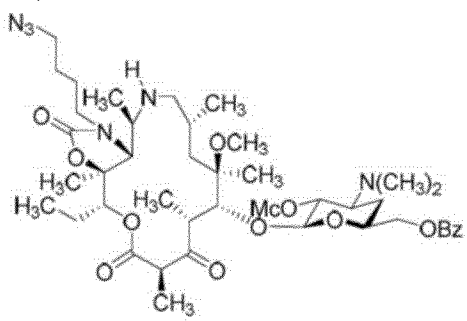

Should be replaced with the formula:

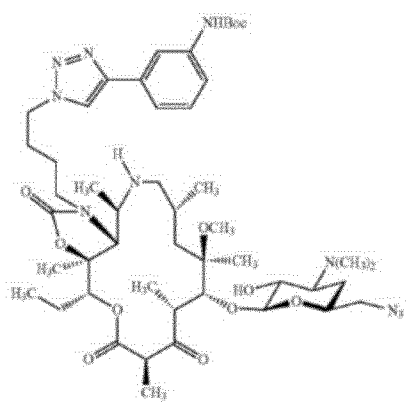

In Claim 12, at Column 315, Lines 5-20, formula:

CERTIFICATE OF CORRECTION (continued)
U.S. Pat. No. 10,640,528 B2

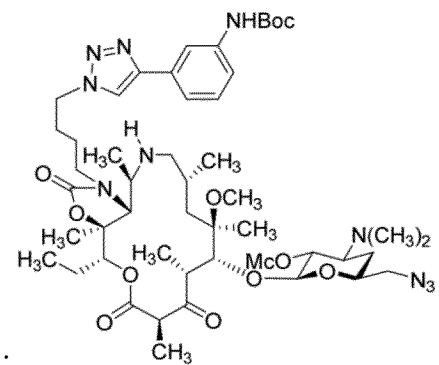

Should be replaced with the formula:

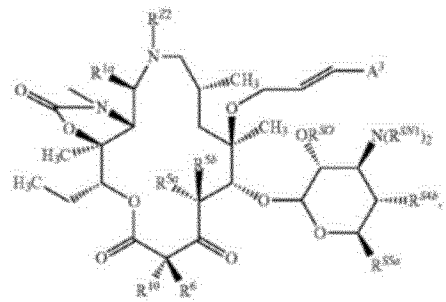

In Claim 16, at Column 323, Lines 50-60, formula:

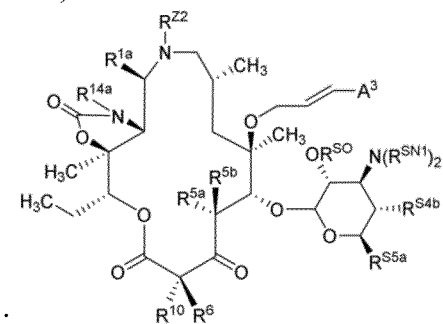

Should be replaced with the formula: